US009880151B2

(12) United States Patent
Watt et al.

(10) Patent No.: US 9,880,151 B2
(45) Date of Patent: Jan. 30, 2018

(54) METHOD OF DETERMINING, IDENTIFYING OR ISOLATING CELL-PENETRATING PEPTIDES

(75) Inventors: Paul Michael Watt, Perth (AU); Richard Hopkins, Perth (AU); Katrin Hoffman, Aubin Grove (AU)

(73) Assignee: Phylogica Limited, Subiaco (AU)

( * ) Notice: Subject to any disclaimer, the term of this patent is extended or adjusted under 35 U.S.C. 154(b) by 0 days.

(21) Appl. No.: 14/112,512

(22) PCT Filed: May 23, 2012

(86) PCT No.: PCT/AU2012/000579
§ 371 (c)(1),
(2), (4) Date: Jan. 27, 2014

(87) PCT Pub. No.: WO2012/159164
PCT Pub. Date: Nov. 29, 2012

(65) Prior Publication Data
US 2014/0141452 A1 May 22, 2014

Related U.S. Application Data

(60) Provisional application No. 61/489,198, filed on May 23, 2011.

(51) Int. Cl.
*G01N 33/50* (2006.01)
*C07K 14/47* (2006.01)
*C40B 60/12* (2006.01)

(52) U.S. Cl.
CPC ..... *G01N 33/5014* (2013.01); *C07K 14/4723* (2013.01); *C07K 2319/00* (2013.01); *C07K 2319/74* (2013.01); *C12N 2503/02* (2013.01); *C40B 60/12* (2013.01)

(58) Field of Classification Search
CPC ............ A61K 38/00; A61K 38/177; A61K 47/48246; A61K 38/162; A61K 47/48238; A61K 49/0056; C12N 2533/52; C12N 2310/3513; G01N 33/566; G01N 2500/00; G01N 2333/005; G01N 33/56983
See application file for complete search history.

(56) References Cited

U.S. PATENT DOCUMENTS

| 5,399,346 | A | 3/1995 | Anderson et al. |
| 5,503,843 | A | 4/1996 | Santus et al. |
| 8,063,012 | B2 * | 11/2011 | Watt .................. C07K 14/4703 514/1.1 |
| 2003/0050243 | A1 * | 3/2003 | Tymianski ............. A61K 38/08 514/8.3 |
| 2003/0170826 | A1 * | 9/2003 | Rabinovich et al. ........ 435/69.7 |

FOREIGN PATENT DOCUMENTS

| WO | WO 2002/066012 | 8/2002 |
| WO | WO 2002/066490 | 8/2002 |
| WO | WO 2003/070735 | 8/2003 |
| WO | WO2009032148 | * 3/2009 |
| WO | WO 2010/094027 | 8/2010 |
| WO | WO2010094027 | * 8/2010 |

OTHER PUBLICATIONS

Nascimento et al. The natural cell-penetrating peptide crotamine targets tumor tissue in vivo and triggers a lethal calcium-dependent pathway in cultured cells. Mol Pharm. Feb. 6, 2012;9(2):211-21.*
Schwarze et al. Protein transduction: unrestricted delivery into all cells? Trends Cell Biol. Jul. 2000;10(7):290-5.*
Ingham et al. Interaction of *Staphylococcus aureus* Fibronectin-binding Protein with Fibronectin: Affinity, Stoichiometry, and Modular Requirements. J. Biol. Chem. 2004, 279:42945-42953.*
Amblard et al. Methods and Protocols of Modern Solid Phase Peptide Synthesis. Molecular Biotechnology. 2006, vol. (33): pp. 239-254. Humana Press Inc. All rights of any nature whatsoever reserved. ISSN: 1073-6085/Online ISSN: 1559-0305/2006/33:3/239.*
Olson et al. In vivo characterization of activatable cell penetrating peptides for targeting protease activity in cancer. Integr Biol (Camb). Jun. 2009;1(5-6):382-93. doi: 10.1039/b904890a. Epub May 11, 2009.*
Chen et al. A Heparan Sulfate-Binding Cell Penetrating Peptide for Tumor Targeting and Migration Inhibition. Hindawi Publishing Corporation BioMed Research International vol. 2015, Article ID 237969, 15 pages. http://dx.doi.org/10.1155/2015/237969.*
Altschul, Stephen, F., et al., (1990), "Basic Local Alignment Search Tool", J. Mol. Biol, 215:403-410.
Amann, Egon and Brosius, Jürgen, (1985), "'ATG vectors' for regulated high-level expression of cloned genes in *Escherichia coli*", Gene, 40:183-190.
Beniaminovitz, Ainat, et al., (2000), "Prevention of Rejection in Cardiac Transplantation by Blockade of the Interleukin-2 Receptor With a Monoclonal Antibody", New Engl. J. Med., 342:613-619.
Bernas, Tytus, et al., (2002), "Mitochondrial and Nonmitochondrial Reduction of MTT: Interaction of MTT With TMRE, JC-1, and NAO Mitochondrial Fluorescent Probes", Cytometry, 47:236-242.
Brady, Leo and Dodson, Guy, (1994), "Reflections on a peptide", Nature, 368:692-693.
Carpino, Louis, A., and Han, Grace, Y., (1972), "The 9-Fluorenylmethoxycarbonyl Amino-Protecting Group", J. Org. Chem., 37:3403-3409.
Chorev, Michael and Goodman, Murray, (1995), "Recent developments in retro peptides and proteins—an ongoing topochemical exploration", Trends Biotech., 13:438-445.

(Continued)

*Primary Examiner* — Satyanarayana R Gudibande
*Assistant Examiner* — Jia-Hai Lee
(74) *Attorney, Agent, or Firm* — Michael B. Rubin; Bozicevic, Field & Francis LLP

(57) ABSTRACT

The present invention provides a method of determining or identifying or isolating a cell-penetrating peptide (CPP) or analog or derivative thereof having cell-type selectivity and/or at least capable of passing through a Blood Brain Barrier of an animal subject. This invention also provides CPPs and analogs and derivatives thereof, such as those set forth in SEQ ID NOs: 1-27 of the Sequence Listing, and compositions comprising one or more of the CPPs, including conjugates in which a CPP or analog or derivative thereof is linked to a cargo molecule. The invention also provides methods for transporting cargo molecules across cell membranes to specific locations within cells, and for treating, preventing and/or diagnosing diseases that are treatable by a cargo molecule to which a CPP or analog or derivative of the invention is attached. The invention also provides tailored peptide libraries for use in identifying or isolating CPPs.

14 Claims, 47 Drawing Sheets

(56) References Cited

OTHER PUBLICATIONS

De Kruif, John, et al., (1995) "Rapid Selection of Cell Subpopulation-Specific Human Monoclonal Antibodies from a Synthetic Phage Antibody Library" Proc Natl Acad Sci USA, 92:3938-3942.
Francoeur, Michael, L., et al., (1990), "Oleic Acid: Its effects on stratum corneum in relation to (Trans)Dermal drug delivery", Pharm. Res., 7(6):621-627.
Ghosh, Subrata, et al., (2003), "Natalizumab for Active Crohn's Disease", New Engl. J. Med., 348:24-32.
Goodman, Murray and Chorev, Michael, (1979), "On the Concept of Linear Modified Retro-Peptide Structures", Accounts of Chemical Research, 12(1): 1-7.
Hanes, Jozef and Plückthun, Andreas, (1997), "In vitro selection and evolution of functional proteins by using ribosome display", Proc. Natl. Acad. Sci. USA, 94:4937-4942.
Hoogenboom, Hennie, R., et al., (1998), "Antibody Phage Display Technology and Its Applications" Immunotechnol 4:1-20.
Houghten, Richard, A., (1985), "General method for the rapid solid-phase synthesis of large Numbers of peptides: Specificity of antigen-antibody interaction at the level of individual amino acids", Proc. Natl. Acad. Sci. USA, 82:5131-5135.
Jameson, Bradford, A., et al., (1994), "A rationally designed CD4 analogue inhibits experimental allergic encephalomyelitis", Nature, 368:744-746.
Koncz, Csaba, et al, (1987), "Expression and assembly of functional bacterial luciferase in plants", Proc. Natl. Acad. Sci., 84:131-135.
Kyte, Jack and Doolittle, Russel, F., (1982), "A Simple Method for Displaying the Hydropathic Character of a Protein", J. Mol. Biol., 157:105-132.
Langel (2011) "Cell-Penetrating Peptides: Methods and Protocols" Methods in Molecular Biology Humana Press Inc., 63 pages.
Lepisto, J., et al., (1992), "Effects of Homodimeric Isoforms of Platelet-Derived Growth Factor (PDGF-AA and PDGF-BB) on Wound Healing in Rat", J. Surg. Res., 53:596-601.
Lipsky, Peter, E., et al., (2000), "Infliximab and Methotrexate in the Treatment of Rheumatoid Arthritis", New Engl. J. Med. 343:1594-1602.
Liu, Puchun, et al., (1991), "Cotransport of Estradiol and Ethanol through Human Skin in Vitro: Understanding the Permeant/Enhancer Flux Relationship", Pharm. Res. 8(7): 938-944.
Matsuda, Hiroshi, et al., (1998), "Role of Nerve Growth Factor in Cutaneous Wound Healing: Accelerating Effects in Normal and Healing-impaired Diabetic Mice", J. Exp. Med., 187:297-306.
Mauer, Norbert, et al., (1999), "Lipid-based systems for the intracellular delivery of genetic drugs", Molecular Membrane Biology, 16:129-140.
Merrifield, R.B., (1963), "Solid Phase Peptide Synthesis. I. The Synthesis of a Tetrapeptide", J. Am. Chern. Soc., 85:2149-2154.
Milgrom, Henry, et al., (1999), "Treatment of Allergic Asthma With Monoclonal Anti-IgE Antibody", New England Journal of Medicine, 341(26)1966-1973.
Mosmann, Tim, (1983), "Rapid Colorimetric Assay for Cellular Growth and Survival: Application to Proliferation and Cytotoxicity Assays", J. Immunol. Methods 65:55-63.
Muller, Alexander, J., et al., (1991), "BCR First Exon Sequences Specifically Activate the BCR/ABL Tyrosine Kinase Oncogene of Philadelphia Chromosome-Positive Human Leukemias", Mol. Cell. Biol., 11(4):1785-1792.
Natsume, Atsushi, et al., (2000), "Cationic Liposome Conjugation to Recombinant Adenoviral Vector Reduces Viral Antigenicity", Jpn. J. Cancer Res. 91:363-367.
Needleman, Saul, B. and Wunsch, Christian, D., (1970), "A General Method Applicable to the Search for Similarities in the Amino Acid Sequence of Two Proteins", J. Mol. Biol. 48:443-453.
Sarpotdar, Pramod, P. and Zatz, Joel, L., (1986), "Evaluation of Penetration Enhancement of Lidocaine by Nonionic Surfactants Through Hairless Mouse Skin In Vitro", J. Pharm. Sci., 75(2): 176-181.
Sela, Michael and Zisman, Einat, (1997), "Different roles of D-amino acids in immune phenomena", FASEB J. 11:449-456.
Shimatake, Hiroyuki and Rosenberg, Martin, (1981), "Purified Δ regulatory protein cll positively activated promoters for lysogenic development", Nature, 292:128-132.
Slamon, Dennis, J., et al., (2001), "Use of Chemotherapy Plus a Monoclonal Antibody Against HER2 for Metastatic Breast Cancer That Overexpresses HER2", New Engl J. Med., 344(11):783-792.
Stemmer, Willem, (1994), "DNA shuffling by random fragmentation and reassembly: In vitro recombination for molecular evolution", Proc. Natl. Acad. Sci. USA, 91:10747-10751.
Studier, F., William and Moffatt, Barbara, A., (1986), "Use of Bacteriophage T7 RNA Polymerase to Direct Selective High-level Expression of Cloned Genes", J. Mol. Biol. 189:113-130.
Tangri, Shabnam, et al., (2005), "Rationally Engineered Therapeutic Proteins with Reduced Immunogenicity", The Journal of Immunology, 174:3187-3196.
Tsubery, Haim, et al., (2004), "Prolonging the Action of Protein and Peptide Drugs by a Novel Approach of Reversible Polyethylene Glycol Modification", J. Biol. Chem, 279(37):38118-38124.
Yoneto, Kunio, et al., (1995), "A Mechanistic Study of the Effects of the 1-Alkyl-2-pyrrolidones on Bilayer Permeability of Stratum Corneum Lipid Liposomes: A Comparison with Hairless Mouse Skin Studies", J. Pharm. Sci., 84(7):853-860.
Puolakkainen, Pauli, A., et al., (1995), "The enhancement in wound healing by transforming growth factor-β (TGF-3) depends on the topical delivery system", J. Surg. Res., 58:321-329.

* cited by examiner

| | Number |
|---|---|
| Phage Screens (n) | 37 |
| Unique sequences (n) | 992 |
| Peptide synthesised | 153 (15%) |
| Recombinant peptides | 13 (1%) |
| FACS +ve (Bend.3/CHO) | 46 (30%, n=166) |
| Microscopy +ve (Bend.3/CHO) | 17 (11%, n=166) |

Figure 6

SEQUENCE LISTING

```
<160> NUMBER OF SEQ ID NOS: 29

<210> SEQ ID NO 1
<211> LENGTH: 13
<212> TYPE: PRT
<213> ORGANISM: artificial
<220> FEATURE:
<223> OTHER INFORMATION: Synthetic peptide

<400> SEQUENCE: 1

Arg Phe Arg Cys Gly Arg Arg Lys Trp Gln Ile Gly Ser
1               5                   10

<210> SEQ ID NO 2
<211> LENGTH: 14
<212> TYPE: PRT
<213> ORGANISM: artificial
<220> FEATURE:
<223> OTHER INFORMATION: Synthetic peptide

<400> SEQUENCE: 2

Trp Thr Ile Ser Ser Arg Arg Arg Lys Val Asn Arg Ala Cys
1               5                   10

<210> SEQ ID NO 3
<211> LENGTH: 58
<212> TYPE: PRT
<213> ORGANISM: artificial
<220> FEATURE:
<223> OTHER INFORMATION: Synthetic peptide

<400> SEQUENCE: 3

Pro Met Val Asp Leu Glu Lys Phe Lys Phe His Ala Arg Ile Asp Asp
1               5                   10                  15

Gly Phe Glu Asp Ser Tyr Ile Gln Leu Leu Leu Asp Ala Ala Ile Asn
            20                  25                  30

Tyr Val Ser Lys Ile Thr Gly Val Pro Asn Asp Glu Asn Ala Pro Pro
        35                  40                  45

Glu Tyr Asp Leu Ala Ile Met Ile Leu Ala
    50                  55

<210> SEQ ID NO 4
<211> LENGTH: 51
<212> TYPE: PRT
<213> ORGANISM: artificial
<220> FEATURE:
<223> OTHER INFORMATION: Synthetic peptide

<400> SEQUENCE: 4
```

```
Leu His Gly Ala Asn Gly Leu Arg Thr Ile Ile Asn Asp Tyr Ala Glu
1               5                   10                  15
Arg Ala Asn Thr Arg Leu Trp Leu Lys Gly Leu Leu Tyr Thr Ala Thr
            20                  25                  30
Val Phe Thr Ile Leu Leu Gly Thr Leu Val Ile Phe Thr Phe Asp Pro
        35                  40                  45
Asn Ile Arg
    50

<210> SEQ ID NO 5
<211> LENGTH: 26
<212> TYPE: PRT
<213> ORGANISM: artificial
<220> FEATURE:
<223> OTHER INFORMATION: Synthetic peptide

<400> SEQUENCE: 5

Pro Tyr Ser Arg Pro His Val Gln Leu Trp Tyr Pro Asn Arg Glu Ser
1               5                   10                  15
Cys Arg Ser Leu Ile Arg Ser Leu Gly Pro
            20                  25

<210> SEQ ID NO 6
<211> LENGTH: 47
<212> TYPE: PRT
<213> ORGANISM: artificial
<220> FEATURE:
<223> OTHER INFORMATION: Synthetic peptide

<400> SEQUENCE: 6

Leu Phe Val Lys Val Gly Gly Glu Glu Tyr Gly Val Pro Ile Lys Asn
1               5                   10                  15
Val Asp Glu Ile Thr Gly Thr Glu Glu Ala Lys Gln Val Asn Gly Gln
            20                  25                  30
Glu Val Ile Lys Arg Asn Asp Glu Thr Ile Glu Gly Val Thr Lys
        35                  40                  45

<210> SEQ ID NO 7
<211> LENGTH: 70
<212> TYPE: PRT
<213> ORGANISM: artificial
<220> FEATURE:
<223> OTHER INFORMATION: Synthetic peptide

<400> SEQUENCE: 7

Arg Val Met Ile Ala Met Glu Leu Ala Cys Asp Pro Glu Leu Ile Ile
1               5                   10                  15
Ala Asp Glu Pro Thr Thr Ala Leu Asp Val Thr Ile Glu Lys Lys Val
            20                  25                  30
Leu Ser Ile Phe Ser Lys Leu Val Glu Glu His Asn Leu Ser Val Leu
        35                  40                  45
Trp Ile Thr His Asp Leu Gly Val Ala Gln Phe Cys Asp Arg Val
    50                  55                  60
Gly Val Met Tyr Ala Gly
65                  70

<210> SEQ ID NO 8
<211> LENGTH: 94
<212> TYPE: PRT
<213> ORGANISM: artificial
<220> FEATURE:
<223> OTHER INFORMATION: Synthetic peptide
```

```
<400> SEQUENCE: 8

Leu Leu Gln Ala Thr Tyr Ile Gly Thr Asp Gly Gln Pro Arg Thr Ile
1               5                   10                  15

Phe Tyr Asp Val Gly Val Val Pro Asp Ser Ser Pro Val Phe Ala Ser
                20                  25                  30

Ser Thr Ser Gly Ala Val Ala Glu Asn Glu Ala Val Gly Thr Val Val
            35                  40                  45

Tyr Arg Ala Glu Ala Thr Ser Asp Leu Glu Asn Asn Pro Leu Ser Tyr
        50                  55                  60

Ser Leu Gly Gly Thr Asp Ala Asp Leu Phe Thr Ile Asp Val Ala Thr
65                  70                  75                  80

Gly Glu Val Thr Leu Lys Asn Pro Ala Asp Tyr Glu Ser Lys
                85                  90

<210> SEQ ID NO 9
<211> LENGTH: 19
<212> TYPE: PRT
<213> ORGANISM: artificial
<220> FEATURE:
<223> OTHER INFORMATION: Synthetic peptide

<400> SEQUENCE: 9

Ala Thr Tyr Trp Lys Lys Ala Thr Ala Ala Arg Pro Thr Arg Cys Arg
1               5                   10                  15

Ala Ile Pro

<210> SEQ ID NO 10
<211> LENGTH: 34
<212> TYPE: PRT
<213> ORGANISM: artificial
<220> FEATURE:
<223> OTHER INFORMATION: Synthetic peptide

<400> SEQUENCE: 10

Pro Tyr Tyr Ser Pro Asp Leu Asn Pro Val Glu Gly Ile Trp Ser Trp
1               5                   10                  15

Leu Arg His Gly Pro Met Ala Asn Thr Ala Phe Thr Asp Pro Asp His
                20                  25                  30

Leu Thr

<210> SEQ ID NO 11
<211> LENGTH: 69
<212> TYPE: PRT
<213> ORGANISM: artificial
<220> FEATURE:
<223> OTHER INFORMATION: Synthetic peptide

<400> SEQUENCE: 11

Pro Asp Gly Gly Gln Val Thr Thr Glu Ser Asn Leu Val Glu Phe Asp
1               5                   10                  15

Glu Glu Ser Thr Lys Gly Ile Val Thr Gly Ala Val Ser Asp His Thr
                20                  25                  30

Thr Val Glu Asp Thr Lys Glu Tyr Thr Thr Glu Ser Asn Leu Ile Glu
            35                  40                  45

Leu Val Asp Glu Leu Pro Glu Glu His Gly Gln Ala Gln Gly Pro Ile
        50                  55                  60

Glu Glu Ile Thr Glu
65
```

<210> SEQ ID NO 12
<211> LENGTH: 69
<212> TYPE: PRT
<213> ORGANISM: artificial
<220> FEATURE:
<223> OTHER INFORMATION: Synthetic peptide

<400> SEQUENCE: 12

Pro Gly Gly Gly Gln Val Thr Thr Glu Ser Asn Leu Val Glu Phe Asp
1               5                   10                  15

Glu Glu Ser Thr Lys Gly Ile Val Thr Gly Ala Val Ser Asp His Thr
            20                  25                  30

Thr Val Glu Asp Thr Lys Glu Tyr Thr Thr Glu Ser Asn Leu Ile Glu
        35                  40                  45

Leu Val Asp Glu Leu Pro Glu Glu His Gly Gln Ala Gln Gly Pro Ile
    50                  55                  60

Glu Glu Ile Thr Glu
65

<210> SEQ ID NO 13
<211> LENGTH: 41
<212> TYPE: PRT
<213> ORGANISM: artificial
<220> FEATURE:
<223> OTHER INFORMATION: Synthetic peptide

<400> SEQUENCE: 13

Leu Glu Asp Thr Lys Glu Tyr Thr Thr Glu Ser Asn Leu Ile Glu Leu
1               5                   10                  15

Val Asp Glu Leu Pro Glu Glu His Gly Gln Ala Gln Gly Pro Ile Glu
            20                  25                  30

Glu Ile Thr Glu Asn Asn His His Ile
        35                  40

<210> SEQ ID NO 14
<211> LENGTH: 14
<212> TYPE: PRT
<213> ORGANISM: artificial
<220> FEATURE:
<223> OTHER INFORMATION: Synthetic peptide

<400> SEQUENCE: 14

Pro Phe Leu Lys Arg Val Pro Ala Cys Leu Arg Leu Arg Arg
1               5                   10

<210> SEQ ID NO 15
<211> LENGTH: 18
<212> TYPE: PRT
<213> ORGANISM: artificial
<220> FEATURE:
<223> OTHER INFORMATION: Synthetic peptide

<400> SEQUENCE: 15

Arg Cys Gly Arg Ala Ser Arg Cys Arg Val Arg Trp Met Arg Arg Arg
1               5                   10                  15

Arg Ile

<210> SEQ ID NO 16
<211> LENGTH: 14
<212> TYPE: PRT
<213> ORGANISM: artificial
<220> FEATURE:
<223> OTHER INFORMATION: Synthetic peptide -continued

<400> SEQUENCE: 16

Trp Gly Cys Cys Gly Arg Ser Ser Arg Arg Arg Thr Arg
1               5                   10

<210> SEQ ID NO 17
<211> LENGTH: 35
<212> TYPE: PRT
<213> ORGANISM: artificial
<220> FEATURE:
<223> OTHER INFORMATION: Synthetic peptide

<400> SEQUENCE: 17

Leu Thr Gly Gly Ile Ile Gly Ser Ala Ser Tyr Ser Tyr Gly Lys Arg
1               5                   10                  15

Asp Asn Gln Ser Ser Leu Thr Thr Val Ala Gly Ala Asp Gln Thr Ser
            20                  25                  30

Asn Thr Leu
        35

<210> SEQ ID NO 18
<211> LENGTH: 15
<212> TYPE: PRT
<213> ORGANISM: artificial
<220> FEATURE:
<223> OTHER INFORMATION: Synthetic peptide

<400> SEQUENCE: 18

Ser Arg Ala Arg Thr Phe Arg Val Gly Phe Thr His Gly Arg Lys
1               5                   10                  15

<210> SEQ ID NO 19
<211> LENGTH: 15
<212> TYPE: PRT
<213> ORGANISM: artificial
<220> FEATURE:
<223> OTHER INFORMATION: Synthetic peptide

<400> SEQUENCE: 19

Ala Asp Ser Gly His Ala Glu Arg Leu Cys Ala Met Ala Glu Val
1               5                   10                  15

<210> SEQ ID NO 20
<211> LENGTH: 37
<212> TYPE: PRT
<213> ORGANISM: artificial
<220> FEATURE:
<223> OTHER INFORMATION: Synthetic peptide

<400> SEQUENCE: 20

Val Thr Ser Leu Ser Asp Ser Thr Ser Thr Asn Ser Gly Ser Glu
1               5                   10                  15

Val Arg Gln His Arg Ser Val Thr Gln Gln Ala Gln Val Asn Pro Ile
            20                  25                  30

Arg Arg Gln His Leu
        35

<210> SEQ ID NO 21
<211> LENGTH: 51
<212> TYPE: PRT
<213> ORGANISM: artificial
<220> FEATURE:
<223> OTHER INFORMATION: Synthetic peptide

<400> SEQUENCE: 21

```
Asp Ser Ala Gly Ser Tyr Ile Lys Ser Asn Glu Lys Asn Asp Asn Lys
1               5                   10                  15

Asp Ile Lys Asp Asp Ser Ser Lys Pro Ser Gly Glu Glu Asp Gln Lys
                20                  25                  30

Ser Asp Glu Asn Glu Asp Glu Asn Thr Asp Gln Thr Asp Thr Thr Gln Asp
        35                  40                  45

Ser Lys Gln
    50
```

<210> SEQ ID NO 22
<211> LENGTH: 24
<212> TYPE: PRT
<213> ORGANISM: artificial
<220> FEATURE:
<223> OTHER INFORMATION: Synthetic peptide

<400> SEQUENCE: 22

```
Ala Gly Ser Pro Ser Ala Gly Asn Ile Ala Glu Leu Asp Ala Ile Ala
1               5                   10                  15

Phe Leu Glu Thr Pro Gly Arg Ser
                20
```

<210> SEQ ID NO 23
<211> LENGTH: 21
<212> TYPE: PRT
<213> ORGANISM: artificial
<220> FEATURE:
<223> OTHER INFORMATION: Synthetic peptide

<400> SEQUENCE: 23

```
Pro Gln Lys Pro Ser Lys Lys Arg Lys Thr Lys Tyr Phe Gly Gly Lys
1               5                   10                  15

Val Lys Ser Gly Asp
                20
```

<210> SEQ ID NO 24
<211> LENGTH: 14
<212> TYPE: PRT
<213> ORGANISM: artificial
<220> FEATURE:
<223> OTHER INFORMATION: Synthetic peptide

<400> SEQUENCE: 24

```
Pro Phe Leu Lys Arg Val Pro Ala Ser Leu Arg Leu Arg Arg
1               5                   10
```

<210> SEQ ID NO 25
<211> LENGTH: 18
<212> TYPE: PRT
<213> ORGANISM: artificial
<220> FEATURE:
<223> OTHER INFORMATION: Synthetic peptide

<400> SEQUENCE: 25

```
Arg Ser Gly Arg Ala Ser Arg Ser Arg Val Arg Trp Met Arg Arg
1               5                   10                  15

Arg Ile
```

<210> SEQ ID NO 26
<211> LENGTH: 14
<212> TYPE: PRT
<213> ORGANISM: artificial
<220> FEATURE:

```
<223> OTHER INFORMATION: Synthetic peptide

<400> SEQUENCE: 26

Trp Gly Cys Cys Gly Arg Ser Ser Arg Arg Arg Thr Arg
1               5                   10

<210> SEQ ID NO 27
<211> LENGTH: 26
<212> TYPE: PRT
<213> ORGANISM: artificial
<220> FEATURE:
<223> OTHER INFORMATION: Synthetic peptide

<400> SEQUENCE: 27

Pro Tyr Ser Arg Pro His Val Gln Leu Trp Tyr Pro Asn Arg Glu Ser
1               5                   10                  15

Cys Arg Ser Leu Ile Arg Ser Leu Gly Pro
            20                  25

<210> SEQ ID NO 28
<211> LENGTH: 11
<212> TYPE: PRT
<213> ORGANISM: artificial
<220> FEATURE:
<223> OTHER INFORMATION: Synthetic peptide

<400> SEQUENCE: 28

Gly Arg Lys Lys Arg Arg Gln Arg Arg Arg Gly
1               5                   10

<210> SEQ ID NO 29
<211> LENGTH: 14
<212> TYPE: PRT
<213> ORGANISM: artificial
<220> FEATURE:
<223> OTHER INFORMATION: Synthetic peptide

<400> SEQUENCE: 29

Gly Leu Gln Arg Arg Arg Gln Gly Tyr Gln Ser Ile Lys Pro
1               5                   10
```

METHOD OF DETERMINING, IDENTIFYING OR ISOLATING CELL-PENETRATING PEPTIDES

RELATED APPLICATION

This application claims priority from U.S. Provisional Application Ser. No. 61/489,198 filed on 23 May 2011, the contents of which are herein incorporated by reference in their entirety.

FIELD OF THE INVENTION

The present invention relates generally to the field of pharmaceutical sciences and, in particular, to the selective targeting of therapeutic compounds such as peptides to organs, tissues, cells and sub-cellular localizations.

malian cells, localize in one or more intracellular compartments, and mediate intracellular delivery of a cargo molecule e.g., a drug or other therapeutic agent, or a diagnostic agent such as an imaging agent.

Arguably, the most widely-studied and utilized CPP is a peptide derived from the human immunodeficiency virus (HIV-1) transactivator of transcription (TAT) protein. A positively-charged fragment of HIV-1 Tat protein comprising residues 47-57 of the full-length protein penetrates cultured mammalian cells. Since the discovery of Tat, other polycationic CPPs such as e.g., penetratin (a fragment of Antennapedia homeodomain) and vp22 (derived from herpes virus structural protein VP22) have been identified and characterized for their ability to translocate and deliver distinct cargos into the cell cytoplasm and nucleus in vitro and in vivo. Exemplary known CPPs are set forth in Table 1.

TABLE 1

Characterized CPPs

| Cell-penetrating peptides (CPP) | Sequence | Origin |
| --- | --- | --- |
| *Amphipathic peptides* | | |
| Penetratin (43-58) | RQIKIWFQNRRMKWKK | *Drosophila melanogaster* |
| Amphipathic model peptide | KLALKLALKALKAALKLA | Synthetic |
| Transportan | GWTLNSAGYLLKINLKALAALAKKIL | Chimeric galanin-mastoparan |
| SBP | MGLGLHLLVLAAALQGAWSQPKKKRKV | Chimeric *Caiman crocodylus* Ig(v) light chain-SV40 large T antigen |
| FBP | GALFLGWLGAAGSTMGAWSQPKKKRKV | Chimeric HIV-1 gp41-SV40 large T antigen |
| *Cationic peptides* | | |
| HIV Tat peptide (48-60) | GRKKRRQRRRPPQ | Viral transcriptional regulator |
| Syn-B1 | RGGRLSYSRRRFSTSTGR | Protegrin 1 |
| Syn-B3 | RRLSYSRRRF | Protegrin 1 |
| homoarginine peptide (Arg)7 and (Arg)9) | RRRRRRR(RR) | Synthetic |

BACKGROUND TO THE INVENTION

Many biologically active compounds require intracellular delivery in order to exert their therapeutic action, either inside the cytoplasm, within the nucleus or other organelles. Selective delivery to particular organs, tissues, cells, or sub-cellular localizations, is highly-desirable to avoid or minimize undesirable side-effects in non-target organs, tissues, cells, or sub-cellular localizations. Thus, the ability to deliver molecules of therapeutic benefit efficiently and selectively is important to drug development.

More than two decades ago it was discovered that certain short sequences, composed mostly of basic, positively-charged amino acids, e.g., Arg, Lys or His, have the ability to transport an attached cargo molecule across the plasma membrane of a cell. These basic sequences are commonly referred to as cell-penetrating peptides (CPPs) or protein transduction domains (PTDs). Prior art CPPs are generally short cationic and/or amphipathic peptide sequences, often between 20 and 50 residues in length, characterized by an ability to translocate across the membrane systems of mam- The precise mechanism(s) by which CPPs achieve their cellular internalization has been somewhat controversial. However, there is consensus that most CPPs are internalized via an endocytic mechanism. Several endocytic pathways exist, and clathrin-dependent endocytosis, caveolae/lipid raft-mediated endocytosis or macropinocytosis may be involved. The first step in cellular entry of a polycationic CPP is thought to be an electrostatic interaction between the polycation and negatively-charged heparin sulphate proteoglycan (HSPG) of the plasma membrane. Proceeding on this basis, a charge distribution and amphipathicity of the CPP are believed to be critical factors for cell internalization, possibly affecting an electrostatic interaction between the CPP and proteoglycans on the plasma membrane. Endocytosis of the CPP following contact with the cell surface is believed to be driven by a variety of parameters including the secondary structure of the CPP, the nature of the cargo to which the CPP is linked (if any), cell type, and membrane composition. As such, cell internalization is a complex and multi-faceted process.

Notwithstanding that certain CPPs may share some common characteristics that facilitate their cell binding and uptake e.g., polycationic and amphipathic sequences, not all CPPs possess sufficient similarity in their primary structure e.g., amino acid sequence, to readily predict their ability to bind to the cell surface and/or enter the cell based on sequence alone. It is not understood how secondary and/or tertiary structure considerations could effect cellular uptake.

Following endocytosis, the internalized CPP needs to escape the endosome to avoid degradation, and to deliver its cargo to an intended intracellular destination. Escape from the endosome may provide a bottleneck to efficient intracellular delivery of macromolecular cargos. For example, the efficiency of endosome escape appears to be low for Tat, penetratin, Rev, VP22 and transferrin e.g., Sugita et al., *Br. J. Pharmacol.* 153, 1143-1152 (2008). Delivery of CPP-cargo conjugates in liposomes may assist their escape from the endocytic vesicle e.g., El-Sayed et al., *The AAPS J.* 11, 13-22 (2009). Moreover, the inclusion of fusigenic peptides, such as the HA2 sequence of influenza (Wadia, Stan and Dowdy, Nat. Med. 2004 March; 10(3):310-5. Epub 2004 Feb. 8) can also enhance endosomal escape somewhat, although much of the cell penetrating peptides remain in the endosome. There remains a need for CPPs having an ability to escape the endocytic vesicle efficiently following their uptake.

One limitation to the in vivo utility of known CPPs for delivery of drug cargos is their non-selectivity. A generalized uptake of many existing CPPs in vivo may limit their clinical application, particularly where targeted drug action is advantageous or necessary, or where non-specific targeting of an organ or tissue type can lead to unwanted side effects. Notwithstanding that selection of a CPP for the presence of polycationic centres may provide peptides that are able to facilitate initiation of the internalization process, peptides selected for a primary structure that is positively charged may not be cell-selective in view of ubiquity of HSPG and phospholipid in the outer leaflet of cell membranes.

There is presently insufficient diversity of cell-type selective CPPs to provide coverage for many clinical applications involving drug delivery to different cells, tissues, organs and across organ systems. Tight junctions (TJs), basolateral membranes, and apical membranes may function to restrict the passage of CPPs into all cell types, especially when administered intravenously. The blood-brain barrier (BBB) is located at the endothelial tight junctions lining the blood vessels surrounding the brain, and the primary physical and/or pharmacological and/or physiological component(s) of the blood-testis barrier (BTB) and blood-epididymis barrier (BEB) consists of tight junctions between adjacent epithelial cells lining the seminiferous tubules (Sertoli cells) and epididymal duct, respectively. Such physical barriers and/or pharmacological barriers and/or physiological barriers may also be provided by the presence of active transporters and channels at the basolateral and/or apical membranes. HIV-1 Tat-derived peptides, penetratin and VP22 appear to have limited cellular uptake across these barriers and in certain cell types, both in vitro and in vivo. See e.g., Trehin and Merkle, *Eur. J. Pharm. Biopharm.* 58, 209-223 (2004). Thus, the existing bank of CPPs may not be sufficient to deliver therapeutic cargos to all cell types, suggesting a need for further functional diversity of CPPs.

Safety is a particular concern for the clinical application of any therapeutic agent, and no less so for CPPs that are utilized to deliver a cargo to one or more cells, tissues, organs or across organ systems of the human or animal body. For example, amphipathic peptides may be cytotoxic by virtue of perturbing the cell membrane, e.g., Sugita et al., *Brit J Pharmacol* 153, 1143-1152 (2008), and it may not be a simple matter to reduce the cytotoxicity of such peptides if their amphipathicity is critical to their interaction with the lipid membrane and subsequent internalization. Similarly, intrastriatal injection of penetratin at 10 µg dosage has been demonstrated to cause neurotoxic cell death, and in vitro delivery at concentrations of 40-100 µM has been demonstrated to induce cell lysis and other cytotoxic effects e.g., Trehin and Merkle, *Eur. J. Pharm. Biopharm.* 58, 209-223 (2004). Poly-L-arginine peptides have also been reported to induce cell membrane damage, increased permeability of cell barriers and reduce cell-cell contacts between epithelial cells in vitro, to the induce an inflammatory response when injected into the pleural cavity of rat lungs e.g., Trehin and Merkle, *Eur. J. Pharm. Biopharm.* 58, 209-223 (2004). Accordingly, there remains a need for CPPs having low or reduced cytotoxic side-effects relative to known CPPs.

Many of the limitations of known CPPS are a consequence of the processes used for their identification, and their subsequent adoption in the art before adequate testing has taken place to determine their uptake and/or release from the endosome and/or cell-type selectivity and/or tissue-type selectivity and/or organ selectivity and/or ability to cross physical barriers and/or pharmacological barriers and/or physiological barriers, and/or their safety limits.

Phage-display approaches have been successfully applied for the identification of cell-penetrating peptides and are efficient as they can be performed in a high throughput manner with many peptides being interrogated simultaneously e.g., Kamada et al., *Biol Pharm Bull* 30, 218-223 (2007). Notwithstanding the widespread and successful use of phage display screening techniques for discovery of new CPPs, existing screening methods do not necessarily select peptides for more than the attribute of cellular uptake, and fail to provide validation of cellular internalization or delivery. There remains a need for improved methods for identifying and isolating CPPs.

SUMMARY OF THE INVENTION

1. General

As used herein, the term "cell-penetrating peptide" or "CPP" or similar term shall be taken to mean peptidyl compound capable of translocating across a membrane system and internalizing within a cell.

By "peptidyl compound" is meant a composition comprising a peptide, or a composition the structure of which is based on a peptide such as an analogue of a peptide.

As used herein, the term "peptide" shall be taken to mean a compound other than a full-length protein that is the expression product of a natural open-reading frame of an organism having a prokaryotic or compact eukaryote genome, and comprising at least 5 or 6 or 7 or 8 or 9 or 10 contiguous amino acid, or amino acid-like, residues. Peptides will generally have an upper length of at least 200 residues or 190 residues or 180 residues or residues or 160 residues or 150 residues or 140 residues or 130 residues or 120 residues or 110 residues or 100 residues, however a peptide may have a length in the range of 10-20 residues or 10-30 residues or 10-40 residues or 10-50 residues or 10-60 residues or 10-70 residues or 10-80 residues or 10-90 residues or 10-100 residues, including any length within said range(s).

In the work leading up to the present invention the inventors sought to develop improved methods of determining, identifying and/or isolating peptides, or analogues and/or or derivatives thereof, having cell-penetrating activity and preferably that provide an advantage over previously-known CPPs. The methods that the inventors have developed test for one or more clinically-relevant factors to CPP-mediated drug delivery e.g., release from the endosome such as at a higher efficiency than one or more previously-known CPPs, and/or cell-type selectivity such as a different cell-type selectivity to one or more previously-known CPPs, and/or tissue-type selectivity such as a different tissue-type selectivity to one or more previously-known CPPs, and/or organ selectivity such as a different organ selectivity to one or more previously-known CPPs, and/or an ability to cross one or more physical barriers and/or pharmacological barriers and/or physiological barriers such as an improved efficiency of crossing the blood-brain barrier (BBB) or blood testis barrier (BTB) or blood-epididymal barrier (BEB) relative to one or more previously-known CPPs, and/or a safety consideration such as reduced cytotoxicity in one or more cell types compared to one or more previously-known CPPs.

As exemplified herein, the inventors employ a whole-cell biopanning of phage display libraries expressing isolated protein domains that are the expression products of genome fragments from prokaryotic genomes and/or compact eukaryotic genomes which are not known or predicted as having cell-penetrating activity in their native environments. These expressed protein domains are either the expression products of fragments of naturally-occurring open-reading frames, or they are encoded by nucleic acid that is not translated in its native context. The inventors adopted the use of such genomic fragments to reduce the contribution of uncharacterized nucleic acid e.g., non-sequenced nucleic acid or non-annotated sequence, and to enhance the diversity of expressed protein domains being screened. Without being bound by theory, this approach is believed to enrich the libraries for sequences which have survived millions to billions of years of evolution, thereby increasing the likelihood of isolating peptides with improved or desired properties such as structural stability, protease resistance, biological compatibility, including reduced toxicity.

The inventors screened highly diverse phage display libraries expressing these protein domains to identify and/or isolate peptides having an ability to penetrate one or more cell types selectively e.g., by performing one or more rounds of selection against binding and/or uptake e.g., negative selection against one or more cell types, to thereby remove peptides having non-selective or a non-desired cell-binding and/or cell-penetrating activity, followed by selection for peptides that bind to and/or penetrate a cell type of interest e.g., a positive selection, to then determine, identify or isolate peptide(s) having a desired cell-binding and/or cell-penetrating activity. The inventors also screened cells carrying the expressed protein domains for their survival. In the exemplified assays, the peptide is tested whilst being displayed on a bacteriophage e.g., M13-derived phage, and then recovered by transfecting cell lysates comprising the phage in a suitable bacterial host cell.

For example, by selecting for selective or specific uptake or penetration of brain endothelial cells as described herein, the present invention is particularly useful for providing CPPs having utility in a method of treating, preventing and/or diagnosing a disease or condition of the central nervous system, said method comprising providing to the central nervous system of a subject in need thereof.

The inventors also provide further improvements to their standard screening methods, wherein endosome-release of the peptides is tested, by employing bait-prey technology to demonstrate delivery of the peptide to the cytosol or more sub-cellular organelles or other sub-cellular location. For example, cells expressing an haloalkane dehalogenase substrate-binding domain in their cytosol are contacted with one or more haloalkane-tagged peptides, and haloalkane-tagged peptide that becomes co-localized with the expressed cytosolic haloalkane dehalogenase substrate-binding domain is recovered. In this example, co-localization of the haloalkane dehalogenase substrate-binding domain and haloalkane-tagged peptide may be determined by their co-immune precipitation (CoIP) or immune histochemistry e.g., using anti-haloalkane dehalogenase substrate-binding domain antibody or antibody against the peptidyl moiety of the complex. In another example, cells expressing a haloalkane dehalogenase substrate-binding domain-actin fusion protein in their cytoskeleton are contacted with one or more haloalkane-tagged peptides and haloalkane-, tagged peptide that becomes co-localized with the expressed cytoskeletal haloalkane dehalogenase substrate-binding domain-actin fusion protein is recovered. In this example, co-localization of the haloalkane dehalogenase substrate-binding domain-actin fusion protein and haloalkane-tagged peptide may be determined by their co-immune precipitation (CoIP) e.g., using anti-actin antibody or antibody against the peptidyl moiety of the complex. Alternatively, the haloalkane-tagged peptide may be labeled with a detectable reporter molecule such as a fluorophore to facilitate detection of the complex between the haloalkane moiety of the haloalkane-tagged peptide and the haloalkane dehalogenase substrate-binding domain or the haloalkane dehalogenase substrate-binding domain moiety of the haloalkane dehalogenase substrate-binding domain-actin fusion protein by virtue of the signal produced by the reporter molecule, and immune histochemistry or CoIP is employed to confirm localization. Alternatively, or in addition, cells expressing an haloalkane dehalogenase substrate-binding domain or alkane-dehalogenase fusion protein are contacted with one or more haloalkane-tagged peptides, and haloalkane-tagged peptide that does not merely co-localize with one or more endosome markers e.g., annexin VI, EEA1, ESCRT, Rab5, Rab7, Lamp1, Rap1, Syntaxin 7, Syntaxin 8, Syntaxin 12, or VAMP-7 (vesicle-associated membrane protein-7), or that does not selectively co-localize with one or more of said endosome markers or that does not predominantly co-localize with one or more of said endosome markers, or otherwise has a high affinity for an early endosome or endosome or endosome-lysosome, is recovered.

The inventors have also provided new cell-penetrating peptides that have passed the various filters of the exemplified methods. Exemplary cell-penetrating peptides of the invention are shown in the accompanying Sequence Listing, and these are expression products of natural open-reading frames of bacterial genomes, or alternatively, capable of being expressed from non-coding regions of compact genomes of eukaryotes or bacteria. The peptides of the invention, or analogues' or derivatives thereof, may be derived from proteins that are classified inter alfa as bacterial and/or viral virulence factors, ATP-binding cassette (ABC) transporter proteins, bacterial anti-sigma factors, taxis sensor proteins, lipoproteins, neurotransmitter:sodium symporter (NSS) family proteins, phage-related DNA packing proteins, membrane anchor proteins, succinate dehydrogenases, proteins comprising CALX-cadherin motifs, serine-rich adhesion proteins, proteins having homology to gp41 proteins of immunodeficiency viruses, transposases, permeases, and fibronectin-binding proteins.

It is to be understood that the cell-penetrating peptides of the present invention are not full-length proteins that occur in nature, but peptides as defined herein, or peptide fragments of proteins, that comprise at least 5 or 6 or 7 or 8 or 9 or 10 contiguous amino acid residues, and have an upper length of at least 200 amino acids or 190 amino acids or 180 amino acids or 170 amino acids or 160 amino acids or 150 amino acids or 140 amino acids or 130 amino acids or 120 amino acids or 110 amino acids or 100 amino acids, including peptides having lengths in the range of 10-20 amino acids or 10-30 amino acids or 10-40 amino acids or 10-50 amino acids or 10-60 amino acids or 10-70 amino acids or 10-80 amino acids or 10-90 amino acids or 10-100 amino acids, or any length within said range(s). Particularly preferred cell-penetrating peptides of the invention have lengths in the range of about 10-about 100 amino acids, including 10-95 amino acids or 11-94 amino acids, or more commonly from about 10 to about 60 amino acids or from about 10 to about 50 amino acids in length.

Alternatively or in addition to their derivation from non-coding regions of genomes or from full-length natural open reading frames encoding full-length proteins, and their length, the cell-penetrating peptides of the present invention are characterized by one or more of the following structural features: a propensity to form an α-helical secondary structure such as an amphipathic α-helical secondary structure and/or an amino acid composition sufficient for the peptide to have a net negative charge and/or an amino acid composition sufficient for the peptide to have a net positive charge and/or an amino acid composition sufficient for the peptide to have a net neutral charge.

Alternatively, or in addition to their derivation and/or any one or more structural and/or physicochemical properties, the cell-penetrating peptides of the invention are characterized functionally by their cell-type selectivity as described herein. For example, the cell-penetrating peptides of the present invention are selective for endothelial cell types e.g., vascular endothelial cells such as HUV-EC-C cells, or alternatively, brain endothelial cells such as b.End.3 cells, as opposed to epithelial cells e.g., ovarian epithelial cells such as SVEC4-10 cells and/or HepG2 cells and/or CHO cells including CHO-K1 cells. Alternatively, or in addition, the cell-penetrating peptides of the present invention are selective for brain endothelial cells such as b.End.3 cells as opposed to other endothelial cells such as HUV-EC-C cells, epithelial cells such as CHO cells and/or HepG2 cells and/or SVEC4-10 cells, or any cells other than brain endothelial cells. Alternatively, or in addition, the cell-penetrating peptides of the present invention are selective for vascular endothelial cells e.g., microvascular endothelial cells such as HUV-EC-C cells as opposed to brain endothelial cells such as b.End.3 cells or other endothelial cell types. Alternatively, or in addition, the cell-penetrating peptides of the present invention are selective for vascular endothelial cells e.g., microvascular endothelial cells such as HUV-EC-C cells as opposed to epithelial cells e.g., ovarian epithelial cells such as SVEC4-10 cells and/or hepG2 cells and/or CHO cells including CHO-K1 cells. Alternatively, or in addition, the cell-penetrating peptides of the present invention are selective for vascular endothelial cells e.g., microvascular endothelial cells such as HUV-EC-C cells as opposed to other endothelial cells such as b.End.3 cells and epithelial cells such as SVEC4-10 cells and/or hepG2 cells and/or CHO cells including CHO-K1 cells. Alternatively, or in addition, the cell-penetrating peptides of the present invention are selective for cells other than vascular endothelial cells e.g., microvascular endothelial cells such as HUV-EC-C cells, or for epithelial cells such as CHO cells including CHO-K1 cells and/or hepG2 cells and/or SVEC4-10 cells as opposed to endothelial cells of vasculature e.g., microvascular endothelial cells such as HUV-EC-C cells or brain endothelial cells such as b.End.3 cells, or cells other than epithelial cells.

The inventors also provide exemplary derivatives of the cell-penetrating peptides of the invention as described herein, which are functional in delivering a cargo molecule to cells, e.g., derivatives wherein one or more amino acids of the cell-penetrating peptide is replaced with a different amino acid residue, such as for example a substitution of one or more cysteine residues for one or more serine residues. Preferred derivatives or analogues of cell-penetrating peptides retain one or more structural and/or physicochemical characteristics of the cell-penetrating peptide from which they are derived apart from their specific sequence. Alternatively, or in addition, preferred derivatives or analogues of cell-penetrating peptides retain one or more functional characteristics of the cell-penetrating peptide from which they are derived e.g., cell-type selectivity and/or cytotoxicity profile.

Exemplary cell-penetrating peptides identified by the inventors that appear to be expression products of non-coding regions of compact genomes of eukaryotes or bacteria, for example in their native contexts, are set forth in SEQ ID NOs: 1, 2, 9, 14-16, 18, and 19 hereof. Of these sequences, at least SEQ ID NOs: 1 and 2 are arginine-rich TAT-like sequences, validating the method employed for the isolation of such sequences.

Proteins encoded by natural open-reading frames of bacterial genomes from which the exemplified cell-penetrating peptides of SEQ ID NOs: 3-8, 10-13, 17, and 20-23 are derived have been classified inter alfa into ATP-binding cassette (ABC) transporter proteins, taxis sensor proteins, lipoproteins, neurotransmitter:sodium symporter (NSS) family proteins, phage-related DNA packing proteins, membrane anchor proteins, succinate dehydrogenases, proteins comprising CALX-cadherin motifs, proteins having homology to gp41 proteins of immunodeficiency viruses, transposases, and fibronectin-binding proteins.

For example: a cell-penetrating peptide derived from a phage-related DNA packing protein is set forth in SEQ ID NO: 3; a cell-penetrating peptide derived from a membrane anchor protein is set forth in SEQ ID NO: 4; a cell-penetrating peptide derived from succinate dehydrogenase is set forth in SEQ ID NO: 4; a cell-penetrating peptide derived from proteins having homology to gp41 proteins of immunodeficiency viruses is set forth in SEQ ID NO: 5; a cell-penetrating peptide derived from a chemotaxis sensor protein is set forth in SEQ ID NO: 6; a cell-penetrating peptides derived from an ATP-binding cassette (ABC) transporter protein is set forth in SEQ ID NO: 7; a cell-penetrating peptide derived from a protein comprising CALX-cadherin motifs is set forth in SEQ ID NO: 8; a cell-penetrating peptide derived from a transposase is set forth in SEQ ID NO: 10; cell-penetrating peptides derived from fibronectin-binding proteins are set forth in SEQ ID NOs: 11-13; a cell-penetrating peptide derived from a lipoprotein is set forth in SEQ ID NO: 17; a cell-penetrating peptide derived from a serine-rich adhesion protein is set forth in SEQ ID NO: 20; a cell-penetrating peptide derived from a bacterial anti-sigma factor is set forth in SEQ ID NO: 21; a cell-penetrating peptides derived from a permease is set forth in SEQ ID NO: 22; and a cell-penetrating peptide derived from a neurotransmitter:sodium symporter (NSS) family protein is set forth in SEQ ID NO: 23.

Exemplary analogues or derivatives of the cell-penetrating peptides of the invention are analogues of or derived from cell-penetrating peptides that appear to be expression products of non-coding regions of compact genomes of eukaryotes or bacteria in their native contexts as described herein, such as those cell-penetrating peptides set forth in SEQ ID Nos: 14-16, or alternatively, from cell-penetrating peptides that are encoded by natural open-reading frames of bacterial genomes, such as a cell-penetrating peptide derived from a protein having homology to a gp41 protein of an immunodeficiency virus, for example SEQ ID NO: 5. In accordance with these examples of the invention, a preferred derivative of a cell-penetrating peptide of the invention comprises an amino acid sequence set forth in any one of SEQ ID Nos: 24-27 as described in Table 10 hereof.

In one example, cell-penetrating peptides and derivatives thereof comprising sequences selected from the group consisting of SEQ ID NOs: 3-8, 10-13, 17, 20-23 and 27 are particularly preferred, and more preferably SEQ ID NOs: 3-8, 10-13, and 17 or SEQ ID NOs: 3-8, 10-13, 17 and 20-23, including any one or more of said SEQ ID NOs.

In another example, cell-penetrating peptides and derivatives thereof comprising sequences selected from the group consisting of SEQ ID NOs: 1, 2, 9, 14-16, and 18-26 are particularly preferred, and more preferably SEQ ID NOs: 1, 2, 9, 14-16, 18, 19, and 24-26, including any one or more of said SEQ ID NOs.

In another example, a preferred cell-penetrating peptide of the invention, or an analogue or derivative thereof, may have a net charge that is neutral or negative.

Throughout this specification, the term "net charge" shall be taken to refer to the summation of charges of ionisable groups of the constituent residues of a peptide, analogue or derivative of the invention, such as at a pH in the range pH 6.0 to pH 7.0 including pH 7.0. For example, a determination of net charge of a peptide comprising natural charged residues may comprise identifying all of the ionizable groups of those natural charged residues including the amino group of the N-terminal residue, the carboxyl group of the C-terminal residue, and ionisable groups of aspartate, glutamate, arginine, lysine, histidine and cysteine residues at the given pH, determining the charge on each ionisable group at the given pH, and summing the charges determined for each ionisable group at the given pH.

For example, a peptide having a net charge that is neutral or negative may have a net charge in a range from 0 to −10 or from 0 to −15 or from 0 to −20, including a net charge of 0, −1, −2, −3, −4, −5, −6, −7, −8, −9, −10, −11, −12, −13, −14, −15, −16, −17, −18, −19, or −20 e.g., a peptide comprising or having the sequence set forth in any one or more of SEQ ID NOs: 3, 4, 6-8, 10-13, 17 or 19, or an analogue or derivative thereof. Such a preferred cell-penetrating peptide of the invention, or an analogue or derivative thereof, may hive a net charge that is neutral or negative, and be capable of delivering a negatively-charged cargo molecule such as nucleic acid or a phospholipid to a cell.

In another example, a preferred cell-penetrating peptide of the invention or derivative thereof may have a net negative charge e.g., a peptide comprising or having the sequence set forth in any one or more of SEQ ID NOs: 3, 4, 6-8, 10-13 or 19, or an analogue or derivative thereof.

In another example, a preferred cell-penetrating peptide of the invention, or an analogue or derivative thereof, may have a net charge that is neutral or positive. For example, the peptide, analogue, or derivative may have a net charge in a range from 0 to +10 or from 0 to +15 or from 0 to +20, including a net charge of 0, +1, +2, +3, +4, +5, +6, +7, +8, +9, +10, +11, +12, +13, +14, +15, +16, +17, +18, +19, or +20 e.g., a peptide comprising or having the sequence set forth in any one or more of SEQ ID NOs: 1, 2, 5, 9, 14-18, or 24-27, or an analogue or derivative thereof.

In another example, a preferred cell-penetrating peptide of the invention, or an analogue or derivative thereof, may have a net positive charge e.g., a peptide comprising or having the sequence set forth in any one or more of SEQ ID NOs: 1, 2, 5, 9, 14-16, 18, or 24-27 or an analogue or derivative thereof.

In another example, a preferred cell-penetrating peptide of the invention, or an analogue or derivative thereof, may have a net neutral charge e.g., a peptide comprising or having the sequence set forth in SEQ ID NO: 17 or an analogue or derivative thereof.

The exemplified peptides or any other cell-penetrating peptide identified and/or isolated or purified by performing a process of the present invention is readily formulated into a conjugate comprising at least one of said cell-penetrating peptides, or an analog and/or derivative thereof, and at least one cargo for delivery to a cell or sub-cellular location, as described herein. For example, a conjugate comprising at least one cell-penetrating peptide or analog and/or derivative thereof capable of crossing the Blood Brain Barrier (BBB) and at least one cargo molecule having therapeutic or diagnostic utility for a disease or condition of the central nervous system provides a significant advance in therapy or diagnosis of the disease or condition. A conjugate is produced by linking at least one cell-penetrating peptide or an analog and/or derivative thereof to a cargo molecule of diagnostic or therapeutic utility. Pharmaceutical compositions e.g., formulated for parenteral administration, are also produced comprising at least one such conjugate and a pharmaceutically-acceptable carrier or excipient. It will also be apparent that a cargo molecule is readily transported across a cell membrane and/or internalized within a cell or a sub-cellular location, by contacting the cell with at least one such conjugate or pharmaceutical composition for a time and under conditions sufficient for the conjugate to cross the cell membrane.

The foregoing classification of cell-penetrating peptides provided by the inventors also provides a basis for producing selective libraries of peptides and/or expression libraries for identifying or isolating one or more cell-penetrating peptides (CPPs) from candidate CPPs. For example, an expression library may comprise fragments of open reading frames encoding proteins selected from the group consisting of bacterial and/or viral virulence factors, ATP-binding cassette (ABC) transporter proteins, bacterial anti-sigma factors, taxis sensor proteins, lipoproteins, neurotransmitter: sodium symporter (NSS) family proteins, phage-related DNA packing proteins, membrane anchor proteins, succinate dehydrogenases, proteins comprising CALX-cadherin motifs, serine-rich adhesion proteins, gp41 proteins (or other proteins involved in viral fusion), transposases, permeases, and fibronectin-binding proteins; and/or fragments of open reading frames encoding orthologues or homologues of any one or more of those proteins and/or fragments of open reading frames encoding domains of any one or more of the proteins or orthologs/homologs. An exemplary library may therefore comprise one or more of SEQ ID NOs: 3-8, 10-13 and 17 and derivatives and analogs thereof. For example, the library may comprise a plurality of peptide derivatives that are sequence variants of one or more of such sequences, such as mutagenesis library of one or more such sequences. In one of such examples, the mutagenesis library is a random mutagenesis library comprising sequence variants produced by random mutagenesis of the base sequence(s) such as across a large portion of the base sequence. In another of such examples, the sequence variation is localised to one or more particular portions of one or more base sequences.

In another example, an expression library may consist of genomic DNA fragments and/or cDNA fragments from 2 or more different species or strains of pathogenic organisms. In a further example, an expression library may consist of genomic DNA fragments and/or cDNA fragments from 2 or more different species or strains of pathogenic organisms from two or more different phylogenetic orders.

It will also be apparent that such a selective library may comprise a combination of the aforementioned nucleic acid fragments, or only fragments that encode peptides of closely-related source proteins e.g., produced by mutagenesis and/or affinity maturation of one or more closely-related base peptides. Alternatively, such a selective library may be a peptide library comprising peptides encoded by such fragments of an expression library.

Because such selective libraries are enriched for CPPs or nucleic acids encoding CPPs, they provide an advance in screening processes for identifying or isolating new CPPs or CPPs having specific activity or cell-type selectivity from candidate CPPs. In use of these selective libraries, a combination of the negative and positive selections of the foregoing assays may be employed, however this is not necessary because the peptides of the library have already been pre-selected for CPP activity by virtue of their classification supra. The selective libraries of the present invention may be used for straightforward positive selection of CPPs by binding a peptide expressed by the library or comprised within it (in the case of peptide library) under conditions sufficient for a peptide to adhere to or penetrate the cell, and cell-penetration activity of the peptide bound to the cell or internalized within the cell can be detected.

A further use of the cell-penetrating peptide or analog and/or derivative thereof, and peptide libraries comprising or expressing such peptides, is in elucidating signaling pathways for internalization of diagnostic and/or therapeutic molecules. For example, cellular receptors involved in cell penetration e.g., mediated by a specific CPP or with respect to a particular cell type, may be isolated or purified from other proteins using the exemplified CPPs and libraries expressing them. The identified or isolated cellular receptor can be characterized e.g., biochemically, by sequence, expression profile, regulation, etc. Accordingly, this invention also encompasses molecules that bind to cell-penetrating peptides as described herein, especially isolated or enriched or purified cellular receptors involved in cell penetration, and more particularly, any isolated or substantially pure form of a cellular receptor involved in cell penetration, for example when enriched, purified, collected, identified or characterized by performing a method according to any example hereof. The invention extends further to isolated nucleic acid encoding such cellular receptors.

Unlike methods which are based on mapping sequences derived from a particular virulence factor or membrane/associated component or receptor, the method described herein allows for the empirical screening of multiple fragments of multiple proteins in parallel, thereby eliminating biases inherent in such conventional methods, while ensuring that the most competitive. CPP's are isolated, regardless of their source or prior knowledge of their function.

The inventors demonstrate the ability of exemplified cell-penetrating peptides of the invention, and exemplary derivatives of the cell-penetrating peptides to deliver a cargo e.g., a fluorescent molecule such as FITC, or a peptide such as neuroprotective peptide or a maltose-binding protein, or a virus particle, to different cell types.

Specific Examples of the Invention

One example of the present invention provides a process of identifying a cell-penetrating peptide (CPP) having cell-type selectivity, said process comprising:

(i) performing n iterations of a method comprising contacting a candidate peptide with a cell of a predetermined cell-type in suitable medium for a time and under conditions sufficient for the peptide to adhere to or penetrate the cell, and separating the cell from the medium to thereby produce a separated medium, wherein n is an integer having a value equal to or greater than 1;

(ii) contacting separated medium following performance of the n iterations at (i) with a cell of a predetermined cell-type that is different from a cell of predetermined cell-type at (i) for a time and under conditions sufficient for a candidate peptide in the separated medium to adhere to and/or penetrate the cell;

(iii) detecting a candidate peptide bound to the cell at (ii) and/or internalized within the cell at (ii), wherein said detected candidate peptide is a cell-penetrating peptide (CPP) having cell-type selectivity e.g., for the cell of predetermined cell-type at (ii) relative to the cell(s) of predetermined cell type(s) at (i).

Alternatively, the invention provides a method of determining or identifying a cell-penetrating peptide (CPP) having cell-type selectivity, said method comprising:

(i) performing n iterations of a method comprising: (a) contacting a candidate CPP with a cell of a predetermined cell-type in suitable medium for a time and under conditions sufficient for a CPP to adhere to or penetrate the cell, and (b) separating the cell from the medium, wherein n is an integer having a value equal to or greater than 1;

(ii) contacting the separated medium with a cell of a predetermined cell-type that is different from a cell of predetermined cell-type at (i) for a time and under conditions sufficient for a peptide in the separated medium to adhere to or penetrate the cell; and (iii) detecting cell-penetration activity of the peptide bound to the cell at (ii) or internalized within the cell at (ii), thereby determining or identifying said detected peptide as a cell-penetrating peptide (CPP) having cell-type selectivity.

The cells at (i) and (ii) are eukaryotic cells of a multicellular organism, preferably animal cells or plant cells, including protoplasts of plant cells in which the cell wall has been removed. In preferred examples, the cells are mammalian cells, including human cells.

The term "cell-type selective" or "moderately cell specific" shall be taken to mean that a CPP is not internalized non-specifically and to the same extent or degree by all cell-types tested in a method of the present invention with respect to which cell-type selectivity or moderate cell specificity is claimed. For example, peptides exhibiting cell-type selectivity or moderate cell specificity adhere to and/or penetrate cells of pre-determined cell-type in a positive selection for said adherence or penetration e.g., at higher efficiency or level than the peptides adhere to or penetrate cells of different pre-determined cell-type in a negative selection for said adherence or penetration. In this context, the term "positive selection" refers to a process of enrichment or selection that identifies a peptide or plurality of peptides that adhere(s) to and preferably penetrate(s) cells of one or more pre-determined cell types, and the term "negative selection" refers to a process of enrichment or selection that identifies a peptide or plurality of peptides that does/do not adhere to and preferably penetrate cells of one or more pre-determined cell types. Preferably, a negative selection involves sequestering or depleting or removing the peptide(s) being selected against, and a positive selection involves enriching or enhancing or purifying the peptide(s) being positively selected.

The integer n may have a value of between 1 and 10, or between 1 and 20 or between 1 and 30 or between 1 and 40 or between 1 and 50, or between 1 and 100. Wherein n is greater than unity, such as wherein n has a value of 2 or 3 or 4 or 5 or 6 or 7 or 8 or 9 or 10 or 20 or 30 or 40 or 50 or more, a plurality of iterations at (i) may be performed using the same cell of predetermined cell type, such that the amount or concentration of peptide that binds to a cell type being selected against is gradually depleted from the surrounding medium. Alternatively, or in addition, a plurality of iterations at (i) may be performed using different cells of the same or different predetermined cell type, such that the selectivity of the peptide is enhanced at each iteration e.g., by selecting against a greater number of different cell types. Preferably, a plurality of iterations at (i) is performed using different cells of different cell-types in each of said plurality.

Contacting of the peptide with one or more predetermined cell types at (i) may be performed consecutively or simultaneously. By "consecutively" in this context is meant that one iteration of the method at (i) is performed following another iteration of the method at (i). During each such consecutive iteration, the concentration of peptides in the medium will be reduced by their binding to the cells of the preceding iteration. By "simultaneously" in this context, it is meant that the peptide is contacted at about the same time with the cell of predetermined cell type such that each iteration of the method at (i) is performed at about the same time e.g., in different batches. Following each such simultaneous iteration, the different batches are pooled and the pooled cells separated from the pooled media, and the pooled separated medium is then contacted with the cell at (ii). An advantage of this assay format is higher throughput than is achieved for consecutive iterations of the method at (i), however selectivity may be compromized slightly for more abundant peptides or promiscuous peptides that are not completely removed or depleted in the performance of the method at (i). Generally, a higher number of simultaneous iterations is performed on each cell type to achieve the same degree of selectivity as consecutive iterations of the method at (i).

It will be apparent that the contacting at (ii) must follow the iteration(s) at (i) in performing the method of the invention.

Preferably, the cell at (i) is washed n times using a buffer or medium compatible with cell viability or survival or that does not adversely affect the ability of another cell downstream in the subject process to internalize the peptide, wherein n is an integer having a value equal to or greater than 1 e.g., 1 or 2 or 3 or 4 or 5 or 6 or 7 or 8 or 9 or 10. Preferably, such washing of the cell at (i) removes peptide that is associated non-selectively with the cell at (i), especially the cell membrane. By "associated non-selectively" is meant that the peptide is in physical relation with the cell other than by means of a mechanism that is capable of transporting the peptide through the membrane of that particular cell or internalizing the peptide in that particular cell. The wash comprising peptide that is associated non-selectively with the cell at (i), especially the cell membrane, may be combined with the separated medium and the combined solution carried forward to the next step of the process.

Accordingly, the term "separated medium" shall be taken to comprise medium that is separated from the cell following one or more iterations of the method at (i), optionally further comprising medium or buffer or other solution obtained by washing cell following any iteration of the method at (i), and any medium, buffer or other solution produced by combining medium, buffer or other solution obtained by performance of an iteration of the method at (i) consecutively with or without washing of the cell following an iteration of the method.

Preferably, the process further comprises separating the medium from the cell at (ii) before detecting the peptide at (iii) by removing unbound and/or non-internalized peptide from the cell to which the positive selection relates, for example to enhance the signal:noise ratio of the assay.

Preferably, the processes or methods of the invention further comprise treating the cell at (ii) to thereby remove peptide that is associated non-selectively with the cell at (ii) or that is non-integral to the cell membrane of said cell or that is non-internalized to said cell. For example, the cell is treated by incubating the cell with a suitable protease, such as for a time and under conditions sufficient to remove extrinsic proteins to the cell membrane without disrupting the cell membrane. Such treatment of the cell is generally performed before detecting the peptide bound to the cell at (ii) and/or internalized within the cell at (ii), however may be performed before or after any optional separation of the medium from the cell at (ii).

To reduce dilution effects and/or surface denaturation of peptides at low concentration in solution, the medium at any step of the subject process may be concentrated, or supplemented with a carrier protein e.g., between iterations of negative selection, or between the final negative selection and the positive selection steps. Such modifications are clearly within the scope of the present invention.

It is also within the scope of the invention to exchange the culture media/medium between iterations of negative selection, or between the final negative selection and the positive selection steps, to maximize or optimise survival of different cell types that are not tolerant to media from the preceding step. For example, the medium may be desalted and lyophilized and the peptide resuspended in a medium compatible with the cells of the following step.

It is clearly within the scope of the invention described herein for the pre-determined cell types in one or more iterations at (i) and/or the pre-determined cell type at (ii) to be within isolated tissue(s) e.g., liver or brain or vascular tissue. Conveniently, tissues are presented in the form of cell cultures or tissue sections or cultures of sections that are amenable to visualization by the detection means employed e.g., fluorescence microscopy or luminescence microscopy or live confocal microscopy or immune histochemistry. Sections should be sufficiently small to facilitate their contacting with peptide and separation from medium. Thin sections such as those generated by a microtome e.g., about 10 microns in thickness, are preferred. Tissue is preferably fresh to maintain active transport mechanisms of the cells.

In other example of the invention, one or more of the pre-determined cell types are within a multicellular organism, such as a transgenic mouse.

One exemplary process of the present invention is useful for providing one or more cell-type selective peptides of any selectivity or moderate specificity, the only requirement being that the positive selection follows the negative selection(s). For example, the process of the invention may be used to provide peptides that are selective for a mechanism of cellular uptake relative to another such mechanism e.g., a clathrin-dependent endocytosis as opposed to caveolae/lipid raft-mediated endocytosis or macropinocytosis, e.g., by using one or more inhibitors of certain uptake mechanisms. Alternatively, or in addition, the process of the invention may be used to provide peptides that are selective for a particular cell membrane composition e.g., lipid content or carbohydrate content or active transporter or channel or junction or charge or other property that selects for transcytosis of peptides having specific secondary structure characteristics or charge conferring their uptake. As exemplified herein, the method provides CPPs that are cell-type selective or moderately cell specific for a range of different cell types e.g., epithelial cells as opposed to endothelial cells, or endothelial cells as opposed to epithelial cells, or brain endothelial cells as opposed to endothelial cells of vasculature e.g., microvascular endothelial cells or other endothelial cell types, or brain endothelial cells as opposed to epithelial cells e.g., ovarian epithelial cells, or brain endothelial cells as opposed to other endothelial cells and epithelial cells, or cells other than brain endothelial cells, or vascular endothelial cells e.g., microvascular endothelial cells as opposed to brain endothelial cells or other endothelial cell types, or vascular endothelial cells e.g., microvascular endothelial cells as opposed to epithelial cells e.g., ovarian epithelial cells, or vascular endothelial cells e.g., microvascular endothelial cells as opposed to other endothelial cells and epithelial cells, or cells other than vascular endothelial cells e.g., microvascular endothelial cells, or epithelial cells as opposed to endothelial cells of vasculature e.g., microvascular endothelial cells or brain endothelial cells, or cells other than epithelial cells. By careful selection of negative and positive selection parameters, especially cell type(s) e.g., in accordance with the description provided herein, broad applicability of the invention can be achieved without undue burden experimentation.

It will be apparent from the preceding description that selectivity does not mean absolute exclusivity or even specificity, however it may encompass exclusive transcytosis across the plasma membrane of a single cell type or a limited number of different cell types.

The peptide may be provided to the cells as a synthetic peptide or a recombinant peptide in a substantially purified form, or alternatively, in association with other molecules e.g., lipid, carbohydrate, salt, nucleic acid, or protein. The peptide may also include D-amino acids or be provided as a racemic mixture e.g., comprising a plurality of isosteres or other peptide analogs, such as a plurality of different peptide analogs each comprising one or more D-amino acids. For example, the peptide may be provided as a mixture of at least two peptides selected from a peptide consisting of L-amino acids, a retroinverted analog of said peptide comprising one or more D-amino acids, an analog of said peptide comprising one or more D-amino acids and an analog of said peptide comprising a reversed amino acid sequence. In a particularly preferred form, the peptide is displayed on the surface of a particle e.g., latex or colored particle or nanoparticle or quantum dot, or on the surface of a cell, bacteriophage, or virus that does not adversely affect the ability of the peptide to be internalized to a cell employed in the process. More preferably, the peptide is displayed on the surface of a particle e.g., latex or colored particle or nanoparticle or quantum dot, or on the surface of a cell, bacteriophage, or virus that is capable of being internalized to the cell at (ii) of the subject process such as by a mechanism that is distinct from the mechanism of peptide penetration to the cell at (ii). As exemplified herein, the peptide may be displayed on the surface of a bacteriophage to facilitate subsequent recovery and characterization of the peptide from the cell at (ii).

Preferably, the peptide is displayed on the surface of a particle such that the peptide assumes stable secondary structure and/or a conformation or peptide fold or assembly of folds sufficient for binding and/or internalization and/or localization to a sub-cellular location other than merely the endosome or endosome-lysosome. It is preferred that the peptide assumes such secondary and/or tertiary structure autonomously in the medium or on contact with the cell, or on contact with a chaperonin of the cell e.g., without a need for intramolecular disulphide bridge formation to produce a loop.

It is within the scope of the present invention for the peptide to be labeled e.g., with one or more detectable reporter molecules to facilitate detection of binding, entry and localization e.g., a fluorophore, haloalkane, radioactive label, colored particle, latex bead, nanoparticle, quantum dot, or stable enzyme such as beta lactamase, etc. Exemplary reporter molecules are described herein.

Alternatively, or in addition to labeling the peptide, the cell may express or otherwise comprise a molecule that facilitates detection of binding, entry and localization of the peptide to/within the cell. For example, the cell may express a prey molecule to which a prey conjugated to the peptide binds, e.g., a haloalkane dehalogenase substrate-binding domain or haloalkane dehalogenase substrate-binding domain fusion protein as described herein.

Alternatively, or in addition, an inactive form of the fluorescent label can be conjugated to the peptide via a labile linkage, such as an ester bond or a specific protease site, so that once the peptide is released to the cytosol it can be cleaved by esterases or proteases, to fluoresce. One example of such an esterase-cleavable die is Oregon Green 488 carboxylic acid diacetate (carboxy-DFFDA)-6-isomer.

Similarly, the cell penetrating peptide may comprise a pair of functional groups suitable for proximity assay e.g., a fluorophore and a quenching group separated by a cleavable linker such that fluorescence is activated by cleavage in the cytoplasm by an enzyme which is not present or active in the endosomal compartment.

The means and manner in which the peptide is detected as being bound to a cell or internalized within a cell during positive selection will vary e.g., depending on whether or not the peptide is labeled and the structure of any label employed. In one example, the peptide is labeled with one or more fluorophores e.g., fluorescein and/or rhodamine and/or green-fluorescent protein, and detected a being bound to or internalized within the cell at (ii) by performing a fluorescence-based assay e.g., fluorescence-activated cell sorting (FACS) or fluorescence microscopy or live confocal microscopy or a combination thereof to detect the fluorophore(s). Alternatively, a fluorophore may be substituted for a fluorophore substrate e.g., diaminofluorescein-2 diacetate. (DAF-2DA) that is converted to the fluorescent triaole DAF-2T by the actions of a cytosolic esterase and nitric oxide, and the DAF-2T detected inside the cell by FACS or fluorescence microscopy or live confocal microscopy or a combination thereof.

Alternatively or in addition, when the peptide is fused to an enzyme cargo such as β-lactamase, it can be detected by means of a fluorescent substrate, such as the cell-permeant FRET-paired fluorescent substrate CCF4-AM which comprises a cephalosporin core linking a 7-hydroxycoumarin to a fluorescein group.

Alternatively, or in addition, immune precipitation or immune localization of the CPP or a protein or other molecule with which the CPP binds at the cell surface and preferably inside the cell is employed to determine binding and/or internalization of the peptide.

In a preferred form, one or more processes or methods of the invention further comprise determining, identifying or isolating a peptide as a cell-penetrating peptide (CPP) having a different cell-type selectivity relative to one or more previously-known CPPs e.g., penetratin (43-58) and/or transportan and/or SBP and/or FBP and/or HIV Tat peptide (48-60) and/or syn-B1 and/or syn-B3 and/or a homoarginine-7 peptide and/or homoarginine-9 peptide. For example, the process may be performed in parallel wherein one set assays a candidate peptide against the cell-types at (i) and (ii) and wherein each other set assays a previously-known CPP control against the same cell-types at (i) and (ii), and a candidate CPP having a different cell-type selectivity relative to the previously-known CPP control(s) is identified. Alternatively, the cell selectivity profile of one or more previously-known CPP control peptides may have been determined previously by any means, and a candidate CPP having a different cell-type selectivity at relative to the previously-known CPP control(s) is identified. These steps apply mutatis mutandis to a process for identifying a CPP having different cell-type selectivity to a previously-known CPP.

The processes or methods of the present invention may be performed in part or in its entirety ex vivo such as on cells or tissues that have been isolated or purified previously, including biopsies, cell cultures, tissue sections, etc. For example, the process of the invention may further comprise one or more steps that are performed ex vivo such as by determining selectivity of the peptide on a cellular sample from an animal e.g., a cellular sample or tissue sample taken previously from an animal that has been administered previously with a peptide for which selectivity is being assayed. Similarly, an ability of the peptide to pass through one or more physical barriers and/or pharmacological barriers and/or physiological barriers e.g., a BBB and/or BTB and/or BEB may be inferred from the tissue or organ localization of the peptide in the brain, testis or epididymus respectively following prior intravenous injection of the peptide.

The processes or methods of the invention may comprise one or more steps that are performed in vivo such as administering the peptide to an animal and determining selectivity of the peptide in vivo. For example, a peptide for which selectivity is being assayed may be administered to an animal and cell-type specificity of the peptide in various cell-types, tissue or organs of the animal is determined as an adjunct to the in vitro assay described herein. Alternatively, or in addition, a peptide for which selectivity is being assayed may be administered to an animal and an ability of the peptide to pass through one or more physical barriers and/or pharmacological barriers and/or physiological barriers e.g., a BBB and/or BTB and/or BEB is determined.

Preferably, the process or method of the invention as described according to any preceding example further comprises determining release of the peptide from the endosome or endosome-lysosome of the cell. Determining release of the peptide from the endosome or endosome-lysosome of the cell may be performed simultaneously with e.g., alongside or in parallel with, the process of determining cell-type selectivity of a peptide, or alternatively, consecutively with e.g., before or after, the process of determining cell-type selectivity of a peptide.

In one example, determining release of the peptide from the endosome or endosome-lysosome of the cell comprises determining localization of the peptide in a sub-cellular location other than the endosome or endosome-lysosome e.g., cytosol, nucleus, endoplasmic reticulum, golgi, vacuole, mitochondrion, plastid such as chloroplast or amyloplast or chromoplast or leukoplast, nucleus, ribosome, cytoskeleton, centriole, microtubule-organizing center (MTOC), acrosome, glyoxysome, melanosome, myofibril, nucleolus, peroxisome, nucleosome or microtubule.

In another example, determining release of the peptide from the endosome or endosome-lysosome of the cell comprises determining localization of the peptide in a sub-cellular location other than in a vesicle of the endomembrane system of the cell e.g., cytosol, nucleus, endoplasmic reticulum, golgi, mitochondrion, plastid, nucleus, ribosome, cytoskeleton, centriole, microtubule-organizing center (MTOC), acrosome, glyoxysome, melanosome, myofibril, nucleolus, peroxisome, nucleosome or microtubule.

For example, determining release of the peptide from the endosome or endosome-lysosome may comprise contacting the cell with an antibody that binds to the peptide in situ and determining localization of the antibody e.g., by standard immune histochemical detection means known in the art, wherein localization of the antibody bound to the peptide in a sub-cellular location other than the endosome or endosome-lysosome or other vesicle of the endomembrane system indicates release of the peptide from the endosome or endosome-lysosome.

Alternatively, the peptide employed in the process may be labeled with a suitable reporter molecule e.g., a fluorophore, radioactive label, haloalkane, luminescent molecule, dye, etc., and determining release of the peptide from the endosome or endosome-lysosome may comprise determining localization of the reporter molecule within the cell, wherein localization of the reporter molecule bound to the reporter molecule in a sub-cellular location other than the endosome or endosome-lysosome or other vesicle of the endomembrane system indicates release of the peptide from the endosome or endosome-lysosome. In a particularly-preferred form of this example, the cells at (ii) express an haloalkane dehalogenase substrate-binding domain in a sub-cellular location other than the endosome or endosome-lysosome or other vesicle of the endomembrane system either naturally or by virtue of having been genetically engineered to do so, and the reporter molecule comprises a haloalkane. In accordance with this preferred example, determining localization of the reporter molecule within the cell comprises determining localization of the haloalkane, wherein localization of the haloalkane bound to the haloalkane dehalogenase substrate-binding domain in a sub-cellular location other than the endosome or endosome-lysosome or other vesicle of the endomembrane system indicates release of the peptide from the endosome or endosome-lysosome. Preferably, the haloalkane is detected by co-immune precipitation (CoIP) or immune histochemistry e.g., using anti-haloalkane dehalogenase substrate-binding domain antibody or antibody against the peptidyl moiety of the complex. Preferably, the haloalkane is localized predominantly in the cytosol e.g., in a complex formed between the haloalkane-tagged peptide and the expressed cytosolic haloalkane dehalogenase substrate-binding domain in this example, however the haloalkane dehalogenase substrate-binding domain may be expressed in other cellular locations by appropriate engineering e.g., by expressing the haloalkane dehalogenase substrate-binding domain as a fusion protein with another protein that is targeted to a different cellular location e.g., a haloalkane dehalogenase substrate-binding domain fusion protein expressed in the cytoskeleton of the cell. Alternatively, the peptide may be labeled with a haloalkane and a second detectable reporter molecule such as a fluorophore or radioactive label or luminescent molecule to facilitate localization of the haloalkane-tag.

As used herein, the term "haloalkane" shall be taken to include any primary, secondary or tertiary alkane molecule comprising one or more halogen atoms e.g., fluorine, chlorine, bromine or iodine, optionally further comprising a spacer molecule or linker or functional group e.g., amine or thiol, to facilitate linkage to a peptidyl moiety. An exemplary haloalkane is 1-chloro-7,10-dioxaoctadecane or 1-bromo-7,10-dioxaoctadecane or 1-fluoro-7,10-dioxaoctadecane, however other haloalkanes are selected from chlorine or bromine or fluorine derivatives of primary alkanes selected from methane, ethane, n-propane, n-butane, n-pentane, n-hexane, n-heptane, n-octane and n-nonane or n-decane are also preferred. Salts and hydrates of such haloalkanes are also within the scope of the term "haloalkane" as used herein. For example, each of the following molecules is a haloalkane that may be employed in any example of the present invention:

1. 18-chloro-3,6,9,12-tetraoxaoctadecan-1-amine hydrochloride;
2. 18-chloro-3,6,9,12-tetraoxaoctadecane-1-thiol;
3. 2,5-dioxopyrrolidino-1-yl-[4-(18-chloro-3,6,9,12-tetraoxaoctadecan-1-amino)-4-oxobutanoate];
4. N-(18-chloro-3,6,9,12-tetraoxaoctadecyl)-2-iodoacetamide; and
5. 2-(2-(6-chlorohexyloxy)ethoxy) ethanamine hydrochloride;
6. 2,5-dioxopyrrolidin-1-yl-[4-(2-(2-(6-chlorohexyloxy)ethoxy)ethylamino)-4-oxobutanoate; and
7. N-(2-(2-(6-chlorohexyloxy)ethoxy)ethyl)-2-iodoacetamide.

The term "haloalkane dehalogenase substrate-binding domain" refers to a polypeptide or protein or protein domain that is capable of binding to a haloalkane-peptide conjugate e.g., a peptide bound covalently to a haloalkane as defined, and preferably does not have the catalytic ability to cleave the haloalkane moiety from the peptide moiety of the haloalkane-peptide conjugate. Haloalkane dehalogenase substrate-binding domains within this definition are known in the art.

When used, a haloalkane dehalogenase substrate-binding domain fusion protein may comprise the haloalkane dehalogenase substrate-binding domain linked covalently to a polypeptide selected from the group consisting of actin, tubulin, talin, p65, p53, N-acetylgalactosaminyltransferase-2, synaptophysin and histone 2B, and/or to a signal sequence selected from the group consisting of the endoplasmic reticulum signal sequence of calreticulin, an endoplasmic reticulum retention signal sequence e.g., the amino acid sequence KDEL, a myristoylation/palmitoylation sequence of a Lck tyrosine kinase enzyme, a leader sequence of E1-alpha pyruvate dehydrogenase, a peroxisomal targeting sequence, and SV40 nuclear localization sequence. The only requirement for such fusion proteins is that they are not expressed on the endosome or endosome-lysosome of the cell, and preferably not within the endomembrane system of the cell.

Optionally, determining release of the peptide from the endosome or endosome-lysosome may further comprise contacting the cell at (ii) with a molecule e.g., an antibody or labeled antibody, that binds to an endosome marker e.g., annexin VI, EEA1, ESCRT, Rab5, Rab7, Lamp1, Rap1, Syntaxin 7, Syntaxin 8, Syntaxin 12, or VAMP-7 (vesicle-associated membrane protein-7), and detecting the molecule, wherein a non-co-localization of the antibody or reporter molecule bound to the peptide with the molecule bound to the endosome marker indicates release of the peptide from the endosome or endosome-lysosome.

Optionally, determining release of the peptide from the endosome or endosome-lysosome may further comprise comparing endosome or endosome-lysosome release of a candidate peptide in the cell at (ii) to the endosome or endosome-lysosome release capability of one or more previously-known CPPs in the cell at (ii) e.g., penetratin (43-58) and/or transportan and/or SBP and/or FBP and/or HIV Tat peptide (48-60) and/or syn-B1 and/or syn-B3 and/or a homoarginine-7 peptide and/or homoarginine-9 peptide, and identifying a peptide having an improved or enhanced capability for achieving endosome or endosome-lysosome release for the cell relative to said one or more previously-known CPPs. The sub-cellular localization ability of one or more previously-known CPPs in the cell at (ii) may be known in the art, or determined empirically such as by performing the process described herein using the cell at (ii) wherein the peptide is substituted for the one or more previously-known CPPs. For example, steps for determining release of the peptide and the one or more previously-known CPPs from the endosome or endosome-lysosome of the cell at (ii) may be performed in two or more sets, wherein one set assays a candidate peptide for endosome release or endosome-lysosome and wherein each other set assays a previously-known CPP against the same cell-type, and identifying having an improved or enhanced capability for achieving endosome or endosome-lysosome release for the cell relative to said one or more previously-known CPPs. These process steps apply mutatis mutandis to a process for identifying a CPP having improved capability of being released from the endosome or endosome-lysosome of a cell.

Preferably, the processes or methods of the invention as described according to any preceding example further comprises culturing the cell at (ii) for a time and under conditions sufficient to determine viability of the cell in the presence and absence of the bound and/or internalized peptide, and determining viability of the cell, wherein viability of the cell in the presence of the bound and/or internalized peptide indicates low cytotoxicity of the peptide. However, it is to be understood that, notwithstanding the desirability of the peptide having no impact on viability of the cell, an absolute equivalence in the viability of the cell in the presence and absence of the peptide is not essential to identifying a peptide having utility as a CPP. Preferably, viability of the cell at (ii) is performed without treatment of the cell to remove peptide that is associated non-selectively with the cell or that is non-integral to the cell membrane of said cell or that is non-internalized to said cell, by a means that, in and of itself, adversely affects cell viability.

In one example, a cell-penetrating peptide of the present invention is employed to protect a cell from apoptosis, and/or to select cell-penetrating peptides having endogenous pro-survival or anti-apoptotic activity, and/or to deliver a pro-survival or anti-apoptotic cargo, and/or to screen candidate molecules for pro-survival or anti-apoptotic activity. For selecting and/or utilizing a cell-penetrating peptide having endogenous pro-survival or anti-apoptotic activity, the peptide is introduced to a cell under selection that normally induces apoptosis e.g., comprising one or more cytotoxic agents or irradiation, and viable cells having the peptide internalized therein are selected, wherein the selected cells are viable by virtue of the cell-penetrating peptide having endogenous pro-survival or anti-apoptotic activity. For selecting and/or utilizing a cell-penetrating peptide having an ability to deliver a pro-survival or anti-apoptotic cargo, a conjugate comprising the peptide and a cargo molecule is introduced to a cell under selection that normally induces apoptosis e.g., comprising one or more cytotoxic agents or irradiation, and viable cells having the conjugate internalized therein are selected, wherein the selected cells are viable by virtue of the cell-penetrating peptide having an ability to deliver the cargo and by virtue of the cargo having pro-survival or anti-apoptotic activity. For selecting and/or utilizing a cargo molecule having pro-survival or anti-apoptotic activity, a conjugate comprising a cell-penetrating peptide of the present invention and a candidate cargo molecule is introduced to a cell under selection that normally induces apoptosis e.g., comprising one or more cytotoxic agents or irradiation, and viable cells having the conjugate internalized therein are selected, wherein the selected cells are viable by virtue of the candidate cargo molecule having pro-survival or anti-apoptotic activity. Using such methods, CPPs are selected which are non-toxic in themselves and/or have utility in delivering a pro-survival cargo to a cell, such as to the cytoplasm of the cell, thereby protecting the cell from apoptosis. Preferably, the CPP is linked covalently to or in association with the cargo molecule in these examples. Exemplary cargo molecules having pro-survival or anti-apoptotic activity include e.g., anti-cancer compounds, Bcl-2 and homologs thereof, AKT, NF-κB, Mcl-1 and other pro-survival proteins, siRNA targeting expression of pro-apoptotic genes, BH3 mimetic compounds, and pinacidil.

In one example, viability of the cell is determined after incubating the cell with a peptide for at least the doubling-time of the cell in the medium employed to perform the assay, and determining viability of the cell comprises determining the doubling rate of the cell e.g., the period of time required for the cell to divide. Any art-recognized method may be employed to determine a doubling rate of a cell e.g., nucleic acid content or cell counting such as by FACS. In accordance with this example, an increase in the doubling time of the cell is indicative of an adverse impact of the peptide on cell viability. Preferably, viability of the cell in the presence of the bound and/or internalized peptide is indicated by an ability of said cell to divide in less than 2-fold or less than 1.5-fold or less than 1.4-fold or less than 1.3-fold or less than 1.2-fold or less than 1.1-fold or less than 1.05-fold the time taken for the cell to divide in the absence of the peptide. More preferably, viability of the cell in the presence of the bound and/or internalized peptide is indicated by an ability of said cell to divide the same time or less than twice the time taken for the cell to divide in the absence of the peptide.

In another example, viability of the cell is determined by measuring a level of one or more metabolic substrates or enzymes that are indicative of cell viability, wherein a reduce level of the one or more metabolic substrates or enzymes in the cell is indicative of reduced viability of the cell. On one example, a level of adenosine triphosphate (ATP) is determined e.g., by measuring an increase in luminescence of luciferin in the presence of cell lysates, by virtue of cellular ATP production providing a substrate for luciferase enzyme. In another example, a level of reductase enzyme activity is determined e.g., by colorimetric assay involving the reduction of a tetrazolium salt dye e.g., 3-(4, 5-dimethylthiazol-2-yl)-2,5-diphenyltetrazolium bromide (MMT) or 2,3-bis-(2-methoxy-4-nitro-5-sulfophenyl)-2H-tetrazolium-5-carboxanilide (XTT) to a corresponding formazan in the presence of cellular reductase enzyme. Preferably, viability of the cell in the presence of the bound and/or internalized peptide is indicated by a level of ATP and/or a level of reductase that is more than 50% or more than 60% or more than 70% or more than 80% or more than 85% or more than 90% or more than 95% the level in the cell in the absence of the peptide. More preferably, viability of the cell in the presence of the bound and/or internalized peptide is indicated by the same level of ATP and/or a reductase in the presence and absence of the peptide.

Optionally, determining viability of the cell may further comprise comparing viability of the cell in the presence of the bound and/or internalized peptide to viability of the cell in the presence of one or more bound and/or internalized previously-known CPPs e.g., penetratin (43-58) and/or transportan and/or SBP and/or FBP and/or HIV Tat peptide (48-60) and/or syn-B1 and/or syn-B3 and/or a homoarginine-7 peptide and/or homoarginine-9 peptide, and identifying a peptide having an reduced cytotoxicity when bound and/or internalized to the cell relative to said one or more previously-known CPPs. The cytotoxicity of the one or more previously-known CPPs in the cell may be known in the art, or determined empirically such as by performing the process described herein using the cell at (ii) wherein the peptide is substituted for the one or more previously-known CPPs. For example, steps for determining viability of the cell at (ii) in the presence of the peptide and the one or more previously-known CPPs may be performed in two or more sets, wherein one set assays viability of the cell with a candidate peptide bound/internalized to it and wherein each other set assays viability of the cell with a previously-known CPP bound/internalized to it, and a peptide identified that is less cytotoxic to the cell than said one or more previously-known CPPs. These process steps apply mutatis mutandis to a process for identifying a CPP having reduced cytotoxicity.

Determining cell viability may be performed simultaneously with e.g., alongside or in parallel with, the process of determining cell-type selectivity of a peptide, or alternatively, consecutively with e.g., before or after, the process of determining cell-type selectivity of a peptide. Determining cell viability may also be performed simultaneously with e.g., alongside or in parallel with determining release of the peptide from the endosome or endosome-lysosome of the cell, or alternatively, consecutively with e.g., before or after determining release of the peptide from the endosome or endosome-lysosome of the cell. The present invention clearly provides a process comprising determinations of cell-type selectivity of the peptide, toxicity of the peptide, and release of the peptide from the endosome or endosome-lysosome of the cell wherein said determinations are performed consecutively in any order or wherein two or three of said determinations are performed in parallel.

In another example, the present invention provides a method of determining or identifying a cell-penetrating peptide (CPP) capable of being released from an endosome or endosome-lysosome of a cell, said process comprising contacting a cell that expresses a haloalkane dehalogenase substrate-binding domain or a fusion protein comprising said domain in a sub-cellular location other than in the endosome or endosome-lysosome or a vesicle of the endomembrane system of the cell with a peptide-haloalkane conjugate for a time and under conditions sufficient for a complex to form between the conjugate and the haloalkane dehalogenase substrate-binding domain or between the conjugate and the fusion protein, and then detecting the complex, wherein detected complex indicates that the cell-penetrating peptide (CPP) is released from the endosome or endosome-lysosome of a cell.

Preferably, the method further comprises obtaining a cell that expresses a haloalkane dehalogenase substrate-binding domain or a fusion protein comprising said domain in a sub-cellular location other than in the endosome or endosome-lysosome or a vesicle of the endomembrane system of the cell.

In preferred examples of the methods and processes of the invention, the cell expresses a haloalkane dehalogenase substrate-binding domain or a fusion protein comprising said domain in the cytosol.

Alternatively, or in addition, the method may further comprise producing a cell that expresses a haloalkane dehalogenase substrate-binding domain or a fusion protein comprising said domain in a sub-cellular location other than in the endosome or endosome-lysosome or a vesicle of the endomembrane system of the cell. For example, the cell may be produced by transfecting a cell with nucleic acid comprising a sequence that encodes the haloalkane dehalogenase substrate-binding domain or fusion protein comprising said haloalkane dehalogenase substrate-binding domain.

Exemplary fusion proteins comprise the haloalkane dehalogenase substrate-binding domain linked covalently to a protein domain that effects delivery of the fusion protein to the cytosol, plasma membrane, nucleus, endoplasmic reticulum, golgi, vacuole, mitochondrion, plastid such as chloroplast or amyloplast or chromoplast or leukoplast, nucleus, ribosome, cytoskeleton, centriole, microtubule-organizing center (MTOC), acrosome, glyoxysome, melanosome, myofibril, nucleolus, peroxisome, nucleosome or microtubule. For example, the fusion protein may comprise the haloalkane dehalogenase substrate-binding domain linked covalently to a polypeptide selected from the group consisting of actin, tubulin, talin, p65, p53, N-acetylgalactosaminyltransferase-2, synaptophysin and histone 2B, and/or to a signal sequence selected from the group consisting of the endoplasmic reticulum signal sequence of calreticulin, an endoplasmic reticulum retention signal sequence e.g., the amino acid sequence KDEL, a myristoylation/palmitoylation sequence of a Lck tyrosine kinase enzyme, a leader sequence of E1-alpha pyruvate dehydrogenase, a peroxisomal targeting sequence, and SV40 nuclear localization sequence. Standard methods known to the skilled artisan are employed to produce a haloalkane dehalogenase substrate-binding domain fusion protein.

As used herein, the term "peptide-haloalkane conjugate" means a molecule comprising a candidate peptide such as a CPP being tested in the subject method and a haloalkane as defined, wherein the candidate peptide is at sufficient distance from the halogen atom of the haloalkane to not interfere with binding to a haloalkane dehalogenase substrate-binding domain. For example, a candidate peptide and n-haloalkane may be linked covalently such that the candidate peptide and at least one halogen atom are at opposing ends of the molecule. Preferably, the peptide is linked to the haloalkane via a alpha-amino group of the peptide or an epsilon-amino group of an internal lysine residue.

In one example, the complex is detected by contacting the cell with an antibody that binds to the peptide-haloalkane conjugate or the haloalkane dehalogenase substrate-binding domain or haloalkane dehalogenase substrate-binding domain fusion partner in situ e.g., by standard immune histochemical detection means known in the art. By "haloalkane dehalogenase substrate-binding domain fusion partner" is meant the protein or signal to which the haloalkane dehalogenase substrate-binding domain is fused in the fusion protein.

Alternatively, the peptide-halolkane conjugate comprises a detectable reporter molecule e.g., a fluorophore, radioactive label, haloalkane, luminescent molecule, dye, etc., and the complex is detected by detecting the reporter molecule within the cell, wherein localization of the reporter molecule bound to the reporter molecule in a sub-cellular location other than the endosome or endosome-lysosome or other vesicle of the endomembrane system indicates release of the peptide from the endosome or endosome-lysosome.

Preferably, the peptide-halolkane conjugate comprises a detectable reporter molecule e.g., a fluorophore, radioactive label, haloalkane, luminescent molecule, dye, etc., and the complex is detected by detecting the reporter molecule and the haloalkane dehalogenase substrate-binding domain or haloalkane dehalogenase substrate-binding domain fusion partner, wherein co-localization of the detectable reporter molecule and the haloalkane dehalogenase substrate-binding domain or haloalkane dehalogenase substrate-binding domain fusion partner in a sub-cellular location other than the endosome or endosome-lysosome or other vesicle of the endomembrane system indicates release of the peptide from the endosome or endosome-lysosome.

Preferably, the method further comprises determining the sub-cellular localization of the peptide-haloalkane conjugate e.g., in the cytosol, nucleus, endoplasmic reticulum, golgi, vacuole, mitochondrion, plastid such as chloroplast or amyloplast or chromoplast or leukoplast, nucleus, ribosome, cytoskeleton, centriole, microtubule-organizing center (MTOC), acrosome, glyoxysome, melanosome, myofibril, nucleolus, peroxisome, nucleosome or microtubule.

Preferably, the method may further comprise obtaining a candidate peptide-haloalkane conjugate.

Alternatively, or in addition, the method may comprise producing a candidate peptide-haloalkane conjugate e.g., by chemical reaction of a CPP with a haloalkane as defined herein. For example, the haloalkane may undergo reductive amination in the presence of a CPP.

Optionally, the method may further comprise contacting the cell with a molecule e.g., an antibody or labeled antibody, that binds to an endosome marker e.g., annexin VI, EEA1, ESCRT, Rab5, Rab7, Lamp1, Rap1, Syntaxin 7, Syntaxin 8, Syntaxin 12, or VAMP-7 (vesicle-associated membrane protein-7), detecting the molecule, and comparing the localization of the detected molecule to the localization of the detected complex, wherein a non-co-localization of the molecule with the complex indicates release of the peptide from the endosome or endosome-lysosome.

Optionally, the method may further comprise comparing endosome or endosome-lysosome release of the peptide-haloalkane conjugate in the cell to the endosome or endosome-lysosome release capability of one or more previously-known CPPs in the cell e.g., penetratin (43-58) and/or transportan and/or SBP and/or FBP and/or HIV Tat peptide (48-60) and/or syn-B1 and/or syn-B3 and/or a homoarginine-7 peptide and/or homoarginine-9 peptide, and identifying a peptidyl moiety of a peptide-haloalkane conjugate having an improved or enhanced capability for achieving endosome or endosome-lysosome release in the cell relative to said one or more previously-known CPPs. The sub-cellular localization ability of one or more previously-known CPPs in the cell may be known in the art, or determined empirically as described herein. For example, release of the peptide-haloalkane conjugate and the one or more previously-known CPPs from the endosome or endosome-lysosome of the cell may be performed in two or more sets, wherein one set assays a candidate peptide-haloalkane conjugate for endosome release or endosome-lysosome release, and wherein each other set assays a previously-known CPP against the same cell-type, and identifying a peptidyl moiety of a peptide-haloalkane conjugate having an improved or enhanced capability for achieving endosome or endosome-lysosome release in the cell relative to said one or more previously-known CPPs. These process steps apply mutatis mutandis to a process for identifying a CPP having improved capability of being released from the endosome or endosome-lysosome of a cell.

In another example, the present invention provides a method of identifying a cell-penetrating peptide (CPP) that is substantially non-toxic to a cell, said process comprising contacting the cell with a candidate CPP for a time and under conditions for the candidate CPP to bind to the cell and/or become internalized, and determining viability of the cell in the presence and absence of the bound and/or internalized peptide, wherein viability of the cell in the presence of the bound and/or internalized peptide indicates substantial non-cytotoxicity of the peptide to the cell.

As used herein the term "substantially non-cytotoxic" shall be taken to mean that the candidate CPP does not result in a substantial reduction in cell viability relative to the viability of the cells in the absence of the candidate CPP. It is to be understood that, notwithstanding the desirability of the candidate CPP to have no adverse impact on viability of the cell, an absolute equivalence in the viability of the cell in the presence and absence of the candidate CPP is not essential.

In one example, viability of the cell is determined after incubating the cell with a candidate CPP for at least the doubling-time of the cell in the medium employed to perform the assay, and determining viability of the cell comprises determining the doubling rate of the cell e.g., the period of time required for the cell to divide. Any method described according to any example hereof for determining the doubling rate of a cell may be employed, and any indicia for interpreting the result of such a method as described according to any example hereof applies mutatis mutandis to this example of the invention.

In the examples described herein for protecting a cell from apoptosis, and/or selecting cell-penetrating peptides having endogenous pro-survival or anti-apoptotic activity, and/or delivering pro-survival or anti-apoptotic cargo to a cell, and/or screening candidate molecules for pro-survival or anti-apoptotic activity, viable cells comprising the CPP(s) which survive the pro-apoptotic selection are selected by virtue of their capacity to grow in media or by FACS sorting for live cells. Other features of the assay formats described herein in relation to those examples apply mutatis mutandis to this example of the invention.

In another example, viability of the cell is determined by measuring a level of one or more metabolic substrates or enzymes that are indicative of cell viability as described according to any example hereof, and indicia for interpreting the result of such measurements apply mutatis mutandis to this example of the invention.

Optionally, the subject method further comprises comparing viability of the cell in the presence of the candidate CPP to viability of the cell in the presence of one or more bound and/or internalized previously-known CPPs e.g., penetratin (43-58) and/or transportan and/or SBP and/or FBP and/or HIV Tat peptide (48-60) and/or syn-B1 and/or syn-B3 and/or a homoarginine-7 peptide and/or homoarginine-9 peptide, and identifying a peptide having an reduced cytotoxicity when bound and/or internalized to the cell relative to said one or more previously-known CPPs. Means for performing such an example of the present invention as described according to any example hereof shall apply mutatis mutandis to this example of the invention. Such steps also apply mutatis mutandis to a process for identifying a CPP having reduced cytotoxicity.

In another example, the present invention provides a process for isolating a cell-penetrating peptide having cell-type selectivity, said process comprising performing a process for identifying a CPP having cell-type selectivity as described according to any example hereof including any preferred or optional feature thereof on a plurality of candidate peptides and isolating a candidate peptide from the plurality that has been detected in said process as a cell-penetrating peptide (CPP) having cell-type selectivity.

For example, the present invention provides a process of isolating a cell-penetrating peptide (CPP) having cell-type selectivity, said process comprising:
(i) performing n iterations of a method comprising contacting a plurality of candidate peptides with a population of cells of a predetermined cell-type in suitable medium for a time and under conditions sufficient for a candidate peptide of said plurality to adhere to or penetrate the cells, and separating the cells from the medium to thereby produce a separated medium comprising at least one candidate peptide, wherein n is an integer having a value equal to or greater than 1;
(ii) contacting separated medium following performance of the n iterations at (i) with a population of cells of a predetermined cell-type that is different from the population of cells of predetermined cell-type at (i) for a time and under conditions sufficient for a candidate in the separated medium to adhere to and/or penetrate the cell;
(iii) recovering a candidate peptide bound to the cells at (ii) and/or internalized within the cells at (ii); and
(iv) optionally, repeating (i) to (iii) for n iterations using the recovered candidate peptide, wherein n is an integer having a value greater than one e.g. 1 or 2 or 3 or 4 or 5 or 6 or 7 or 8 or 9 or 10,
wherein a recovered candidate peptide at (iii) or (iv) is an isolated cell-penetrating peptide (CPP) having cell-type selectivity e.g., for the cell of pre-determined cell-type at (ii) relative to the cell(s) of pre-determined cell type(s) at (i).

As used herein, the term "plurality of candidate peptides" shall be construed broadly to mean more than one peptide molecule in any structural or enantiomeric form e.g., a mixture of peptides or library of peptides presented as a mixture notwithstanding that each peptide may be displayed separately from any other peptide in the mixture or library. For example, a phage display library wherein each peptide is displayed on a different phage particle, or a solid matrix comprising polymeric pins wherein each pin displays a different peptide, may constitute a plurality of candidate peptides within the present context. A "peptide library" is a plurality of peptides e.g., synthetic peptides or peptides produced by recombinant means, optionally wherein each recombinant peptide is contained within or secreted from a cell comprising a vector that encodes the peptide or wherein each recombinant peptide is displayed on the vector or cell or ribosome that encodes or otherwise produces it e.g., as in phage display or cell display or ribosome display.

Conveniently, the plurality of peptides consists of or is comprised within a peptide library, more preferably a phage display library or virus display library or in vitro display library such as covalent display library ribosome display library, or mRNA display library. A benefit of employing phage display or virus display libraries is in facilitating recovery of a candidate peptide bound to the cells at (ii) and/or internalized within the cells at (ii). For example, a candidate peptide bound to the cells at (ii) and/or internalized within the cells at (ii) is recovered by transfecting host cells of a phage vector or virus, vector expressing the candidate peptide with a lysate of the cells at (ii) for a time and under conditions sufficient to amplify the phage or virus, respectively, and then recovering the amplified phage or virus. The recovered phage or virus is then retained as a source of the candidate peptide or nucleic acid encoding said candidate peptide.

Wherein the library is a phage display library, the method of the invention may further comprise transfecting host cells with a lysate of cells to which the peptide binds or into which the peptide is internalized to thereby amplify phage expressing the candidate peptide or comprising nucleic acid encoding the candidate peptide. Phage expressing the candidate peptide or comprising nucleic acid encoding the candidate peptide may then be isolated or amplified. The recovered phage may be used as a source of the candidate peptide or nucleic acid encoding said candidate peptide.

Phage are sufficiently flexible to allow fluorescent labelling or the expression of enzymes which may be detected by the use of fluorescent substrates. For example, enzymes such as β-lactamase can be expressed from or displayed on phage (Girja et al., *Protein Engineering, Design and Selection* 23, 431-440 (2010). Accordingly, any art-recognized fluorescent detection method may be employed to detect an expressed or displayed cell-penetrating peptide expressed from or displayed in a phage display library of the present invention.

Wherein the library is a virus display library, the method of the invention may further comprise transfecting host cells with a lysate of cells to which the peptide binds or into which the peptide is internalized to thereby amplify virus expressing the candidate peptide or comprising nucleic acid encoding the candidate peptide. Virus expressing the candidate peptide or comprising nucleic acid encoding the candidate peptide may then be isolated or amplified. The recovered virus may be used as a source of the candidate peptide or nucleic acid encoding said candidate peptide.

In an alternative embodiment, the expression library is an in vitro display library i.e., the peptides encoded by the prokaryote or compact eukaryote nucleic acid fragments of the expression library are displayed using in vitro display wherein the expressed peptide is linked to the nucleic acid from which it was expressed such that said peptide is presented in the absence of a host cell. Accordingly, expression libraries produced by in vitro display technologies are not limited by transformation or transfection efficiencies. Accordingly any such library is of much higher complexity than an in vivo display library. Examples of methods of in vitro display include a method selected from the group comprising but not limited to, ribosome display, covalent display and mRNA display.

A ribosome display library directly links mRNA encoded by the expression library to the peptide that it encodes. Means for producing a ribosome display library require that the nucleic acid fragment be placed in operable connection with an appropriate promoter sequence and ribosome binding sequence, ie. form a gene construct. Preferred promoter sequences are the bacteriophage T3 and T7 promoters. Preferably, the nucleic acid fragment is placed in operable connection with a spacer sequence and a modified terminator sequence with the terminator sequence removed. As used herein the term "spacer sequence" shall be understood to mean a series of nucleic acids that encode a peptide that is fused to the peptide. The spacer sequence is incorporated into the gene construct, as the peptide encoded by the spacer sequence remains within the ribosomal tunnel following translation, while allowing the peptide to freely fold and interact with another protein or a nucleic acid. A preferred spacer sequence is, for example, a nucleic acid that encodes amino acids 211-299 of gene III of filamentous phage M13 mp19. The display library is transcribed and translated in vitro using methods well known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Examples of systems for in vitro transcription and translation include, for example, the TNT in vitro transcription and translation systems from Promega. Cooling the expression reactions on ice generally terminates translation. The ribosome complexes are stabilized against dissociation from the peptide and/or its encoding mRNA by the addition of reagents such as, for example, magnesium acetate or chloroamphenicol. Such in vitro display libraries are screened by a variety of methods, as described herein.

A ribosome inactivation display library requires the nucleic acid fragment to be operably linked to a nucleic acid encoding a first spacer sequence. It is preferred that this spacer sequence is a glycine/serine rich sequence that allows a peptide encoded by the expression library of the present invention to freely fold and interact with a target protein or nucleic acid. The first spacer sequence is linked to a nucleic acid that encodes a toxin that inactivates a ribosome. It is preferred that the toxin comprises the ricin A chain, which inactivates eukaryotic ribosomes and stalls the ribosome on the translation complex without release of the mRNA or the encoded peptide. The nucleic acid encoding the toxin is linked to another nucleic acid that encodes a second spacer sequence. The second spacer is required as an anchor to occupy the tunnel of the ribosome, and allow both the peptide and the toxin to correctly fold and become active. Examples of such spacer sequences are sequences derived from gene III of M13 bacteriophage. Ribosome inactivation display libraries are generally transcribed and translated in vitro, using a system such as the rabbit reticulocyte lysate system available from Promega. Upon translation of the mRNA encoding the toxin and correct folding of this protein, the ribosome is inactivated while still bound to both the encoded polypeptide and the mRNA from which it was translated.

An mRNA display library requires the nucleic acid fragment to be operably linked to a nucleic acid encoding a spacer sequence, such as a glycine/serine rich sequence that allows a peptide encoded by the expression library of the present invention to freely fold and interact with a target protein or nucleic acid. The nucleic acid encoding the spacer sequence is operably linked to a transcription terminator. Such mRNA display libraries are generally transcribed in vitro, using methods well known in the art, such as, for example, the HeLaScribe Nuclear Extract in vitro Transcription System available from Promega. Encoded mRNA is subsequently covalently linked to a DNA oligonucleotide that is covalently linked to a molecule that binds to a ribosome, such as, for example, puromycin, using techniques well known in the art and are described in, for example, Roberts and Szostak, *Proc. Natl. Acad. Sci. USA*, 94, 12297-12302 (1997). Preferably, the oligonucleotide is covalently linked to a psoralen moiety, whereby the oligonucleotide is photo-crosslinked to a mRNA encoded by the expression library of the present invention. The mRNA transcribed from the expression library is then translated using methods well known in the art and are described for example, in Ausubel et al., In: Current Protocols in Molecular Biology. Wiley Interscience, ISBN 047 150338, (1987) or Sambrook et al., In: Molecular Cloning: Molecular Cloning: A Laboratory Manual, Cold Spring Harbor Laboratories, New York, Third Edition (2001). When the ribosome reaches the junction of the mRNA and the oligonucleotide, the ribosome stalls and the puromycin moiety enters the phosphotransferase site of the ribosome and thus covalently links the encoded polypeptide to the mRNA from which it was expressed.

In a covalent display library, the nucleic acid fragment is operably linked to a second nucleic acid fragment that encodes a protein that interacts with the DNA from which it was encoded. Examples of a protein that interacts with the DNA from which it interacts include, but are not limited to, the *E. coli* bacteriophage P2 viral A protein (P2A) and equivalent proteins isolated from phage 186, HP1 and PSP3. The P2A protein is particularly preferred. The P2A protein recognizes a defined initiator sequence TCGGA positioned within the nucleic acid encoding the P2A protein and nicks one of the strands while forming a covalent bond with one of the free end nucleotides. Accordingly, it is preferred that at least the sequence TCGGA is included in the gene construct containing the expression library of the present invention. It is particularly preferred that the protein attachment site is positioned such that a nucleic acid fragment is covalently linked to the peptide that it encodes. A covalent display gene construct is transcribed and translated in vitro, using a system such as the rabbit reticulocyte lysate system available from Promega. Upon translation of the fusion of the peptide and the P2A protein, the P2A protein nicks the nucleic acid of the initiator sequence and forms a covalent bond therewith. Accordingly, a nucleic acid fragment is covalently linked to the peptide that it encodes.

A library, when used in a method or process of the invention, may be any library described herein.

In each of the foregoing examples, the library may comprise or consist essentially of genomic DNA and/or cDNA fragments of pathogenic organisms e.g., pathogenic bacteria and viruses.

In one preferred form, the library comprises:
(a) fragments of open reading frames encoding proteins selected from the group consisting of bacterial and/or viral virulence factors, ATP-binding cassette (ABC) transporter proteins, bacterial anti-sigma factors, taxis sensor proteins, lipoproteins, neurotransmitter:sodium symporter (NSS) family proteins, phage-related DNA packing proteins, membrane anchor proteins, succinate dehydrogenases, proteins comprising CALX-cadherin motifs, serine-rich adhesion proteins, gp41 proteins, transposases, permeases, and fibronectin-binding proteins; and/or
(b) fragments of open reading frames encoding bacterial or viral homologs of any one or more of the proteins at (a); and/or
(c) fragments of open reading frames encoding domains of any, one or more of the proteins at (a) or the bacterial or viral homologs at (b); and/or
(d) combinations of the fragments at (a) and/or (b) and/or (c).

In another preferred form, the library consists of genomic DNA fragments and/or cDNA fragments from two or more different species or strains of pathogenic organisms, and in certain of such forms the pathogenic organisms are from two or more different phylogenetic orders.

The library may comprise genomic DNA or cDNA fragments of open reading frames encoding bacterial and/or viral virulence factors. Alternatively, or in addition, the library comprises genomic DNA or cDNA fragments of open reading frames encoding ATP-binding cassette (ABC) transporter proteins or domains thereof. Alternatively, or in addition, the library comprises genomic DNA or cDNA fragments of open reading frames encoding bacterial ATP-binding cassette (ABC) transporter proteins or domains thereof. For example, the domains may be transmembrane domains (TMDs) or membrane-spanning domains (MSDs) or integral membrane (IM) domains that normally function in binding a substrate of a functional ATP-binding cassette (ABC) transporter protein. Alternatively, or in addition, the library comprises genomic DNA or cDNA fragments of open reading frames encoding bacterial anti-sigma factors. Alternatively, or in addition, the library comprises genomic DNA or cDNA fragments of open reading frames encoding CALX-cadherin motifs. Alternatively, or in addition, the library comprises genomic DNA or cDNA fragments of open reading frames encoding taxis sensor proteins e.g., bacterial taxis sensor proteins or chemotaxis sensor proteins such as bacterial chemotaxis proteins that sense amino acids. Alternatively, or in addition, the library comprises genomic DNA or cDNA fragments of open reading frames encoding lipoproteins. Alternatively, or in addition, the library comprises genomic DNA or cDNA fragments of open reading frames encoding neurotransmitter:sodium symporter (NSS) family proteins. Alternatively, or in addition, the library comprises genomic DNA or cDNA fragments of open reading frames encoding phage-related DNA packing proteins. Alternatively, or in addition, the library comprises genomic DNA or cDNA fragments of open reading frames encoding membrane anchor proteins such as succinate dehydrogenases. Alternatively, or in addition, the library comprises genomic DNA or cDNA fragments of open reading frames encoding to serine-rich adhesion proteins or bacterial proteins having homology thereto. Alternatively, or in addition, the library comprises genomic DNA or cDNA fragments of open reading frames encoding gp41 proteins or bacterial proteins having homology thereto. Alternatively, or in addition, the library comprises genomic DNA or cDNA fragments of open reading frames encoding transposases. Alternatively, or in addition, the library comprises genomic DNA or cDNA fragments of open reading frames encoding permeases. Alternatively, or in addition, the library comprises genomic DNA or cDNA fragments of open reading frames encoding fibronectin-binding proteins.

A suitable library of the present invention for use in isolating CPPs, may express candidate peptides that assume conformations or secondary structures sufficient for said candidate peptides to bind or penetrate the cell. In one example, the peptides are Phylomer peptides produced by Phylogica Limited, Western Australia, Australia. In such libraries, nucleic acid fragments of genomic DNA from prokaryotes and/or eukaryotes or viruses having compact genomes that are substantially sequenced may be employed as a source of the expressed peptides, and such libraries may be constructed from two or more genomes of and/or cDNA populations from different species or strains of such organisms or viruses e.g., two or more genomes of and/or cDNA populations from different species or strains of pathogenic organisms or viruses. In this example, the candidate CPPs are generally encoded by portions of open, reading frames of the genomic DNA comprised within the nucleic acid fragments, wherein said open reading frames encode polypeptides having sequences that are known to be expressed in the prokaryote and/or eukaryote and/or virus. Alternatively, the candidate CPPs are encoded by nucleic acid fragments that do not encode polypeptides having sequences that are known to be expressed in the prokaryote and/or eukaryote and/or virus. It is also within the scope of the present invention to produce and/or use libraries of peptides, and/or analogs and/or derivatives thereof, that have a net charge that is neutral or negative e.g., a net charge in a range from 0 to −10 or from 0 to −15 or from 0 to −20, including a net charge of 0, −1, −2, −3, −4, −5, −6, −7, −8, −9, −10, −11, −12, −13, −14, −15, −16, −17, −18, −19, or −20, or alternatively, a net charge that is negative. It is also within the scope of the present invention to produce and/or use libraries of peptides that have a net charge that is neutral or positive e.g., a net charge in a range from 0 to +10 or from 0 to +15 or from 0 to +20, including a net charge of 0, +1, +2, +3, +4, +5, +6, +7, +8, +9, +10, +11, +12, +13, +14, +15, +16, +17, +18, +19, or +20, or alternatively a net positive charge. It is also within the scope of the present invention to produce and/or use libraries of peptides that have a net neutral charge. Net charges of peptides, or analogs and/or derivatives thereof, may be determined as described herein.

An exemplary library comprises one or more of SEQ ID NOs: 1-27, or any one or more of SEQ ID NOs: 1, 2, 9, 14-16, 18, and 19, or any one or more of SEQ ID NOs: 1, 2, 9, 14-16, 18, 19 and 24-26, or any one or more of SEQ ID NOs: 1, 2, 5, 9, 14-16, 18, and 19, or any one or more of SEQ ID NOs: 1, 2, 5, 9, 14-16, 18, 19 and 24-26, or any one or more of any one or more of SEQ ID NOs: 1, 2, 5, 9, 14-18, and 20-23, or any one or more of SEQ ID NOs: 3-8, 10-13, 17, and 20-23, or any one or more of any one or more of SEQ ID NOs: 1, 2, 5, 9, 14-16, 18, and 20-23, or any one or more of SEQ ID NOs: 3-8, 10-13, and 17, or any one or more of SEQ ID NOs: 3-8, 10-13, 17, 20-23, and 27, or any one or more of SEQ ID NOs: 3, 4, 6-8, 10-13, 17, or 19, or any one or more of SEQ ID NOs: 3, 4, 6-8, 10-13 or 19, or any one or more of SEQ ID NOs: 1, 2, 5, 9, 14-18, or 24-27, or any one or more of SEQ ID NOs: 1, 2, 5, 9, 14-16, 18, or 24-27, or any one or more of SEQ ID NOs: 1, 2, 9, 14-16, 18 and 19, or comprising or having the sequence set forth in SEQ ID NO: 17, including any one of said SEQ ID NOs, or including an analogue or derivative thereof as described according to any example hereof. Another exemplary library comprises a plurality of peptide derivatives that are sequence variants of one or more of such sequences, such as mutagenesis library as described herein.

In another example, an expression library comprises genomic DNA fragments and/or cDNA fragments from two or more different species or strains of pathogenic organisms. In a further example, an expression library comprises genomic DNA fragments and/or cDNA fragments from two or more different species or strains of pathogenic organisms or viruses from two or more different phylogenetic orders.

In preferred examples of the invention, when a library of component of a library is used as a "source" of the (candidate) peptide includes that the peptide is isolated, identified and/or characterised by means of such "source". In alternative examples, the source can be used to generate or produce a desired amount of such peptide.

As used herein, and unless the context requires otherwise, the term "population of cells" shall be construed broadly to include a plurality of cells of the same or similar cell-type which are in culture together or otherwise collected to form a group. For example, a population of cells may comprise a mixture of primary epithelial cells of human origin in culture with primary epithelial cells of non-human origin. In another example, a population of cells comprises fibroblast cells derived from multiple human subjects. In another example, a population of cells comprises endothelial cells of neuronal origin or non-vascular e.g., brain endothelial cells. In another example, a population of cells comprises endothelial cells of non-neuronal origin e.g., vascular endothelial cells. In another example, a population of cells comprises epithelial cells of ovarian origin. In yet another example, a population of cells comprises a purified cell line e.g., human brain astrocytoma cells.

In the examples described herein for protecting a cell from apoptosis, and/or selecting cell-penetrating peptides having endogenous pro-survival or anti-apoptotic activity, and/or delivering pro-survival or anti-apoptotic cargo to a cell, and/or screening candidate molecules for pro-survival or anti-apoptotic activity, the cell-penetrating peptides may be isolated from the viable cells e.g., by culturing the cells in the selective media or by FACS sorting of viable or living cells. Other features of those assay formats described herein in relation to those examples apply mutatis mutandis to this example of the invention.

In the examples described herein wherein a cell-penetrating peptide is fused to an enzyme cargo such as β-lactamase, and detected by means of a fluorescent substrate, such as CCF4-AM, selecting cells in which there is low enzyme expression in the endosome and preferably elevated expression in the cytosol, and recovering or isolating the cell-penetrating peptide from the selected cells. In this example, the expression of the enzyme, such as indicated by fluorescence of a substrate of the enzyme, is also indicative of the cell-penetrating peptide being capable of delivering a protein cargo, and being capable of internalization as determined by endosomal escape. Other features of examples employing enzyme cargos as described herein, especially enzyme cargos that have fluorescent substrates, apply mutatis mutandis to this example of the invention.

In an alternative example, the present invention provides a process for isolating a cell-penetrating peptide capable of being released from an endosome or endosome-lysosome of a cell, said process comprising performing a process for identifying a CPP capable of being released from an endosome or endosome-lysosome of a cell as described according to any example hereof on a plurality of candidate peptides and isolating a candidate peptide from the plurality that has been detected in said process as a cell-penetrating peptide (CPP) capable of being released from an endosome or endosome-lysosome of a cell. The preferred features of a process for identifying a CPP capable of being released from an endosome or endosome-lysosome of a cell according to any example hereof including any optional feature thereof shall also apply mutatis mutandis to this example of the invention. Such steps also apply mutatis mutandis to a process for isolating a CPP having improved capability of being released from an endosome or endosome-lysosome of a cell relative to a previously-known CPP.

For example, the present invention provides a process for isolating a cell-penetrating peptide capable of being released from an endosome or endosome-lysosome of a cell, said process comprising:

(i) contacting a population of cells with a plurality of peptide-haloalkane conjugates, wherein the cells of the population express a haloalkane dehalogenase substrate-binding domain or a fusion protein comprising said domain in a sub-cellular location other than in an endosome or endosome-lysosome or a vesicle of the endomembrane system, and wherein the peptide-haloalkane conjugates differ at least with respect to their peptidyl moieties, and wherein said contacting is for a time and under conditions sufficient for complexes to form between the haloalkane moieties of the peptide-haloalkane conjugates and the haloalkane dehalogenase substrate-binding domain or between the haloalkane moieties of the peptide-haloalkane conjugates and the fusion proteins;

(ii) detecting cells in which a complex is formed between the haloalkane moieties of the peptide-haloalkane conjugates and the haloalkane dehalogenase substrate-binding domain or in which a complex is formed between the haloalkane moieties of the peptide-haloalkane conjugates and the fusion proteins;

(iii) recovering a peptide-haloalkane conjugate from the detected cells; and (iv) optionally, repeating (i) to (iii) for n iterations using the recovered peptide-haloalkane conjugate, wherein n is an integer having a value greater than one e.g. 1 or 2 or 3 or 4 or 5 or 6 or 7 or 8 or 9 or 10 or more.

The preferred features of a process for identifying a CPP having cell-type selectivity as described according to any example hereof including any preferred or optional feature thereof on a plurality of candidate peptides shall also apply mutatis mutandis to this example of the invention. Such steps also apply mutatis mutandis to a process for isolating a CPP having different cell-type specificity relative to a previously-known CPP.

In yet another example, the present invention provides a process for isolating a cell-penetrating peptide (CPP) that is substantially non-toxic to a cell, said process comprising performing a process for identifying a CPP a cell-penetrating peptide (CPP) that is substantially non-toxic to a cell as described according to any example hereof on a plurality of candidate peptides and isolating a candidate peptide from the plurality that has been detected in said process as CPP that is substantially non-toxic to a cell. The preferred features of a process for identifying a CPP that is substantially non-toxic to a cell according to any example hereof including any optional feature thereof shall also apply mutatis mutandis to this example of the invention. Such steps also apply mutatis mutandis to a process for isolating a CPP having reduced cytotoxicity relative to a previously-known CPP.

For example, the present invention provides a process of isolating a cell-penetrating peptide (CPP) that is substantially non-toxic to a cell, said process comprising:

(i) contacting a population of cells with a plurality of candidate CPPs for a time and under conditions for the candidate CPPs to bind to the cells and/or become internalized;

(ii) isolating substantially viable cells e.g., by culturing the cells to achieve at least one cell doubling;

(iii) recovering the candidate CPP from the substantially viable cells; and (iv) optionally, repeating (i) to (iii) for n iterations using the recovered candidate CPP, wherein n is an integer having a value greater than one e.g. 1 or 2 or 3 or 4 or 5 or 6 or 7 or 8 or 9 or 10 or more.

A further example of the present invention provides a cell-penetrating peptide e.g., a peptide identified or isolated by performing a process or method according to any example hereof, or an analog and/or derivative thereof.

This invention also provides a cell-penetrating peptide, or an analog, or derivative thereof, wherein the peptide comprises a sequence of a protein selected from the group consisting of:

(a) a protein selected from the group consisting of bacterial and/or viral virulence factors, ATP-binding cassette (ABC) transporter proteins, bacterial anti-sigma factors, taxis sensor proteins, lipoproteins, neurotransmitter:sodium symporter (NSS) family proteins, phage-related DNA packing proteins, membrane anchor proteins, succinate dehydrogenases, proteins comprising CALX-cadherin motifs, serine-rich adhesion proteins, gp41 proteins, transposases, permeases, and fibronectin-binding proteins; and (b) a bacterial or viral homolog of any one or more of the proteins at (a); and (c) a domain or other portion of any one or more of the proteins at (a) or any one or more of the bacterial or viral homologs at (b).

As used herein, the term "analog" in reference to a peptide shall be taken in its broadest context to mean any structurally-modified polymeric amino acid sequence, and more particularly a polymeric amino acid sequence comprising one or more modifications to L-amino acid side-chains or to the alpha-amino acid backbone.

The term "derivative" shall be taken to mean a composition that is derived by mutation, fragmentation or addition to a peptide of the present invention.

An analog of a peptide of the invention may consist of an analog of a derivative of a peptide of the invention. Similarly, a derivative of a peptide of the invention may consist of a derivative of an analog of a peptide of the invention. Accordingly, the invention also provides for moieties that may be considered both analogs and derivatives of any peptide of the invention disclosed herein.

A preferred analog and/or derivative of any peptide of the invention disclosed herein is an analog and/or derivative that has cell-penetrating activity, or one that has a cell-penetrating functionality of the base peptide. Other preferred derivatives or analogues of cell-penetrating peptides retain one or more structural and/or physicochemical characteristics of the cell-penetrating peptide from which they are ultimately derived apart from their specific sequence. Alternatively, or in addition, preferred derivatives or analogues of cell-penetrating peptides retain one or more functional characteristics of the cell-penetrating peptide from which they are derived e.g., cell-type selectivity and/or cytotoxicity profile.

The cell-penetrating peptide or derivative thereof may comprise a sequence of a bacterial and/or viral virulence factor or domain or other portion thereof. Alternatively, or in addition, the cell-penetrating peptide or derivative thereof may comprise a sequence of an ATP-binding cassette (ABC) transporter protein or domain thereof. Alternatively, or in addition, the cell-penetrating peptide or derivative thereof comprises a sequence of a bacterial ATP-binding cassette (ABC) transporter protein or domain or other portion thereof. For example, the domain or other portion may be a transmembrane domain (TMD) or membrane-spanning domain (MSD) or integral membrane (IM) domain that normally functions in binding a substrate of a functional ATP-binding cassette (ABC) transporter protein. Alternatively, or in addition, the cell-penetrating peptide or derivative thereof comprises a sequence of a bacterial anti-sigma factor or domain or other portion thereof. Alternatively, or in addition, the cell-penetrating peptide or derivative thereof comprises a sequence of a polypeptide comprising a CALX-cadherin motif or domain or other portion thereof. Alternatively, or in addition, the cell-penetrating peptide or derivative thereof comprises a sequence of a taxis sensor protein or domain or other portion thereof e.g., a bacterial taxis sensor protein or a chemotaxis sensor protein such as a bacterial chemotaxis protein that senses amino acids. Alternatively, or in addition, the cell-penetrating peptide or derivative thereof comprises a sequence of a lipoprotein or domain or other portion thereof. Alternatively, or in addition, the cell-penetrating peptide or derivative thereof comprises a sequence of a neurotransmitter:sodium symporter (NSS) family protein or domain or other portion thereof. Alternatively, or in addition, the cell-penetrating peptide or derivative thereof comprises a sequence of a phage-related DNA packing protein or domain or other portion thereof. Alternatively, or in addition, the cell-penetrating peptide or derivative thereof comprises a sequence of a membrane anchor protein such as succinate dehydrogenase or a domain or other portion thereof. Alternatively, or in addition, the cell-penetrating peptide or derivative thereof comprises a sequence of a serine-rich adhesion protein or bacterial protein having homology thereto or a domain or other portion thereof. Alternatively, or in addition, the cell-penetrating peptide or derivative thereof comprises a sequence of a gp41 protein of an immunodeficiency virus or a bacterial protein having homology thereto or a domain or other portion thereof. Alternatively, or in addition, the cell-penetrating peptide or derivative thereof comprises a sequence of a transposase or domain or other portion thereof. Alternatively, or in addition, the cell-penetrating peptide or derivative thereof comprises a sequence of a permease or domain or other portion thereof. Alternatively, or in addition, the cell-penetrating peptide or derivative thereof comprises a sequence of a fibronectin-binding protein or domain or other portion thereof.

Alternatively, or in addition, the cell-penetrating peptide or derivative thereof comprises an amino acid sequence of a base peptide selected from the group consisting of SEQ ID NOs: 1-27, or any one or more of SEQ ID NOs: 1, 2, 9, 14-16, 18, and 19, or any one or more of SEQ ID NOs: 1, 2, 9, 14-16, 18, 19 and 24-26, or any one or more of SEQ ID NOs: 1, 2, 5, 9, 14-16, 18, and 19, or any one or more of SEQ ID NOs: 1, 2, 5, 9, 14-16, 18, 19 and 24-26, or any one or more of any one or more of SEQ ID NOs: 1, 2, 5, 9, 14-18, and 20-23, or any one or more of SEQ ID NOs: 3-8, 10-13, 17, and 20-23, or any one or more of any one or more of SEQ ID NOs: 1, 2, 5, 9, 14-16, 18, and 20-23, or any one or more of SEQ ID NOs: 3-8, 10-13, and 17, or any one or more of SEQ ID NOs: 3-8, 10-13, 17, 20-23, and 27, or any one or more of SEQ ID NOs: 3, 4, 6-8, 10-13, 17, or 19, or any one or more of SEQ ID NOs: 3, 4, 6-8, 10-13 or 19, or any one or more of SEQ ID NOs: 1, 2, 5, 9, 14-18, or 24-27, or any one or more of SEQ ID NOs: 1, 2, 5, 9, 14-16, 18, or 24-27, or any one or more of SEQ ID NOs: 1, 2, 9, 14-16, 18 and 19, or comprising or having the sequence set forth in SEQ ID NO: 17, including any one of said SEQ ID NOs, or including an analogue or derivative thereof as described according to any example hereof having a cell-penetrating activity or functionality of the base peptide. Alternatively, or in addition, the cell-penetrating peptide comprises an amino acid sequence of an analog and/or derivative of such a base peptide having cell-penetrating activity or having a cell-penetrating functionality of the base peptide.

Exemplary analogs of the foregoing CPPs may consist of an isostere comprising one or more D-amino acid substituents relative to the amino acid sequence of a base peptide, or comprise one or more conservative amino acid substitutions relative to the sequence of a base peptide, or comprise a reversed sequence relative to the sequence of a base peptide. Particularly-preferred analogs are retro-inverso peptide analogs.

Exemplary derivatives consist of a fragment of the peptide comprising at least about 5 contiguous amino acids of amino acid sequence of a base peptide.

In another example, the invention provides an isostere comprising one or more D-amino acid substituents relative to a fragment of the peptide comprising at least about 5 contiguous amino acids of amino acid sequence of a base peptide.

In particular examples the derivative comprises a conjugate comprising a peptide, or an analog and/or other derivative, described herein and a cargo for delivery to a cell or sub-cellular location. For example, derivatives may comprise a peptide, analog or other derivative in association with or covalently linked to a cargo selected from the group consisting of small molecules, carbohydrates, lipids, nucleic acids, peptides, polypeptides, proteins, cells, bacteriophage particles, virus particles, synthetic polymers, resins, latex particles, and dyes. Preferably, the cargo is covalently-linked to the peptide, analog or other derivative via a linker or spacer molecule. Conjugates may be solid matrices comprising one or more of the peptides, analogs, or derivatives. Preferred conjugates comprise cargo molecules having therapeutic utility or diagnostic utility e.g., for transport of a therapeutic or diagnostic molecule across the Blood Brain Barrier (BBB) or Blood Testes Barrier (BTB) or Blood Epididymal Barrier (BEB) in association with or covalently linked to said cell-penetrating peptide, analog, or derivative. For example, the conjugate may have utility in therapy or diagnosis of a disease or condition of the central nervous system.

In another example, a conjugate may comprise a peptide, or an analog and/or derivative thereof, as described herein, in association with linked covalently to a detectable molecule, especially for diagnostic purposes. For example, the peptide, analog and/or derivative may be linked covalently to a detectable molecule selected from the group comprising a haloalkane moiety, fluorophore, radioactive label, luminescent molecule, nanoparticle, contrast agent, and quantum dot.

In another example, a conjugate may comprise a peptide, or an analog and/or derivative thereof, as described herein, in association with linked covalently to a second peptide, a polypeptide or a protein.

In another example, a conjugate may comprise the peptide or an analog and/or derivative thereof linked covalently to a second peptide, a polypeptide or a protein.

The present invention extends to a cell-penetrating peptide, analog, or derivative according to any example hereof in an isolated or substantially-pure form. A substantially-pure form includes a form of a referenced composition that includes greater than about 50%, 60%, 70%, 80%, 90%, 92%, 95%, 98%, 99%, 99.5% or 99.9% of such referenced composition, and/or has less than about 40%, 30%, 20%, 10%, 8%, 5%, 2%, 1%, 0.5%, or 0.1% of a second-most prevalent composition other than the referenced composition. Methods to determine the purity of a referenced composition will be well known to the person of ordinary skill, and for a peptide may include the use of HPLC.

The present invention also extends to composition comprising a plurality of the cell-penetrating peptides and/or analogs and/or derivatives according to any example hereof, including any conjugate(s) described herein.

In a preferred example, the cell-penetrating peptide comprises or consists of an amino acid sequence selected from the group consisting of SEQ ID NOs: 1-27, SEQ ID NOs: 1-27, or any one or more of SEQ ID NOs: 1, 2, 9, 14-16, 18, and 19, or any one or more of SEQ ID NOs: 1, 2, 9, 14-16, 18, 19 and 24-26, or any one or more of SEQ ID NOs: 1, 2, 5, 9, 14-16, 18, and 19, or any one or more of SEQ ID NOs: 1, 2, 5, 9, 14-16, 18, 19 and 24-26, or any one or more of any one or more of SEQ ID NOs: 1, 2, 5, 9, 14-18, and 20-23, or any one or more of SEQ ID NOs: 3-8, 10-13, 17, and 20-23, or any one or more of any one or more of SEQ ID NOs: 1, 2, 5, 9, 14-16, 18, and 20-23, or any one or more of SEQ ID NOs: 3-8, 10-13, and 17, or any one or more of SEQ ID NOs: 3-8, 10-13, 17, 20-23, and 27, or any one or more of SEQ ID NOs: 3, 4, 6-8, 10-13, 17, or 19, or any one or more of SEQ ID NOs: 3, 4, 6-8, 10-13 or 19, or any one or more of SEQ ID NOs: 1, 2, 5, 9, 14-18, or 24-27, or any one or more of SEQ ID NOs: 1, 2, 5, 9, 14-16, 18, or 24-27, or any one or more of SEQ ID NOs: 1, 2, 9, 14-16, 18 and 19, or comprising or having the sequence set forth in SEQ ID NO: 17, including any one of said SEQ ID NOs, or including an analogue or derivative thereof as described according to any example hereof. In more preferred examples, the analog of any one of said SEQ ID NOs has a cell-penetrating activity or has a cell-penetrating functionality of the base peptide, and/or the derivative, such as a fragment, of any one of said SEQ ID Nos has a cell-penetrating activity or has a cell-penetrating functionality of the base peptide.

By "a cell-penetrating functionality of the base peptide" in this context is meant that the analog and/or derivative inter alia has the same or similar ability as the base peptide to bind to a cell and/or be internalized, and/or the same cell-type selectivity or specificity as the base peptide, and/or the same cytotoxicity as the base peptide or a reduced cytotoxicity relative to the base peptide, and/or the same ability as the base peptide to be released from the endosome or endosome-lysosome or a reduced retention in the endosome or endosome-lysosome relative to the base peptide.

A preferred analog of a peptide of the invention disclosed herein, such as any one of SEQ ID NOs: 1-27 selected or grouped according to any example hereof will consist of an isostere, an analog comprising one or more D-amino acid substituents e.g., one or more D-amino acid stereoisomers of L-amino acids in the sequence of a base peptide with respect to which it is, an analog, or an analog comprising one or more conservative amino acid substitutions relative to the sequence of a base peptide with respect to which it is an analog, or an analog comprising a reversed sequence relative to the sequence of a base peptide with respect to which it is an analog. Retro-inverso peptide analogs are particularly preferred.

A preferred derivative of a peptide of the invention disclosed herein, such as any one of SEQ ID NOs: 1-27 selected or grouped according to any example hereof, will consist of a fragment of the peptide, such as a fragment comprising a sufficient number of contiguous amino acids to retain a cell-penetrating activity, or to retain a cell-penetrating functionality of the base peptide with respect to which it is a fragment. Preferred fragments of a peptide disclosed herein will comprise at least about 5 contiguous amino acids of the base peptide or at least about 10 contiguous amino acids of the base peptide or at least about 15 contiguous amino acids of the base peptide or at least about 20 contiguous amino acids of the base peptide or at least about 25 contiguous amino acids of the base peptide, including at least about 5 or 6 or 7 or 8 or 9 or 10 or 11 or 12 or 13 or 14 or 15 or 16 or 17 or 18 or 19 or 20 or 21 or 22 or 23 or 24 or 25 contiguous amino acids of the base peptide. Such fragments may be comprised in, i.e., form part of, a larger molecule such as a polypeptide. For example, a fragment of a peptide disclosed herein may form part of a fusion-protein or a specific sequence or structural domain of a polypeptide (or peptide-like) chain.

A particularly preferred derivative of a peptide of the invention disclosed herein, such as any one of SEQ ID NOs: 1-27 selected or grouped according to any example hereof comprises or consists of a conjugate comprising the peptide or an analog and/or derivative thereof and a cargo for delivery to a cell or sub-cellular location. Exemplary cargos are small molecules, carbohydrates, lipids, nucleic acids (e.g., DNA, RNA, siRNA duplex or simplex molecule, or miRNA), peptides, polypeptides, proteins, cells, bacteriophage or virus particles, synthetic polymers, resins, latex particles, dyes or other detectable molecules that are covalently linked to the peptide directly or indirectly via a linker or spacer molecule e.g., a carbon spacer or linker consisting of amino acids of low immunogenicity. Solid matrices e.g., polymeric pins or microtiter plates comprising one or more peptides, analogs, or derivatives of the invention are encompassed by the term "conjugate". Preferred conjugates comprise cargo molecules having therapeutic utility or diagnostic utility. For example, a conjugate may comprise the subject peptide, analog and/or derivative linked covalently to a detectable molecule e.g., a haloalkane moiety, fluorophore, radioactive label, luminescent molecule, nanoparticle, contrast agent, or quantum dot. In another example, the conjugate comprises a fusion protein comprising a peptide of the present invention or an analog and/or derivative thereof linked covalently to a second peptide, polypeptide or protein. For example, the second peptide, polypeptide or protein may be an enzyme that is detectable by fluorescence of a substrate, e.g., the β-lactamase enzyme as described herein.

In yet another example, the present invention provides a conjugate comprising at least one cell-penetrating peptide or comprising an analog and/or derivative thereof according to any example hereof, and at least one cargo for delivery to a cell or sub-cellular location. In preferred examples, the derivative is itself not a conjugate. The cargo may be selected from the group consisting of small molecules, carbohydrates, lipids, nucleic acids, peptides, polypeptides, proteins, cells, bacteriophage particles, virus particles, synthetic polymers, resins, latex particles, and dyes, and is generally associated with or covalently-linked to the at least one cell-penetrating peptide, analog and/or derivative. Preferably, the cargo is covalently-linked to the peptide via a linker or spacer molecule. Conjugates may be solid matrices comprising one or more of the peptides, analogs, or derivatives. Preferred conjugates comprise cargo molecules having therapeutic utility or diagnostic utility e.g., conjugates for transport of a therapeutic or diagnostic molecule (as cargo) across the Blood Brain Barrier (BBB) or Blood Testes Barrier (BTB) or Blood Epididymal Barrier (BEB) in association with or covalently linked to said cell-penetrating peptide, analog, or derivative. For example, the conjugate may have utility in therapy or diagnosis of a disease or condition of the central nervous system.

In another example, a conjugate may comprise at least one cell-penetrating peptide or comprising an analog and/or derivative thereof according to any example hereof, and associated with or linked covalently to a detectable molecule, especially for diagnostic purposes. For example, the peptide or an analog and/or derivative thereof may be linked covalently to a detectable molecule selected from the group comprising a haloalkane moiety, fluorophore, radioactive label, luminescent molecule, nanoparticle, contrast agent, and quantum dot.

In another example, a conjugate may comprise at least one cell-penetrating peptide or comprising an analog and/or derivative thereof according to any example hereof, and associated with or linked covalently to a second peptide, a polypeptide or a protein, such as a second peptide, a polypeptide or a protein as a cargo for delivery to a cell or sub-cellular location.

The conjugate of any example herein may be provided in an isolated or substantially-pure form.

In yet another example, the present invention provides a pharmaceutical composition comprising a conjugate and a pharmaceutically-acceptable carrier or excipient, wherein the conjugate comprises a cell-penetrating peptide of the present invention, or an analog and/or derivative thereof as described according to any example hereof. Preferred pharmaceutical compositions are formulated for therapeutic or diagnostic use e.g., for parenteral administration such as by intravenous injection, or for inhalation or oral administration.

Alternatively, a pharmaceutical composition of the invention may comprise a pharmaceutical composition comprising at least one conjugate according to any example hereof and a pharmaceutically-acceptable carrier or excipient. The pharmaceutical composition may be formulated for parenteral administration.

In yet another example, the present invention provides use of a cell-penetrating peptide of the present invention, or an analog and/or derivative thereof, as described according to any example hereof for use in medicine. In a preferred such example, the cell-penetrating peptide, analog or derivative is used as a conjugate further comprising a cargo molecule having therapeutic or diagnostic utility.

In yet another example, the present invention provides a method of transporting a cargo molecule across a cell membrane or internalizing a cargo molecule within a cell or a sub-cellular location, said method comprising contacting the cell with a conjugate comprising the cargo molecule and a cell-penetrating peptide of the present invention, or an analog and/or derivative thereof, as described according to any example hereof, for a time and under conditions sufficient for the conjugate to cross the cell membrane. Preferably, the method further comprises providing the conjugate. Alternatively, or in addition, the method further comprises producing the conjugate by a process comprising associating or linking covalently the cargo molecule to the peptide, analog or derivative.

In yet another example, the present invention provides a method of producing a conjugate capable of crossing a cell membrane or being internalized within a cell, said method comprising associating or linking covalently a cell-penetrating peptide of the present invention, or an analog and/or derivative thereof, as described according to any example hereof, to a second molecule e.g., a cargo molecule described herein.

In yet another example, the present invention provides a library e.g., an expression library or peptide library, such as one specifically adapted, for use in a method of identifying or isolating one or more cell-penetrating peptides (CPPs) from candidate CPPs.

In one example, the library comprises:
(a) fragments of open reading frames encoding proteins selected from the group consisting of bacterial and/or viral virulence factors, ATP-binding cassette (ABC) transporter proteins, bacterial anti-sigma factors, taxis sensor proteins, lipoproteins, neurotransmitter:sodium symporter (NSS) family proteins, phage-related DNA packing proteins, membrane anchor proteins, succinate dehydrogenases, proteins comprising CALX-cadherin motifs, serine-rich adhesion proteins, gp41 proteins, transposases, permeases, and fibronectin-binding proteins; and/or
(b) fragments of open reading frames encoding bacterial or viral homologs of any one or more of the proteins at (a); and/or
(c) fragments of open reading frames encoding domains of any one or more of the proteins at (a) or the bacterial or viral homologs at (b); and/or
(d) peptides encoded by the fragments at (a) and/or (b) and/or (c).

In another example, the library may comprise fragments encoding or a plurality of peptide derivatives that are sequence variants of one or more of the sequences represented by (a), (b), (c) and/or (d) above, such as mutagenesis library of one or more such sequences. In one of such examples, the mutagenesis library is a random mutagenesis library e.g., comprising sequence variants across a large portion of the base sequence(s). In another of such examples, the sequence variation is localised to one or more particular portions of one or more given base sequences.

In another example, the library consists of genomic DNA fragments and/or cDNA fragments from 2 or more different species or strains of pathogenic organisms or viruses. For example, suitable libraries may consist of genomic DNA fragments and/or cDNA fragments from between 2 and about 50 different species or strains of pathogenic organisms or viruses, such as between about 5 and about 10, between about 10 and about 25 or between about 25 and 50 different species or strains of pathogenic organisms or viruses. In other examples, the different pathogenic organisms or viruses used for the construction of such libraries are found within between 2 and about 30 different phylogenetic orders, such as between about 5 and about 10, between about 10 and about 20 or between about 20 and 30 different phylogenetic orders.

The DNA or cDNA within such libraries may be obtained from organisms, such as bacteria and/or viruses, that are pathogenic to eukaryotic other organisms, such as are pathogenic to mammals including humans. The identity of bacteria and virus that are pathogenic to humans will be known to the person of ordinary skill, and include those described in Ecker et al, 2005 (*The Microbial Rosetta Stone Database: A compilation of global and emerging infectious microorganisms and bioterrorist threat agents*; BMC Microbiol. 5: 19).

In one example, the libraries of the invention may comprise or consist of genomic DNA fragments and/or cDNA fragments obtained from 2 or more pathogenic organisms that are found in two or more different phylogenetic orders. For example, pathogenic bacteria may be selected from species or strains found at 2 or more phylogenic orders (with example species) selected from the group: Bacillales (*B. anthracis, B. cereus, S. aureus, L. monocytogenes*); Lactobacillales (*S. pneumoniae, S. pyogenes*); Clostridiales (*C. botulinum, C. difficile, C. perfringens, C. tetani*); Spirochaetales (*Borrelia burgdorferi, Treponema pallidum*); Chlamydiales (*Chlamydia trachomatis, Chlamydophila psittaci*); Actinomycetales (*C. diphtheriae, Mycobacterium tuberculosis, M. avium*): Rickettsiales (*R. prowazekii, R. rickettsii, R. typhi, A. phagocytophilum, E. chaffeensis*); Rhizobiales (*Brucella melitensis*); Burkholderiales (*Bordetella pertussis, Burkholderia mallei, B. pseudomallei*); Neisseriales (*Neisseria gonorrhoeae, N. meningitides*); Campylobacterales (*Campylobacter jejuni, Helicobacter pylori*); Legionellales (*Legionella pneumophila*); Pseudomonadales (*A. baumannii, Moraxella catarrhalis, P. aeruginosa*); Aeromonadales (*Aeromonas* sp.); Vibrionales (*Vibrio cholerae, V. parahaemolyticus*); Thiotrichales; Pasteurellales (*Haemophilus influenza*); and Enterobacteriales (*Klebsiella pneumoniae, Proteus mirabilis, Yersinia pestis, Y. enterocolitica, Shigella flexneri, Salmonella enterica, E. coli*). Alternatively, or in addition to the aforementioned pathogenic bacterial orders, pathogen viruses may be selected from species or strains found at 2 or more phylogenic groups or orders (with example sub-orders/species): Single-Stranded DNA Viruses (Parvoviridae); Double-Stranded DNA Viruses (Papillomaviridae, Polyomaviridae, Poxyiridae, Herpesviridae); Astroviridae (Human astrovirus); Coronaviridae (SARS coronavirus); Caliciviridae (Norwalk virus); Togaviridae (Rubivirus: Rubella virus; Alphavirus: Chikungunya virus, O'nyong-nyong virus, Ross River virus, Eastern equine encephalitis virus, Western equine encephalitis virus, Venezuelan equine encephalitis virus); Flaviviridae (Hepacivirus: Hepatitis C virus; Flavivirus: Dengue virus, Japanese encephalitis virus, St. Louis encephalitis virus, West Nile virus, Kyasanur forest disease virus, Yellow fever virus); Picornaviridae (Hepatovirus: Hepatitis A virus; Rhinovirus: Human rhinovirus A-B; Enterovirus: Human enterovirus A-D, Human poliovirus 1-3); Reoviridae (Rotavirus: Rotavirus A-C; Coltivirus: Colorado tick fever virus; Seadornavirus: Banna virus); Retroviridae (Deltaretrovirus: Human T-lymphotropic virus 1-2; Lentivirus: HIV 1-2); and Hepadnaviridae (Orthohepadnavirus: Hepatitis B virus).

For example, a library of the present invention may comprise or consist of genomic DNA fragments from two or more different pathogenic bacterial species or cDNA fragments produced from RNA expressed thereby, wherein the pathogenic bacterial species are selected from the following species: *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtheriae, Enterococcus faecalis, Enterococcus faecium*, Enterotoxigenic *Escherichia coli* (ETEC), Enteropathogenic *E. coli, Francisella tularensis, Haemophilus influenzae, Helicobacter pylori, Legionella pneumophila, Leptospira interrogans, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Streptococcal pharyngitis, Treponema pallidum, Vibrio cholerae*, and *Yersinia pestis.*

Alternatively, or in addition to the aforementioned pathogenic bacterial species, a library of the present invention may comprise or consist of genomic DNA fragments from two or more different pathogenic viruses or cDNA fragments produced from RNA expressed thereby, wherein the pathogenic viruses are selected from the following: Parvovirus B19, Rhinoviruses, Coxsackieviruses, Echoviruses, Hantaviruses, Togaviruses, Reoviruses, Adenoviruses, Orthomyxoviruses, Coronaviruses, Morbilliviruses, Varicella-zoster virus, Arenaviruses, Filoviruses such as Marburg virus, Parainfluenza viruses, Respiratory Syncytial Virus, Poxviruses such as Variola virus and Vaccinia viruses, Monkeypox virus, and Paramyxoviruses.

In another example, the libraries of the invention may comprise or consist of genomic DNA fragments and/or cDNA fragments obtained from 2 or more pathogenic organisms that can cross the blood brain barrier. The identity of such pathogens will be known to the person of ordinary skill, and include those described in Kim 2008 (*Nat Rev Microbiol* 6: 625-634). In one such example, the libraries of the invention may comprise or consist of genomic DNA fragments and/or cDNA fragments obtained from 2 or more organisms selected from the list consisting of: *Escherichia coli, Listeria monocytogenes, Neisseria meningitides, Streptococcus pneumonia, Streptococcus agalactiae, Haemophilus influenza, Mycobacterium influenza, Crytpococcus neoformans* (a eukaryotic yeast) and *Plasmodium falciparum* (a eukaryotic protozoa).

Exemplary libraries are phage display libraries or virus display libraries. Preferably, each candidate CPP is displayed on a different phage or virus particle of such a library.

Especially preferred libraries of the present invention are enriched for CPPs, for example to increase the probability of obtaining a functional CPP relative to conventional libraries. Other preferred libraries may comprise peptides that are derived from a peptide having CPP functionality e.g., products of mutagenesis or affinity maturation, or nucleic acid encoding such derivatives. Such mutagenic or affinity matured libraries permit selection of CPPs having modified cell-type selectivity, or enhanced activity or affinity for particular cells or cell types relative to the base peptide from which they are derived. A clear benefit of selected libraries comprising CPP peptides or derivatives thereof is that the peptides have, to some extent already been selected for CPP functionality. A negative selection may not be required for screening such libraries.

The libraries of the present invention are preferably Phylomer libraries (for example as described in U.S. Pat. No. 7,270,969 the contents of which are incorporated herein by reference in their entirety. Exemplary Phylomer libraries are capable of expressing or displaying peptides that assume conformations sufficient for CPP functionality e.g., binding and/or penetration of a cell, wherein the libraries comprise nucleic acid fragments of genomic DNA from viruses and/or prokaryotes and/or eukaryotes having compact genomes that are substantially sequenced, such as from two or more different species or isolates of such organisms In using such libraries, the candidate CPPs are generally encoded by portions of open reading frames of the genomic DNA comprised within the nucleic acid fragments, wherein said open reading frames encode polypeptides having sequences that are known to be expressed in the virus, prokaryote or eukaryote. Alternatively, the candidate CPPs are encoded by nucleic acid fragments that do not encode polypeptides having sequences that are known to be expressed in the virus, prokaryote or eukaryote.

Exemplary libraries of the present invention may consist essentially of genomic DNA fragments and/or cDNA fragments of pathogenic organisms, such as pathogenic bacteria and viruses, such as do not comprise genomic DNA fragments or cDNA fragments from bacteria and viruses that are not pathogenic to a second organism, including humans.

In preferred examples, the library may comprise genomic DNA fragments and/or cDNA fragments of open reading frames encoding bacterial and/or viral virulence factors, such as may consist essentially of such genomic DNA fragments and/or cDNA fragments and/or do not comprise genomic DNA fragments or cDNA fragments from bacteria or viruses that are not pathogenic to a second organism, including humans.

Alternatively, or in addition, the library comprises genomic DNA or cDNA fragments of open reading frames encoding ATP-binding cassette (ABC) transporter proteins or domains thereof. Alternatively, or in addition, the library comprises genomic DNA or cDNA fragments' of open reading frames encoding bacterial ATP-binding cassette (ABC) transporter proteins or domains thereof. Alternatively, or in addition, the library comprises genomic DNA or cDNA fragments of open reading frames encoding bacterial anti-sigma factors. Alternatively, or in addition, the library comprises genomic DNA or cDNA fragments of open reading frames encoding CALX-cadherin motifs. Alternatively, or in addition, the library comprises genomic DNA or cDNA fragments of open reading frames encoding taxis sensor proteins. Alternatively, or in addition, the library comprises genomic DNA or cDNA fragments of open reading frames encoding lipoproteins. Alternatively, or in addition, the library comprises genomic DNA or cDNA fragments of open reading frames encoding neurotransmitter:sodium symporter (NSS) family proteins. Alternatively, or in addition, the library comprises genomic DNA or cDNA fragments of open reading frames encoding phage-related DNA packing proteins. Alternatively, or in addition, the library comprises genomic DNA or cDNA fragments of open reading frames encoding membrane anchor proteins such as succinate dehydrogenases. Alternatively, or in addition, the library comprises genomic DNA or cDNA fragments of open reading frames encoding to serine-rich adhesion proteins or bacterial proteins having homology thereto. Alternatively, or in addition, the library comprises genomic DNA or cDNA fragments of open reading frames encoding gp41 proteins or viral or bacterial proteins having homology thereto. Alternatively, or in addition, the library comprises genomic DNA or cDNA fragments of open reading frames encoding transposases. Alternatively, or in addition, the library comprises genomic DNA or cDNA fragments of open reading frames encoding permeases. Alternatively, or in addition, the library comprises genomic DNA or cDNA fragments of open reading frames encoding fibronectin-binding proteins.

As an alternative to phage or virus display or in vitro display, the libraries of the invention may display candidate CPPs on a solid matrix comprising polymeric pins wherein each pin displays a different candidate CPP, or displays different pools or mixtures of candidate CPPs.

A particularly preferred example of the present invention provides a library comprising peptides or nucleic acid encoding same, wherein the peptides are selected from peptides comprising one or more of the amino acid sequences set forth in SEQ ID NOs: 1-27 selected or grouped according to any example hereof, and/or derivatives and/or analogs thereof. Preferably the library comprises at least about 10% or 20% or 30% or 40% or 50% or 60% or 70% or 80% or 90% of said SEQ ID NOs and/or derivatives and/or analogs thereof.

In yet another example, the present invention provides for use of a library according to any example hereof in a method or process to determine, identify or isolate a cell-penetrating peptide (CPP) from candidate CPPs, wherein the candidate CPPs are expressed by said, library, such as to determine, identify or isolate a CPP having cell-type selectivity.

For example, the present invention provides a method of identifying a peptide having cell-penetrating activity (a cell penetrating peptide (CPP)), said method comprising:
(i) providing a peptide from or comprised in a library according to any example hereof;
(ii) contacting the peptide with a cell for a time and under conditions sufficient for a peptide to adhere to or penetrate the cell; and
(iii) detecting cell-penetration activity of the peptide bound to the cell at (ii) or internalized within the cell at (ii), thereby identifying said detected peptide as a cell-penetrating peptide (CPP).

In particular examples, such process further comprises:
(A) after (i) and before (ii), performing n iterations of a method comprising: (a) contacting a candidate said peptide with a cell of a predetermined cell-type different to the cell-type in (ii) in suitable medium for a time and under conditions sufficient for a peptide to adhere to or penetrate the cell, and (b) separating the cell from the medium, wherein n is an integer having a value equal to or greater than 1; and (B) using peptide comprised in the separated medium of (A) in (ii).

In yet another example, the present invention provides a method for enriching, purifying or depleting a cellular receptor involved in cell penetration from a pool of proteins comprising at least one cellular receptor involved in cell penetration, said method comprising:
(i) immobilizing at least one cell-penetrating peptide or analog and/or derivative thereof according to any example hereof or at least one conjugate according to any example hereof on a support;
(ii) contacting the support with a pool of proteins comprising at least one cellular receptor involved in cell penetration for a time and under conditions sufficient for a cellular receptor involved in cell penetration to bind to an immobilized cell-penetrating peptide or analog and/or derivative thereof, said binding indicating that the bound protein is a cellular receptor involved in cell penetration; and
(iii) separating proteins not bound to an immobilized cell-penetrating peptide or analog and/or derivative thereof from one or more proteins bound to an immobilized cell-penetrating peptide or analog and/or derivative thereof, thereby enriching, purifying or depleting a cellular receptor involved in cell penetration from the pool of proteins.

The method may further comprise releasing the one or more proteins bound to an immobilized cell-penetrating peptide or analog and/or derivative thereof, wherein the released protein is a cellular receptor involved in cell penetration.

The method may further comprise collecting the released protein cellular receptor involved in cell penetration.

The method may further comprise identifying or characterizing the released protein cellular receptor involved in cell penetration.

The present invention clearly extends to any isolated or substantially pure form of a cellular receptor involved in cell penetration: (i) when enriched, purified, collected, identified or characterized by performing this method according to any example hereof; and/or (ii) that binds to or is involved in cell penetration of at least one cell-penetrating peptide or analog or derivative described herein, and to any isolated nucleic acid encoding the isolated or substantially pure cellular receptor involved in cell penetration.

Throughout this specification, unless specifically stated otherwise or the context requires otherwise, reference to a single step, composition of matter, group of steps or group of compositions of matter shall be taken to encompass one and a plurality (e.g. one or more) of those steps, compositions of matter, groups of steps or group of compositions of matter Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and/or all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts:
1. Sambrook, Fritsch & Maniatis, whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactiva, Germany);
10. Sakakibara, D., Teichman, J., Lien, E. Land Fenichel, R. L. (1976). *Biochem. Biophys. Res. Commun.* 73, 336-342
11. Merrifield, R. B. (1963). *J. Am. Chem. Soc.* 85, 2149-2154.
12. Barany, G. and Merrifield, R. B. (1979) in *The Peptides* (Gross, E. and Meienhofer, J. eds.), vol. 2, pp. 1-284, Academic Press, New York.
13. Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart.
14. Bodanszky, M. (1984) *Principles of Peptide Synthesis*, Springer-Verlag, Heidelberg.
15. Bodanszky, M. & Bodanszky, A. (1984) *The Practice of Peptide Synthesis*, Springer-Verlag, Heidelberg.
16. Bodanszky, M. (1985) *Int. J. Peptide Protein Res.* 25, 449-474.
17. Handbook of Experimental Immunology, Vols. I-IV (D. M. Weir and C. C. Blackwell, eds., 1986, Blackwell Scientific Publications).
18. McPherson et al., *In: PCR A Practical Approach*., IRL Press, Oxford University Press, Oxford, United Kingdom, 1991.
19. Methods in Yeast Genetics: A Cold Spring Harbor Laboratory Course Manual (D. Burke et al., eds) Cold Spring Harbor Press, New York, 2000 (see whole of text).
20. Guide to Yeast Genetics and Molecular Biology. In Methods in Enzymology Series, Vol. 194 (C. Guthrie and G. R. Fink eds) Academic Press, London, 1991 2000 (see whole of text).

The present invention is described further in the following non-limiting examples, and/or as shown in the figures.

DETAILED DESCRIPTION OF THE PREFERRED EMBODIMENTS

1. Cell-Type Selectivity

Figure 1:
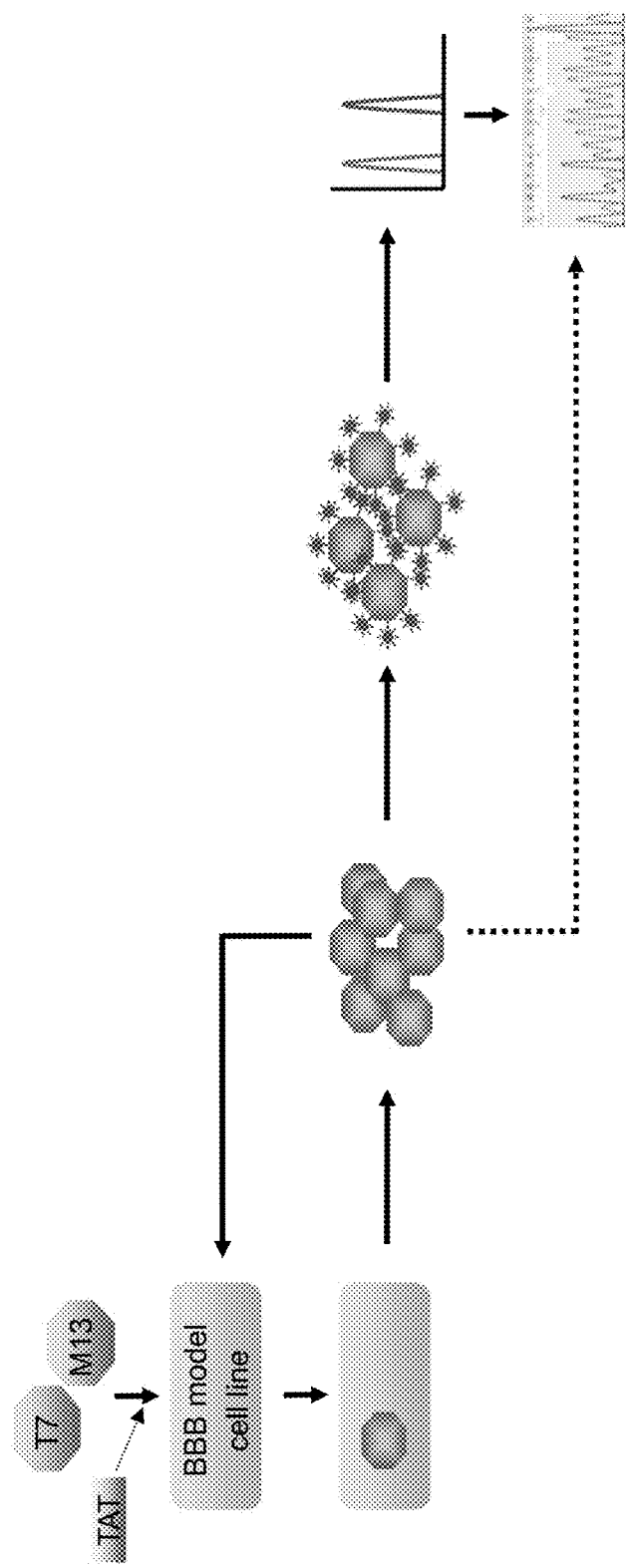
FIG. 1 provides a schematic representation one screening method of the invention for cell penetrating peptides from Phylomer libraries.
Figure 2:
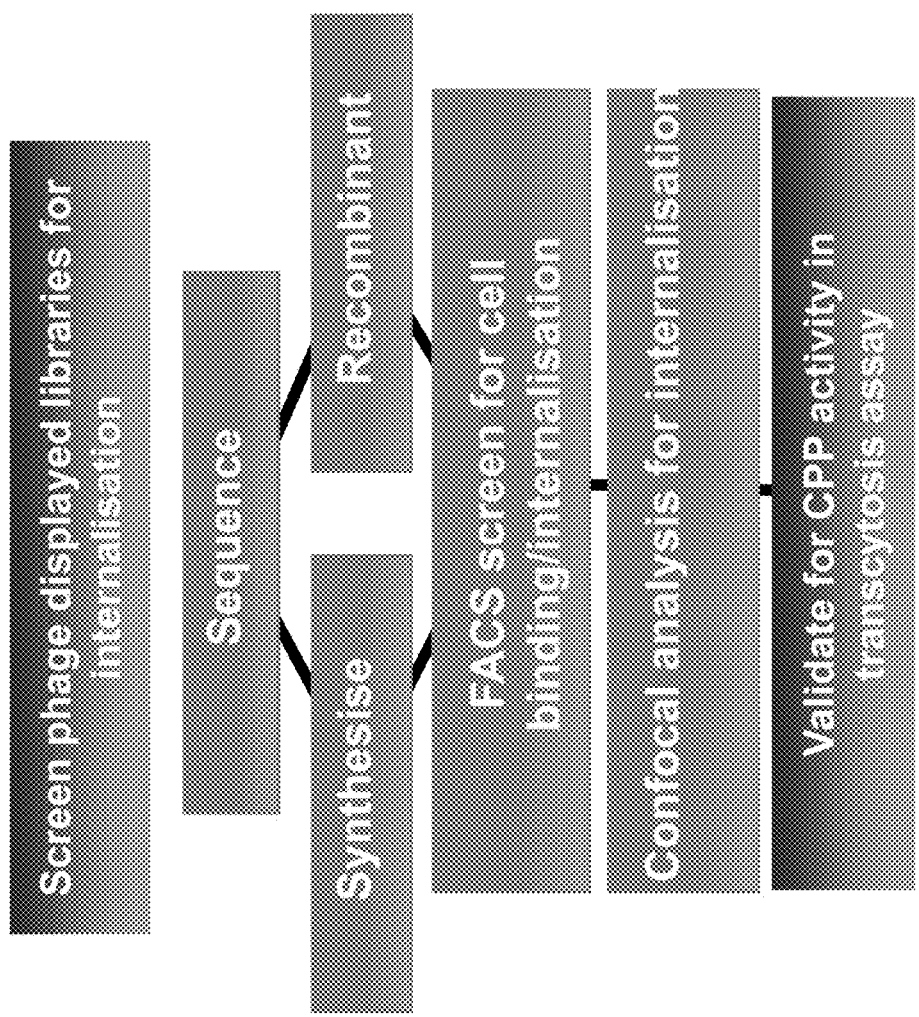
FIG. 2 is a schematic representation showing a workflow for screening cell penetrating peptides.
Figure 3:
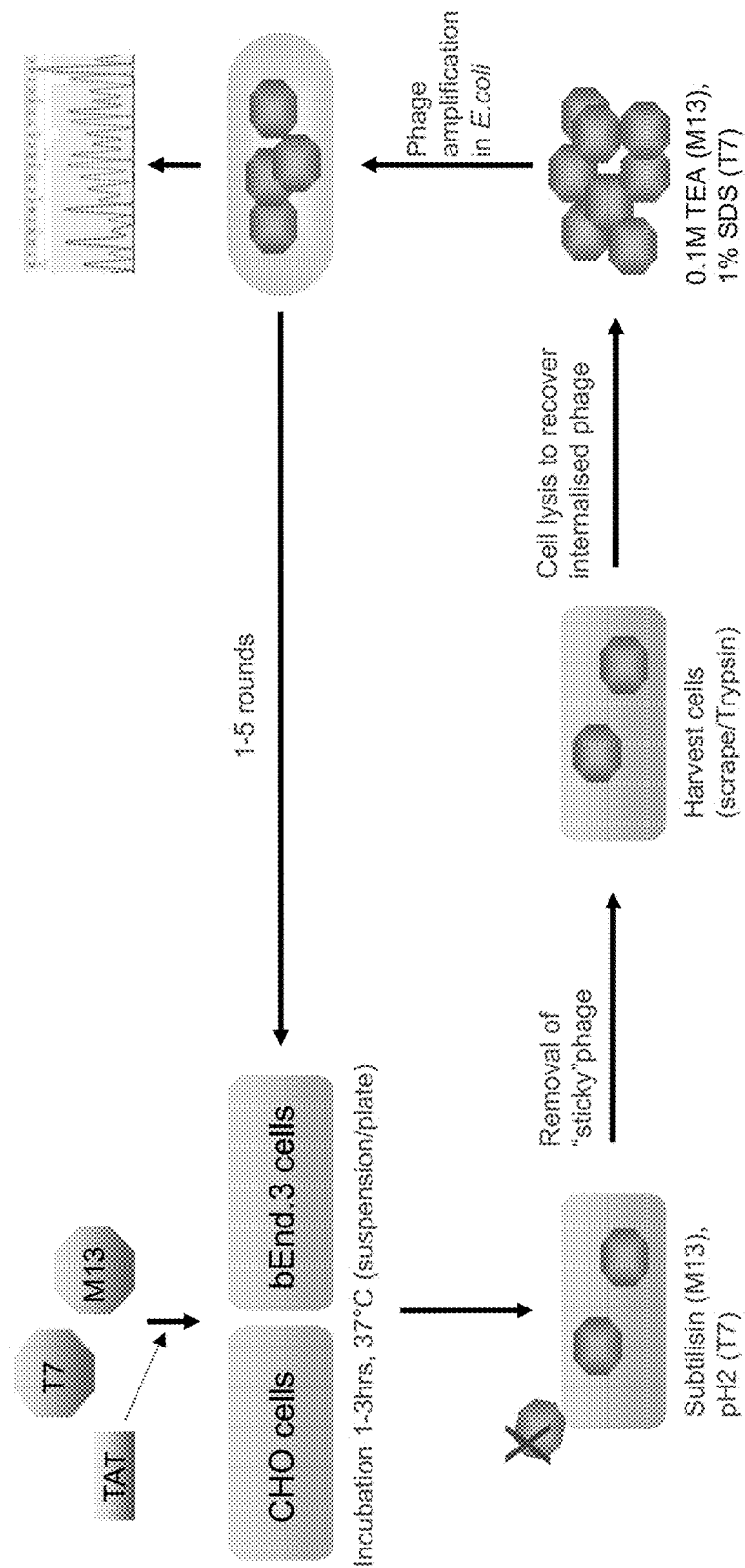
FIG. 3 provides a schematic representation showing one procedure for CPP selections according to the invention. Cells are incubated with various phage libraries before being treated to remove surface-bound phage, harvested and then lysed to release internalised phage. Recovered phage are amplified in *E. coli* and used as input for subsequent rounds of selection. PCR and sequence analysis is performed after every round.
Figure 4:
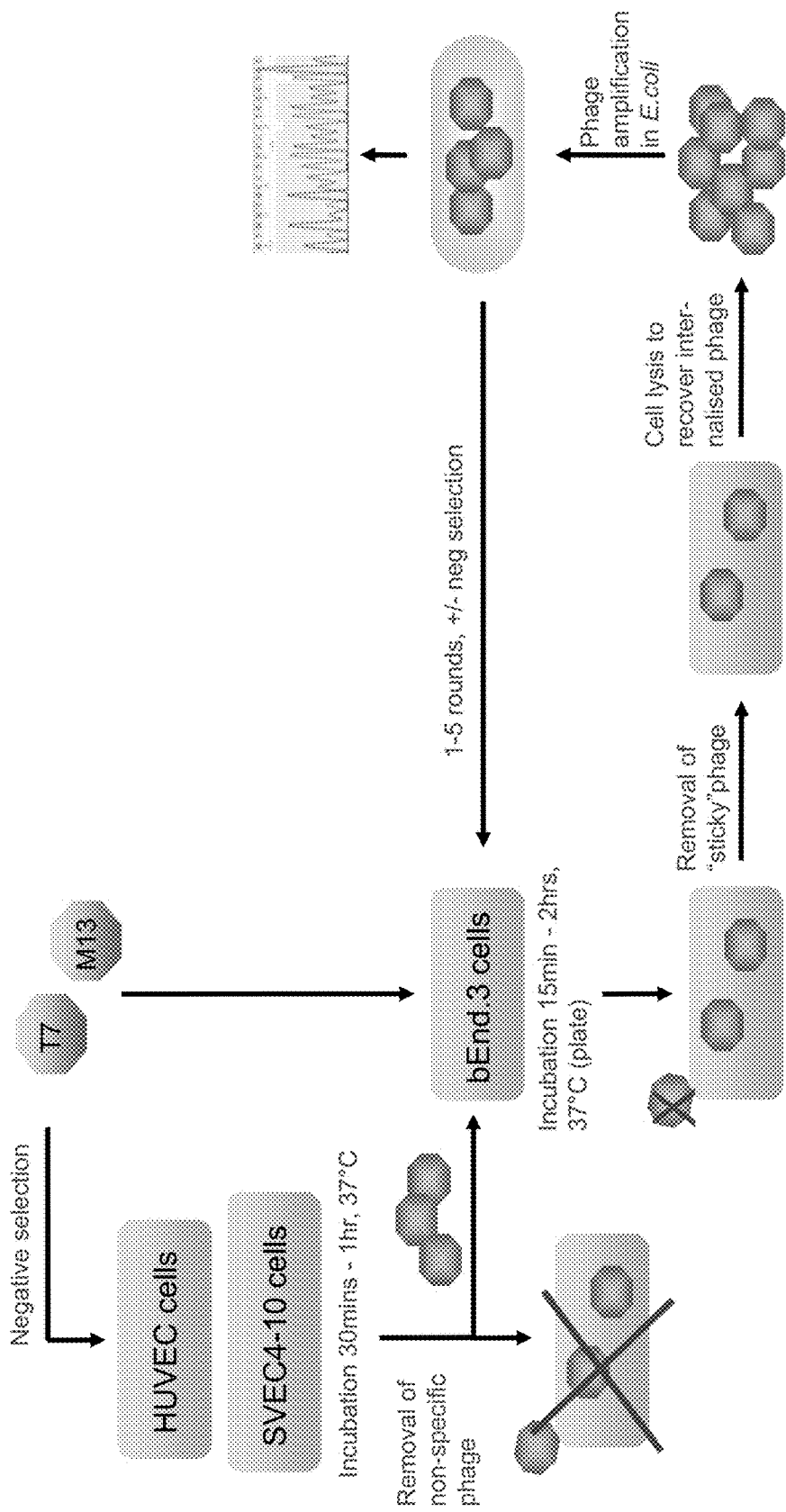
FIG. 4 provides a schematic representation showing another procedure for CPP selections according to the invention. An additional negative selection step is introduced to minimise non-specific phage binding to mammalian cells. After selection against bEnd.3 surface-bound phage is removed, cells harvested and lysed. The recovered internalised phage are amplified in *E. coli* and used as input for further rounds of selections. PCR and sequence analysis is performed after every round.
Figure 5:
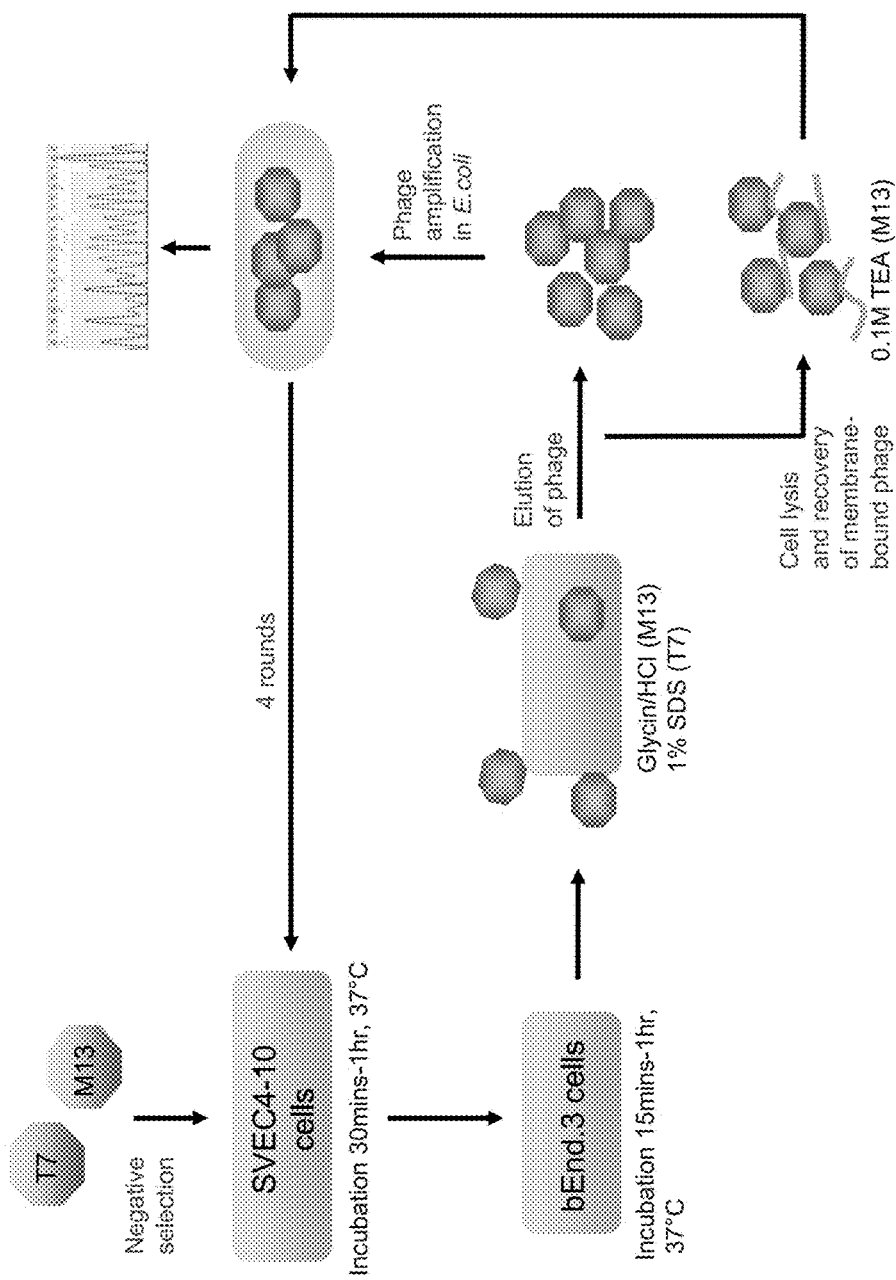
FIG. 5 provides a schematic representation showing another procedure for CPP selections according to the invention. Negative selections using SVEC-10 cells are performed to eliminate peptides that recognise common receptors before positive (+ve) selection against bEnd.3 cells. Surface-bound M13 phage from each round are eluted with Glycine/HCl or T7 phage with 1% SDS and then analysed via PCR sequencing FIG. 6 provides a graphical representation showing a statistical summary of cell penetrating peptides and cell binding selections as conducted by the inventors.
Figure 7:
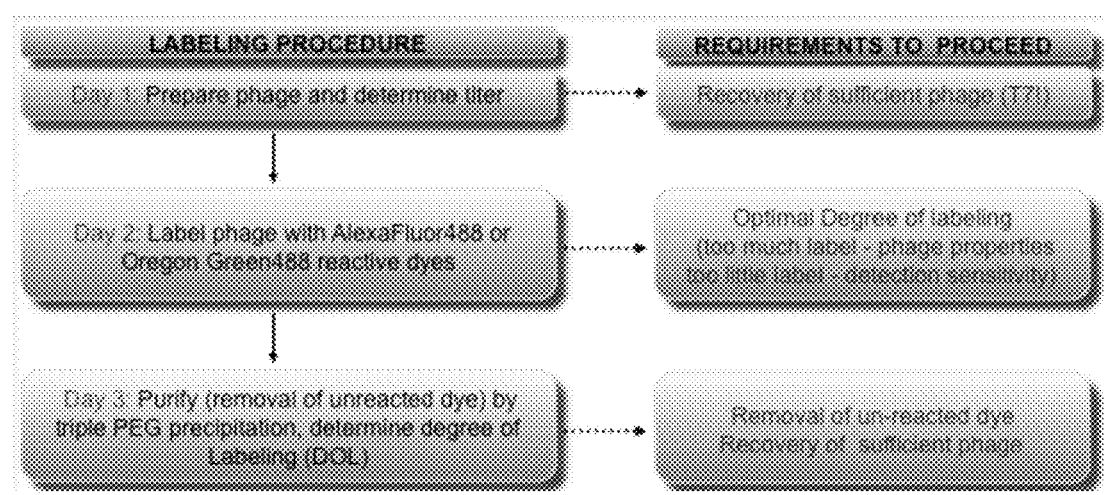
FIG. 7 provides a schematic representation showing a procedure for labelling T7 and M13 phage with either AlexaFluor 488® or Oregon Green® followed by purification by triple PEG precipitation.
Figure 8:
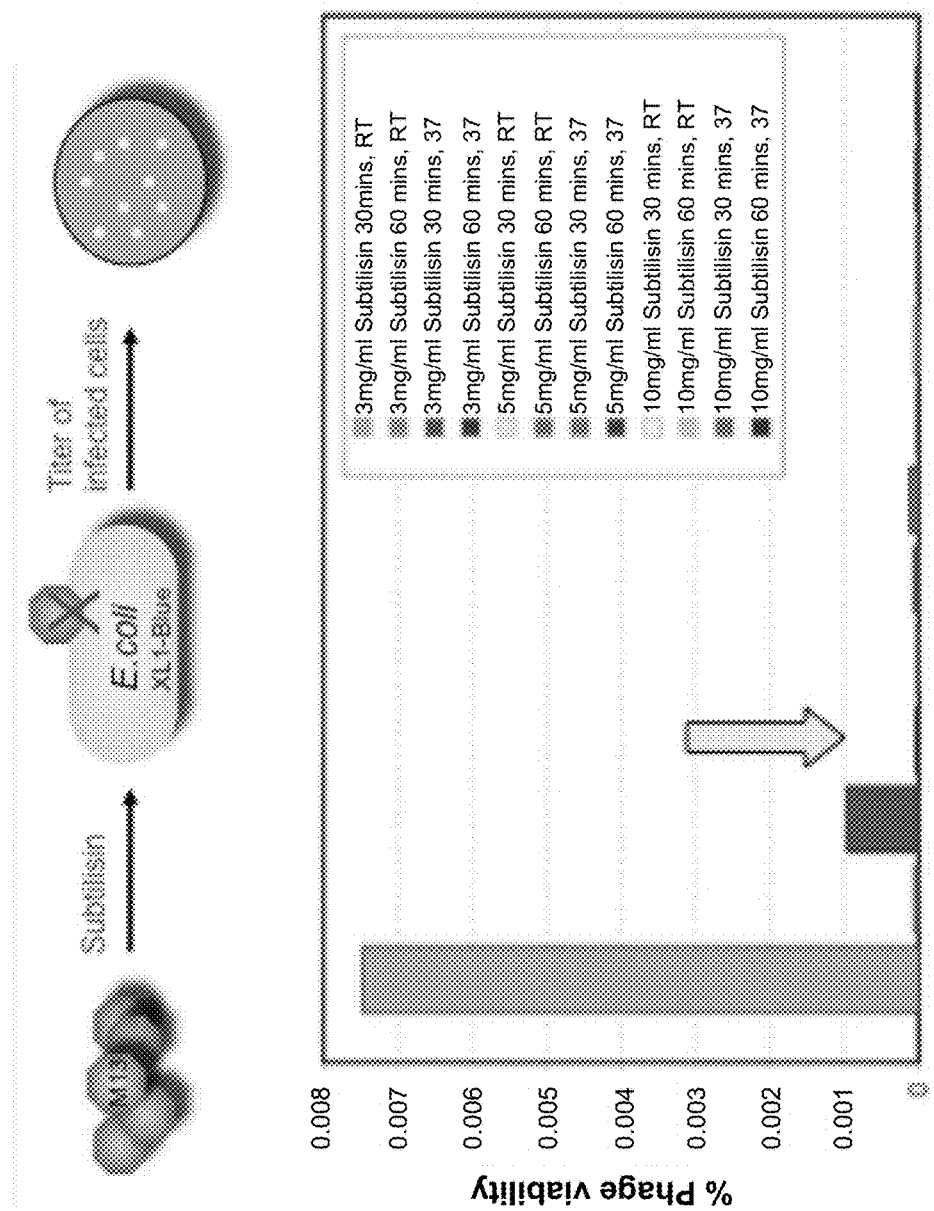
FIG. 8 provides a graphical representation showing the viability of M13 phage after incubation with various concentrations of subtilisin at room temperature or at 37° C. Viability was assessed via infection of *E. coli* and subsequent titration of plaques isolated from infected cells.
Figure 9:
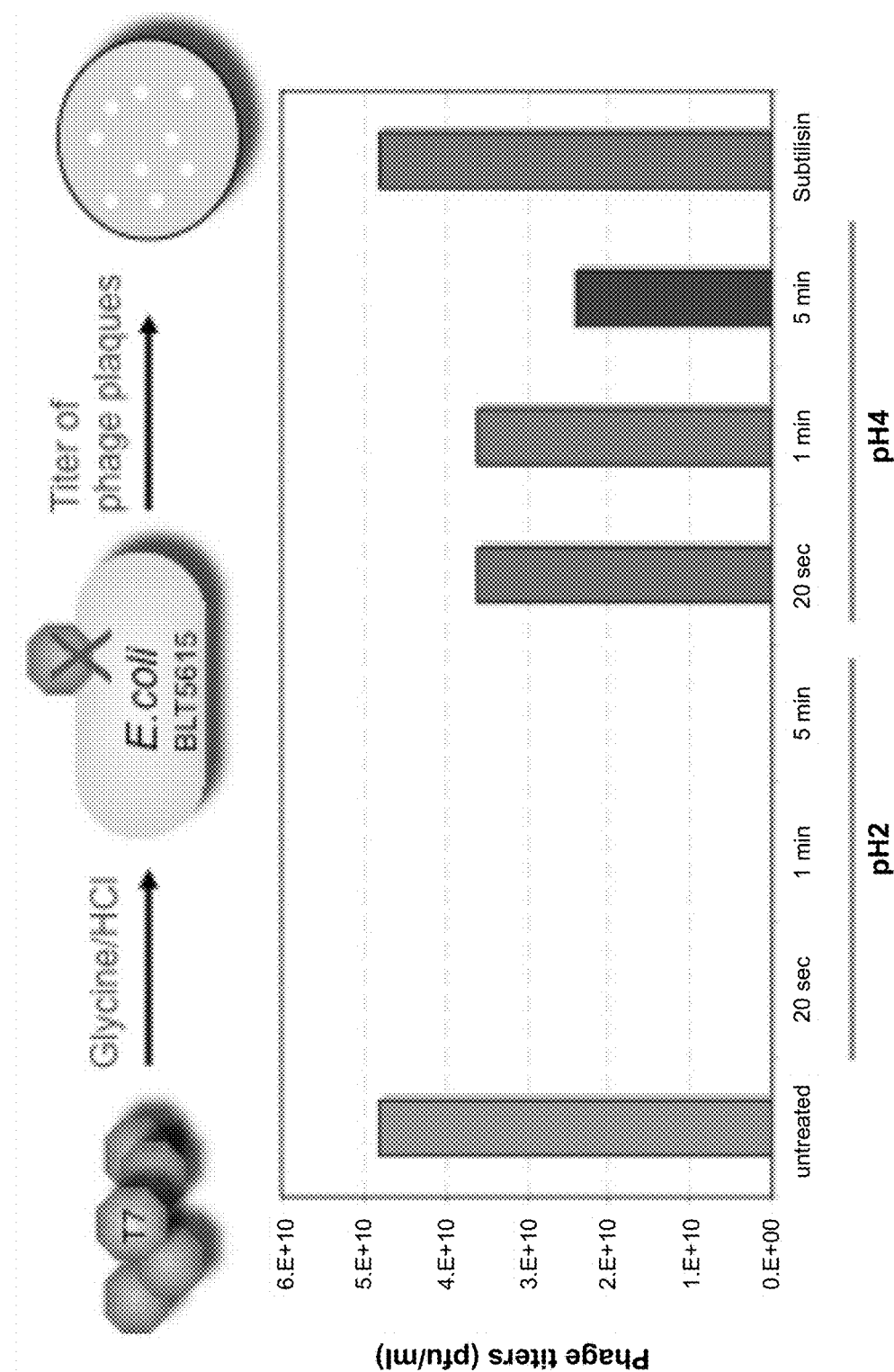
FIG. 9 provides a graphical representation showing the viability T7 phage after exposure to Glycine and HCl at pH 2 and pH 4 in PBS or RPMI medium for 20 seconds to 5 minutes. Viability was assessed via infection of *E. coli* and subsequent titration of plaques isolated from infected cells.
Figure 10:
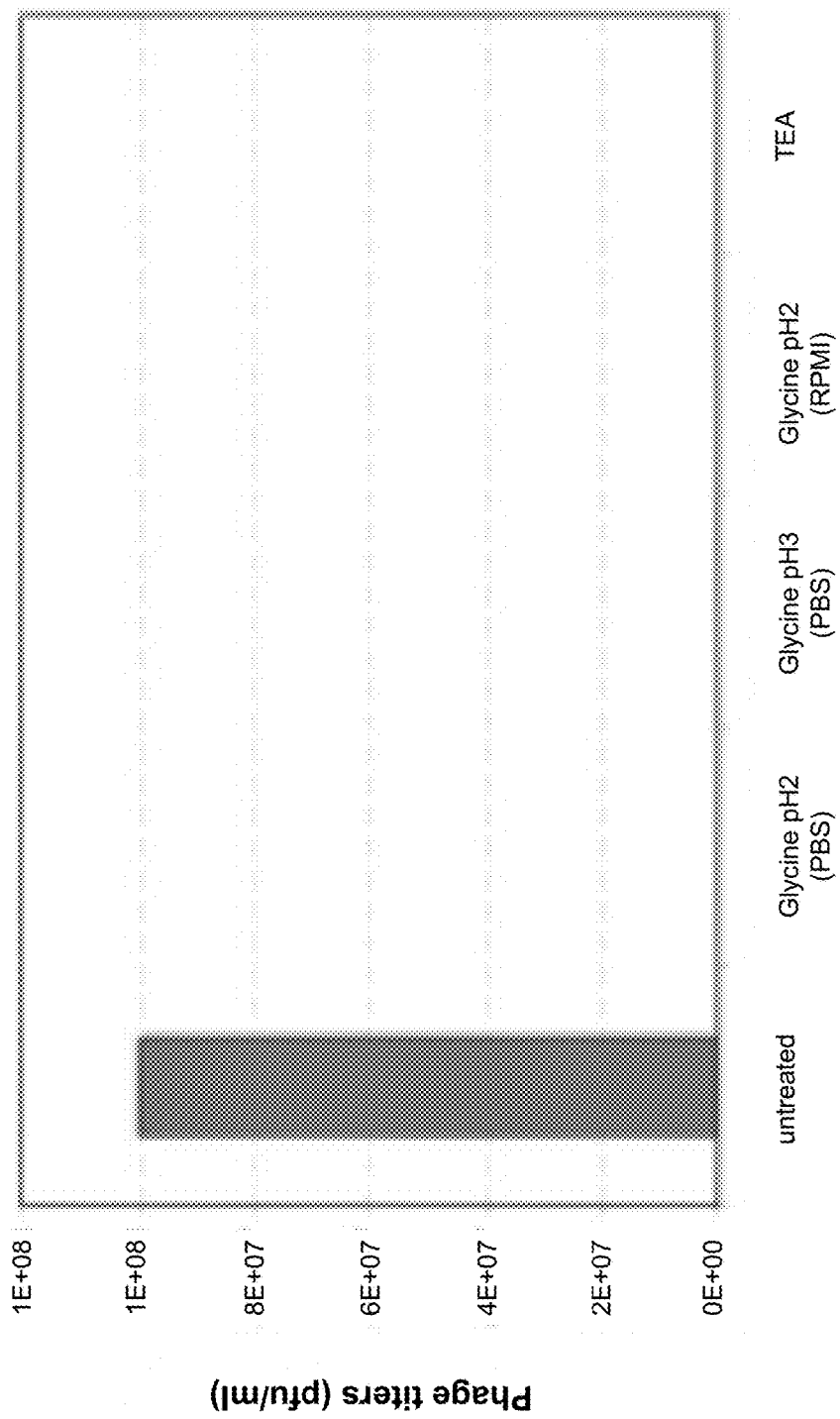
FIG. 10 provides a graphical representation showing the viability T7 phage after exposure to Glycine and HCl at pH 2 and pH 3 in PBS or RPMI medium for 10 seconds. Viability was assessed via infection of *E. coli* and subsequent titration of plaques isolated from infected cells.
Figure 11:
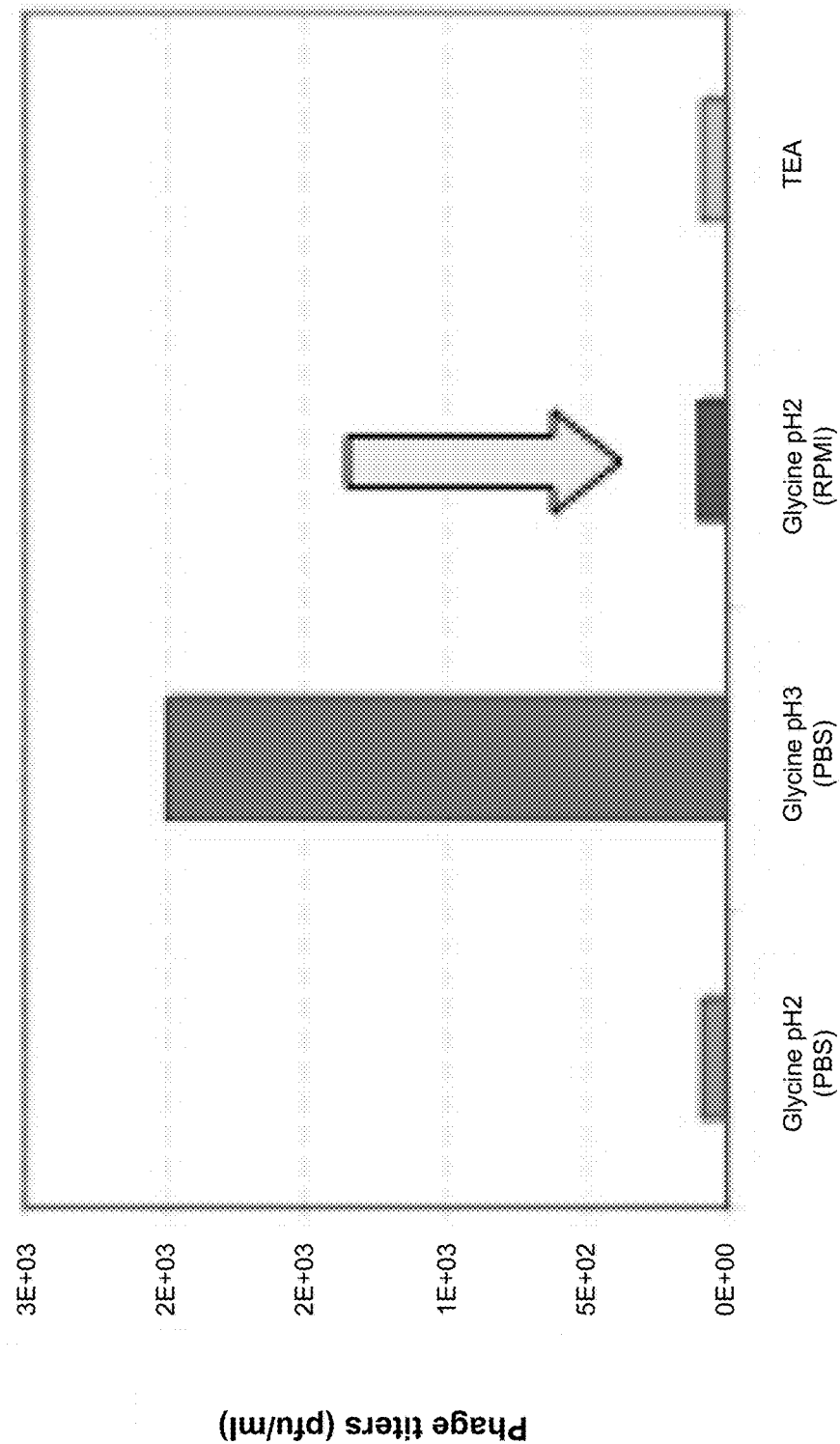
FIG. 11 provides a graphical representation showing the essentially the same data as the preceding figure, however the untreated control histogram shown in such figure has been removed and the scale of the y-axis has been adjusted by several orders of magnitude to properly display the differences between the remaining samples.
Figure 12:
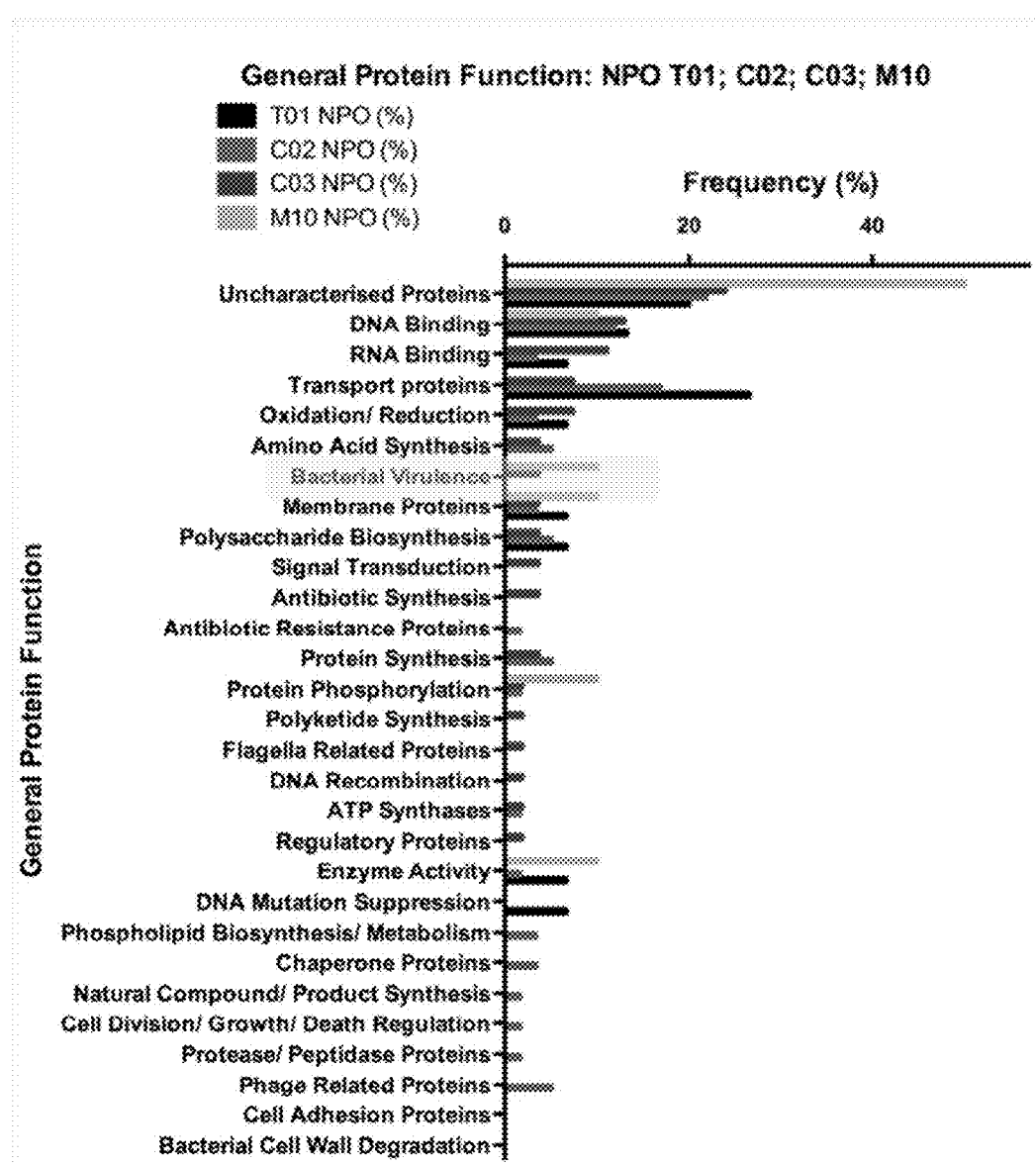
FIG. 12 provides a graphical representation showing the classification of naïve library sequences into functional protein categories. The column representing sequences from bacterial virulence factors has been highlighted.
Figure 13:
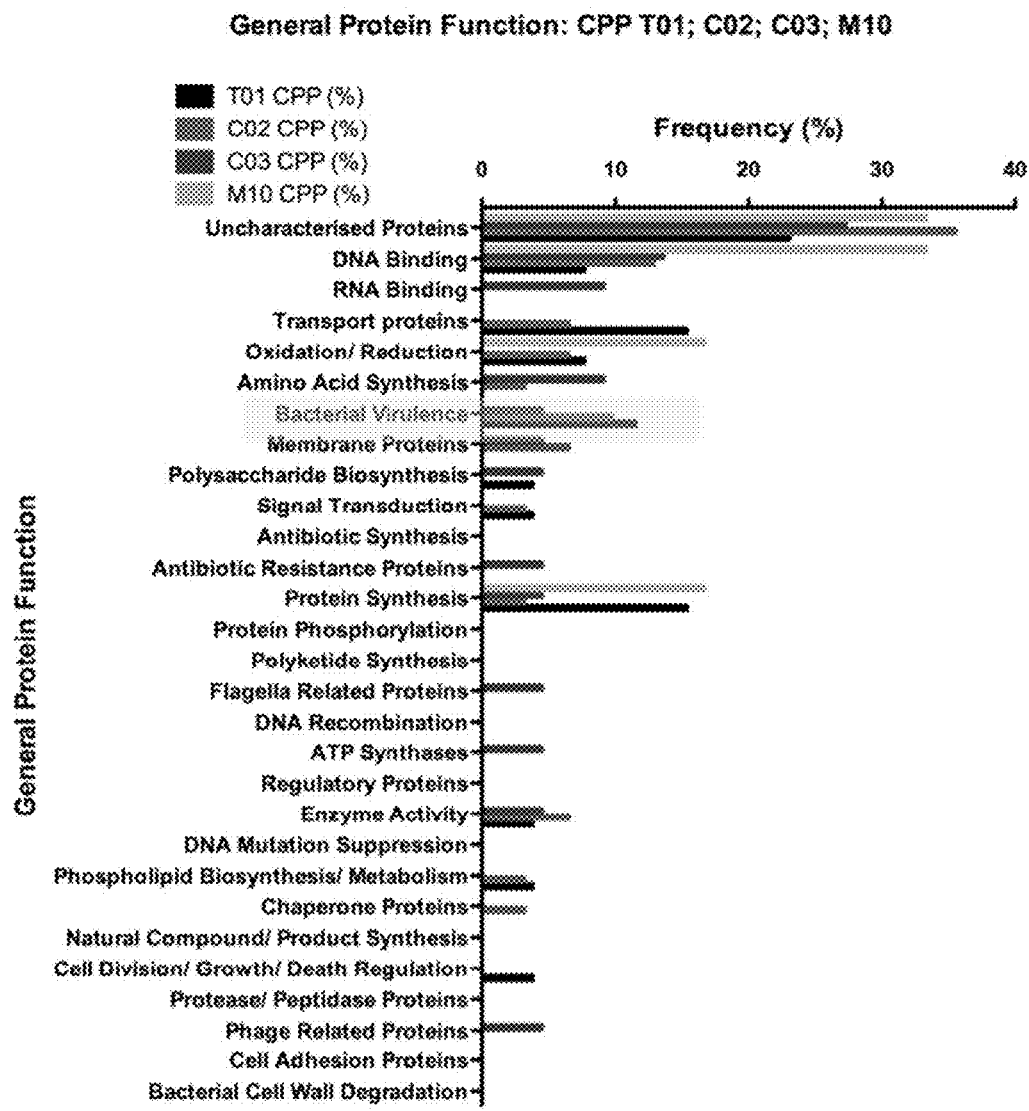
FIG. 13 provides a graphical representation showing the classification of CPPs identified from the screens conducted by the inventors into functional protein categories. The column representing sequences from bacterial virulence factors has been highlighted. Comparison to the corresponding column in the preceding figure shows that such sequences have been enriched following selection compared to the naïve libraries.
Figure 14:
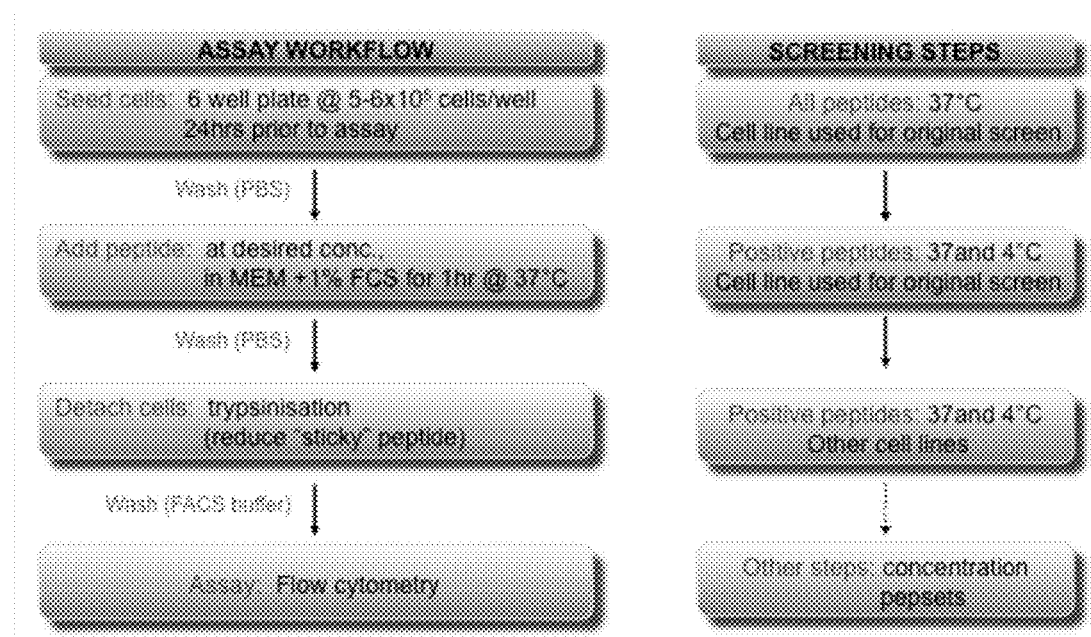
FIG. 14 provides a schematic representation showing a procedure for flow cytometry assessment of peptide cell binding/internalisation activity.
Figure 15:
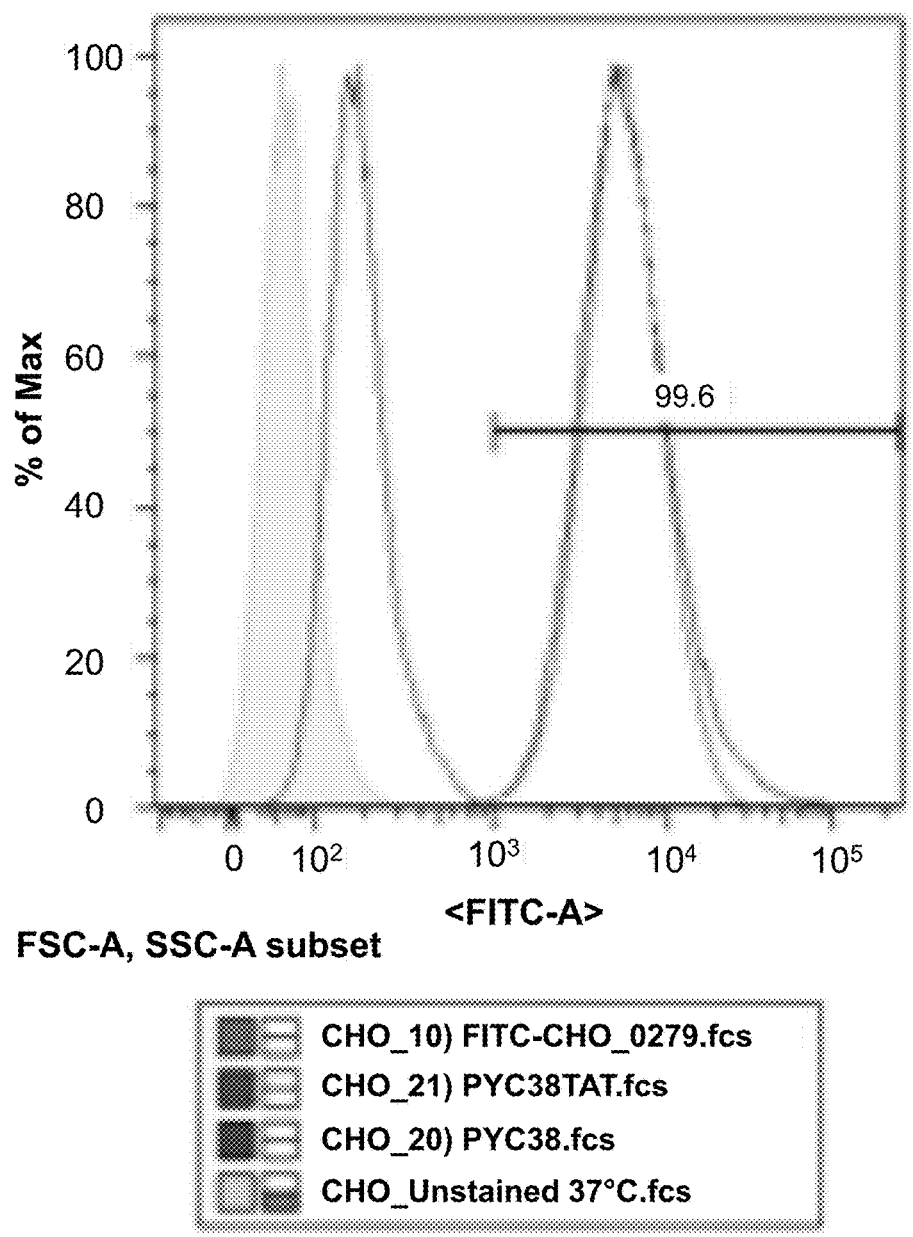
FIG. 15 provides a graphical representation showing the results of flow cytometry analysis of the uptake of 10 μM CPP identified by a method of the invention (SEQ ID NO: 1 [RFRCGRRKWQIGS], described herein as "CHO_0279" or "0279") into CHO-K1 cells compared to 10 μM PYC38 and 10 μM PYC38-TAT (as negative and positive controls, respectively) at 37° C. The curve for the CPP largely overlaps with that for the positive control. "PYC38" is a retro-inverso peptide having the sequence: rhaplarGswrGqpqqGpqrrGqlGG.
Figure 16:
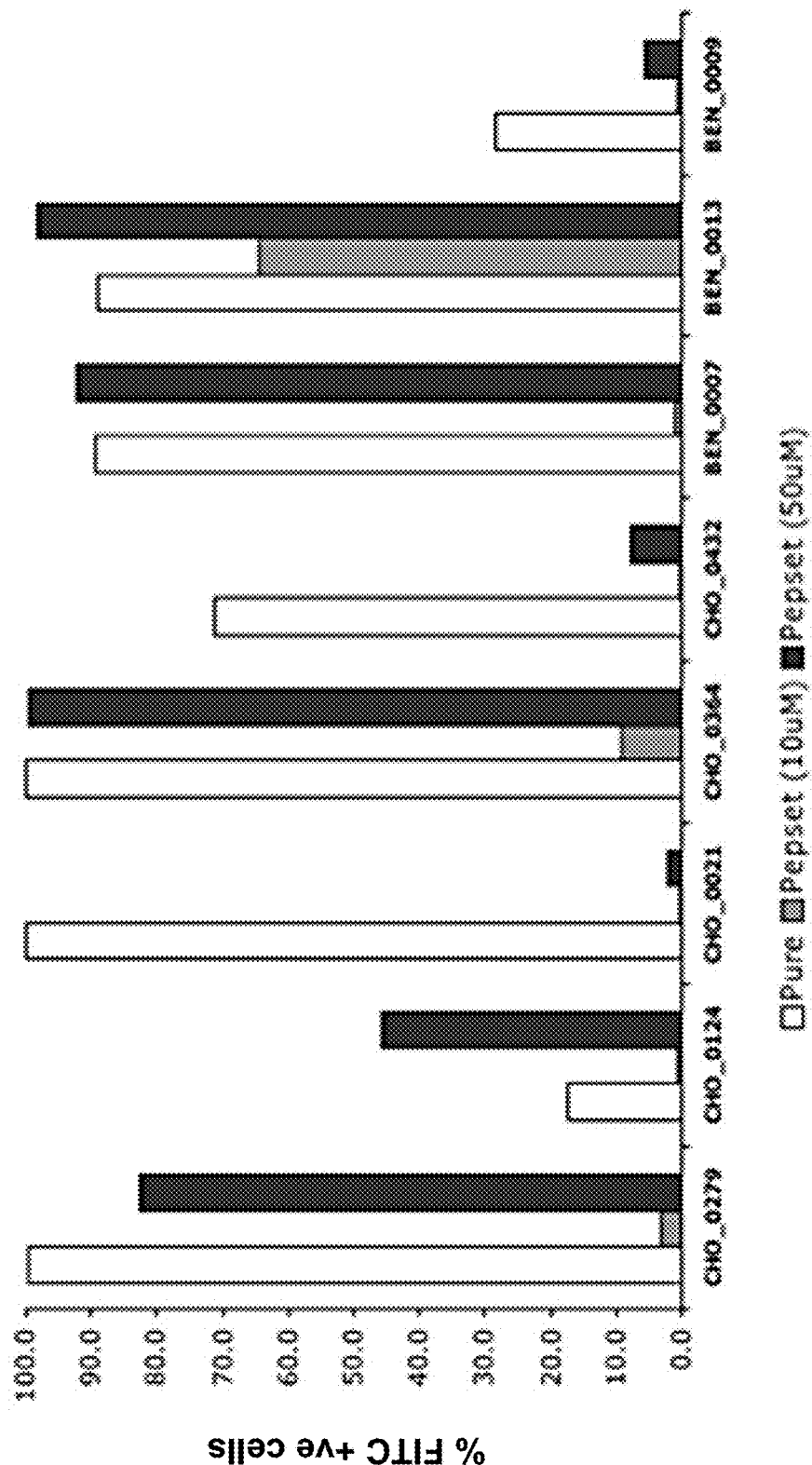
FIG. 16 provides a graphical representation showing the results of flow cytometry analysis of the uptake of 10 μM pure and crude ("PepSet" synthesis from Mimotopes) peptide preparations (including CPPs identified by a method of the invention) into CHO-K1 cells.
Figure 17:
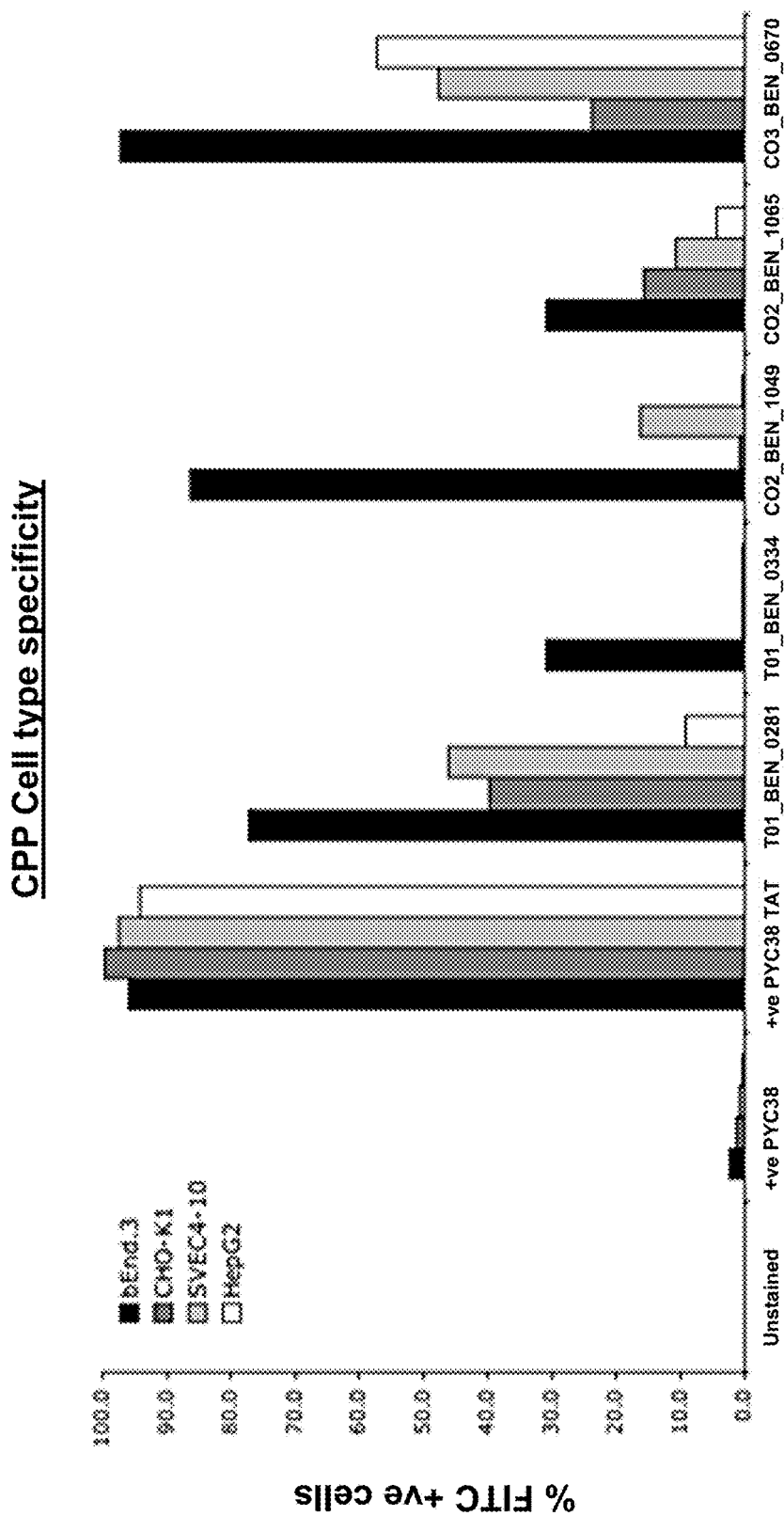
FIG. 17 provides a graphical representation showing the results of flow cytometry analysis of the uptake of CPPs identified by a method of the invention into bEnd.3, CHO-K1, SVEC4-10 and HepG2 cells at 37° C.
Figure 18:
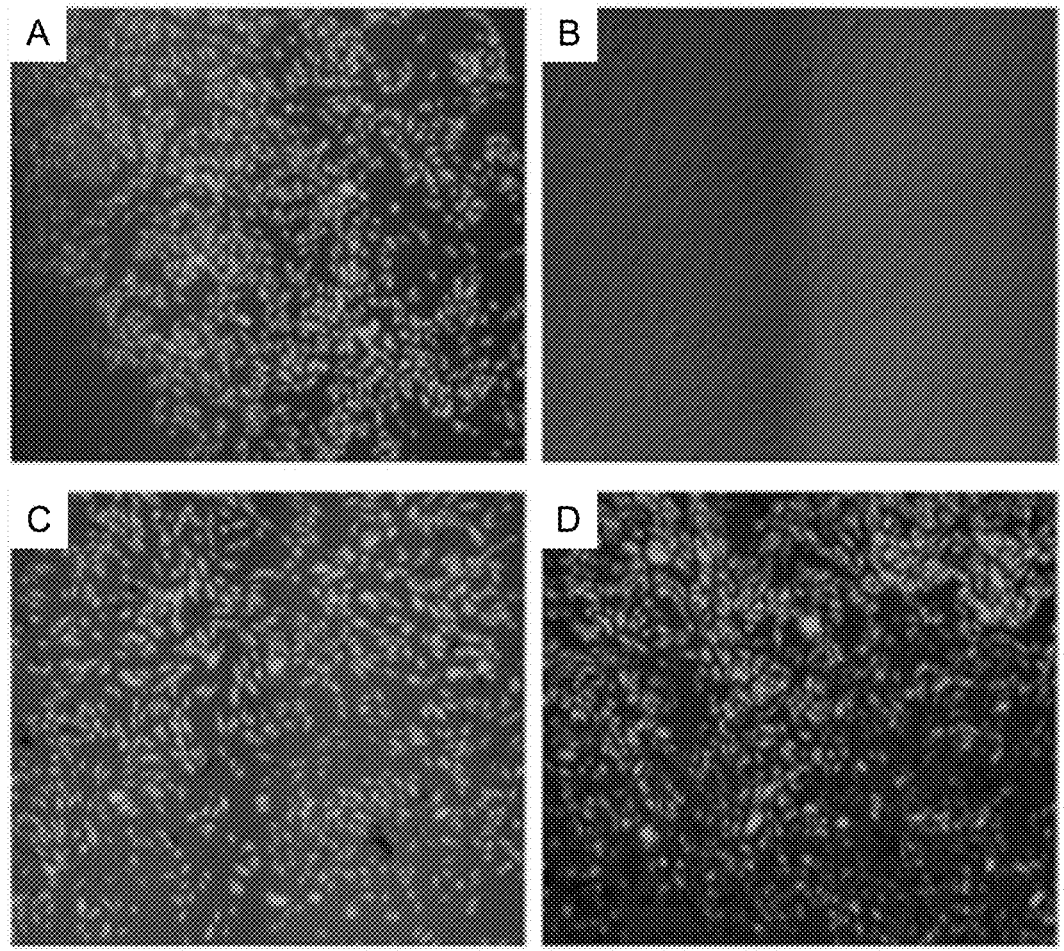
FIG. 18 provides photographic representation of confocal microscopy of CHO-K1 cells after incubation with FITC-labelled peptides. Panel A shows the uptake of FITC-D-PYC38TAT into CHO-K1 cells 60 minutes after incubation with 5 μM peptide. Panel B shows no detectable evidence of uptake of FITC-D-PYC38 into CHO-K1 cells 60 minutes after incubation with 5 μM of such peptide. Panel C shows evidence of the uptake of a CPP identified by a method of the invention (SEQ ID NO: 2 [WTISSRRRKVNRAC], described herein as "CHO_0364" or "0364") labelled with FITC into CHO-K1 cells 60 minutes after incubation with 10 μM of such peptide. Panel C shows the uptake of the same construct into CHO-K1 cells 60 minutes after incubation with 30 μM if such peptide.
Figure 19:
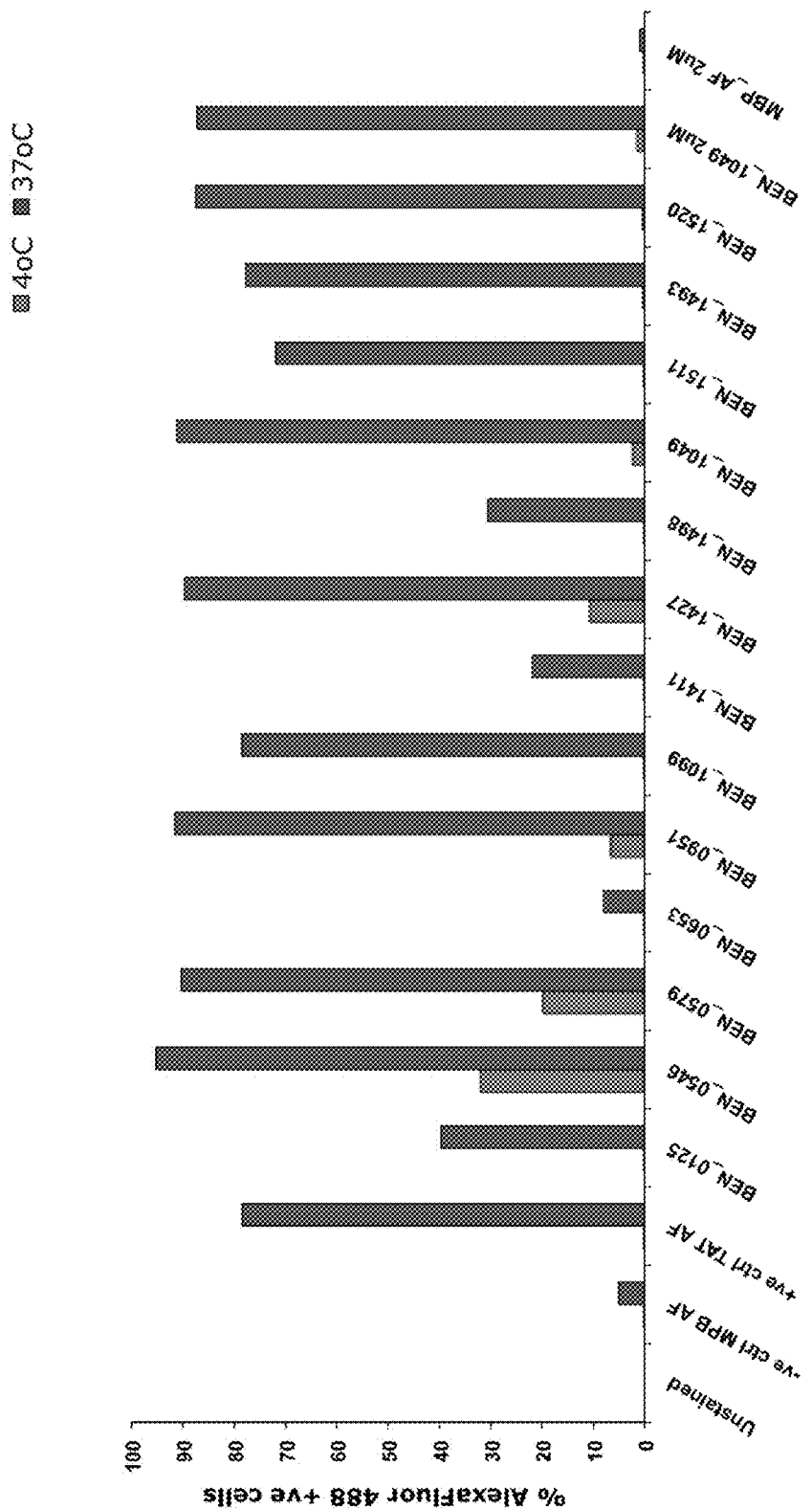
FIG. 19 provides a graphical representation showing the results of flow cytometry analysis of recombinant MBP-CPP fusion proteins (and controls) incubated with bEnd.3 cells at 5 μM (or 2 μM where noted) at 4° C. or 37° C.
Figure 20:
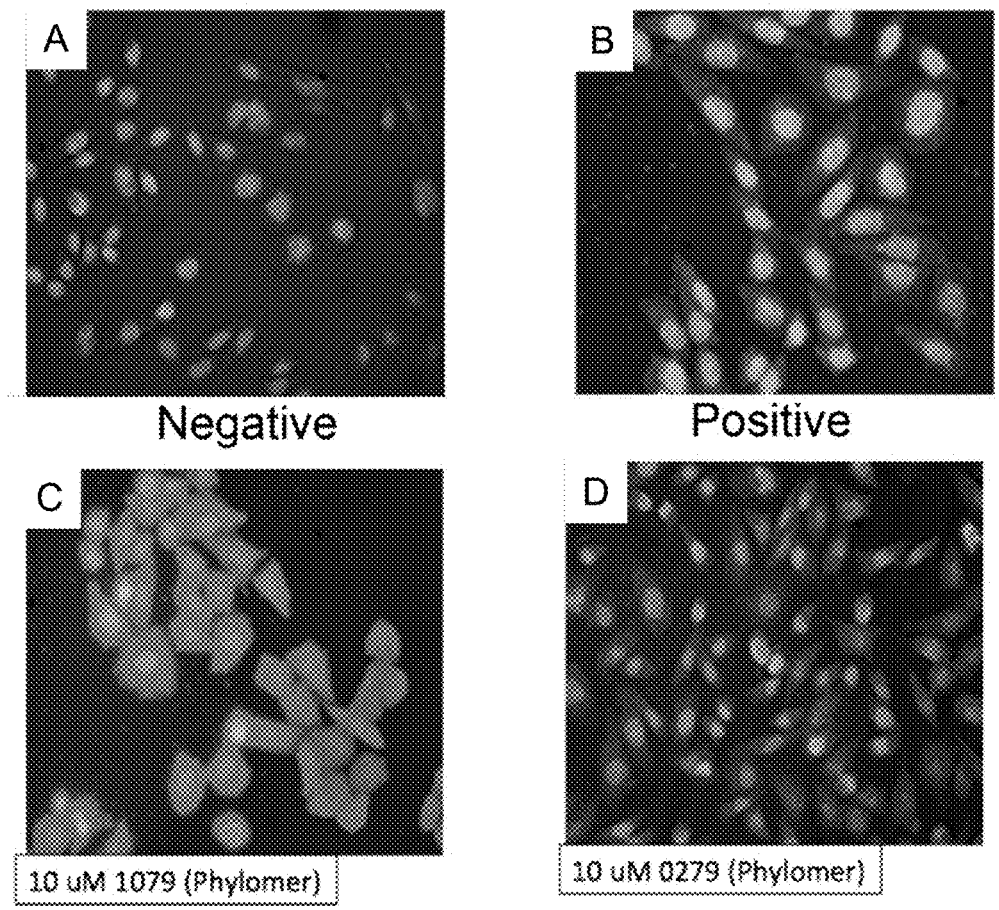
FIG. 20 provides photographic representation of confocal microscopy of cellular uptake of CPPs identified by a method of the invention. Panel A shows an exemplary result of negative cellular uptake using a negative control. Panel B shows an exemplary result of evidence for positive cellular uptake using a positive control. Panel C shows evidence for cellular uptake of CPP (Peptide ID: 9170; shown in the figure as "1079"; SEQ ID NO: 15) after incubation at 10 μM. Panel D shows evidence for cellular uptake of another CPP (SEQ ID No: 1 [RFRCGRRKWQIGS]) after incubation at 10 μM.
Figure 21:
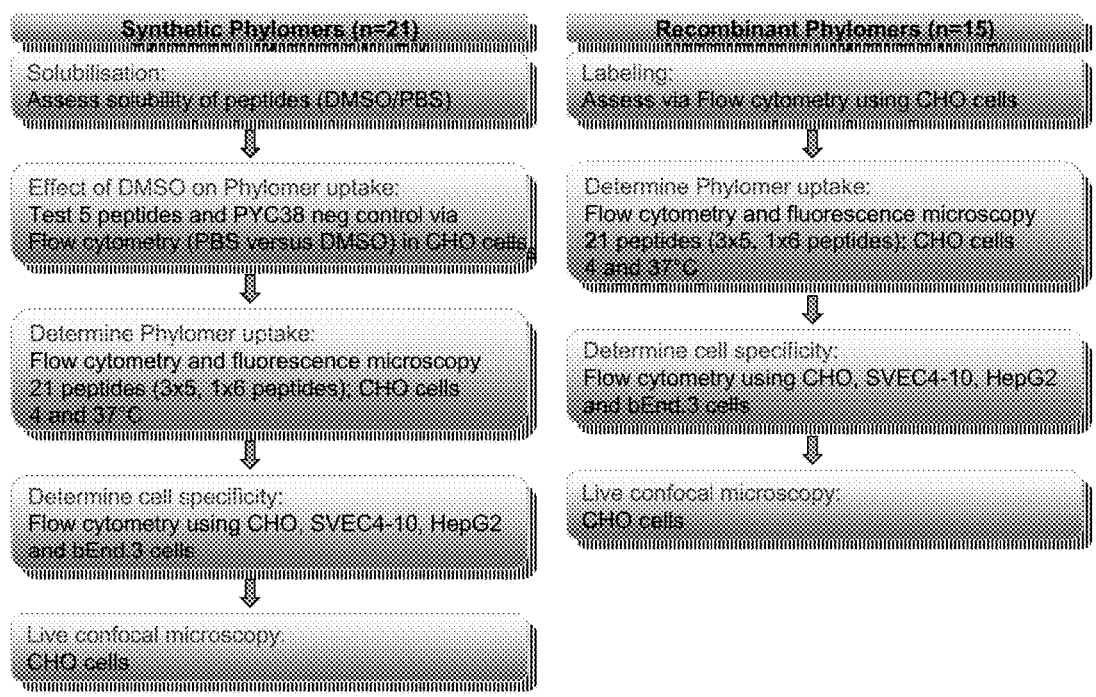
FIG. 21 provides a schematic representation showing the procedure for assessment of synthetic and recombinant CPPs.
Figure 22:
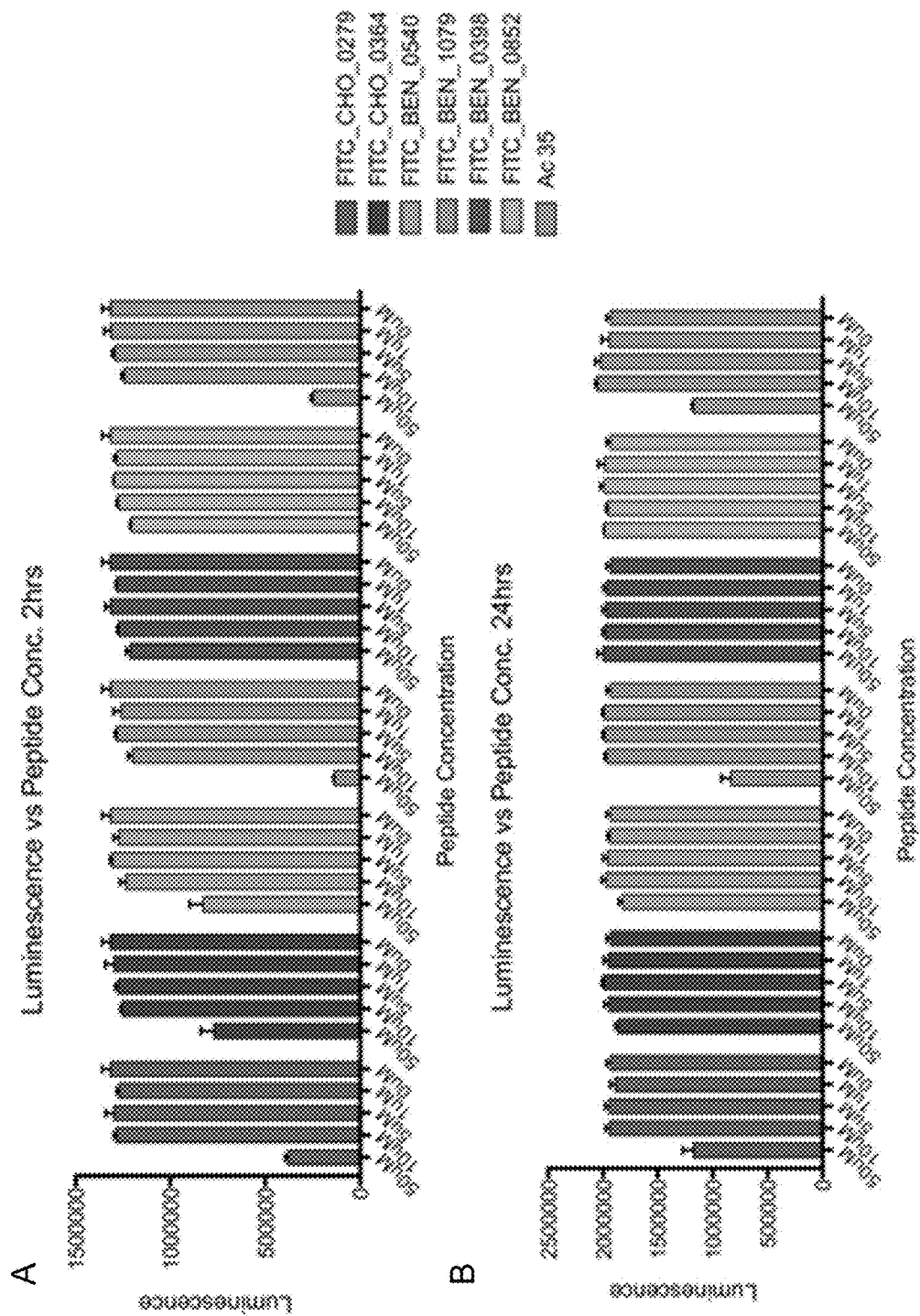
FIG. 22 provides a graphical representation showing the results of CellTiter-Glo viability assays assessing cytotoxicity of various CPPs identified by a method of the invention in CHO-K1 cells. Panel A shows the results for CPPs including Peptide IDs: 0045 (shown as FITC_BEN_0540 in the figure; SEQ ID NO: 14), 9170 (shown as FITC_BEN_1079 in the figure; SEQ ID NO: 15) and 8093 (shown as FITC_BEN_0398 in the figure; SEQ ID NO: 9), and for Ac35 as control, incubated with CHO-K1 cells for 2 hours at 0 μM, 1 μM, 5 μM, 10 μM and 50 μM. Panel B shows the results for the same peptides incubated with CHO-K1 cells for 24 hours at 0 μM, 1 μM, 5 μM, 10 μM and 50 μM.
Figure 23:
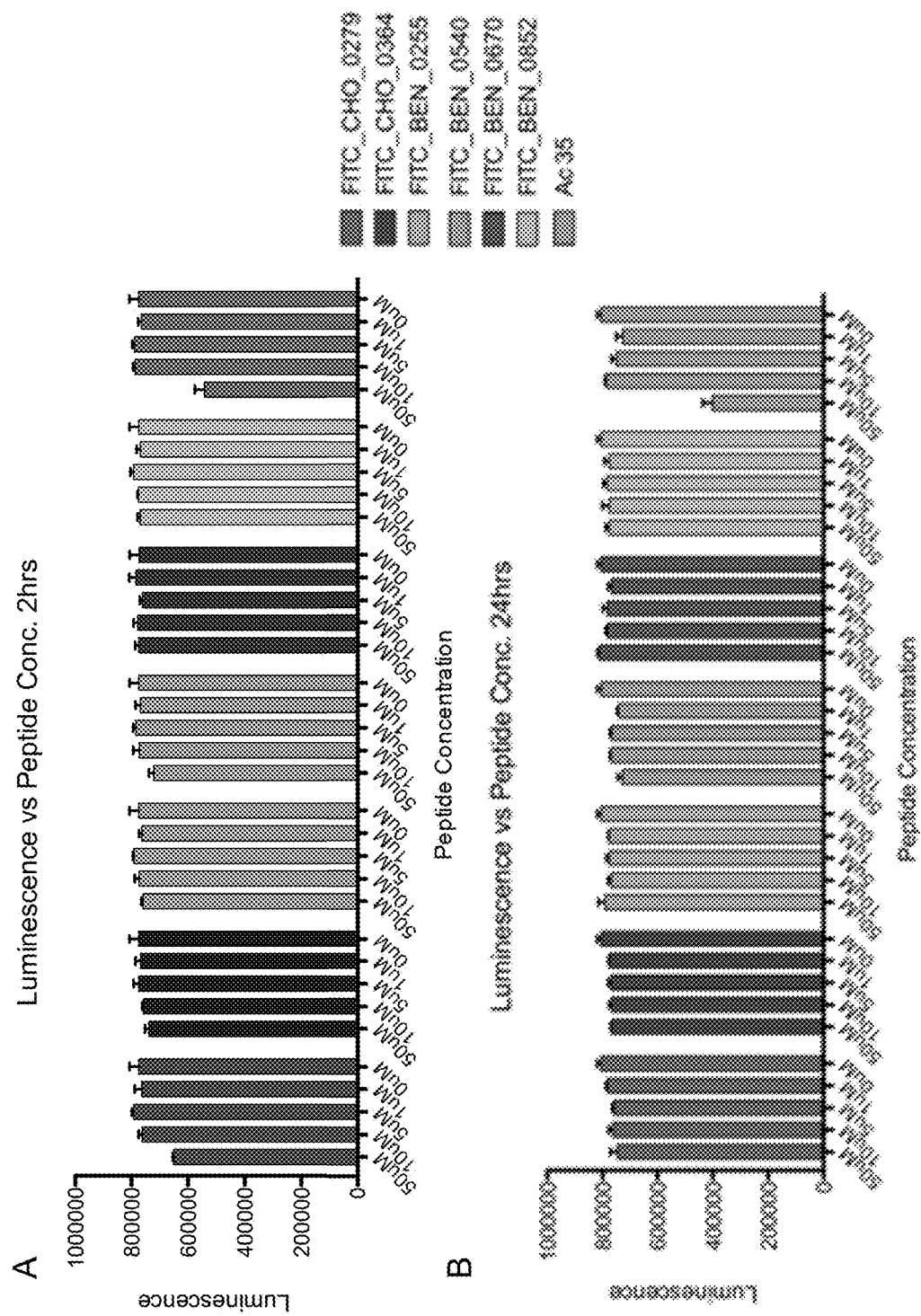
FIG. 23 provides a graphical representation showing the results of CellTiter-Glo viability assays assessing cytotoxicity of various CPPs identified by a method of the invention in bEnd.3 cells. Panel A shows the results for CPPs including Peptide IDs: 0045 (shown as FITC_BEN_0540 in the figure; SEQ ID NO: 14) and 0076 (shown as FITC_BEN_0670 in the figure SEQ ID NO: 10), and for Ac35 as control, incubated with bEnd.3 cells for 2 hours at 0 μM, 1 μM, 5 μM, 10 μM and 50 μM. Panel B shows the results for the same peptides incubated with bEnd.3 cells for 24 hours at 0 μM, 1 μM, 5 μM, 10 μM and 50 μM.
Figure 24:
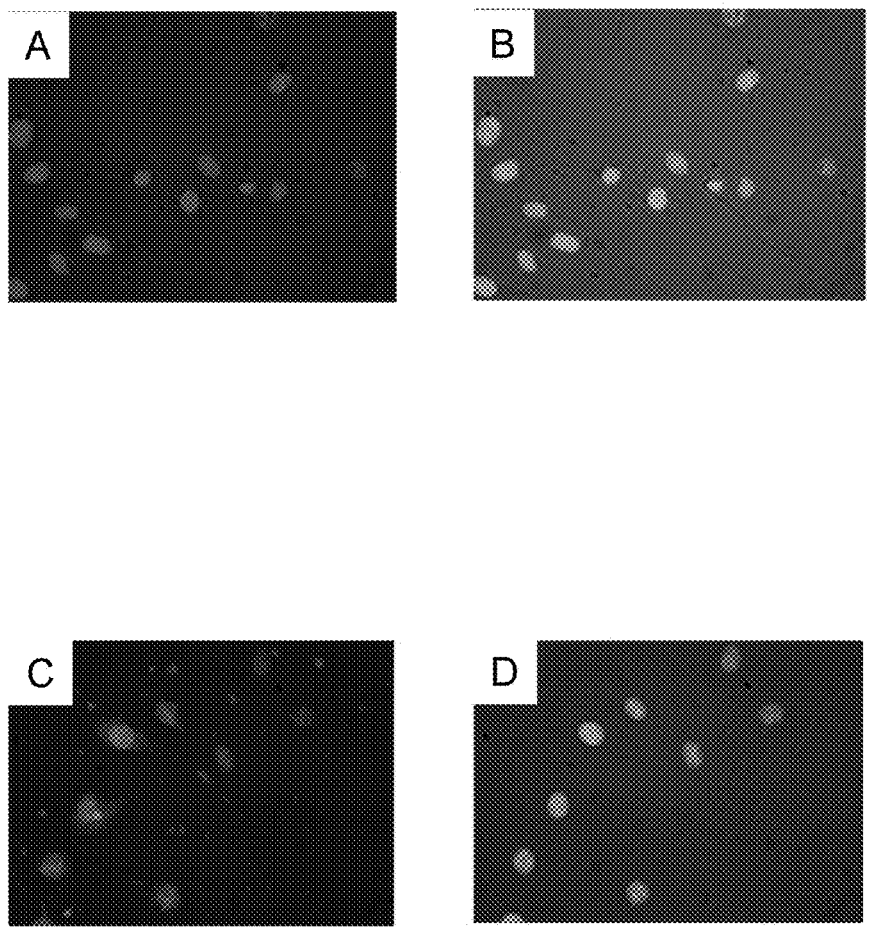
FIG. 24 provides photographic representation of fluorescent microscopy of bEnd.3 mouse brain endothelial cells. Panel A is a 40× magnification of bEnd.3 mouse brain endothelial cells incubated in 5 μM PYC38 SF. Panel B is a 40× magnification of bEnd.3 mouse brain endothelial cells incubated in 5 μM PYC38 SF dyed with DAPI and BF. Panel C is a 40× magnification of bEnd.3 mouse brain endothelial cells incubated in 5 μM PYC38-TAT SF. Panel D is a 40× magnification of bEnd.3 mouse brain endothelial cells incubated in 5 μM PYC38-TAT SF dyed with DAPI and BF. These figures show evidence for internalisation of the peptide into bEnd.3 cells.
Figure 25:
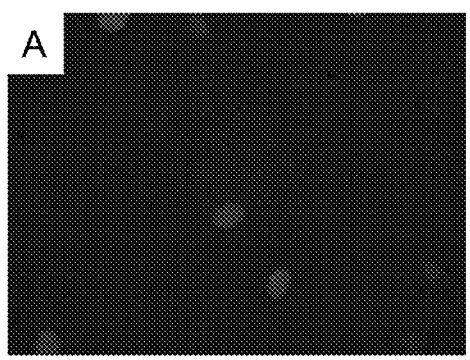
FIG. 25 provides photographic representation of fluorescent microscopy of bEnd.3 mouse brain endothelial cells. Panel A is a 40× magnification of bEnd.3 mouse brain endothelial cells incubated in 10 μM CPP (Peptide ID: 0076; SEQ ID NO: 10) CM. Panel B is a 40× magnification of bEnd.3 mouse brain endothelial cells incubated in 10 μM CPP CM dyed with DAPI and BF. Panel C is a 40× magnification of bEnd.3 mouse brain endothelial cells incubated in 10 μM CPP SF. Panel D is a 40× magnification of bEnd.3 mouse brain endothelial cells incubated in 10 μM CPP SF dyed with DAN and BF. These figures show evidence for internalisation of the peptide into bEnd.3 cells.
Figure 25:
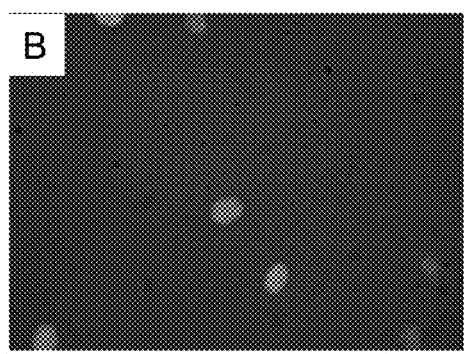
Figure 25:
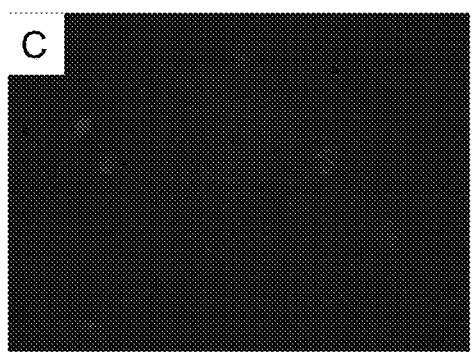
Figure 25:
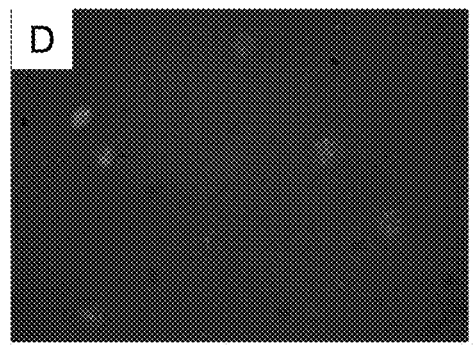
Figure 26:
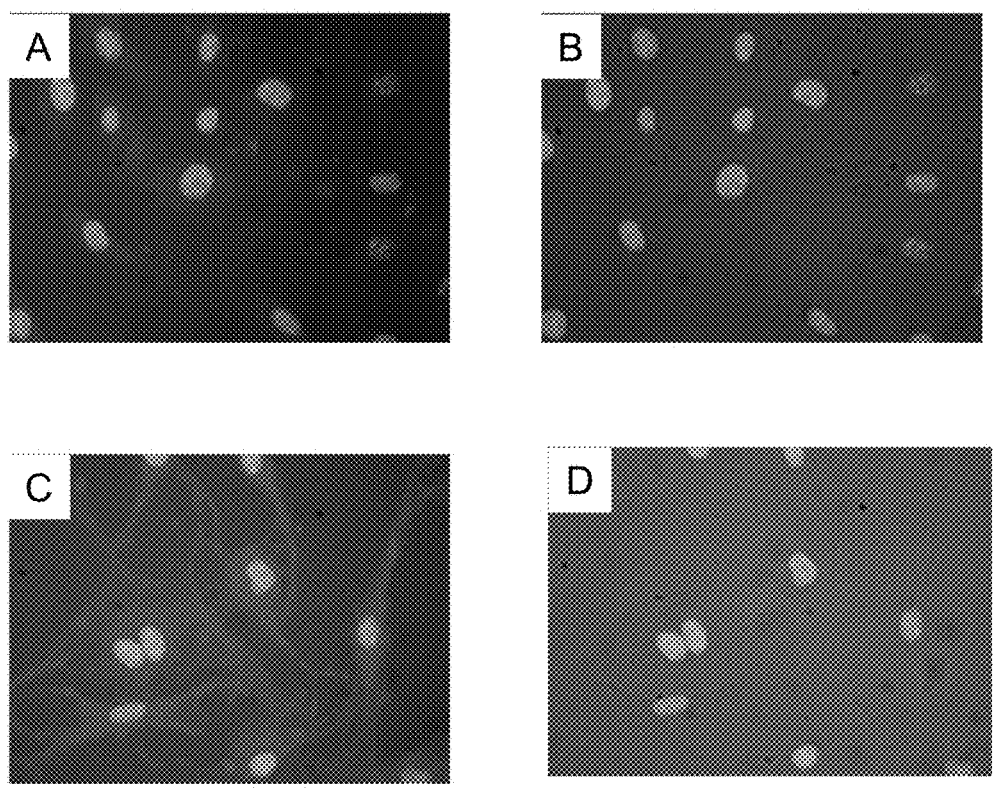
FIG. 26 provides photographic representation of fluorescent microscopy of bEnd.3 mouse brain endothelial cells. Panel A is a 40× magnification of bEnd.3 mouse brain endothelial cells incubated in 10 μM CPP (Peptide ID: 5008; SEQ ID NO: 5) CM. Panel B is a 40× magnification of bEnd.3 mouse brain endothelial cells incubated in 10 μM CPP CM dyed with DAPI and BF. Panel C is a 40× magnification of bEnd.3 mouse brain endothelial cells incubated in 10 μM CPP SF. Panel D is a 40× magnification of bEnd.3 mouse brain endothelial cells incubated in 10 μM CPP SF dyed with DAPI and BF. These figures show evidence for internalisation of the peptide into bEnd.3 cells.
Figure 27:
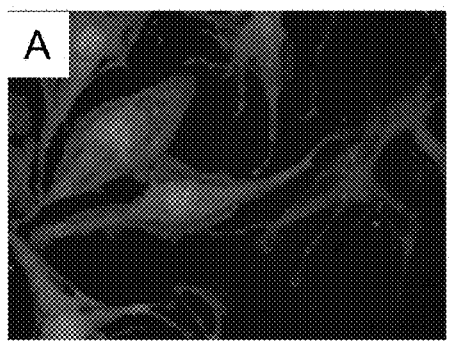
FIG. 27 provides photographic representation of fluorescent microscopy of bEnd.3 mouse brain endothelial cells. Panel A is a 40× magnification of bEnd.3 mouse brain endothelial cells incubated in 10 μM CPP (Peptide ID: 9170; SEQ ID NO: 15) CM. Panel B is a 40× magnification of bEnd.3 mouse brain endothelial cells incubated in 10 μM CPP CM dyed with DAPI and BF. Panel C is a 40× magnification of bEnd.3 mouse brain endothelial cells incubated in 10 μM CPP SF. Panel D is a 40× magnification of bEnd.3 mouse brain endothelial cells incubated in 10 μM CPP SF dyed with DAPI and BF. These figures show evidence for internalisation of the peptide into bEnd.3 cells.
Figure 27:
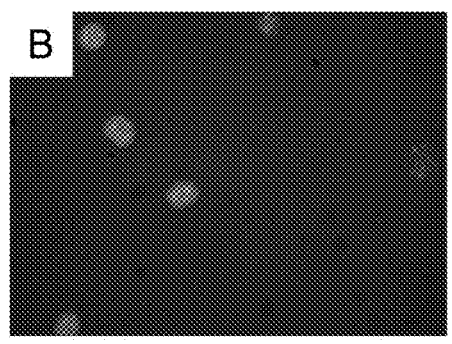
Figure 27:
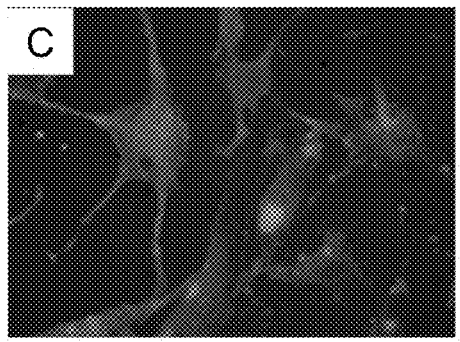
Figure 27:
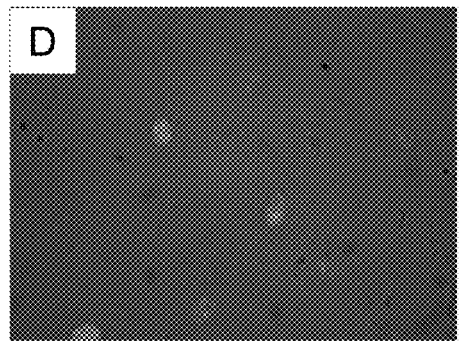
Figure 28:
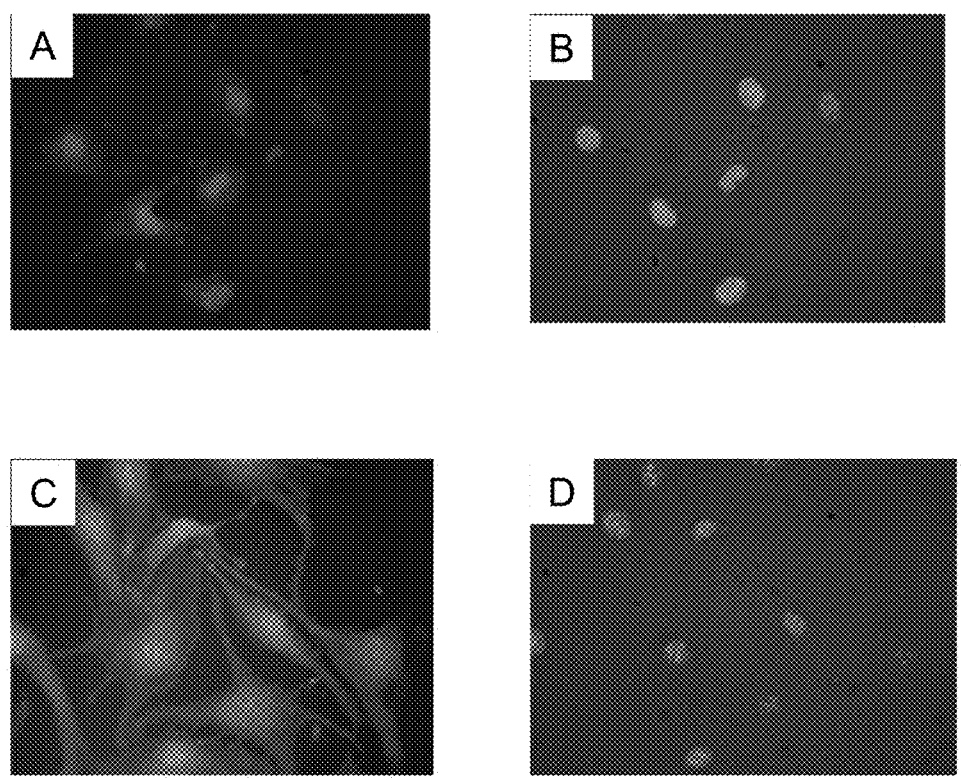
FIG. 28 provides photographic representation of fluorescent microscopy of bEnd.3 mouse brain endothelial cells. Panel A is a 40× magnification of bEnd.3 mouse brain endothelial cells incubated in 10 μM CPP (Peptide ID: 0045; SEQ ID NO: 14) CM. Panel B is a 40× magnification of bEnd.3 mouse brain endothelial cells incubated in 10 μM CPP CM dyed with DAPI and BF. Panel C is a 40× magnification of bEnd.3 mouse brain endothelial cells incubated in 10 μM CPP SF. Panel D is a 40× magnification of bEnd.3 mouse brain endothelial cells incubated in 10 μM CPP SF dyed with DAPI and BF. These figures show evidence for internalisation of the peptide into bEnd.3 cells.
Figure 29:
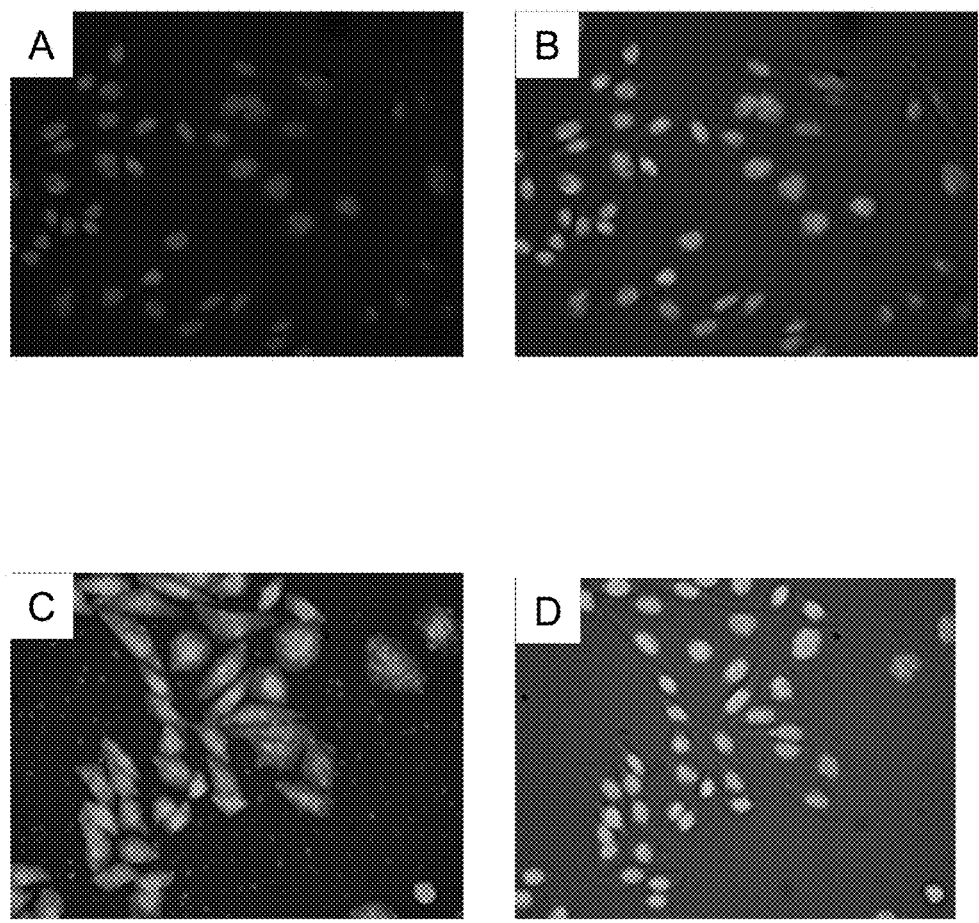
FIG. 29 provides photographic representation of fluorescent microscopy of CHO-K1 cells. Panel A is a 40× magnification of CHO-K1 cells incubated in 5 µM PYC38 SF. Panel B is a 40× magnification of CHO-K1 cells incubated in 5 µM PYC38 SF dyed with DAPI and BF. Panel C is a 40× magnification of CHO-K1 cells incubated in 5 µM PYC38-TAT SF. Panel D is a 40× magnification of CHO-K1 incubated in 5 µM PYC38-TAT SF dyed with DAPI and BF. These figures show evidence for internalisation of the peptide into CHO-K1 cells.
Figure 30:
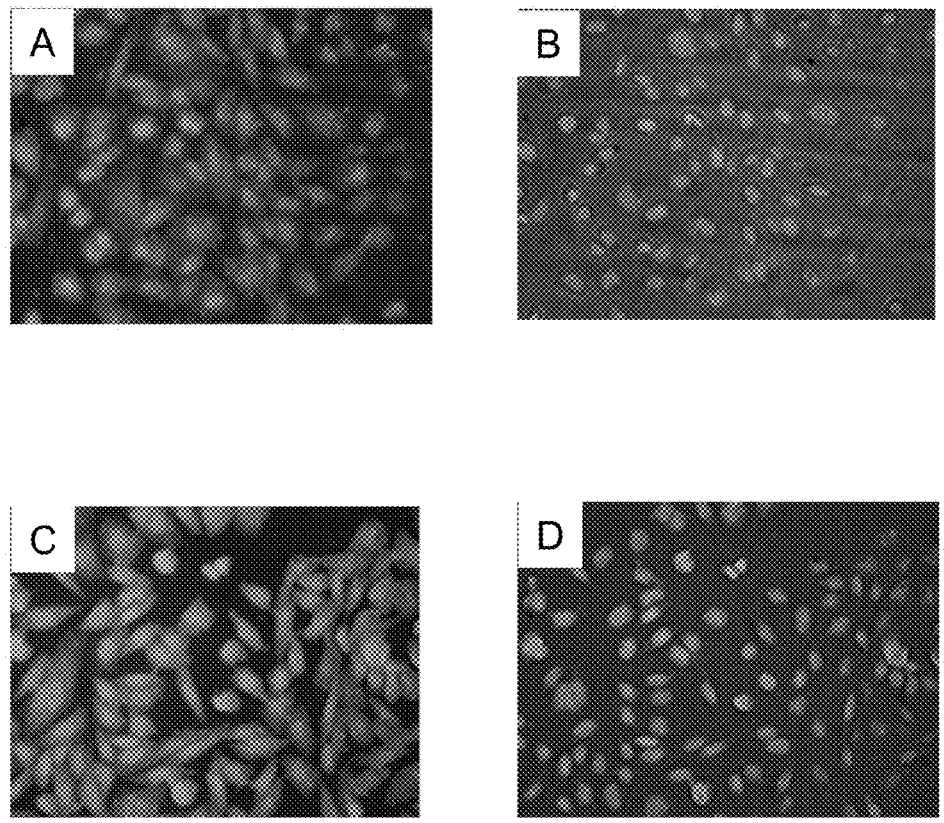
FIG. 30 provides photographic representation of fluorescent microscopy of CHO-K1 cells. Panel A is a 40× magnification of CHO-K1 cells incubated in 10 µM CPP (Peptide ID: 5008; SEQ ID NO: 5) CM. Panel B is a 40× magnification of CHO-K1 cells incubated in 10 µM CPP CM dyed with DAPI and BF. Panel C is a 40× magnification of CHO-K1 cells incubated in 10 µM CPP SF. Panel D is a 40× magnification of CHO-K1 incubated in 10 µM CPP SF dyed with DAPI and BF. These figures show evidence for internalisation of the peptide into CHO-K1 cells.
Figure 31:
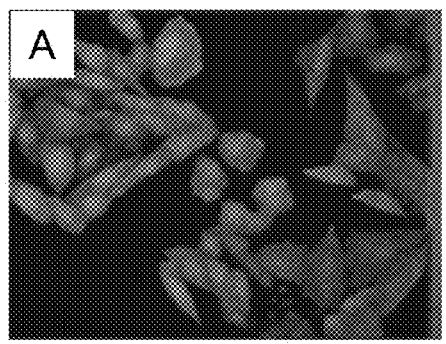
FIG. 31 provides photographic representation of fluorescent microscopy of CHO-K1 cells. Panel A is a 40× magnification of CHO-K1 cells incubated in 10 µM CPP (Peptide ID: 9170; SEQ ID NO: 15) CM. Panel B is a 40× magnification of CHO-K1 cells incubated in 10 µM CPP CM dyed with DAPI and BF. Panel C is a 40× magnification of CHO-K1 cells incubated in 10 µM CPP SF. Panel D is a 40× magnification of CHO-K1 cells incubated in 10 µM CPP SF dyed with DAPI and BF. These figures show evidence for internalisation of the peptide into CHO-K1 cells.
Figure 31:
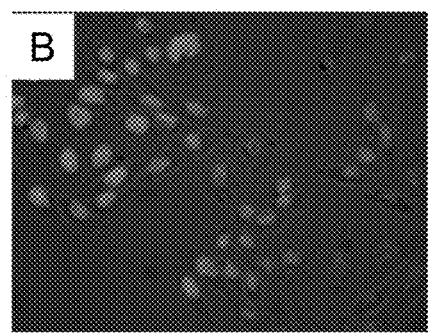
Figure 31:
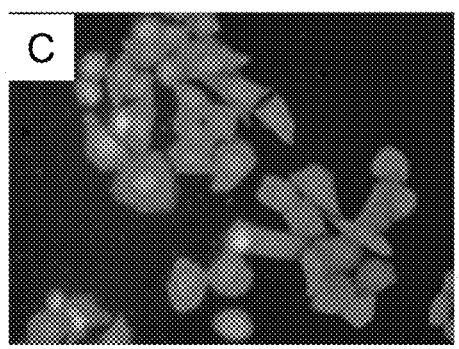
Figure 31:
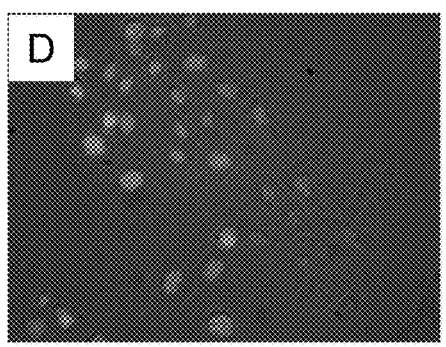
Figure 32:
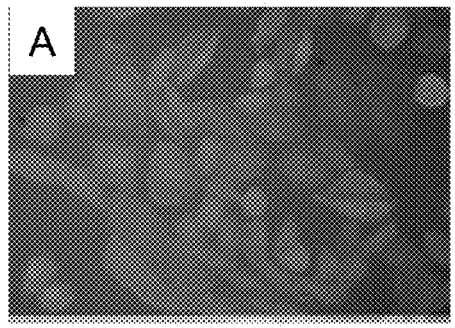
FIG. 32 provides photographic representation of fluorescent microscopy of CHO-K1 cells. Panel A is a 40× magnification of CHO-K1 cells incubated in 10 µM CPP (Peptide ID: 0045; SEQ ID NO: 14) CM. Panel B is a 40× magnification of CHO-K1 cells incubated in 10 µM CPP CM dyed with DAPI and BF. Panel C is a 40× magnification of CHO-K1 cells incubated in 10 µM CPP SF. Panel D is a 40× magnification of CHO-K1 incubated in 10 µM CPP SF dyed with DAPI and BF. These figures show evidence for internalisation of the peptide into CHO-K1 cells.
Figure 32:
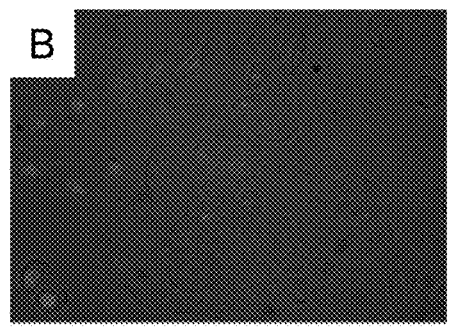
Figure 32:
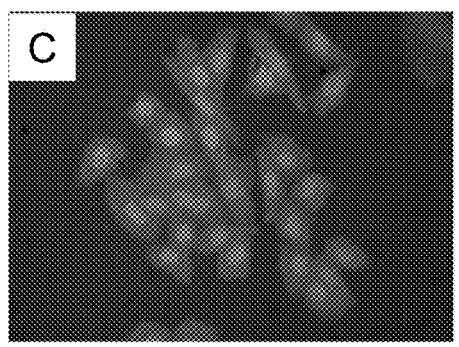
Figure 32:
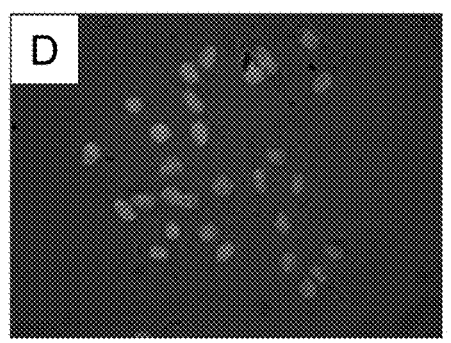
Figure 33:
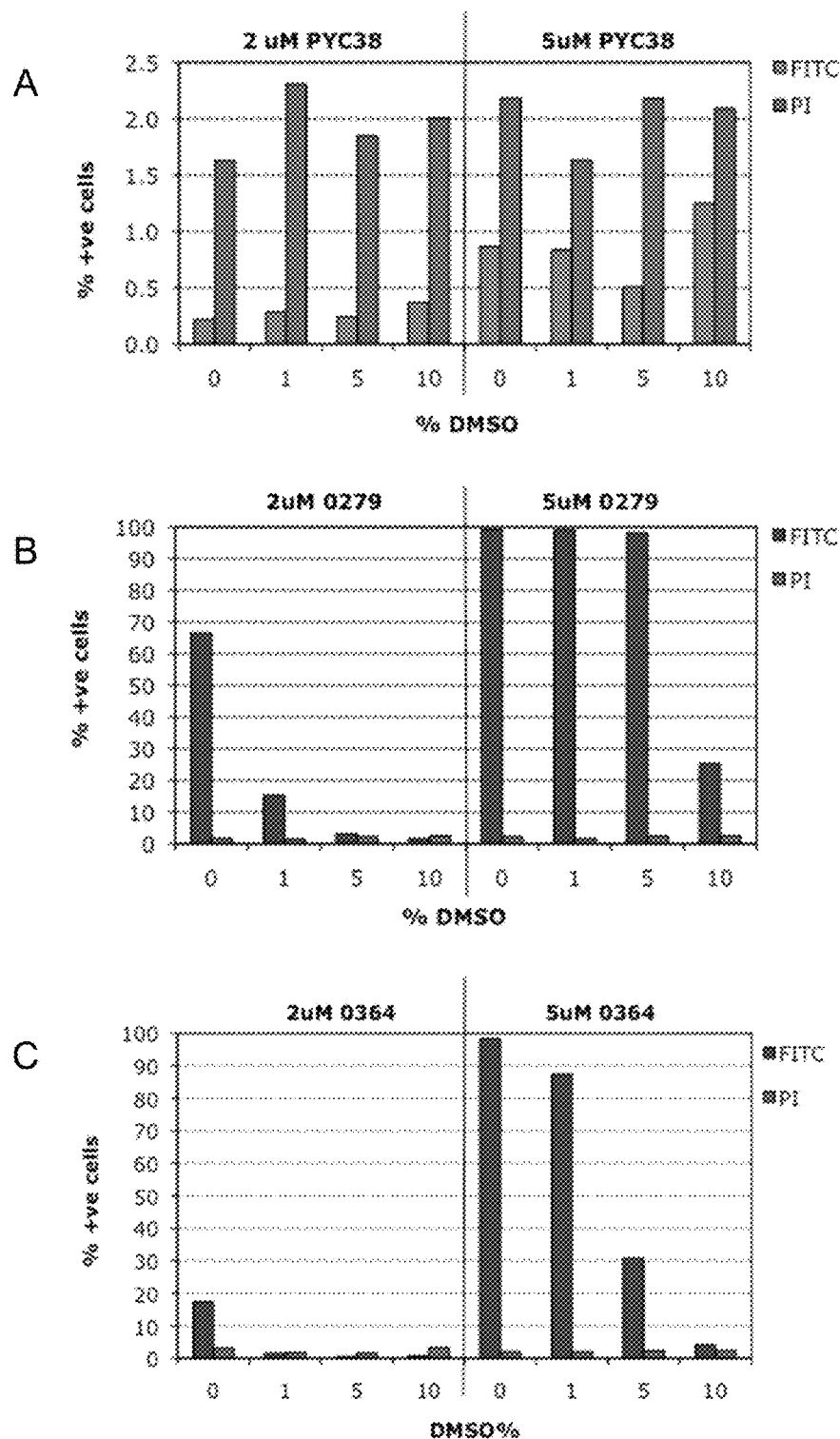
FIG. 33 provides a graphical representation showing the effect of increasing levels of DMSO on cellular uptake of CPPs. Panel A shows the FITC and Propidium Iodide staining results of CHO-K1 cells incubated in 2 µM PYC38 and 5 µM PYC38 at 0%, 1%, 5% and 10% DMSO. Panel B shows the FITC and Propidium Iodide staining results of CHO-K1 cells incubated in 2 µM of a CPP identified by a method of the invention (SEQ ID No 1: [RFRCGRRKWQIGS]) and 5 µM of such CPP at 0%, 1%, 5% and 10% DMSO. Panel C shows the FITC and Propidium Iodide staining results of CHO-K1 cells incubated in 2 µM of another CPP identified by a method of the invention (SEQ ID NO: 2: [WTISSRRRKVNRAC]) and 5 µM of such CPP at 0%, 1%, 5% and 10% DMSO.
Figure 34:
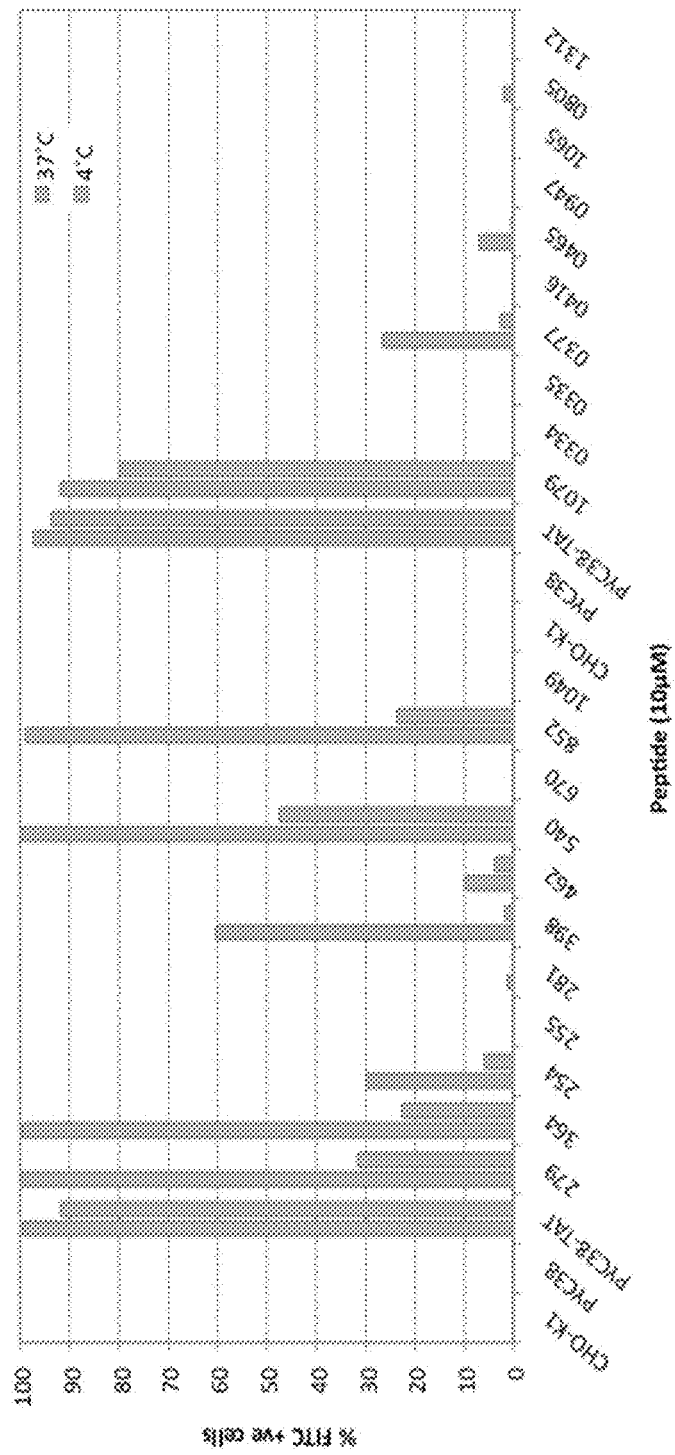
FIG. 34 provides a graphical representation showing the cellular uptake of various CPPs, including peptide IDs: 0045 (shown as "540" in the figure; SEQ ID NO: 14), 8093 (shown as "398" in the figure; SEQ ID NO: 9), 0076 (shown as "670" in the figure; SEQ ID NO: 10), and 9170 (shown as "1079" in the figure; SEQ ID NO: 15) showing high uptake, and controls, into CHO-K1 at 37° C. and 4° C.
Figure 35:
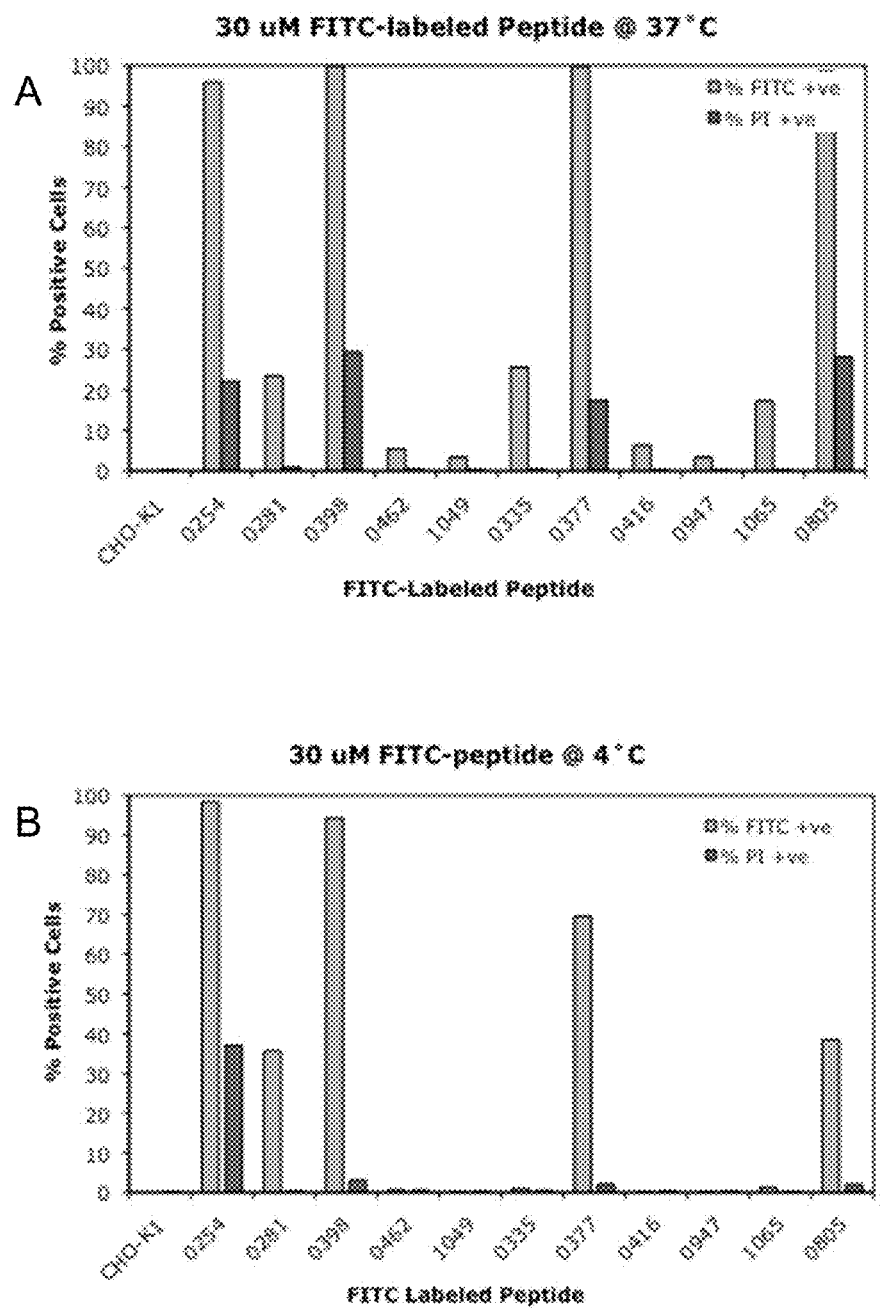
FIG. 35 provides a graphical representation showing the cellular uptake of various CPPs, including peptide IDs: 4052 (shown as "0254" in the figure; SEQ ID NO: 16), 8093 (shown as "0398" in the figure; SEQ ID NO: 9) and 5008 (shown as "0805" in the figure; SEQ ID NO: 5) showing greater than 40% uptake, and controls, into CHO-K1 incubated with 10 µM DMSO. Panel A shows the FITC and Propidium Iodide staining results of CHO-K1 cells incubated with CPPs at 30 µM at 37° C. Panel B shows the FITC and Propidium Iodide staining results of CHO-K1 cells incubated with CPPs at 30 µM at 4° C.
Figure 36:
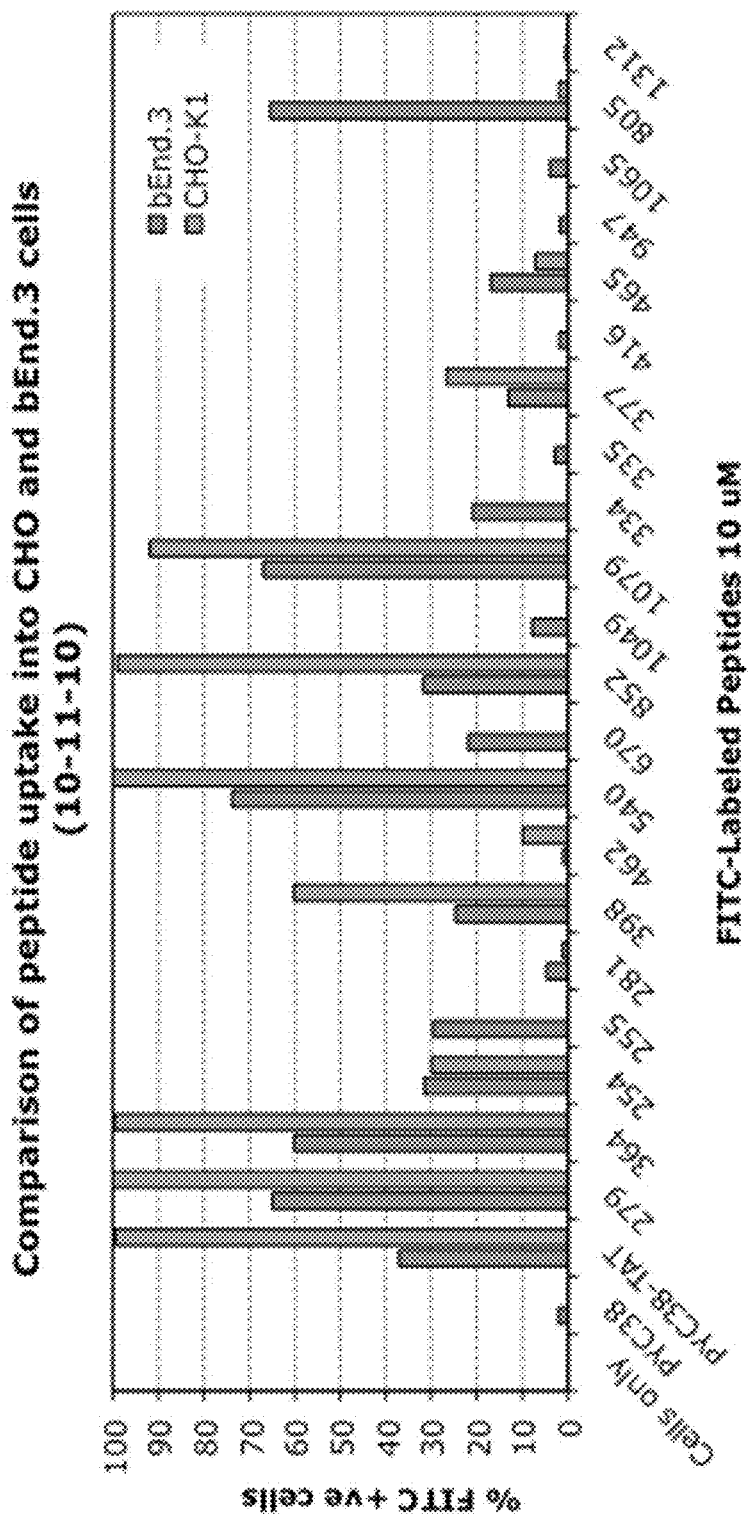
FIG. 36 provides a graphical representation showing the cellular uptake of various CPPs, including peptide IDs: 4052 (shown as "254" in the figure; SEQ ID NO: 16), 8093 (shown as "398" in the figure; SEQ ID NO: 9), 9170 (shown as "1079" in the figure; SEQ ID NO: 15) and 5008 (shown as "805" in the figure; SEQ ID NO: 5) showing high uptake, and 0076 (shown as "670" in the figure; SEQ ID NO: 10) showing bEnd.3 specific uptake, and controls, into bEnd.3 and CHO-K1 cells measured using FITC.
Figure 37:
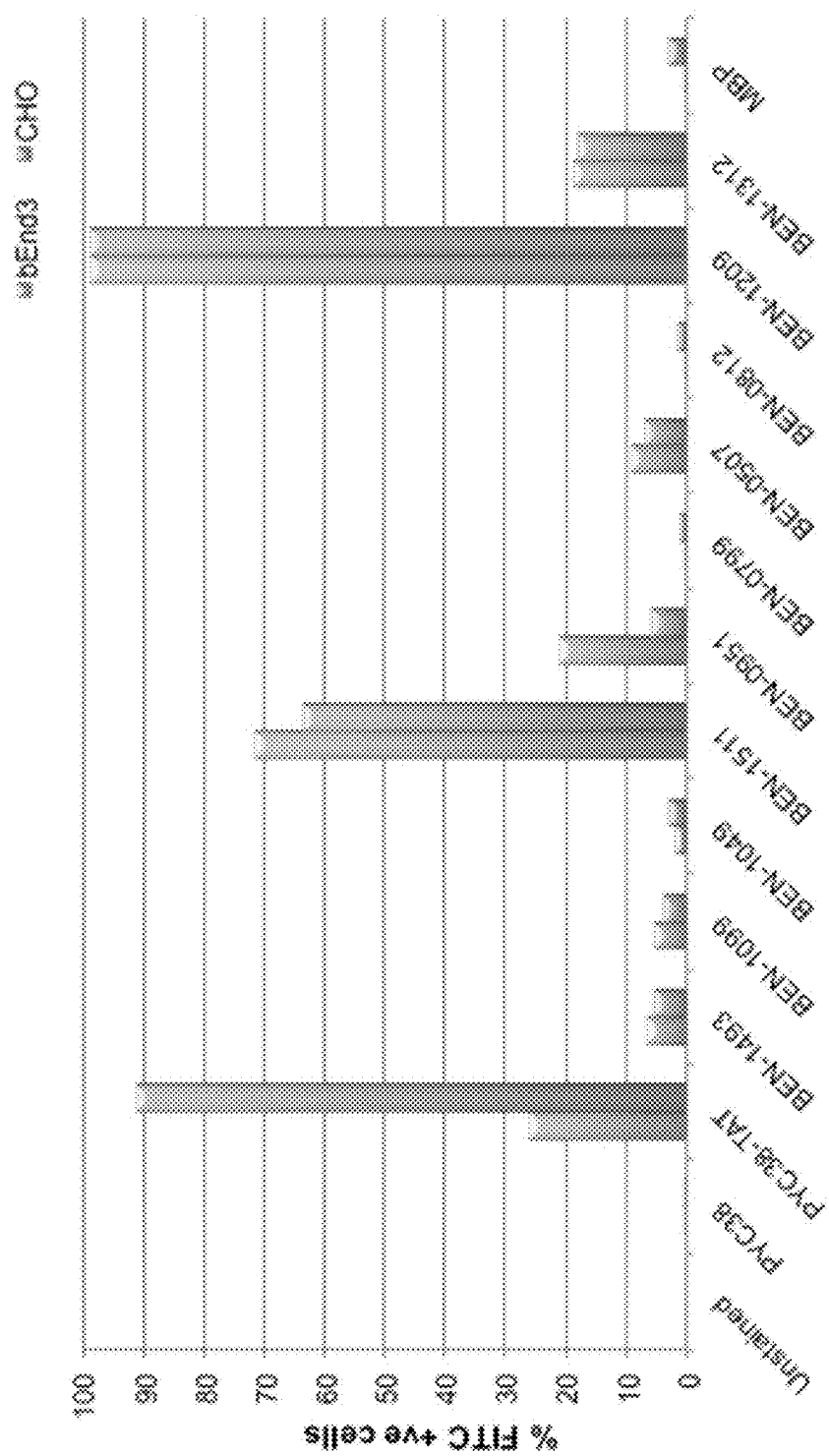
FIG. 37 provides a graphical representation showing the results of flow cytometry analysis of the cellular uptake of bEnd.3 and CHO-K1 cells incubated with recombinant CPPs, including peptide ID: 1115 (shown as "1511" in the figure; SEQ ID NO: 7) and 9102 (shown as "1209" in the figure; SEQ ID NO: 11) showing greater than 50% uptake for both b.End.3 and CHO cells, and controls, at 10 µM at 37° C. for 1 hour.
Figure 38:
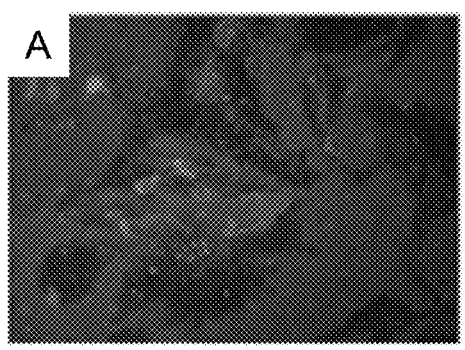
FIG. 38 provides photographic representation of fluorescent microscopy of bEnd.3 mouse brain endothelial cells. Panel A is a 40× magnification of bEnd.3 mouse brain endothelial cells incubated in 10 µM CPP (Peptide ID: 0125; SEQ ID NO: 8) fused with MBP SF fusion protein. Panel B is a 40× magnification of bEnd.3 mouse brain endothelial cells incubated in 10 µM of the fusion protein SF. Panel C is a 40× magnification of bEnd.3 mouse brain endothelial cells incubated in 10 µM of the fusion protein SF dyed with DAPI and BF. Panel D is a 40× magnification of bEnd.3 mouse brain endothelial cells incubated in 10 µM of the fusion protein SF. These figures show evidence for internalisation of the peptide-MBP fusion protein into bEnd.3 cells.
Figure 38:
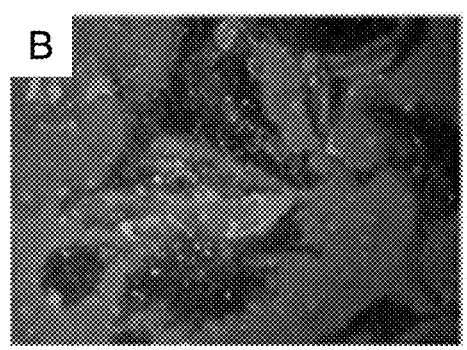
Figure 38:
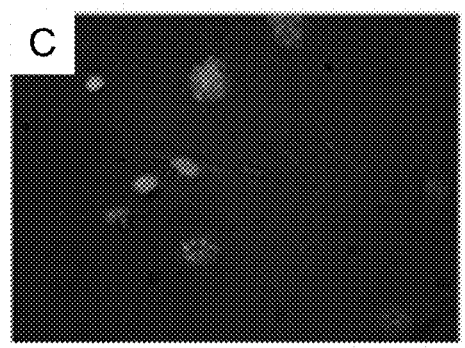
Figure 38:
Figure 39:
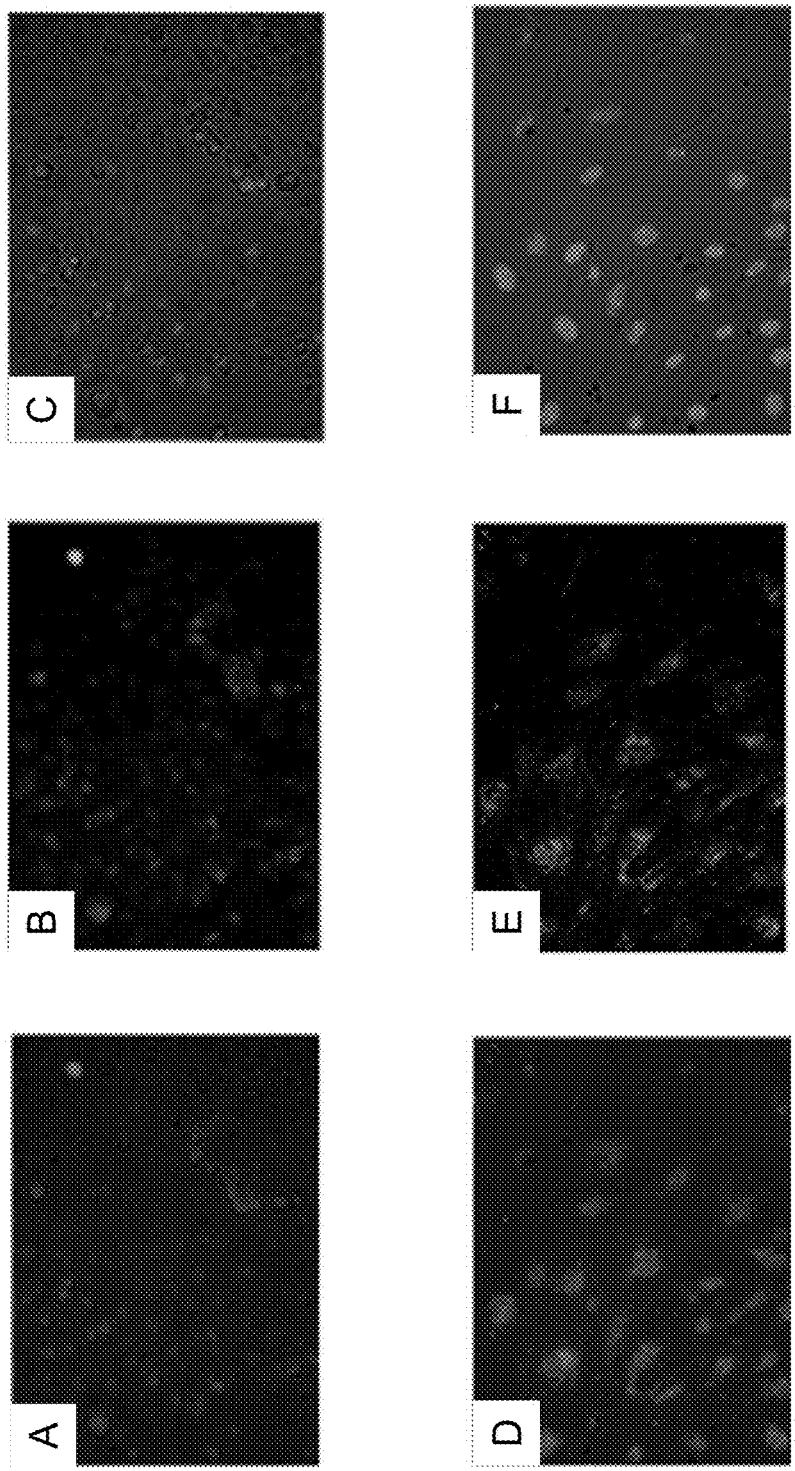
FIG. 39 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 3194; SEQ ID NO: 6) SF. Panel B is a 40× magnification of CHO-K1 epithelial cells incubated in 1 µM CPP SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into bEnd.3 and/or CHO-K1 cells.
Figure 40:
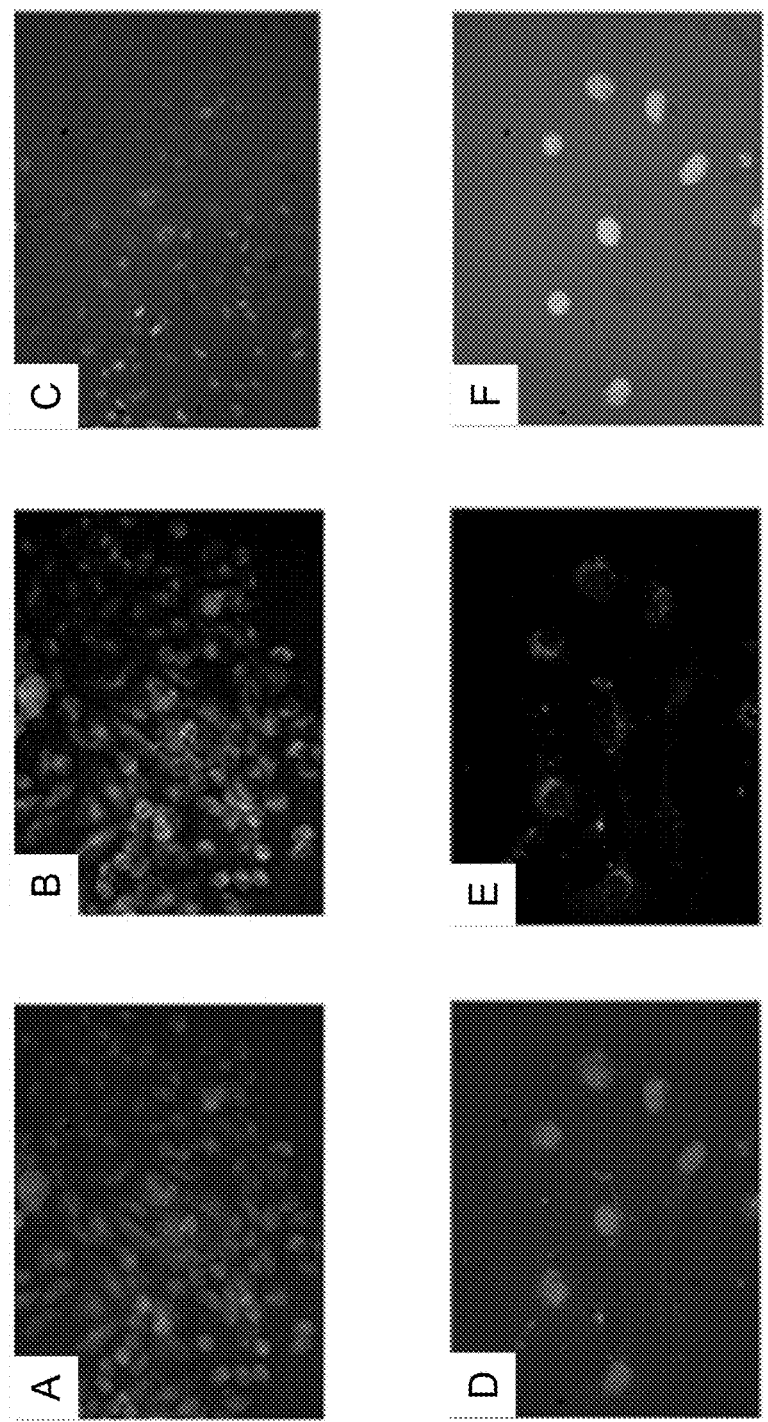
FIG. 40 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 1059; SEQ ID NO: 4) SF. Panel B is a 40× magnification of CHO-K1 epithelial cells incubated in 1 µM 0951 SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into bEnd.3 and/or CHO-K1 cells.
Figure 41:
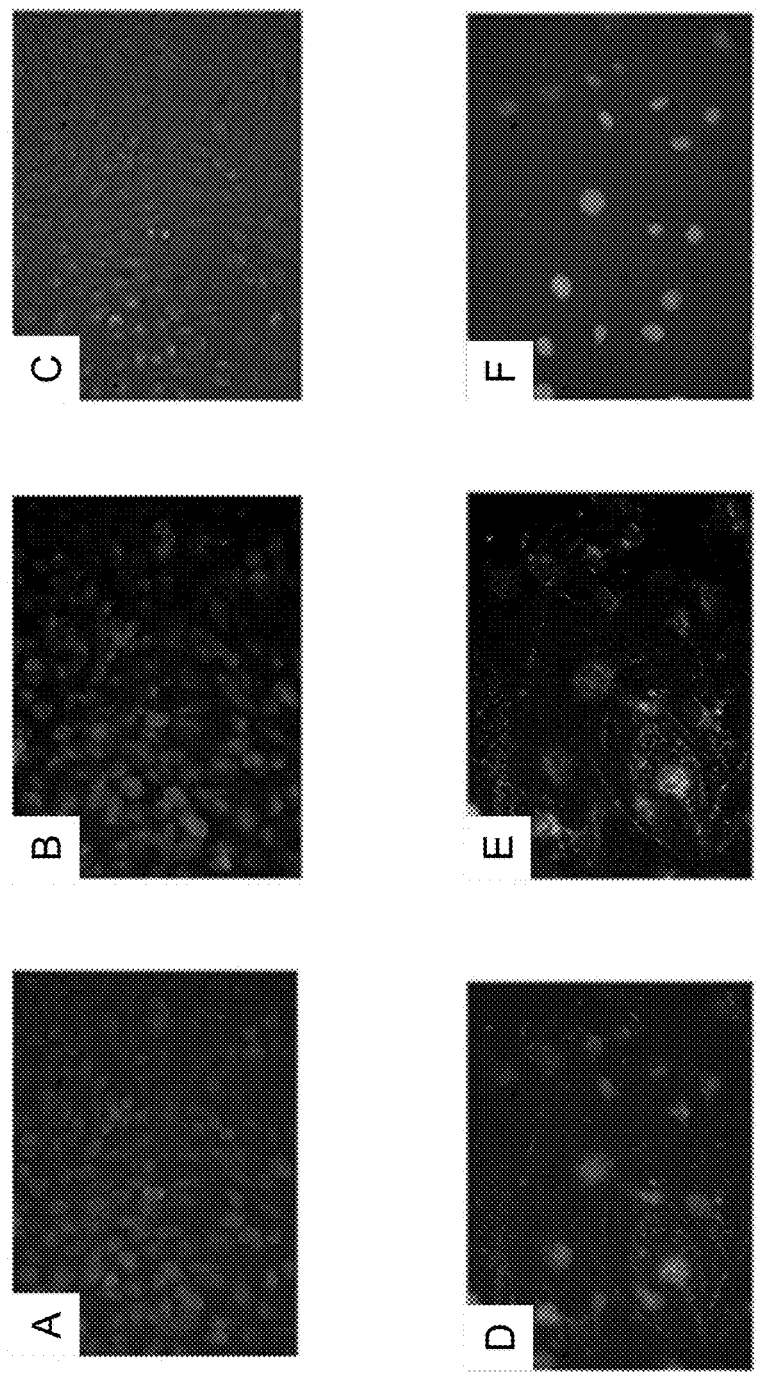
FIG. 41 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 1115; SEQ ID NO: 7) SF. Panel B is a 40× magnification of CHO-K1 epithelial cells incubated in 1 µM CPP SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into bEnd.3 and/or CHO-K1 cells.
Figure 42:
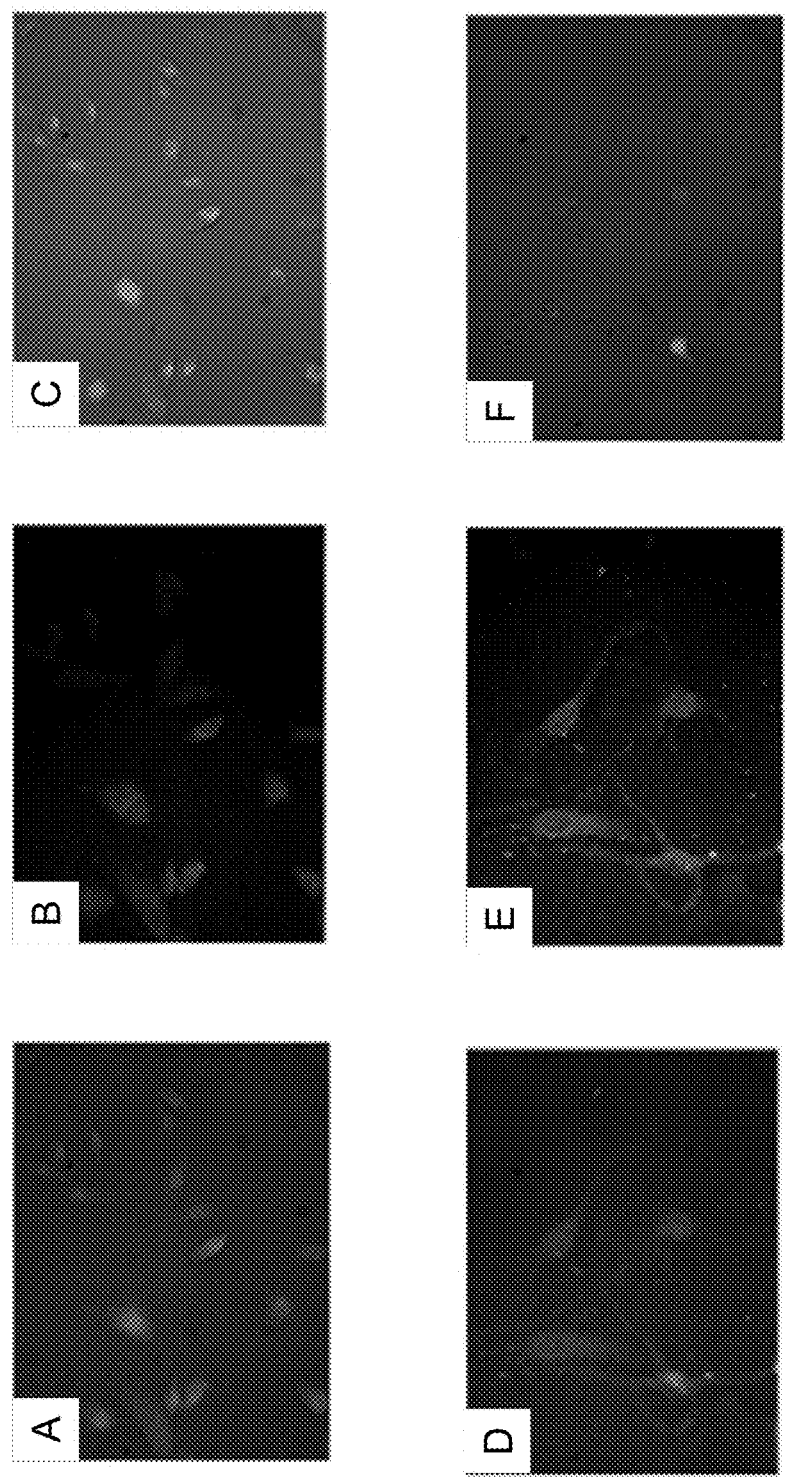
FIG. 42 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 9102; SEQ ID NO: 11) SF. Panel B is a 40× magnification of CHO-K1 epithelial cells incubated in 1 µM CPP SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into bEnd.3 and/or CHO-K1 cells.
Figure 43:
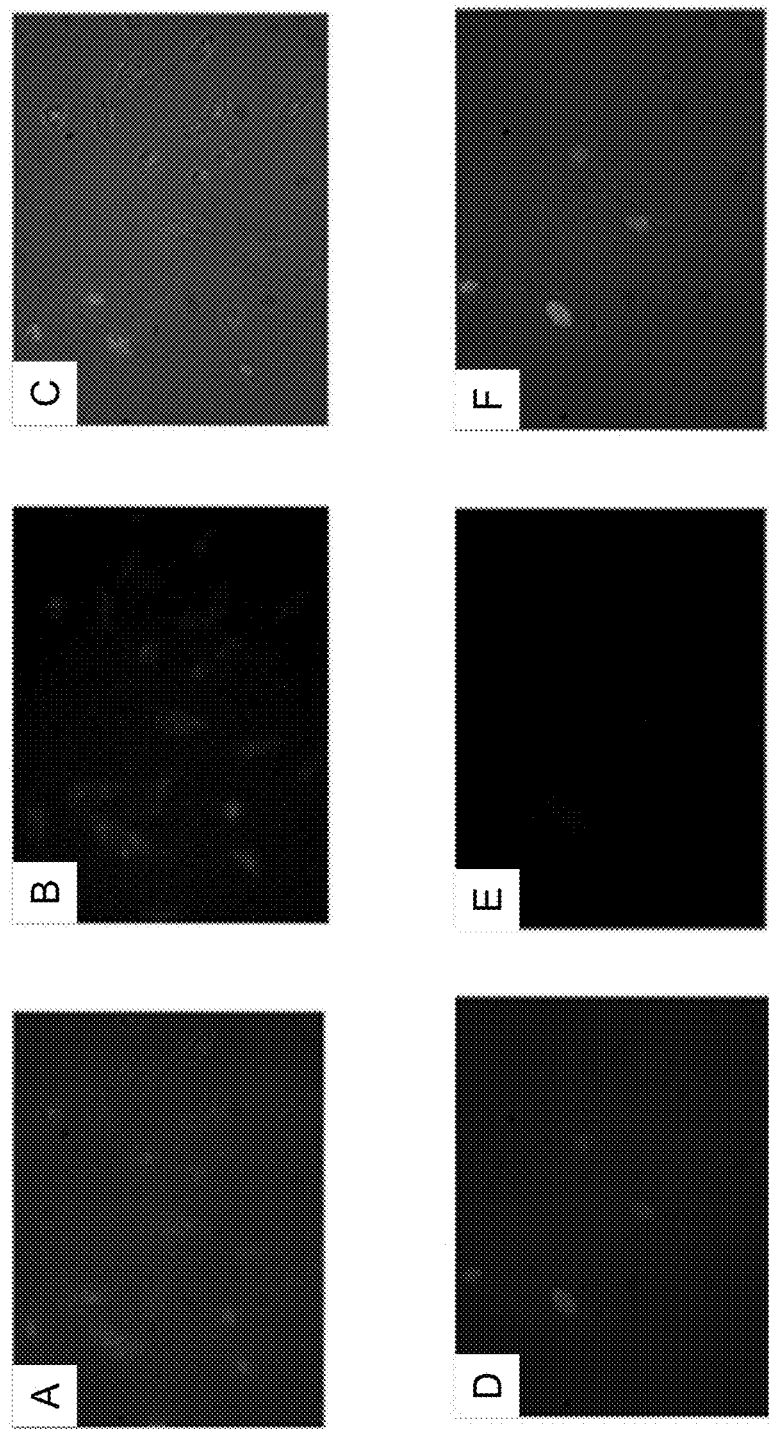
FIG. 43 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 2113; SEQ ID NO: 13) SF. Panel B is a 40× magnification of CHO-K1 epithelial cells incubated in 1 µM CPP SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into CHO-K1 cells.
Figure 44:
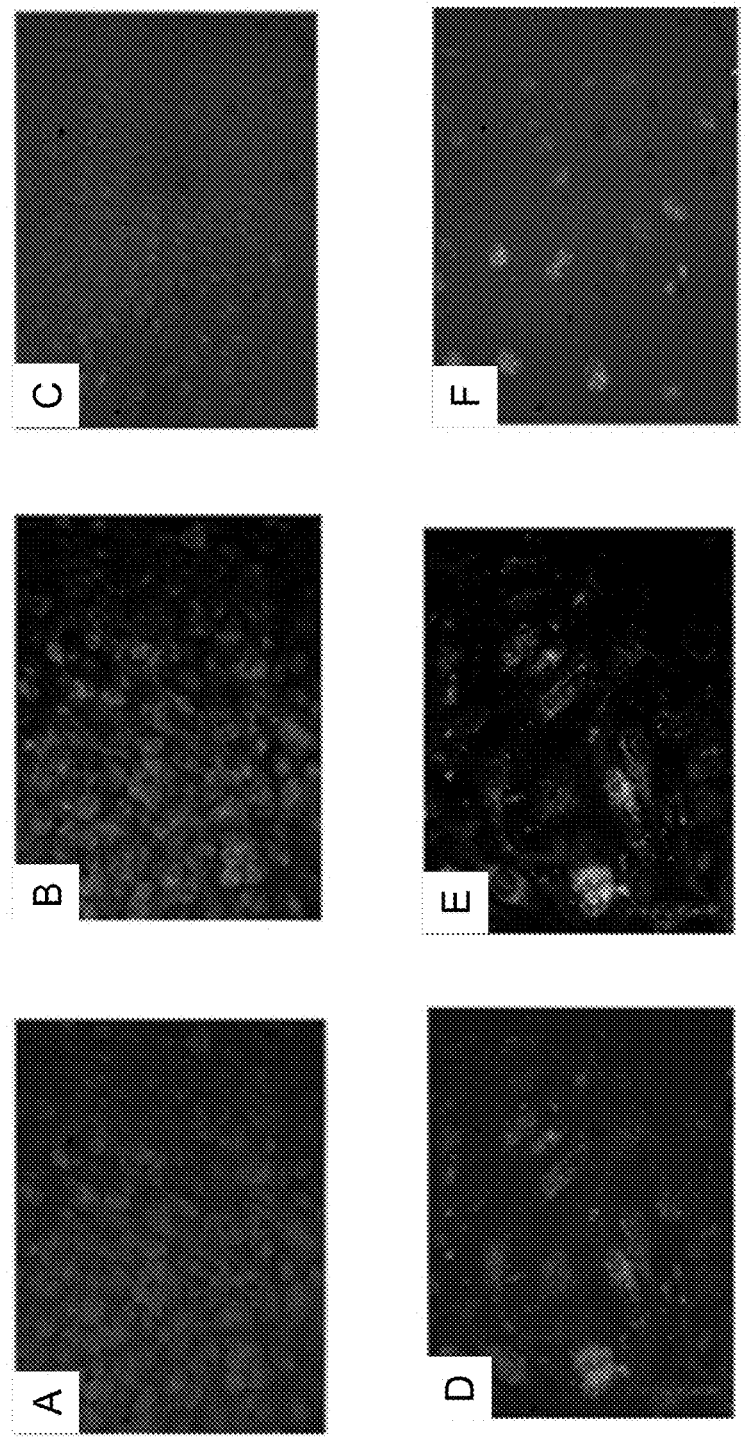
FIG. 44 provides photographic representation of fluorescent microscopy of CHO-K1 epithelial and bEnd.3 mouse brain endothelial cells. Panel A is a 40× magnification of CHO-K1 epithelial cells incubated in 1 µM CPP (Peptide ID: 9190; SEQ ID NO: 3) SF. Panel B is a 40× magnification of CHO-K1 epithelial cells incubated in 1 µM CPP SF dyed with FITC. Panel C is a 40× magnification of CHO-K1 epithelial cells incubated in 1 µM CPP SF dyed with DAPI and BF. Panel D is a 40× magnification of b.End3 mouse brain endothelial cells incubated in 1 µM CPP SF. Panel E is a 40× magnification of b.End3 mouse brain endothelial cells incubated in 1 µM CPP SF dyed with FITC. Panel F is a 40× magnification of b.End3 mouse brain endothelial cells incubated in 1 µM CPP SF dyed with DAPI and BF. These figures show evidence for internalisation of the peptide into bEnd.3 and/or CHO-K1 cells.

Identification of cell-specific or cell-selective cell-penetrating peptides is achieved by differentially selecting peptides based on their ability to penetrate distinct cell types, whilst not penetrating others. It is well known that cell membrane compositions vary substantially between different cell types and indeed different tissue types. Cell membranes are composed generally of phospholipids, proteins and carbohydrates arranged in such a way so as to control which molecules can move in and out of those cell. As such, the skilled person will understand that cell membrane characteristics and properties can therefore be used to select for peptide molecules which are internalized within a target cell type and to exclude those peptides which are not to be internalized within a target cell type. In such an approach, negative and positive selections can be employed using distinct cell populations.

As used herein, the term "negative selection" broadly describes the process of incubating peptides with a non-target population of cells in medium for a period of time and under conditions sufficient to allow peptides to adhere to the cell surface or become internalized within those cells resulting in those peptides being sequestered from the medium. Subsequent removal of the non-target population of cells from the medium will result in a proportion of peptides which have adhered to or internalized within those cells being removed e.g., this negative selection may remove peptides with an affinity for adhering to, or penetrating, a broad range of cell types as distinct from those peptides that penetrate target cell types specifically or selectively.

As used herein, the term "positive selection" broadly describes the process of contacting the medium containing peptides from the one or more negative selections with a desirable target population of cells and incubation of those peptides and cells for a period of time and under conditions sufficient to allow peptides to adhere to the cell surface or become internalized within the target population of cells thereby isolating cell-specific or cell selective peptides.

A population of cells used in the negative and positive selections in accordance with the invention method can comprise any cell type, as long as the cell types used in the respective negative and positive selections are sufficiently different from one another in their cell membrane characteristics and/or properties so as to permit the differential selection of cell-penetrating peptides which are internalized. The cell populations supported by the data herein are commercially available cell lines. However, in alternative embodiments the cell populations may comprise for example, primary cells, hybridomas, immortalised cells or any combination thereof.

The data provided in the specific examples supports a method of identifying, validating and recovering cell specific cell-penetrating peptides which are differentially selective or at least moderately specific for penetrating endothelial cells, epithelial cells and/or epithelial-like cells. In particular, exemplified cell lines used in the respective positive and negative selections are mouse bEnd.3, mouse SVEC4-10 and CHO cells. However, any number of other endothelial and epithelial cell lines can be used in the selections e.g., CADMEC, HAOEC, HBcAEC, HBEpC, HCAEC, HCtAEC, RAOEC. Moreover, whilst the cells exemplified in the specific examples are endothelial and epithelial cells, it will be appreciated by those of ordinary skill in the art that any cell types may be employed as long as the population of cells used in respective negative and positive selections are sufficiently distinct from one another to permit the differential selection of cell specific or selective cell-penetrating peptides. Other types of cell that may be used in the method include, for example, endothelial cells, epithelial cells, astrocytes, fibroblasts, T-cells, B-Cells, smooth muscle cells, chondrocytes, stromal cells, mesenchymal cells, osteoblasts, keratinocytes, stem cells, pluripotent cells, hepatocytes and renocytes.

It will also be appreciated by those of ordinary skill in the art that populations of cells used in the negative and positive selections in accordance with the method of the invention may be derived from any tissue source. As exemplified by the data presented herein, the method of the invention is capable of identifying cell specific cell-penetrating peptides which selectively or specifically penetrate cells derived from cerebral cortex tissue, lymph node vascular epithelium and ovarian tissue. However, the method could conceivably be performed using populations of cells derived from any tissue type e.g., cells could be derived from the heart, pancreas, lung, kidney, liver, spleen, brain, thymus, skin, ovarian, testes, muscle, uterus, embryo, lymphatic tissue, tongue, mammary gland, colon, stomach, intestine, cartilage, bone, connective tissue, bronchia, esophagus, rectum, vascular tissue, skeletal tissue, and marrow.

Whilst the exemplified cell types supported by the data are derived from mouse and human, it will also be appreciated by those of ordinary skill in the art that populations of cells used in the negative and positive selections in accordance with the invention method may be derived from any organism. Suitable organisms may include any organism selected from the taxonomic Domains Eukaryota and Prokaryota.

More broadly, the cell populations used in negative and positive selections in accordance with the present invention may further be distinguished by the pathways and mechanisms they employed for internalization of peptides into the cell if this is known e.g., receptor mediated transcytosis (RMT), Fluid-phase mediated transcytosis (FMT) and/or adsorptive-mediated transcytosis (AMT). RMT requires the interaction of peptides with specific receptor moieties on the cell surface. Several RMT pathways are known in the art. Exemplary RMT pathways can include, but are not limited to, iron-transferrin receptor system, insulin receptor system and cholesterol receptor system. FMT involves soluble molecules being randomly taken up by vesicles of the plasma membrane for transport into the cell interior. Exemplary FMT mechanisms can include, but are not limited to, caveolae vesicles or caveolae lipid-rafts mediated transcytosis, and clathrin-coated pits/vesicles mediated transcytosis. AMT involves the interaction of cationic or polycationic molecules with the negatively charged cell surface and subsequent cell internalization.

Appropriate culture media and conditions for culturing the above-described cell populations and cell lines are known in the art. With respect to the conditions necessary and sufficient for peptides to internalize the cells, these should be determined empirically.

2. Detection of CPP Localization

To detect peptides which have been internalized within the target cell population a suitable visualisation method or other means of detection is required. A number of methods are well known in the art. The data presented herein supports a fluorescent-based assay approach wherein peptides are labeled with suitable fluorophores prior to the positive and negative selections being performed, and subsequent internalized cell-penetrating peptides are detected using an art recognised fluorescence detection means.

The specific peptide examples presented herein support the use of peptides, in the form of peptide-presenting phage, labeled with either AlexaFluor 488 (AlexaFluor® 488 carboxylic acid 2,3,5,6-tetrafluorophenyl ester 5-isomer), Oregon Green 488 (Oregon Green® 488 carboxylic acid, succinimidyl ester 5-isomer) or FITC (fluorescein isothiocyanate). However, in accordance with the invention it is permissible that the peptides are labeled or tagged with any detectable dye or reporter which permits detection e.g., by visualisation, and thus validation of cell internalization of cell-penetrating peptides. Suitable fluorescent labels that may be used in accordance with the invention include, but are not limited to, fluorescent, chemiluminescent, phosphorescent, and/or radioactive labels. In some embodiments, the fluorescent label or moiety could include, for example, other Alexafluor dyes, ATTO dyes, fluorescein and fluorescein derivatives, rhodamine dyes, coumarin, cyanine dyes, dabcyl, dabsyl, FITC, TRITC, California red, Rox etc. Any fluorescent label or moiety that can be associated with a peptide and that can be detected can be utilized in accordance with the invention. In some embodiments, peptides comprise at least one radioactive amino acid e.g., an amino acid containing $^{32}P$ or $^{35}S$. In some embodiments, peptides comprise at least one amino acid that is attached to at least one radioactive moiety. In an alternative embodiment, the fluorescent label is a peptide or protein moiety fused to the cell-penetrating peptide. Fluorescent proteins may be fused to the cell-penetrating peptide in order to facilitate fluorescent-based detection of peptide cell internalization as well as biodistribution of the peptide e.g., subcellular localisation of the cell-penetrating peptide. Exemplary fluorescent proteins can include, but are not limited to, green fluorescent protein (GFP), enhanced green fluorescent protein (EGFP), AcGFP, TurboGFP, Emerald, Azami Green, ZsGreen, EBFP, Sapphire, T-Sapphire, ECFP, mCFP, Cerulean, CyPet, AmCyanl, Midori-Ishi Cyan, mTFPI (Teal), enhanced yellow fluorescent protein (EYFP), Topaz, Venus, mCitrine, YPet, PhiYFP, ZsYellow1, mBanana, Kusabira Orange, mOrange, dTomato, dTomato-Tandem, AsRed2, mRFP1, JRed, mCherry, HcRed1, mRaspberry, HcRed1, HcRed-Tandem, mPlum, and AQ 143.

As described herein, fluorescent labeling of peptides with a fluorescent label will permit end point analysis of target cells using standard flow cytometric methods to identify cell populations which have internalized cell-penetrating peptides. As supported by the data presented herein, validation of cell-penetrating peptide internalization following cell-based negative and positive screens, may require treatment of the cells with a protease subtilisin or other suitable serine protease to remove peptides that are bound to the cell surface but not internalized, followed by visualisation of cells using flow cytometry, fluorescence activate cell sorting (FACS), fluorescence microscopy or live confocal microscopy. The above mentioned visualisation methods are capable of detecting fluorescent signal emitted by internalized fluorescent-labeled peptides, thereby validating the presence of cell specific or cell selective CPPs contained within respective cells. Since the above-mentioned detection/visualisation strategies are well known in the art detailed methodologies shall not be described further herein.

In an alternative embodiment of the invention method, distinction between fluorescently labeled CPP which are bound to the cell surface and fluorescently-labeled CPP which have been internalized is achieved using of an extracellular quencher. As used herein, a "quencher" refers to a photon-reducing agent which absorbs energy emitted by the fluorophore or reporter without re-emitting fluorescence energy. Extracellular quenchers are not necessarily cell permeant and can be light absorbing fluorescent compounds having a fluorescence that can be easily separated from that of the fluorescent dye. As supported by the data presented herein, quenching of cell surface bound peptides labeled with FITC may be achieved using Trypan Blue. However, other types of extracellular quenchers may be used with alternative fluorophore including, but are not limited to, tartrazine and amaranth, acid red 37, congo red, brilliant black or a mixture of such quenchers. Quenchers are described in the Sigma-Aldrich Handbook of Dyes, Stains, and Indicators (Floyd G. Green, 1990, St. Louis, Mo., USA).

Since CPPs are reported to frequently be retained within the endosomal compartment following cell internalization, it is further embodiment of the invention method to provide a means for distinguishing between those cell specific or cell selective CPPs which are trapped in the endosome and those which are able to escape into the cytoplasm and other subcellular compartment. Since flow cytometry is unable to accurately differentiate between internalized and cell surface bound peptides, an alternative detection approach is necessary. Herein, we describe a methods wherein fluorescently labeled CPPs are detected and localised to subcellular compartments and/or organelles using live confocal microscopy. The data supports the detection and visualisation of fluorescently labeled CPPs by live confocal microscopy and localisation of CPP in the cytoplasm and the nucleus of CHO cells and bEnd.3 cells. It is, however, conceivable that the approach described herein for validation of CPP endocytic escape may be applied to any cell type in which fluorescently labeled CPP are internalized. In another example, to circumvent the need for CPP to have a bulky chemical fluorophore attached prior to cell-based screens, which may in some cases hinder cell internalization, CPPs are fused to a fluorescent proteins to facilitate visualisation by live confocal microscopy. Suitable fluorescent proteins are discussed supra. In another example, the CPP may be provided as a recombinant fusion protein comprising the CPP and a detectable fusion protein partner. The data provided herein supports the internalization of recombinant CPP fusion protein comprising a CPP fused to maltose binding protein (MBP). As such, it is possible that other fusion protein partners can be employed in the method. In another preferred embodiment the fusion protein partner is a protein which emits a detectable fluorescent signal and can be directly visualised under a live confocal microscope. Alternatively, in another embodiment the detectable fusion protein partner might be a bait protein which can be detected indirectly following the addition of an appropriate prey protein which covalently binds it and which is detectable under a confocal microscope. Bait-prey systems are well known in the art for the study of protein-protein, protein-peptide and protein-DNA interaction and will be discussed in further detail below. Suitable systems for use in a bait-prey approach may be for example, FLAG-tag, his-tag, or haloalkane tag. In one example the bait-prey system might comprise a labeled antibody, which after exposure to an appropriate reactive substrate, emits a fluorescence signal which can be detected and visualised under a live confocal microscope. In a further example the CPP may be conjugated to biotin or avidin/streptavidin molecule which, after internalization, can be indirectly visualised using live confocal microscopy following complexing to an anti-avidin/streptavidin or anti-biotin antibody with a suitable detectable label. Various methods of visualising proteins using antibodies are well known in the art.

In one embodiment of the invention, endosomal escape and subcellular localisation of internalized CPPs is preferred. In such an embodiment, CPP haloalkane ligand fusions which are fluorescently labeled are screened using the cell-based assays. In this cell-based assay the target cell population is further transfected with an expression vector expressing a protein tag fusion comprising a modified haloalkane dehalogenase substrate-binding domain and a protein partner. The protein partner can theoretically be any native protein expressed within the cell interior e.g., cytoplasm, nucleus, mitochondria etc., and may in certain preferred embodiments be a protein which is isolated to a specific subcellular compartment or organelle. CPP-haloalkane ligand fusions which are successfully internalized within the target cell, and which escapes the endosome, are designed to covalently bind the modified haloalkane dehalogenase substrate-binding domain of the protein tag fusion and form a detectable complex by virtue of the fluorophore which emits a fluorescent signal. Using this approach, fluorescently labeled CPP haloalkane ligand fusions that escape the endosome and which are subsequently directed to specific subcellular compartments and/or organelles by virtue of the haloalkane ligand's affinity for binding the protein tag fusion can detected using live confocal microscopy.

As used herein, the term "expression vector" refers to a nucleic acid molecule that has the ability confer expression of a nucleic acid fragment to which it is operably connected, in a cell or in a cell free expression system. Within the context of the present invention, it is to be understood that an expression vector may comprise a promoter as defined herein, a plasmid, bacteriophage, phagemid, cosmid, virus sub-genomic or genomic fragment, or other nucleic acid capable of maintaining and or replicating heterologous DNA in an expressible format. The expressible format is in the form of an RNA molecule which is then processed into a mature protein product by virtue of the cell's translation machinery. Many expression vectors are commercially available for expression in a Variety of cells. Selection of appropriate vectors is within the knowledge of those having skill in the art.

Expression vectors that contain suitable promoter sequences for expression in mammalian cells or mammals include, but are not limited to, the pcDNA vector suite supplied by Invitrogen, the pCI vector suite (Promega), the pCMV vector suite (Clontech), the pM vector (Clontech), the pSI vector (Promega), the VP16 vector (Clontech) and the pDISPLAY vectors (Invitrogen). The pDISPLAY vectors are of particular use in mammalian display studies with the expressed nucleic acid fragment targeted to the cell surface with the Igκ leader sequence, and bound to the membrane of the cell through fusion to the PDGFR transmembrane domain. The pM and VP16 vectors are of particular use in mammalian two-hybrid studies.

Numerous expression vectors for expression of recombinant polypeptides in bacterial cells and efficient ribosome binding sites have been described, such as for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio-TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer Inc., CT, USA); the pQE series of expression vectors (QIAGEN, CA, USA), or the pL series of expression vectors (Invitrogen), amongst others.

A variety of suitable expression vectors, containing suitable promoters and regulatory sequences for expression in insect cells are known in the art, and include, but are not limited to the pAC5 vector, the pDS47 vector, the pMT vector suite (Invitrogen) and the pIB vector suite (Invitrogen).

Furthermore, expression vectors comprising promoters and regulatory sequences for expression of polypeptides in plant cells are also known in the art and include, for example, a promoter selected from the group, pSS, pB1121 (Clontech), pZO1502, and pPCV701 (Kuncz et al, *Proc. Natl. Acad. Sci. USA,* 84 131-135, 1987).

Methods of cloning DNA into nucleic acid vectors for expression of encoded polypeptides are known in the art and are described for example in, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

3. Recovery of CPPs

Following cellular internalization of cell specific or cell selective CPPs, their recovery is necessary for peptide characterisation and downstream application of the respective CPP. As such, a further embodiment of the invention involves the recovery of CPPs from the interior of target cell populations following their cellular internalization. In a preferred embodiment, which is supported by the specific examples, the CPPs are presented on the surface of phage display particles. After undergoing the steps of negative and positive cell-based selection for cell specific or cell selective CPPs, and subsequent removal of cell surface bound CPPs as described supra, the target cell population are harvested and lysed by standard cell culture techniques known in the art to release internalized CPP-presenting phage. Recovered CPP-presenting phage can be used to infect *E. coli* for subsequent amplification of the CPP-presenting phage particle. Following the recovery of a sufficient amount of CPP-presenting phage, polymerase chain reaction (PCR) is performed either directly or following additional preparations for amplification of the CPP encoding nucleic acid sequence. Subsequent nucleic acid sequencing reactions are performed on PCR amplicons from which a nucleic acid sequence encoding the peptides is obtained and from which the CPP amino acid sequence can be extrapolated. Methods described above are known to those skilled in the art. See for example, Sambrook et al., "Molecular Cloning, A Laboratory Manual"; CSH Press, Cold Spring Harbor, 1989. Following recovery of the CPP amino acid sequence, bioinformatic analysis is performed for further characterisation of resulting novel cell specific or cell selective CPPs.

In an alternative embodiment of the invention, the method includes the recovery of cell internalized CPPs using a "bait-prey" approach coupled with co-immunoprecipitation (Co-IP) of the bait-prey complex. In such an embodiment the CPP is provided as a fusion to a haloalkane ligand and the target cell population is transfected with an expression vector expressing a protein tag fusion comprising a modified haloalkane dehalogenase substrate-binding domain and a protein partner. Following subsequent cell-based selection steps, CPP-haloalkane ligand successfully internalized within the target cell population and which escapes the endosome will covalently bind the modified haloalkane dehalogenase substrate-binding domain which is present in the intracellular environment and subsequently form a protein complex. Following formation of a protein complex the target cells can be lysed and the protein complex comprising the CPP recovered from the cell lysate using standard Co-IP methodologies which are known in the art. Briefly, this technique involves precipitating the protein complex out of the cell lysate using an antibody known to specifically bind the protein partner of the complex. The antibody is immobilised on a solid support such that its binding to the protein partner in the complex recovers the CPP from the lysate. Following recovery of the complex from the lysate the peptide is characterised by standard molecular techniques known in the art to obtain the amino acid sequence. Other systems may be employed for the recovery of cell specific internalized CPP including, for example, glutathione S-transferase (GST) to create the GST fusion system, FLAG octapeptide (FLAG-tag) and polyhistidine tag (His-tag).

Although historically the standard solid-phase support for immobilisation of protein complexes during immunoprecipitation is a highly-porous agarose bead (also referred to as agarose resin), alternative supports may be employed to accommodate different capture systems to suit the invention method. For example, in one embodiment the peptides screened for cell penetrating ability in a target population of cells are CPP-haloalkane ligand fusions. CPP sequences that facilitate the transit of CPP-haloalkane ligand fusions across the cell membrane may be recovered by harvesting and lysing the respective cells followed by covalently capturing CPP-haloalkane ligand fusions with modified haloalkane dehalogenase substrate-binding domain fused beads or resin.

Following immobilization of a CPP to a solid support, further detection and validation may be performed using an ELISA-based assay or other suitable detection technique. Alternatively, in another example wherein CPP presenting-phage-haloalkane ligand fusions are screened in a cell-based assay, then following immobilisation on modified haloalkane dehalogenase substrate-binding domain fused beads or resin, the CPP presenting-phage can simply be released from the bead or resin and used to infect *E. coli* for subsequent amplification of the CPP-presenting phage particle. CPP amino acid characterisation can then be performed on the *E. coli* cultures according to standard molecular techniques known in the art and previously described.

4. Identifying/Isolating CPPs Having Low Cytotoxicity.

In a preferred embodiment of the invention, the method of identifying and isolating CPPs or analog and/or derivative thereof involves an in vitro method of detecting cell penetrating peptides that display a low level of toxicity to cells e.g., mammalian cells, in amounts which are of potentially therapeutically effective value. As used herein, the term "low level of toxicity" shall be taken to mean that the CPP induces cell death in less than about 20% of cells to which it is internalized. Preferably, the peptide induces cell death in less than about 15% of cells to which it is internalized. More preferably, the peptide induces cell death in less than about 10% of cells to which it is internalized. Even more preferably, the peptide induces cell death in less than about 5% of cells to which it is internalized. Preferably, the cell used to test the toxicity is a human cell, such as, for example, an endothelial cell, or alternatively a cell that is a recognised cell model, for example, CHO cells. Accordingly, it is preferable that the CPP or analog and/or derivative thereof induces a low level toxicity in the cell to which they are internalized.

As used herein and unless otherwise indicated, the phrase "therapeutically effective" in the context of the amount of peptide is measured by the therapeutic effectiveness of the administered peptide, wherein at least one adverse effect is ameliorated or alleviated. The therapeutic effect is dependent upon the disorder being treated or the biological effect desired.

In a preferred embodiment of the method which is supported by the data presented herein, CPPs which are internalized within target cells following cell-based screens and which display a low level of cytotoxicity are identified using an assay that relies on cellular ATP content as a marker of cell viability. More specifically, ATP-based cell viability assay can include bioluminescence for detection, whereby ATP is the limiting reagent for the luciferase reaction which emits detectable light. Suitable ATP-based cell viability assays are commercially available, for example, CellTiter-Glo Luminescent Cell Viability Assay (Promega), and can be used in mammalian cells e.g., bEnd.3 and CHO, to assess cell viability and cytotoxicity of internalized CPPs or other compounds. As exemplified herein, an ATP-based cell viability assay is used to identify CPP with low level of cytotoxicity at CPP concentrations of 0 uM, 1 uM, 5 uM, 10 uM and 50 uM over incubations ranging from 2 hours to 24 hours. However, this assay can conceivably be employed to identify CPP with low level cytotoxicity at a range of peptide concentrations and incubation periods.

In an alternative embodiment of the invention, the method includes the identification of CPPs which are internalized within target cells following cell-based screens and which display a low level of cytotoxicity using vital dyes which are known in the art, such as, for example, Trypan blue. Vital dyes may be employed in the method for an exclusion assay to assess membrane integrity of cells which have internalized CPPs following cell-based screens. As used herein, the term "exclusion assay" refers to an assay for assessing cell viability by determining the number of viable cells present based on the principle that live cells possess intact cell membranes that exclude certain dyes, such as, for example, trypan blue, eosin, or propidium, whereas dead cells do not. As such, one example of the method includes an exclusion assay for differential staining of cells using a vital dye to detect viable cells which have internalized CPPs and the subsequent identification of the CPP amino acid sequence.

Although an in vitro ATP-based cell viability assay and exclusion assay are supported by the data for identifying CPPs internalized within target cells following cell-based screens and which display a low level of cytotoxicity, other methods of assessing cytotoxicity are known in the art and can be employed, for example, an LDH-release assays that determine the release of lactate dehydrogenase as an indicator of a viable cell, MTT (3-(4,5-Dimethylthiazol-2-yl)-2,5-diphenyltetrazolium bromide) and MTS (3-(4,5-dimethylthiazol-2-yl)-5-(3-carboxymethoxyphenyl)-2-(4-sulfophenyl)-2H-tetrazolium) colorimetric assays which measure potential of cells to reduce MTT and MTS to a purple formazan in viable cells, WST (water soluble tetrazolium salts) based assay which are a serious of water soluble MMT assays developed to give different absorption spectra of the formed formazans in viable cells, and electric cell substrate impedence sensing (ESIC) which measures the response of cells in real time based on the electric impedence measurements when cells are grown on gold-film electrodes. http://en.wikipedia.org/wiki/MTT_assay-cite_note-WSTs-3#cite_note-WSTs-3MTT and MTS assays are colorimetric assays for measuring the activity of enzymes that reduce MTT or close dyes e.g., XTT, MTS, or WSTs to formazan dyes, giving a purple color. Such assays provide an assessment of the viability of cells and their proliferation, and are used generally to determine cytotoxicity of potential medicaments and other agents that potentially stimulate or inhibit cell viability and growth. See e.g., Mosmann, *J. Immunol. Methods* 65, 55-63 (1983); Cory et al., *Cancer Comm.* 3, 207-212 (1991); Wilson, In: (Masters, John R. W. ed.) Animal Cell Culture: A Practical Approach. Vol. 1 (3rd ed.), Oxford University Press ISBN 978-0199637966 (1991); Bernas et al., *Cytometry* 47, 236-242 (2002).

5. CPP Production

In one embodiment, the peptides or peptide libraries for use in the invention may be readily prepared by standard, well-established solid-phase peptide synthesis (SPPS) as described by Stewart et al. (Solid Phase Peptide Synthesis, 2nd Edition, 1984, Pierce Chemical Company, Rockford, Ill.) and as described by Bodanszky and Bodanszky (The Practice of Peptide Synthesis, 1984, Springer-Verlag, New York). In another embodiment peptides of the present invention may be produced as recombinant peptides or protein or nucleic acid fusions. In a further example, the peptides of the present invention are produced as recombinant peptides or protein or as fusions with nucleic acid or other cargo molecules. In a further example, the peptides are analogs or peptides derivatives as described according to any example hereof.

5.1 Peptide Synthesis

A cell-penetrating peptide of the invention or an analog and/or derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Nα-amino protected 9-fluorenyl-methoxycarbonyl (Fmoc) amino acids described by Carpino and Han, J. Org. Chem., 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized, in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at, a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a cell-penetrating peptide of the present invention or an analog and/or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The a cell-penetrating peptides, analog and/or derivative of the present invention can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

As will be apparent to the skilled artisan based on the description herein, an analog and/or derivative of cell-penetrating peptide of the invention may comprise D-amino acids, a combination of D- and L-amino acids, and various unnatural amino acids (e.g., α-methyl-amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine. Methods for the synthesis of such peptides will be apparent to the skilled artisan based on the foregoing.

5.2 Recombinant Peptide Production

In one embodiment, a cell-penetrating peptide or analog and/or derivative thereof or fusion protein comprising same is produced as a recombinant protein. To facilitate the production of a recombinant peptide or fusion protein nucleic acid encoding same is preferably isolated or synthesized. Typically the nucleic acid encoding the constituent components of the fusion protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For example, nucleic acid (e.g., genomic DNA or RNA that is then reverse transcribed to form cDNA) from a cell or organism capable of expressing a cell-penetrating peptide of the invention is isolated using a method known in the art and cloned into a suitable vector. The vector is then introduced into a suitable organism, such as, for example, a bacterial cell. Using a nucleic acid probe from a known cell-penetrating peptides encoding gene a cell comprising the nucleic acid of interest is isolated using methods known in the art and described, for example, in Ausubel et al (In: Current Protocols in Molecular Biology. Wiley Interscience, ISBN 047 150338, 1987), Sambrook et al (In: Molecular Cloning: Molecular Cloning: A Laboratory. Manual, Cold Spring Harbor Laboratories, New York, Third Edition 2001).

Alternatively, nucleic acid encoding a cell-penetrating peptide of the invention is isolated using polymerase chain reaction (PCR). Methods of PCR are known in the art and described, for example, in Dieffenbach (ed) and Dveksler (ed) (In: PCR Primer: A Laboratory Manual, Cold Spring Harbour Laboratories, NY, 1995). Generally, for PCR two non-complementary nucleic acid primer molecules comprising at least about 20 nucleotides in length, and more preferably at least 25 nucleotides in length are hybridized to different strands of a nucleic acid template molecule, and specific nucleic acid molecule copies of the template are amplified enzymatically. Preferably, the primers hybridize to nucleic acid adjacent to a nucleic acid encoding a cell-penetrating peptide of the invention, thereby facilitating amplification of the nucleic acid that encodes the subunit. Following amplification, the amplified nucleic acid is isolated using a method known in the art and, preferably cloned into a suitable vector.

Other methods for the production of a nucleic acid of the invention will be apparent to the skilled artisan and are encompassed by the present invention.

For expressing protein by recombinant means, a protein-encoding nucleotide sequence is placed in operable connection with a promoter or other regulatory sequence capable of regulating expression in a cell-free system or cellular system. For example, nucleic acid comprising a sequence that encodes a cell-penetrating peptide of the present invention in operable connection with a suitable promoter is expressed in a suitable cell for a time and under conditions sufficient for expression to occur. Nucleic acid encoding cell-penetrating peptides of the present invention is readily derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with" "in connection with" or "operably linked to" means positioning a promoter relative to a nucleic acid (e.g., a transgene) such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/transgene and/or promoter/selectable marker gene combinations), it is generally preferred to position the promoter at a distance from the gene transcription start site that is approximately the same as the distance between that promoter and the nucleic acid it controls in its natural setting, e.g., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in. Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, Nature 292, 128, 1981); pKK173-3 (Amann and Brosius, Gene 40, 183, 1985), pET-3 (Studier and Moffat, J. Mol. Biol. 189, 113, 1986); the pCR vector suite (Invitrogen), pGEM-T Easy vectors (Promega), the pL expression vector suite (Invitrogen) the pBAD/TOPO or pBAD/thio-TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRatkneo (Muller et al., *Mol. Cell. Biol.*, 11, 1785, 1991).

A wide range of additional host/vector systems suitable for expressing a cell-penetrating peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

5.3 Peptide/Analog/Derivative/Fusion Protein Isolation

Following production/expression/synthesis, a cell-penetrating peptide of the invention or derivative or analog thereof or fusion protein comprising same is purified using a method known in the art. Such purification preferably provides a peptide of the invention substantially free of conspecific protein, acids, lipids, carbohydrates, and the like. Antibodies and other affinity ligands are particularly preferred for producing isolated protein. Preferably, the protein will be in a preparation wherein more than about 90% (e.g. 95%, 98% or 99%) of the protein in the preparation is a cell-penetrating peptide of the invention or derivative or analog thereof or fusion protein comprising same.

Standard methods of peptide purification are employed to obtain an isolated peptide of the invention, including but not limited to various high-pressure (or performance) liquid chromatography (HPLC) and non-HPLC peptide isolation protocols, such as size exclusion chromatography, ion exchange chromatography, phase separation methods, electrophoretic separations, precipitation methods, salting in/out methods, immunochromatography, and/or other methods.

A preferred method of isolating peptide compounds useful in compositions and methods of the invention employs reversed-phase HPLC using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate a peptide based on its charge.

Alternatively, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is preferably immobilized on a solid support. A sample comprising a fusion protein is then contacted to the immobilized antibody or compound for a time and under conditions sufficient for binding to occur. Following washing to remove any unbound or non-specifically bound protein, the fusion protein is eluted.

The degree of purity of the peptide compound may be determined by various methods, including identification of a major large peak on HPLC. A peptide compound that produces a single peak that is at least 95% of the input material on an HPLC column is preferred. Even more preferable is a polypeptide that produces a single peak that is at least 97%, at least 98%, at least 99% or even 99.5% of the input material on an HPLC column.

To ensure that a peptide obtained using any of the techniques described above is the desired peptide for use in compositions and methods of the present invention, analysis of the composition of the peptide is determined by any of a variety of analytical methods known in the art. Such composition analysis may be conducted using high resolution mass spectrometry to determine the molecular weight of the peptide. Alternatively, the amino acid content of a peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine the sequence of the peptide. Since some of the peptide compounds contain amino and/or carboxyl terminal capping groups, it may be necessary to remove the capping group or the capped amino acid residue prior to a sequence analysis. Thin-layer chromatographic methods may also be used to authenticate one or more constituent groups or residues of a desired peptide.

5.4 Derivatives and Analogs

In a preferred embodiment, the present invention provides an cell-penetrating peptides comprising at least seven or eight or ten or fifteen or twenty amino acids of an amino acid selected from the group consisting of SEQ ID NOs: 1-27, or selected or grouped according to any example hereof, including any one or more of said SEQ ID NOs. Preferably, the peptide comprises at least about ten amino acids of an amino acid selected from the group consisting of SEQ ID NOs: 1-27, or selected or grouped according to any example hereof including any one or more of said SEQ ID NOs. More preferably, the peptide comprises at least fifteen amino acids of an amino acid selected from the group consisting of SEQ ID NOs: 1-27, or selected or grouped according to any example hereof including any one or more of said SEQ ID NOs. Still more preferably, the peptide comprises at least twenty amino acids of an amino acid selected from the group consisting of SEQ ID NOs: 1-27, or selected or grouped according to any example hereof including any one or more of said SEQ ID NOs.

Preferably, the cell-penetrating peptides, analog and/or derivative comprises an amino acid sequence at least about 65% identical to an amino acid selected from the group consisting of SEQ ID NOs: 1-27 or selected or grouped according to any example hereof, including any one or more of said SEQ ID NOs. Preferably, the degree of sequence identity is at least about 70%. More preferably, the degree of sequence identity is at least about 75%. Even more preferably, the degree of sequence identity is at least about 80%. Still more preferably, the degree of sequence identity is at least about 85%. Even more preferably, the degree of sequence identity is at least about 90%. Still more preferably, the degree of sequence identity is at least about 95%. Still more preferably, the degree of sequence identity is at least about 99%, for example, 100%.

In determining whether or not two amino acid sequences fall within the defined percentage identity limits supra, those skilled in the art will be aware that it is possible to conduct a side-by-side comparison of the amino acid sequences. In such comparisons or alignments, differences will arise in the positioning of non-identical residues depending upon the algorithm used to perform the alignment. In the present context, references to percentage identities and similarities between two or more amino acid sequences shall be taken to refer to the number of identical and similar residues respectively, between said sequences as determined using any standard algorithm known to those skilled in the art. In particular, amino acid identities and similarities are calculated using software of the Computer Genetics Group, Inc., University Research Park, Madison, Wis., United States of America, e.g., using the GAP program of Devereaux et al., *Nucl. Acids Res.* 12, 387-395, 1984, which utilizes the algorithm of Needleman and Wunsch, *J. Mol. Biol.* 48, 443-453, 1970.

Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment.

Alternatively, a suite of commonly used and freely available sequence comparison algorithms is provided by the National Center for Biotechnology Information (NCBI) Basic Local Alignment Search Tool (BLAST) (Altschul et al. *J. Mol. Biol.* 215: 403-410, 1990), which is available from several sources, including the NCBI, Bethesda, Md. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

As used herein the term "NCBI" shall be taken to mean the database of the National Center for Biotechnology Information at the National Library of Medicine at the National Institutes of Health of the Government of the United States of America, Bethesda, Md., 20894.

In this respect, non-natural amino acids shall be considered to be identical to their natural counterparts. Accordingly, a peptide comprising only non-natural amino acids (e.g., D-amino acids) equivalent to those set forth in any one of SEQ ID NOs: 1-27, SEQ ID NOs: 1-27, or any one or more of SEQ ID NOs: 1, 2, 9, 14-16, 18, and 19, or any one or more of SEQ ID NOs: 1, 2, 9, 14-16, 18, 19 and 24-26, or any one or more of SEQ ID NOs: 1, 2, 5, 9, 14-16, 18, and 19, or any one or more of SEQ ID NOs: 1, 2, 5, 9, 14-16, 18, 19 and 24-26, or any one or more of any one or more of SEQ ID NOs: 1, 2, 5, 9, 14-18, and 20-23, or any one or more of SEQ ID NOs: 3-8, 10-13, 17, and 20-23, or any one or more of any one or more of SEQ ID NOs: 1, 2, 5, 9, 14-16, 18, and 20-23, or any one or more of SEQ ID NOs: 3-8, 10-13, and 17, or any one or more of SEQ ID NOs: 3-8, 16-13, 17, 20-23, and 27, or any one or more of SEQ ID NOs: 3, 4, 6-8, 10-13, 17, or 19, or any one or more of SEQ ID NOs: 3, 4, 6-8, 10-13 or 19, or any one or more of SEQ ID NOs: 1, 2, 5, 9, 14-18, or 24-27, or any one or more of SEQ ID NOs: 1, 2, 5, 9, 14-16, 18, or 24-27, or any one or more of SEQ ID NOs: 1, 2, 9, 14-16, 18 and 19, or comprising or having the sequence set forth in SEQ ID NO: 17, including any one of said SEQ ID NOs, or including an analogue or derivative thereof as described according to any example hereof, shall be considered to have an amino acid sequence 100% identical to the respective sequence of SEQ ID NOs: 1-27, including any one or more of said SEQ ID NOs.

Preferably, an cell-penetrating peptide or analog and/or derivative thereof is between about 6 to about 100 residues long (or any value there between), preferably from about 15 to 75 residues (or any value there between), preferably from about 20 to about 50 residues (or any value there between), and even more preferably from about 24 to about 40 residues (or any value there between).

Suitable peptide analogs include, for example, a cell-penetrating peptide comprising one or more conservative amino acid substitutions. A "conservative amino acid substitution" is one in which the amino acid residue is replaced with an amino acid residue having a similar side chain.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), .beta.-branched side chains (e.g., threonine, valine, isoleucine) and aromatic side chains (e.g., tyrosine, phenylalanine, tryptophan, histidine).

Analogs of the peptides of the invention are intended to include compounds in which one or more amino acids of the peptide structure are substituted with a homologous amino acid such that the properties of the original modulator are maintained. Preferably conservative amino acid substitutions are made at one or more amino acid residues.

The importance of the hydropathic amino acid index in conferring interactive biological function on a protein is generally understood in the art (Kyte & Doolittle, J. Mol. Biol. 157, 105-132, 1982). It is known that certain amino acids may be substituted for other amino acids having a similar hydropathic index or score and still retain a similar biological activity, for example, the ability to bind to a membrane of an organism or translocate a cell membrane. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within +/−0.2 is preferred. More preferably, the substitution will involve amino acids having hydropathic indices within +/−0.1, and more preferably within about +/−0.05.

It is also understood in the art that the substitution of like amino acids is made effectively on the basis of hydrophilicity. As detailed in U.S. Pat. No. 4,554,101, the following hydrophilicity values have been assigned to amino acid residues: arginine (+3.0); lysine (+3.0); aspartate (+3.0+/− 0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05

The present invention also contemplates non-conservative amino acid changes. For example, of particular interest are substitutions of charged amino acids with another charged amino acid and with neutral or positively charged amino acids. Preferably, the latter of these substitutions results in a cell-penetrating peptide analog having reduced positive charge, thereby improving the characteristics of the cell-penetrating peptide.

Additional preferred peptide analogs have reduced immunogenicity compared to a cell-penetrating peptide of the invention. Alternatively, or in addition, a preferred peptide analog has enhanced stability compared to cell-penetrating peptides of the invention.

It also is contemplated that other sterically similar compounds may be formulated to mimic the key portions of the peptide structure. Such compounds, which may be termed peptidomimetics, may be used in the same manner as the peptides of the invention and hence are also analogs of a peptide of the invention. The generation of such an analog may be achieved by the techniques of modeling and chemical design known to those of skill in the art. It will be understood that all such sterically similar cell-penetrating peptide analogs fall within the scope of the present invention.

Another method for determining the "equivalence" of modified peptides involves a functional approach. For example, a given peptide analog is tested for its cell penetrating ability e.g., using any cell-based screening method described herein.

Particularly preferred analogs of a peptide of the invention will comprise one or more non-naturally occurring amino acids or amino acid analogs. For example, a cell-penetrating peptide of the invention may comprise one or more naturally occurring non-genetically encoded L-amino acids, synthetic L-amino acids or D-enantiomers of an amino acid. For example, the peptide comprises only D-amino acids. More particularly, the analog may comprise one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, p-aminophenylalanine, N-methylvaline, homocysteine, homoserine, ε-amino hexanoic acid, δ-amino valeric acid, 2,3-diaminobutyric acid and mixtures thereof.

Commonly-encountered amino acids that are not genetically encoded and which can be present, or substituted for an amino acid in an analog of cell-penetrating peptides of the invention include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer).

Other amino acid residues that are useful for making the peptides and peptide analogs described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (e.g., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ[CONR]), or backbone cross-linking to construct lactams and other cyclic structures. Other derivatives of the peptides of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another embodiment, the peptide analog is a retro peptide analog (Goodman et al., Accounts of Chemical Research, 12:1-7, 1979). A retro peptide analog comprises a reversed amino acid sequence of cell-penetrating peptides of the present invention.

In a preferred embodiment, an analog of a cell-penetrating peptide of the invention is a retro-inverted peptide (Sela and Zisman, FASEB J. 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverted peptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved.

An advantage of retro-inverted peptides is their enhanced activity in vivo due to improved resistance to proteolytic degradation, e.g., the peptide has enhanced stability. (e.g., Chorev et al., Trends Biotech. 13, 438-445, 1995).

Retro-inverted peptide analogs may be complete or partial. Complete retro-inverted peptides are those in which a complete sequence of a cell-penetrating peptide of the invention is reversed and the chirality of each amino acid in a sequence is inverted. Partial retro-inverted peptide analogs are those in which some or all of the peptide bonds are reversed (e.g., completely reversed sequence) and the chirality of some, but not all, amino acid residues is inverted in which the N-terminal and C-terminal amino acid residues are D-amino acids and the entire sequence is reversed relative to the base peptide sequence. Partial retro-inverted peptide analogs can also have only some of the peptide bonds are reversed and the chirality of only those amino acid residues in the reversed portion inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverted peptide analogs.

In another embodiment, an analog of a peptide is modified to reduce the immunogenicity of said analog. Such reduced immunogenicity is useful for a peptide that is to be injected into a subject. Methods for reducing the immunogenicity of a peptide will be apparent to the skilled artisan. For example, an antigenic region of a peptide is predicted using a method known in the art and described, for example, in Kolaskar and Tongaonkar FEBS Letters, 276: 172-174, 1990. Any identified antigenic region may then be modified to reduce the immunogenicity of a peptide analog, provided that said analog is a cell-penetrating peptide analog.

Alternatively, or in addition, Tangri et al., The Journal of Immunology, 174: 3187-3196, 2005, describe a process for identifying an antigenic site in a peptide and modifying said site to thereby reduce the immunogenicity of the protein without significantly reducing the activity of said protein. The approach is based on 1) the identification of immune-dominant epitopes, e.g., by determining binding to purified HLA molecules; and 2) reducing their binding affinity to HLA-DR molecules to levels below those associated with naturally occurring helper T lymphocyte epitopes. Generally, the approach is based on quantitative determination of HLA-DR binding affinity coupled with confirmation of these epitopes by in vitro immunogenicity testing.

Preferred derivatives include, for example, a fragment or processed form of an cell-penetrating peptide of the invention. Preferred derivatives have reduced immunogenicity. For example, by deleting an antigenic determinant from a cell-penetrating peptide of the invention, a derivative is produced having reduced immunogenicity.

Alternatively, or in addition, a preferred derivative of a cell-penetrating peptide of the invention has enhanced cell penetrating capability.

Alternatively, or in addition, a preferred derivative of a cell-penetrating peptide of the invention has enhanced stability Methods for producing additional derivatives of a cell-penetrating peptide of the invention will be apparent to the skilled artisan and include recombinant methods. For example, a nucleic acid encoding a cell-penetrating peptide of the invention or an analog thereof is amplified using mutagenic. PCR and the resulting nucleic acid expressed to produce a peptide using a method known in the art and/or described herein.

In a preferred embodiment, the nucleic acid fragments are modified by amplifying a nucleic acid fragment using mutagenic PCR. Such methods include a process selected from the group consisting of (i) performing the PCR reaction in the presence of manganese; and (ii) performing the PCR in the presence of a concentration of dNTPs sufficient to result in mis-incorporation of nucleotides.

Methods of inducing random mutations using PCR are known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene).

In one embodiment, PCR reactions are performed in the presence of at least about 200 µM manganese or a salt thereof, more preferably at least about 300 µM manganese or a salt thereof, or even more preferably at least about 500 µM or at least about 600 µM manganese or a salt thereof. Such concentrations manganese ion or a manganese salt induce from about 2 mutations per 1000 base pairs (bp) to about 10 mutations every 1000 bp of amplified nucleic acid (Leung et al *Technique* 1, 11-15, 1989).

In another embodiment, PCR reactions are performed in the presence of an elevated or increased or high concentration of dGTP. It is preferred that the concentration of dGTP is at least about 25 µM, or more preferably between about 50 µM and about 100 µM. Even more preferably the concentration of dGTP is between about 100 µM and about 150 µM, and still more preferably between about 150 µM and about 200 µM. Such high concentrations of dGTP result in the mis-incorporation of nucleotides into PCR products at a rate of between about 1 nucleotide and about 3 nucleotides every 1000 bp of amplified nucleic acid (Shafkhani et al *BioTechniques* 23, 304-306, 1997).

PCR-based mutagenesis is preferred for the mutation of the nucleic acid fragments of the present invention, as increased mutation rates are achieved by performing additional rounds of PCR.

Alternatively, or in addition, a nucleic acid encoding a cell-penetrating peptide of the invention or a derivative thereof is inserted or introduced into a host cell that is capable of mutating nucleic acid. Such host cells are generally deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are known in the art, such as, for example the XL-1Red, XL-mutS and XL-mutS-Kanr bacterial cells (Stratagene).

Alternatively the nucleic acid is cloned into a nucleic acid vector that is preferentially replicated in a bacterial cell by the repair polymerase, Pol I. By way of exemplification, a Pol I variant strain will induce a high level of mutations in the introduced nucleic acid vector, thereby enhancing sequence diversity of the nucleic acid encoding the cell-penetrating peptides or derivative thereof. Such a method is described, for example, in Fabret et al (In: *Nucl Acid Res,* 28: 1-5 2000).

Alternatively, derivatives of a cell-penetrating peptide of the present invention can be generated through DNA shuffling, e.g., as disclosed in Stemmer, *Nature* 370:389-91, 1994, Stemmer, *Proc. Natl. Acad. Sci. USA* 91:10747-51, 1994 and WO 97/20078. Briefly, nucleic acid encoding a derivative of the invention is generated by in vitro homologous recombination by random fragmentation of a parent DNA (e.g., encoding a cell-penetrating peptide of the invention) followed by reassembly using PCR, resulting in randomly introduced mutations. This technique can be modified by using a family of parent DNAs, such as, for example, nucleic acid encoding other cell-penetrating peptide, to introduce additional variability into the process. Reassembled nucleic acids are then expressed to produce a derivative peptide and assessed for cell penetrating activity and/or reduced immunogenicity and/or resistance to degradation using a method known in the art and/or described herein. Screening for the desired activity, followed by additional iterations of mutagenesis and assay provides for rapid "evolution" of sequences by selecting for desirable mutations while simultaneously selecting against detrimental changes.

For example, a derivative of the invention is produced by combining nucleic acids encoding two or more cell-penetrating peptides of the invention, or nucleic acid encoding one or more cell-penetrating peptides of the invention and nucleic acid encoding another cell-penetrating peptide in a reaction vessel. The nucleic acids are then digested using a nuclease (e.g., DNase I). The resulting fragments are then reassembled by repeated cycles of denaturing and annealing in the presence of a DNA polymerase. Homologous regions of fragments then induce DNA replication of fragments, e.g., from different source templates, to thereby regenerate a nucleic acid encoding a peptide analog. Such a method is described, for example, in Stemmer, *Proc. Natl. Acad. Sci. USA* 91:10747-51, 1994. An analog produced using this method may then be screened for cell penetrating activity, e.g., using a method described herein.

The present invention additionally encompasses the production of a derivative of a cell-penetrating peptide of the invention by performing a combination of random mutagenesis and DNA shuffling.

Alternatively, a derivative of a cell-penetrating peptide of the invention is produced by performing site-directed mutagenesis. Suitable methods of site-directed mutagenesis are known in the art and/or described in Dieffenbach (ed) and Dveksler (ed) (In: PCR Primer: A Laboratory Manual, Cold Spring Harbour Laboratories, NY, 1995).

Peptide derivatives of the present invention also encompass a cell-penetrating peptide or an analog thereof as described herein in any embodiment that is modified to contain one or more-chemical moieties other than an amino acid. The chemical moiety may be linked covalently to the peptide or analog e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound (e.g., its cell penetrating activity).

An "amino terminal capping group" of a peptide compound described herein is any chemical compound or moiety that is covalently linked or conjugated to the amino terminal amino acid residue of a peptide or analog. An amino-terminal capping group may be useful to inhibit or prevent intramolecular cyclization or intermolecular polymerization, to protect the amino terminus from an undesirable reaction with other molecules, or to provide a combination of these properties. A peptide compound of this invention that possesses an amino terminal capping group may possess other beneficial activities as compared with the uncapped peptide, such as enhanced efficacy or reduced side effects. Examples of amino terminal capping groups that are useful in preparing peptide derivatives according to the invention include, but are not limited to, 1 to 6 naturally occurring L-amino acid residues, preferably, 1-6 lysine residues, 1-6 arginine residues, or a combination of lysine and arginine residues; urethanes; urea compounds; lipoic acid ("Lip"); glucose-3-O-glycolic acid moiety ("Gga"); or an acyl group that is covalently linked to the amino terminal amino acid residue of a peptide, wherein such acyl groups useful in the compositions of the invention may have a carbonyl group and a hydrocarbon chain that ranges from one carbon atom (e.g., as in an acetyl moiety) to up to 25 carbons (e.g., palmitoyl group, "Palm" (16:0) and docosahexaenoyl group, "DHA" (C22:6-3)). Furthermore, the carbon chain of the acyl group may be saturated, as in Palm, or unsaturated, as in DHA. It is understood that when an acid, such as docosahexaenoic acid, palmitic acid, or lipoic acid is designated as an amino terminal capping group, the resultant peptide compound is the condensed product of the uncapped peptide and the acid.

A "carboxy terminal capping group" of a peptide compound described herein is any chemical compound or moiety that is covalently linked or conjugated to the carboxy terminal amino acid residue of the peptide compound. The primary purpose of such a carboxy terminal capping group is to inhibit or prevent intramolecular cyclization or intermolecular polymerization, to promote transport of the peptide compound across the blood-brain barrier, and to provide a combination of these properties. A peptide compound of this invention possessing a carboxy terminal capping group may also possess other beneficial activities as compared with the uncapped peptide, such as enhanced efficacy, reduced side effects, enhanced hydrophilicity, enhanced hydrophobicity. Carboxy terminal capping groups that are particularly useful in the peptide compounds described herein include primary or secondary amines that are linked by an amide bond to the α-carboxyl group of the carboxy terminal amino acid of the peptide compound. Other carboxy terminal capping groups useful in the invention include aliphatic primary and secondary alcohols and aromatic phenolic derivatives, including flavenoids, with 1 to 26 carbon atoms, which form esters when linked to the carboxylic acid group of the carboxy terminal amino acid residue of a peptide compound described herein.

Other chemical modifications of a peptide or analog, include, for example, glycosylation, acetylation (including N-terminal acetylation), carboxylation, carbonylation, phosphorylation, PEGylation, amidation, addition of trans olefin, substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

As discussed in previous sections the present invention provides an additional derivative of a cell-penetrating peptide of the invention, such as, for example a fusion protein comprising one or more of the cell-penetrating peptides and/or analogs of the invention. For example, the cell-penetrating peptide or analog is fused to a tag or label. Such a tag or label may have a varied role, but may facilitate purification, isolation, detection, immobilization and/or directed targeting of the cell penetrating, peptide and/or analog and/or derivative or detection of the peptide, analog and/or derivative. Suitable tags will be apparent to the skilled artisan and include, for example, influenza virus hemagglutinin tag (HA tag), Simian Virus 5 tag (V5 tag), polyhistidine tag (his tag), FLAG tag or haloalkane tag. Indeed the use of a haloalkane ligand is exemplified herein.

6 Pharmaceutical Formulations

Cell-penetrating peptides, and analogs and derivatives thereof, as described according to any example hereof, are useful in treatment of a range of diseases and/or disorders, particularly where drugs compounds are not able to permeate the cell membrane unassisted or where efficacy and/or efficiency of drug delivery to the intracellular environment is poor. As such, the present invention encompasses the use of any one or combination of a cell-penetrating peptide or a derivative or analog thereof according to any example hereof in medicine. Additionally, the present invention encompasses a cell-penetrating peptide or a derivative or analog thereof according to any example hereof when identified or isolated by a method or process of the present invention and used in medicine.

A cell-penetrating peptide, or an analog and/or derivative thereof, is readily formulated into a composition for administration. Preferably, the composition is a pharmaceutical composition.

To prepare pharmaceutical or sterile compositions including a cell-penetrating peptide, analog, or any derivative thereof, the cell-penetrating peptide is attached to a therapeutic compound and mixed with a pharmaceutically acceptable carrier or excipient. Compositions comprising a cell-penetrating peptide are prepared, for example, by conjugating the cell-penetrating peptide to the therapeutic compound and mixing this with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

As used herein the terms "therapeutic compound" or "therapeutic agent" shall broadly mean any substance which is intended to furnish pharmacological activity or other direct effect in the diagnosis, cure, mitigation, treatment, or prevention of disease or to affect the structure and function of the body or other biological system. These substances may include but are not limited to, for example, nucleic acid molecules, peptides and proteins, small molecules and macromolecule.

One embodiment of the present invention provides a pharmaceutical composition wherein cell-penetrating peptides are provided for the delivery of nucleic acids to cells in vivo or in vitro. In some embodiments, for example, the nucleic acid may have therapeutic activity and may not by itself be able to enter the interior of a cell, but is able to enter the interior of a cell when delivered with a cell-penetrating peptide. In other embodiments, for example, the nucleic acids in accordance with the invention may not by themselves have therapeutic activity but may direct expression of an RNA and/or protein that has therapeutic activity.

As used herein, the term "nucleic acid" in its broadest sense, includes any compound and/or substance that is or can be incorporated into an oligonucleotide chain, whether they are synthetic or naturally-occurring entities that have been isolated from their natural environments. Exemplary nucleic acids which may be candidates for CPP-mediated intracellular delivery for use in formulating a pharmaceutical composition in accordance with the present invention may include, but is not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers and expression vectors.

Formulation of a pharmaceutical compound may comprise cell-penetrating peptides provided for the delivery of nucleic acids which include agents that mediate RNA interference (RNAi). RNAi is a mechanism that inhibits expression of specific genes. RNAi typically inhibits gene expression at the level of translation, but can function by inhibiting gene expression at the level of transcription. RNAi targets include any RNA that might be present in cells, including but not limited to, cellular transcripts, pathogen transcripts e.g., from viruses, bacteria, fungi etc., transposons and vectors.

As used herein, the term "RNAi agent" refers to an RNA molecule, optionally including one or more nucleotide analogs or modifications, having a structure characteristic of molecules that can mediate inhibition of gene expression through an RNAi mechanism. Exemplary RNAi agents can include, for example, short interfering RNA (siRNA), short hairpin RNA (shRNA), and/or micro RNA (miRNA) that induce an RNAi affect.

As used herein, the term "RNAi-inducing agent" encompasses any entity that delivers, regulates, and/or modifies the activity of an RNAi agent e.g., an RNAi expression vector which expresses one or more RNAs that self-hybridize or hybridize to each other to form an RNAi agent e.g., siRNA, shRNA, and/or miRNA.

As used herein, an "siRNA" refers to an RNAi agent comprising an RNA duplex (referred to herein as a "duplex region") that is approximately 19 base pairs (bp) in length and optionally further comprises one or two single-stranded overhangs.

As used herein, an "shRNA" refers to an RNAi agent in a stemloop form comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop.

As used herein, a "microRNA" or "miRNAs" refers to an RNAi agent comprising genomically encoded non-coding RNAs of about 21-23 nucleotides in length that help regulate gene expression.

In some embodiments, nucleic acids which are suitable for attachment to cell-penetrating peptides for formulation of a pharmaceutical composition include antisense RNAs. As referred to herein, "antisense RNAs" are typically RNA strands of various length that bind to target transcripts and block their translation e.g., either through degradation of mRNA and/or by sterically blocking critical steps of the translation process.

Formulation of a pharmaceutical compound may also comprise cell-penetrating peptides for the delivery of ribozymes or deoxyribozymes. As referred to herein, a "ribozyme" (from ribonucleic acid enzyme; also called RNA enzyme or catalytic RNA) is an RNA molecule that catalyzes a chemical reaction. As used herein, "Deoxyribozymes" are DNAs that bind to RNA substrates, typically via Watson-Crick base pairing, and site-specifically cleave target transcripts, similarly to ribozymes.

In another example, a nucleic acids which is suitable for attachment to cell-penetrating peptides for formulation of a pharmaceutical composition includes aptamers. As used herein "aptamers" are oligonucleic acid molecules that exhibit binding activity towards specific target molecules owing to their three-dimensional structure. An example of aptamers for use in treatment includes, but is not limited to, age-related macular degeneration (AMD). See MACUGEN (OSI Pharmaceuticals).

Other exemplified therapeutic agents which are candidates for CPP-mediated intracellular delivery in accordance with the invention for use in formulating a pharmaceutical composition include proteins or peptides. In some embodiments, the protein or peptide may have therapeutic activity and is unable to cross the plasma membrane unassisted. In other embodiments, the protein or peptide may not be capable to cross the plasma membrane with high efficiency and/or efficacy. The cell-penetrating peptides in accordance with the invention may themselves have therapeutic activity.

Other exemplified therapeutic agents which are candidates for CPP-mediated intracellular delivery in accordance with the invention for use in formulating a pharmaceutical composition include small molecule and macromolecule. In a preferred embodiment, the small molecule or macromolecule are unable to transit the cell membrane unassisted. Preferably, though not necessarily, the drug is one that has already been deemed safe and effective for use in humans or animals by the appropriate governmental agency or regulatory body. All listed drugs are considered acceptable for use in accordance with the present invention.

Formulation of a pharmaceutical compound will vary according to the route of administration selected (e.g., solution, emulsion, capsule). For solutions or emulsion's, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the active compound is a peptidyl compound, it may be possible and desirable for it to be administered via in vivo expression of the recombinant protein. In vivo expression can be accomplished via somatic cell expression according to suitable methods (see, e.g. U.S.

Pat. No. 5,399,346). In this embodiment, nucleic, acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, dimethyl sulfoxide (DMSO), and glycols are preferred liquid carriers, particularly (when isotonic) for solutions. Suitable pharmaceutical carriers and excipients include starch, cellulose, glucose, lactose, sucrose, gelatin, malt, rice, fluor, chalk, silica gel, magnesium stearate, sodium stearate, glycerol monostearate, sodium chloride, glycerol, propylene glycol, water, ethanol, and the like.

The skilled artisan will be aware that a suitable carrier or excipient should not inhibit the cell penetrating ability of CPP or its associated compound.

The formulations can be subjected to conventional pharmaceutical expedients, such as sterilization, and can contain a conventional pharmaceutical additive, such as a preservative and/or a stabilizing agent and/or a wetting agent and/or an emulsifying agent and/or a salt for adjusting osmotic pressure and/or a buffer and/or other additives known in the art. Other acceptable components in the composition of the invention include, but are not limited to, isotonicity-modifying agents such as water and/or saline and/or a buffer including phosphate, citrate, succinate, acetic acid, or other organic acids or their salts.

In an example, a formulation includes one or more stabilizers, reducing agents, anti-oxidants and/or anti-oxidant chelating agents. The use of buffers, stabilizers, reducing agents, anti-oxidants and chelating agents in the preparation of compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In another example, a formulation as described herein according to any embodiment additionally comprises a compound that enhances or facilitates uptake of a compound. Suitable enhancers are, for example, a lipid disrupting agent (LDA), a solubility enhancer, or a surfactant.

LDAs are typically fatty acid-like molecules proposed to fluidize lipids in the human skin membrane. Suitable LDAs are described, for example, in Francoeur et al., *Pharm. Res.*, 7: 621-627, 1990 and U.S. Pat. No. 5,503,843. For example, a suitable LDA is a long hydrocarbon chain with a cis-unsaturated carbon-carbon double bond. These molecules have been shown to increase the fluidity of the lipids, thereby increasing drug transport. For example, oleic acid, oleyl alcohol, decanoic acid, and butene diol are useful LDAs.

Solubility enhancers act by increasing the maximum concentration of drug in a composition, thus creating a larger concentration gradient for diffusion. For example, a lipophilic vehicle isopropyl myristate (IPM) or an organic solvent ethanol or N-methylpyrrolidone (NMP) or dimethyl sulfoxide (DMSO) are suitable solubility enhancers (Liu et al., *Pharm. Res.* 8: 938-944, 1991; and Yoneto et al., *J. Pharm. Sci.* 84: 853-860, 1995).

Surfactants are amphiphilic molecules capable of interacting with the polar and lipid groups in the skin. These molecules have affinity to both hydrophilic and hydrophobic groups, which facilitate in traversing complex regions of the dermis. Suitable surfactants include, for example, an anionic surfactant lauryl sulfate (SDS) or a nonionic surfactant polysorbate 80 (Tween 80). Suitable surfactants are described, for example, in Sarpotdar et al., *J. Pharm. Sci.* 75: 176-181, 1986)

In another example, the formulation is a microemulsion. Characteristics of such microemulsion systems are submicron droplet size, thermodynamic stability, optical transparency, and solubility of both hydrophilic and hydrophobic components. Microemulsion systems have been shown to be useful for delivery of compounds and to exhibit improved solubility of hydrophobic drugs as well as sustained release profiles (Lawrence, et. al. *Int. Journal of Pharmaceutics* 111: 63-72, 1998).

In another example, a formulation comprises a peptidyl moiety conjugated to a hydrolysable polyethylene glycol (PEG) essentially as described by Tsubery et al., *J. Biol. Chem.* 279 (37) pp. 38118-38124. Without being bound by any theory or mode of action, such formulations provide for extended or longer half-life of the cell-penetrating peptide moiety in circulation.

In another example, a formulation comprises a nanoparticle comprising the cell-penetrating peptide moiety and other active ingredient bound to it or encapsulated within it. Without being bound by any theory or mode of action, delivery of a peptidyl composition from a nanoparticle may reduce renal clearance of the peptide(s).

In another example, a formulation comprises a liposome carrier or excipient to facilitate uptake of an inhibitor into a cell. Liposomes are considered to interact with a cell by stable absorption, endocytosis, lipid transfer, and/or fusion (Egerdie et al., *J. Urol.* 142:390, 1989). For example, liposomes comprise molecular films, which fuse with cells and provide optimal conditions for wound healing (K. Reimer et al., *Dermatology* 195(suppl. 2):93, 1999). Generally, liposomes have low antigenicity and can be used to encapsulate and deliver components that cause undesirable immune responses in patients (Natsume et al., *Jpn. J. Cancer Res.* 91:363-367, 2000)

For example, anionic or neutral liposomes often possess excellent colloidal stability, since substantially no aggregation occurs between the carrier and the environment. Consequently their biodistribution is excellent, and their potential for irritation and cytotoxicity is low.

Alternatively, cationic liposomal systems, e.g. as described in Mauer et al., *Molecular Membrane Biology*, 16: 129-140, 1999 or Maeidan et al., *BBA* 1464: 251-261, 2000 are useful for delivering compounds into a cell. Such cationic systems provide high loading efficiencies. Moreover, PEGylated cationic liposomes show enhanced circulation times in vivo (Semple *BBA* 1510, 152-166, 2001).

Amphoteric liposomes are a recently described class of liposomes having an anionic or neutral charge at pH 7.4 and a cationic charge at pH 4. Examples of these liposomes are described, for example, in WO 02/066490, WO 02/066012 and WO 03/070735. Amphoteric liposomes have been found to have a good biodistribution and to be well tolerated in animals and they can encapsulate nucleic acid molecules with high efficiency.

U.S. Ser. No. 09/738,046 and U.S. Ser. No. 10/218,797 describe liposomes suitable for the delivery of peptides or proteins into a cell.

Injectable formulations comprising cell-penetrating peptide(s) of the invention or other active ingredient and a suitable carrier or excipient preferably have improved stability and/or rapid onset of action, and are for intravenous, subcutaneous, intradermal or intramuscular injection.

For parenteral administration, the peptidyl component and other active ingredient, may be administered as injectable doses of a solution or suspension in a physiologically acceptable diluent with a pharmaceutical carrier which can be a sterile liquid such as water or oil e.g., petroleum, animal, vegetable or synthetic oil including any one or more of peanut oil, soybean oil, mineral oil, etc. Surfactant and other pharmaceutically acceptable adjuvants or excipients may be included. In general, water, saline, aqueous dextrose or other related sugar solution, ethanol or glycol e.g., polyethylene glycol or propylene glycol, is a preferred carrier.

Formulations may also contain a chelator e.g., EDTA, and/or a dissolution agent e.g., citric acid. Such components may assist rapid absorption of the active ingredient into the blood stream when administered by injection.

One or more solubilizing agents may be included in the formulation to promote dissolution in aqueous media. Suitable solubilizing agents include e.g., wetting agents such as polysorbates, glycerin, a poloxamer, non-ionic surfactant, ionic surfactant, food acid, food base e.g., sodium bicarbonate, or an alcohol. Buffer salts may also be included for pH control.

Stabilizers are used to inhibit or retard drug decomposition reactions in storage or in vivo which include, by way of example, oxidative reactions, hydrolysis and proteolysis. A number of stabilizers may be used e.g., protease inhibitors, polysaccharides such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semi-synthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. In one example, the stabilizer may be a combination of glycerol, bacteriostatic agents and isotonic agents.

In one example, the peptidyl component or other active ingredient of an injectable formulation is provided as a dry powder in a sterile vial or ampoule. This is mixed with a pharmaceutically acceptable carrier, excipient, and other components of the formulation shortly before or at the time of administration. Such an injectable formulation is produced by mixing components such as a carrier and/or excipient e.g., saline and/or glycerol and/or dissolution agent and/or chelator etc to form a solution to produce a "diluent", and then and sterilizing the diluent e.g., by heat or filtration. The peptidyl component or other active agent is added separately to sterile water to form a solution, sterile-filtered, and a designated amount is placed into each of a number of separate sterile injection bottles. The peptide or other active agent solution is then lyophilized to form a powder and stored e.g., separately from the diluent to retain its stability. Prior to administration, the diluent is added to the injection bottle containing the dried peptidyl component or other active agent. After the predetermined amount of formulation is injected into the patient, the remaining solution may be stored, e.g., frozen or refrigerated.

In another example, the formulation is prepared as a frozen mixture ready for use upon thawing. For example, the peptidyl component or other active agent is combined with the diluent, sterile filtered into multi-use injection bottles or ampoules and frozen prior to use.

In another example of the invention, a formulation comprises an additional component or compound e.g., a compound associated with increased re-epithelialization. For example, the formulation can comprise a growth factor, such as, for example, transforming growth factor β and/or platelet derived growth factor and/or nerve growth factor and/or heparin binding epidermal growth factor and/or epidermal growth factor and/or keratinocyte growth factor and/or platelet derived activating factor and/or platelet derived epithelial growth factor and/or a fibroblast growth factor an/or a keratinocyte growth factor. For example, Puolakkainen et al., *J. Surg. Res.*, 58: 321-329, 1995 describe formulations comprising transforming growth factor β; compositions comprising platelet derived growth factor have been described by Lepisto et al., *J. Surg. Res.*, 53: 596-601, 1992; formulations comprising fibroblast growth factor are described, for example, in Brown et al., *Surg.*, 121: 372-380, 1997; formulations comprising nerve growth factor are described in, for example, Matsuda et al., *J. Exp. Med.*, 187: 297-306, 1998.

Modes of Administration

The present invention contemplates any mode of administration of a medicament or formulation as described herein, however one or a plurality of intranasal and/or injected doses is preferred. Combinations of different administration routes are also encompassed e.g., intranasal and intravenous injection.

The skilled person will understand that selecting an administration regimen for a pharmaceutical composition depends on several factors, including the serum or tissue turnover rate of the entity, the level of symptoms, the immunogenicity of the entity, and the accessibility of the target cells in the biological matrix. Preferably, an administration regimen maximizes the amount of therapeutic compound delivered to the patient consistent with an acceptable level of side effects. Accordingly, the amount of composition delivered depends in part on the particular entity and the severity of the condition being treated.

Guidance in selecting appropriate doses of peptides are available (see, e.g., Milgrom, et al. *New Engl. J. Med.* 341:1966-1973, 1999; Slamon, et al. *New Engl. J. Med.* 344:783-792, 2001; Beniaminovitz, et al. *New Engl. J. Med.*

342:613-619, 2000; Ghosh, et al. *New Engl. J. Med.* 348: 24-32, 2003; or Lipsky, et al. *New Engl. J. Med.* 343:1594-1602, 2000).

Determination of the appropriate dose of the formulation is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of the disease and/or disorder being treated. Preferably, a compound that will be used is derived from or adapted for use in the same species as the subject targeted for treatment, thereby minimizing a humoral response to the reagent.

Standard methods are used to administer injectable formulations of the present invention.

The present invention is described further in the following non-limiting examples.

Example 1

Materials and Methods

Lyophilized Dye Stock for Labeling of Phage

Dye is solubilized in anhydrous DMSO at 5 mg/mL, and stored at −20° C. with desiccant. Frozen dye aliquots are thawed slowly to room temperature (to prevent condensation)

Preparation of Phage for Labeling

Phage are purified by two PEG precipitations, resuspended in PBS, filtered through a 0.2 µM syringe filter, and cfu/mL or pfu/mL determined. Phage are concentrated by a further PEG precipitation and resuspended in labeling buffer (50 mM sodium tetraborate/40 mM NaCl, pH 9.1 (M13) or PBS (T7)). Phage should be prepared 'fresh' (label one day after preparation). Once phage resuspended in labeling buffer, they should undergo the labeling reaction within 1-2 hours.

Labeling Reaction

For consistent level of labeling, about 200 molecules of dye per phage the following quantities were used:

$4 \times 10^{12}$ phage particles (in 50-100 µL volume)

10 µL of 5 mg/mL dye solution (=50 µg)

Phage and dyes solution were mixed and reaction proceeded overnight 12-16 h at room temperature protected from light. To increase the degree of labeling, the ratio of dye:phage is increased, however increasing dye concentration greater than 100 µg affects phage infectivity. GE Healthcare Sephacryl S-200 HR columns are used to remove unincorporated dye from phage.

Internalization of Labelled Phage Via Flow Cytometry

Trypsinized cells from T-75 flasks are counted, washed with MEM and aliquoted $1 \times 10^5$ into FACS tubes. About $1 \times 10^{12}$ phage are added per FACS sample, mixed gently and incubated for 1 h at 37° C. in 5% $CO_2$ (protected from light). Samples are centrifuged for 3 min at 500 rcf and aspirated, and the collected cells are washed with 0.5 mL 0.5% BSA/PBS. The wash is repeated twice. Samples are then incubated with staining reagent or antibody at 4° C. for 20-30 min, centrifuged, and washed as before. The staining procedure is continued until sample preparation is complete. Samples are resuspended in 300 µL 0.5% BSA/PBS, filtered through gauze before reading on BD LSRII flow cytometer. Samples are stored at 4° C. protected from light in 300 µL 0.5% BSA/PBS prior to analysis.

Reagents for Surface Staining of Cells Incubated with Phage
GeneTex, Inc. M13[E1] antibody (biotin); #GTX 17269 50 µg (1 mg/mL); Working concentration: 1 µg/$10^6$ cells
BD Pharmingen PE Streptavidin; #554061, 0.5 mg/mL; Working concentration: 5
Anti-fluorescein/OregonGreen®488 #A889/0.5 mL; rabbit IgG fraction stock 1 mg/mL
Anti-AlexaFluor®488 #A11094/0.5 mL stock; rabbit IgG fraction 1 mg/mL; Working concentration: 5 µg/mL
Novagen biotinylated T7 tag monoclonal antibody #69968/0.2 Working concentration: 2.5 µg/mL
Abcam T7 tag polyclonal antibody (rabbit) (Phycoerythrin) #AB72563/100 µg/mL; Working concentration: 2.5 µg/mL M13 Cell Bio Panning Protocol Media is aspirated from cultured cells, and the cells are washed with PBS and pre-incubated with chloroquine at 37° C. for 1-2 hours. The phage are added to the cells, and the mixtures incubated at 37° C. for 15 minutes-3 hours. The cells are washed 5 times with PBS/DMEM media solution, incubated with subtilisin at 37° C. for 1 hour, washed as before, and then detached from the culture flask and washed 3 times as before.

For binding screens, the phage are infected into *E. coli* XL-1 blue cells for 30 minutes.

For internalization screens, cells are lysed with triethylamine and neutralized, and the lysate is used to infect *E. coli* XL-1 blue cells for 30 minutes.

Eluates are titered and amplified, and used for next round of panning

T7 Cell Bio Panning Protocol

Aspirate media from cells, wash with PBS and pre-incubate cells with chloroquine at 37° C. for 1-2 hours, add phage to cells and incubate at 37° C. for 15 minutes-3 hours, wash cells 2 times with RPMI media solution, incubate cells briefly with Glycine/RPMI solution (this step omitted in cell binding screens), detach cells from flask and wash 2 times with RPMI media solution.

For binding screens: Infect whole cells into BLT5615 for 2-3 hours.

For internalization screens: Lyse cells with 1% SDS. Infect lysate into BLT5615 for 2-3 hours Then, clear T7 lysate by centrifugation, titer lysate and add PEG to remainder, and use PEG precipitate lysate for next round of panning.

Flow Cytometry Analysis of FITC-Labeled Peptides

CHO-K1 and bEnd.3 cells were seeded in 6-well plates at $5 \times 10^5$ cells/well in culture medium and incubated for 24 h at 37° C. in 5% $CO_2$. Culture media was aspirated, and cells washed once with PBS to remove debris. Then, 1 mL of media containing 10 or 20 µM of FITC-peptide was added to wells, and plates were incubated for 1 h at 37° C. in 5% $CO_2$. The cells were washed twice with 1×PBS, and 1 mL of 0.25% trypsin/EDTA added per well, and incubated at 37° C. for 4 min. Reactions were stopped by dilution of trypsin with 2 mL complete media. Cells were dislodged by gentle titration and transferred to flow cytometry tubes, washed twice with FACS buffer (0.5% BSA/0.01% $NaN_3$/PBS), collected by centrifugation for 4 min at 1500 rpm, and resuspended in 0.3 mL fixing buffer solution (1% formaldehyde in PBS). Cells were filtered through gauze before reading on BD LSRII flow cytometer.

Live Confocal Microscopy of FITC-Labeled Peptides bEnd.3 and CHO-K1 cells were seeded at $3 \times 10^4$/well and $5 \times 10^4$/well respectively, on 8-well Lab-Tek H chambered coverglass slides. Slides were incubated for 24 h prior to analysis at 37° C. at 5% $CO_2$. Wells were washed twice with medium containing 1% FBS, and 5-10 µM FITC-labeled peptide in 1% FBS media was added to wells, and cells were imaged at 30 and 60 minutes later.

Recombinant Expression of Peptide-MBP Fusion Proteins

For recombinant protein expression and purification of 6×His-MBP tagged protein constructs, 20 mL of LB media supplemented with carbenicillin (50 µg/mL) and chloramphenicol (30 µg/mL) was inoculated with transformed RoSetta 2(DE3) cells and incubated at 37° C. overnight. Then 500 mL of 2YT supplemented with the aforementioned antibiotics and 0.4% glucose was inoculated with the overnight culture. When culture growth was $OD_{595}$ at 0.6, protein expression was induced by the addition of 1.0 mM IPTG, and the culture incubated for an additional 2.0 hours. Cells were harvested by centrifugation at 4,700×g for 20 minutes, media decanted, and cells resuspended in 200 mL of PBS pH 8.0. Cells were again harvested by centrifugation at 4,700×g for 20 minutes, the PBS decanted, and cells resuspended in 50 mL of lysis buffer (PBS pH 8.0/1× Complete protease inhibitor tablet/1.0 mM PMSF). Cells were disrupted by sonication for 2×1.0 minute at 80% duty cycle, and the soluble fraction obtained from the cell lysate by centrifugation at 43,146×g for 20 minutes.

The expressed protein was isolated from the soluble fraction using MBP-Trap column on the AKTAxpress equilibrated in PBS. The column was washed with 7 volumes (35 mL) of PBS pH 8.0, and fusion protein was eluted using elution buffer (10 mM maltose/PBS pH 8.0) gradient Protein purity and integrity was assessed by electrophoresis on a 12% (w/v) SDS-polyacrylamide gel. Protein yield was determined using the bicinchoninic acid (BCA) assay.

Alexa Fluor 488 Labeling of 6×His-MBP Tagged CPPs

Protein solutions were concentrated in to a final volume of 1.0 mL. Alexa Fluor 488 (1 mg) was reconstituted in 200 µL of DMSO, and 50 µL of Alexa Fluor 488 added to 1.0 mL of protein. Reactions were incubated in the dark for 2.0 hours at room temperature. The protein/label solution was diluted to a final volume of 2.5 mL in PBS pH 8.0, loaded onto a PD10 column pre-equilibrated in PBS pH 8.0, and the flow-through discarded. The protein was eluted by addition of 3.0 mL of PBS pH 8.0. Unconjugated label is retained on the column.

Protein concentration and the degree of labeling (DOL) are determined by measuring the absorbance at 280 nm and 495 nm, and corrected for the contribution of the dye to the absorbance at A280 according to standard procedures.

Fluorescent Microscopy-Assessment of CPP in CHO and bEnd.3 Cells

CHO-K1 cells are seeded at 70,000 cells/slide chamber, and bEnd.3 cells are seeded at 40,000 cells/slide chamber. Cells are cultured for 24 h at 37° C. in 5% $CO_2$, washed with PBS 1×, and FITC-labeled peptide (10 uM) is added to cells in 10% FBS (CM).

Alternatively, cells in serum-free (SF) medium are incubated for 1 h at 37° C., washed twice in PBS, fixed in 10% formaladehyde/PBS (15 min at RT), washed as before, incubated in, 300 nM DAPI/PBS solution for 5 mM at RT, washed as before, and mounted onto slides.

Example 2

Cell Penetration Assays

Positive Cell-Penetrating Peptide (CPP) Control

A sequence previously reported to facilitate internalization into cells was chosen as a positive CPP control. RGD integrin-binding peptide was recovered from a whole-cell phage internalization screen. The positive control sequences were cloned into both M13 and T7 phage display vectors.

The CPP control sequence was successfully cloned into five different M13 phagemid display vectors (pNp8cys, pNp8, pNp3cys, pNp3, pJufop3_v2) and the T7 phage genome (Select10-3B). The integrity of all clones was confirmed via sequencing.

Phage Display of CPP Control

The efficiency of CPP display on the surface of phage was determined by ELISA. High display levels were observed for the RGD peptide, regardless of the vector system used. The RGD peptide displayed well in all vector systems and had previously been shown to facilitate internalization of phage into mammalian cells.

Labeling of Phage with Fluorophores

PEG precipitated T7 and M13 phage, were labelled with either AlexaFluor 488 (AlexaFluor® 488 carboxylic acid 2,3,5,6-tetrafluorophenyl ester 5-isomer) or Oregon Green 488 (Oregon Green® 488 carboxylic acid, succinimidyl ester 5-isomer). Approximately $10^{12}$ phage particles were incubated with 50 µg of fluorescent dye followed by purification from un-reacted dye by triple PEG precipitation or size exclusion chromatography (SEC, S200-HR). The number of dye molecules per phage particle was calculated using Beer-Lambert's Law.

Various experiments were performed to optimise i) phage recovery pre- and post labeling, and ii) the degree of labeling (DOL) to ensure maximum sensitivity while minimising the potential for label to alter phage-binding properties.

M13 and T7 phage were successfully labelled with two different fluorophores using amine-reactive chemistries and then detected using flow cytometry. A starting population of at least $4 \times 10^{12}$ phage particles was preferred to ensure sufficient phage were recovered, after labeling and purification, for detection in the flow cytometry assay. Labeling of T7 phage with either AlexaFluor 488 (AF488) or Oregon Green 488 (OG 488) yielded an extremely high number of dye molecules/phage (1000-8000). Whilst the degree of labeling (DOL) could be reduced to 500 molecules/virion, it was subsequently found that detection of T7 phage in the flow cytometry assay preferred at least 4000 dye molecules/phage. Labeling of M13 phage with either AF488 or OG 488 yielded an average of 100-400 dye molecules/phage. Increasing the amount of dye, improved the DOL/phage and overall assay sensitivity, although once a threshold of ~2000 dye molecules/phage was exceeded, a significant reduction in phage infectivity was observed (data not shown). Phage labelled with equivalent amounts of AF488 or OG488 yielded similar signal intensities in the FACS.

Labeling with fluorophores may alter the binding properties of phage in a dose-dependent manner. Wild-type phage labelled with fluorophores were found to exhibit much higher levels of non-specific binding to mammalian cells when incubated at 4° C., relative to the non-labelled phage controls. This behaviour became more pronounced when the DOL was increased, suggesting the background binding effect was mediated by the label itself (data not shown). Accordingly, this problem could be avoided by generating higher purity phage preparations. Phage could be purified by cesium chloride gradient centrifugation.

Negative Selections in SVEC-4 cells, HUVEC Cells, HepG2 Cells and CHO Cells

For negative phage selections, the mouse epithelial cell line SVEC4-10 and the human endothelial cell line HUVEC were used. In addition, the human epithelial cell line HepG2, the mouse fibroblast cell line L929 and the chinese hamster ovarian cell line, CHO-K1, were used for optimization and CPP screening (Table 2).

TABLE 2

Cell lines for phage screens and internalization assays.

| Cell line | bEnd.3 | HUV-EC-C | Hep G2 | SVEC4-10 | L929 | CHO |
|---|---|---|---|---|---|---|
| Source | ATCC | ATCC | ATCC | ATCC | In house | In house |
| Organism | mouse | human | human | mouse | mouse | Chinese hamster |
| Morphology | endothelial | endothelial | epithelial | epithelial | fibroblast | epithelial-like |
| Tissue | cerebral cortex | Umbilical vein vascular endothelium | liver | Axillary lymph-node vascular epithelium | subcutaneous connective tissue | ovary |
| Disease | endothelioma | normal | hepatocellular carcinoma | normal | normal | normal |
| Established | ✓ | ✓ | ✓ | ✓ | ✓ | ✓ |
| Scale-up | ✓ | ✓ | ✓ | ✓ | ✓ | ✓ |
| Phage screens | positive selection | negative selection | | negative selection | | trial selection |
| Peptide validation | Confocal; Flow cytometry | Flow cytometry | Flow cytometry | Flow cytometry | Flow cytometry | Confocal; Flow cytometry |

To maximise the diversity of phage display peptides, a panel of 6 different phage display libraries were screened including (i) constrained and linear libraries displayed as fusions to the M13 p3 or p8 coat proteins, (ii) a T7 library and (iii) a M13 library constructed using the high stringency pJuFo phagemid (Table 3).

Cell-based selection protocols were successfully optimized to screen phage display libraries for peptides with CPP activity in CHO and bEnd.3 cells. Optimized conditions included performing selections with adherent cells, and harvesting the cells via scraping, rather than trysinization.

To remove surface-bound M13 phage, cells were treated with the protease subtilisin, which renders M13 virions non-infective via cleavage of phage coat proteins. Treatment with 3 mg/ml of subtilisin for 60 min, at 37° C. resulted in almost complete loss of infectivity, however staining with Trypan Blue showed that cell viability was not affected by subtilisin treatment (data not shown). As T7 phage are resistant to the effects of subtilisin, the inventors developed an alternative method in which surface-bound T7 phage particles were removed by brief (<10 sec) exposure to Glycine/HCl pH2, followed immediately by neutralization with Tris pH8. No loss in cell viability was evident.

Data showed that suspended cell populations yielded much greater numbers of phage due to the fact that larger numbers of cells could be screened. However, the viability of cells screened in suspension were found to lower than for adherent cells. As cell viability was considered more important for maintaining screening quality, subsequent screens were performed using adherent cells.

The inventors also determined the impact that the different solutions used during the screening process might have on cell viability. Results showed that cell viability was best

TABLE 3 phage display libraries used for CPP selections.

| Library | Vector | Library feature | Phage | Phage system | Display | Peptide display | Library complexity |
|---|---|---|---|---|---|---|---|
| M06 | pNp8cys | constrained | M13 | phagmid | p8, polyvalent | N-terminal | $2.43 \times 10^9$ |
| M07 | pNp8 | linear | M13 | phagmid | p8, polyvalent | N-terminal | $3.41 \times 10^9$ |
| M08 | pNp3cys | constrained | M13 | phagmid | p3 monovalent | N-terminal | $1.72 \times 10^9$ |
| M09 | pNp3 | linear | M13 | phagmid | p3 monovalent | N-terminal | $3.59 \times 10^9$ |
| M11 | pJuFo(p3)_v2 | linear | M13 | phagmid | p3 monovalent | C-terminal | $1.89 \times 10^9$ |
| T01 | Select 10-3B | linear | T7 | full phage | polyvalent | C-terminal | $5.1 \times 10^7$ |

Positive Selection in bEnd.3 and CHo-K1 Cell Lines

The bEnd.3 mouse endothelial cell line was chosen as the primary target for positive selections in phage CPP screening as it has previously been used as model for the blood brain barrier, making it appropriate for a study aimed at generating BBB-specific CPPs. The cell line was purchased from ATCC and was readily established in culture. Cell-lines were successfully established in-house. Where preferred, cultures were scaled to provide sufficient cell numbers for cell-based phage selections. A human BBB model cell line, such as the hCMEC/D3 cell line is also preferred for the generation of human-specific CPPs.

CHO-K1 cells were also employed.

In brief, phage display libraries ($5 \times 10^{12}$ phage) were incubated for various times with CHO-K1 or bEnd.3 cells ($2 \times 10^6$), either held in suspension or attached to plates. After treatment to remove surface-bound phage, cells were harvested, either by trypsinization or cell scraping, and then lyzed to recover internalized phage. Between 1-5 iterative rounds of biopanning were performed for each screen.

In addition, selected screens were spiked with phage displaying the TAT peptide at various ratios (1:200 and 1:1000) to determine if the selection conditions could enrich for positive control CPPs.

To maximise the diversity of phage display peptides, a panel of 6 different phage display libraries were screened maintained in full culture medium (ie. RPMI) or a combination of ½ PBS and ½ medium compared to PBS alone. In addition cell viability was further improved by maintaining solutions at 37° C. during the selection process.

Following selections, maximum recovery of viable cells was achieved when cells were harvested via scraping compared to trypsinization.

Thus, conditions were optimized herein for efficient removal of non-specific surface-bound T7 and M13 phage that might otherwise contaminate the output from the internalization screens. Additional proteases could be screened for the ability to specifically remove surface-bound T7 phage.

Combined Negative and Positive CPP Selections

Screens were performed according the protocol described herein above, except for the inclusion of a cell-based subtractive screen, designed to enrich for cell-specific binders. To achieve this, phage libraries (Table 3) were pre-incubated either with a murine epithelial cell-line (SVEC4-10) or a human endothelial cell-line (HUVEC) for 30-60 mins prior to CPP selection against the bEnd.3 brain endothelial cell-line. Peptides that scored as highly positive for cell-binding/uptake against bEnd.3 cells were also screened using flow cytometry against a panel of unrelated cell-lines consisting of CHO-K1, SVEC4-10 and HepG2 cells.

A total of 27 independent screens were performed using various screening conditions (Table 4).

TABLE 4

Summary of combined screens

| Library | Screens (n) | Rounds | Variable screening parameter |
|---|---|---|---|
| M13 p3 | 8 | 4-5 | Phage/cell incubation times +/−HUVEC neg selection +/−SVEC4-10 neg selection |
| M13 p8 | 10 | 4-5 | Phage/cell incubation times +/−HUVEC neg selection +/−SVEC4-10 neg selection |
| M13 pJuFo | 2 | 4-5 | Phage/cell incubation times +/−HUVEC neg selection |
| T7 | 7 | 4-5, 1 screen to rd 9 | Phage/cell incubation times +/−HUVEC neg selection +/−SVEC4-10 neg selection +/−chloroquine |
| Total | 27 | | |

Results showed that while a number of peptides bound/internalized with equal efficiency across all cell lines, similar to the behaviour of the PYC38-TAT control peptide, others showed evidence of cell-selectivity.

The inclusion of a negative selection step had no obvious impact on the efficiency of phage recovery, with titres ranging from $10^4$ to $10^5$ virions/round (data not shown), which was consistent with the output from the pilot screens. While these screens were designed to select for peptides with cell-specific CPP activity, the inventors also expect that sequences, which do not discriminate between different cell types will be rescued Flow Cytometry-Based Detection of Peptide Internalization RDG-displaying T7 and M13 phage were labelled with either AF488 or OG 488 according to the procedure described in Section 2.3. Adherent CHO cells were then trypsinized and washed, before approximately $5 \times 10^5$ cells were incubated with ~$10^{10}$ labelled phage for 1 hour at 37° C. protected from light. Subsequently, cells were washed, to remove surface-bound phage, and analysed using flow cytometry. The level of phage internalization was assessed by comparing fluorescence signals for phage displaying the RGD peptide versus wild-type phage. To differentiate between internalized and surface-bound phage, intact cells were also incubated with either a PE-conjugated anti-M13antibody or anti-AF488/anti-OG488 quenching antibodies.

Flow cytometry analysis revealed clearly discernable differences in signal levels between wild-type and RGD-displaying phage labelled with either AF488 or OG488. Analysis of T7 phage showed that significantly higher signal strengths were observed for phage displaying the RGD peptide relative to the wild-type population. Moreover, the limited reduction in signal that occurred following the addition of an anti-OG488 quenching antibody suggests the majority of signal was due to internalized phage. Higher signals were also observed for M13 phage displaying the RGD peptide compared to the wild-type controls, although the signal differential was lower than that observed with T7 phage. This apparent reduction in sensitivity is most likely due to differences in the levels of input phage as the ratio of wild-type to RDG-displaying phage used was ~100:1. Use of higher concentrations of wild-type phage would correlate with higher levels background binding and/or non-specific cell uptake.

In summary, a flow cytometry-based method can successfully detect peptide-mediated internalization of fluorescently labelled phage into mammalian cells. This is the first example of such a method being used to directly validate CPP activity of phage-displayed peptide.

Use of Live Confocal Microscopy Method to Screen for Cell Internalization

Briefly, bEnd.3 and CHO cells were seeded at subconfluent density (~50%) on 8-well chambered coverglasses, incubated for 24 hrs, washed with culture medium containing 1% FBS and then incubated with 5-30 µM of labelled peptide for 1 hr in culture media containing 1% FBS before being imaged using confocal microscopy.

A total of 13 FITC-labelled peptides were screened for CPP activity using confocal microscopy. Analysis revealed that 7/13 peptides showed evidence for internalization in either CHO or bEnd.3 cells, corresponding to a functional hit rate of 54% (for peptides tested). Importantly, strong uptake was observed for the positive control peptide PYC38_TAT while no uptake was seen for PYC38, confirming the flow cytometry results for these two peptides.

The positive control peptide PYC38-TAT showed strong nuclear localization in both CHO and bEnd.3 cells, which has previously been reported for this peptide. Analysis of the phage display peptides showed that while some were widely dispersed throughout the cytoplasm and the nucleus, others appeared to be concentrated in the nucleus.

Other Methods of Detecting Peptide Internalization

To detect or confirm internalization of phage-displayed CPP peptides, the inventors also consider the following methods to have utility:

1. Flow cytometry to detect phage internalization following fixation and permeabilization of cells and subsequent detection using an appropriate combination of primary and secondary antibodies. Alternatively, M13 or T7-specific fluorophore-labelled antibodies could be pre-incubated with phage and then monitored for internalization.

2. Immunhistochemistry to detect of unlabelled phage following fixation and permeabilization of cells followed by detection using an appropriate combination of primary and secondary antibodies.

3. Phage titration to determine the efficiency of internalization.

Example 3

Validation of Internalisation Capability of CPPs

A selection of 152 peptides from the screens were also synthesized with N-terminal FITC labels. Peptides (n=52) were also produced in Pepset format. For a positive CPP control, the inventors chose a TAT-PYC38 phage display fusion, which has previously been validated for CPP activity in mammalian cells using confocal microscopy and various other functional assays. PYC38 (+/−TAT) peptides, along with the CPP controls listed in Table 1, were synthesized with N-terminal AF488- or FITC-fluorophores (Table 8).

Cells were seeded in 6-well plates and then grown for 24 hours before peptide was added for 1 hour at 37° C. Cells were harvested via trypsinization, and then assayed for peptide internalization/binding by flow cytometry.

The flow cytometry procedure was initially optimized using fluorophore-labelled TAT-PYC38. Subsequently, FITC-labelled peptides from the Phase 1-Pilot and Phase 2-CPP screens were assessed at 10 µM concentrations for internalization using CHO and bEnd3 cells. Peptides that scored as positive in the cell binding/internalization assay were subjected to further analysis using different temperatures and cell lines to determine cell selectivity. The cell-binding/uptake activity of pure (>85% purity) and Pepset (purity ranges from 40-80%) peptides was also compared to determine whether peptide purity affected CPP activity.

A comparison of labelled pure and crude (Pepset) peptide preparations revealed a close correlation between the cell binding/uptake activities of peptides synthesized by either method, although significant differences were observed in terms of the respective peptide concentrations preferred to confirm cell-binding/uptake. In general, Pepsets preferred higher concentrations to achieve the same level of activity as their 'pure' peptide counterparts, presumably due to the lower yields of full-length labelled peptide achieved by the crude synthesis approach. While encouraging, it should be noted these results were obtained using a limited set of hits shown to be positive for cell binding/uptake.

Flow cytometry analysis showed that the FITC-labelled PYC38-TAT peptide exhibited significantly higher levels of cell binding/internalization than the PYC38 control. This result suggests that the increase in signal is due the presence of the TAT CPP motif. Duplicate samples showed excellent reproducibility (panels A and C) highlighting the robust nature of the detection procedure. Incubation of cells with increasing concentrations of PYC38-TAT (ranging from 10 µM to 100 µM) resulted in a dose-dependent increase in cell-binding/uptake. A similar result was observed with FITC-labelled PYC38 although the overall level of cell-binding/uptake was significantly lower that for PYC38-TAT. As CPP uptake is thought to be an energy-dependent process, the inventors compared the cell-binding/uptake activity of peptides incubated with cells at 4° C. and 37° C. Analysis revealed significantly higher levels of cell binding/uptake were observed for PYC38-TAT incubated at 37° C. compared to 4° C. This is consistent with reports in the literature. While a similar temperature-dependent increase in cell-uptake/binding was observed for PYC38, both the degree of increase and the overall level of signal strength were much lower than for PYC38-TAT. Uptake of PYC38-TAT was observed as early as 5 minutes after addition of the peptide and reached maximum levels after ~30 minutes (data not shown).

Of 52 peptides derived from the Phase 1 screen assessed for cell binding/uptake using flow cytometry, 7 peptides scored as positive for cell/binding uptake in CHO cells, corresponding to a hit rate of 13.5%. Analysis of a further 100 synthetic peptides derived from the Phase 2-CPP screens were subjected to cell-binding/internalization analysis using bEnd.3 cells. A total of 29 peptides (29%) scored as positive for cell-binding/uptake activity although this number was reduced to 10 peptides (10%) when a threshold of at least 60% FITC-positive cells was applied. Notably, a number of these candidates were rescued on multiple occasions from independent CPP screens.

Example 4

Ability of CPPS to Deliver Cargo

Thirteen clones obtained from the CPP and cell-binding screens against bEnd.3 cells were expressed as recombinant fusions to the Maltose-binding protein (MBP), evaluate the ability of CPP candidates to deliver large cargoes (ie. MBP) into cells.

All 13 recombinant fusions were successfully expressed in E. coli, purified via affinity chromatography (AKTAxpress) and then labelled with AF488 using primary amine reactive chemistries. Labeling efficiency was determined to be 1 molecule of AF488/recombinant protein. Labelled MBP-fusions were then analysed via flow cytometry for binding/uptake into bEnd.3 cells. Recombinant TAT-MBP (rTAT-MBP) and MBP (rMBP) were used as positive and negative CPP controls respectively.

Of the 13 recombinant phage displays tested, 9 scored as positive for cell binding/uptake when incubated with bEnd.3 at 37° C. In contrast, rMBP-control gave little or no signal when tested at the same concentrations (5 µM), whereas the rTAT-MBP fusion gave a high signal. Minimal binding was observed for the majority of phage display fusions incubated at 4° C. at 5 µM concentrations, however 70% of recombinant phage display-MBP fusions scored as positive for cell binding/uptake. A strong correlation was observed between synthetic and recombinant peptides for cell binding/uptake. Result suggests that CPP candidates can facilitate cell binding/uptake when attached to large cargoes. Recombinant expression is a viable option to assess peptides that are not amenable to synthesis.

These results also provide strong evidence to suggest the cell-binding screens can enrich for CPPs that are able to transport large cargo across the cell membrane.

Example 5

Recovery and Characterization of Cell-Penetrating Peptides

Clones from each screen described in Example 2 were PCR-amplified, sequenced and subsequently analyzed using Phylogica's BioLIM system. Analysis included i) an external BLAST search to identify the organism and genomic origin for each fragment and ii) an internal BLAST search against all existing entries in the database, to identify sibling sequences or overlapping fragments that might confirm enrichment for a particular clone or motif. A bioinformatic analysis was also used to assess peptides for CPP-like characteristics based amphipathicity, hydrophobicity, charge, size and presence of arginine and lysine residues. In addition a comprehensive bioinformatic analysis of all natural open reading frames (nORF) was performed using the following databases:

UniprotKb (http://www.uniprot.org)
Conserved domain database—CDD (http://www.ncbi.nlm.nih.gov/Structure/cdd/wrpsb.cgi)
Pfam (http://pfam.sanger.ac.uk/search)
Protonet (http://www.protonet.cs.huji.ac.il/class_your_prot.php)
InterproScan (http://www.ebi.ac.uk/Tools/InterProScan/
PDB (http://www.rcsb.org/pdb/home/home.do)
ModBase (http://modbase.compbio.ucsf.edu/modbase-cgi/index.cgi)
Swiss Model Repository (http://swissmodel.expasy.org/)
Psipred Secondary Structure Prediction (http://bioinf.cs.ucl.ac.uk/psipred/)

Table 5 provides a preliminary grouping of 576 peptides obtained by the screening method.

TABLE 5

Summary of sequences obtained from CPP screens using bEnd.3 cells.

|  | M13 p3 | M13 p8 | M13 pJuFo | T7 | Total |
|---|---|---|---|---|---|
| Screens sequenced (n) | 7 | 4 | 2 | 7 | 20 |
| Unique sequences (n) | 178 | 102 | 37 | 259 | 576 |
| Sequences with CPP characteristics (n)* | 22 (12.4%) | 16 (15.7%) | 3 (8.1%) | 31 (11.9%) | 72 (12.5%) |
| Sibling sequences all screens (n) | 2 | 8 | 0 | 17 | 28 |
| Sibling sequences different screens (n) | 2 (1 is partial overlap) | 0 | 0 | 2 | 4 |
| Sibling sequences different libraries (n) | 2 (1 is partial overlap) | 4 | 1 | 3 | 10 |

*mainly resembling arginine-rich CPPs with low amphipathicity, e.g. Tat and Penetratin Bioinformatic analysis revealed that 7.5%-12% of sequences obtained in any single screen of phage display libraries could be assigned to one of three CPP-like categories:

Class 1: peptides with low amphipathicity where the charge contribution originates mostly from arginine residues.
Class 2: peptides with a high degree of amphipathicity, where the charge contribution originates mostly from lysine residues.
Class 3: peptides where charged and hydrophobic residues are separated lengthwise in the chain.

Interestingly, a propensity for a peptide to exhibit cell selectivity appeared to correlate with sequence composition. For example, TAT-like peptides were more likely to bind across all cell types while sequences derived from natural open reading frames or with neutral charge were more likely to show cell selectivity.

The data set was also subjected to a comprehensive bioinformatic analysis using a range of relevant variables (eg. charge, amino acid composition and frequency, hydrophobicity, hydrophilicity). Analysis failed to reveal any significant differences between screened and naïve libraries, with the exception of charge. Interestingly, while sequences from the T7 CPP screens showed a distinct shift towards more negatively charged peptides, CPP sequences obtained from screening the M13 p8 libraries were more positively charged compared to the naïve library sequences (data not shown).

An additional bioinformatic analysis was undertaken using a subset of peptides derived from natural open reading frames (nORFs), corresponding to known proteins. A variety of on-line databases (see above) were used to assign sequences to different protein families defined according to function. Of particular interest, was the apparent enrichment for bacterial virulence factors (as defined by Pfam) in the Phase 2-CPP screen relative to the naïve phage display libraries.

The presence of multiple copies of the same sequence or sibling within a screen and between different screens and libraries suggests there was selective pressure for particular clones. Enrichment for sibling sequences were observed in several screens, particularly in the later screening rounds. The same sequences were also recovered from independent screens and from different phage display libraries.

High levels of sequence diversity observed within the pool of non-CPP like sequences, suggests the phage display libraries can serve as a discovery platform for novel classes of CPPs.

In summary, a highly diverse population of phage displays was recovered from the screens described herein. Recovery of such a large number of unique clones was not surprising given the range of different screening conditions used and the fact that clones were recovered from all rounds within each screen. The finding of specific enrichment for sibling sequences with CPP-like characteristics provides some evidence that screens were selecting for cell penetration. Moreover, the fact that the same sequences were recovered multiple times from different screens and libraries indicates there was a strong selection bias for these clones. Enrichment for CPP-like sequences was observed across all phage display libraries.

Tables 6-9 demonstrate exemplary CPPs obtained by performing a method or process of the present invention as described according to any example hereof.

TABLE 6

Cell selectivity profile of exemplary CPPs by flow cytometry

| PEPTIDE ID | SEQ ID NO: | Peptide Charge | Peptide length | Flow cytometry (10 μM) | | |
|---|---|---|---|---|---|---|
|  |  |  |  | bEnd.3 | CHO | SVEC 4-10 |
| 8093 | 9 | +5 | 19 | + | ++ | ++ |
| 0045 | 14 | +5 | 14 | ++ | +++ | ++ |
| 9170 | 15 | +9 | 18 | ++ | +++ | ++ |
| 0076 | 10 | −3 | 34 | + | − | − |
| 4052 | 16 | +6 | 14 | + | + | ++ |
| 2113 | 13 | −11 | 41 | − | − | − |
| 5008 | 5 | +3 | 30 | ++ | − | ++ |
| 3194 | 6 | −4 | 47 | − | − |  |
| 9190 | 3 | −7 | 64 | − | − |  |
| 1059 | 4 | +2 | 51 | + | − |  |
| 1115 | 7 | −6 | 70 | ++ | +++ |  |
| 0125 | 8 | −10 | 94 | NT | +++ |  |
| 9102 | 11 | −17 | 69 | + | ++ |  |
| 5112 | 12 | −16 | 69 | + | + |  |
| 9072 | 1 | +5 | 13 | ++ | +++ | ++ |
| 4063 | 2 | +5 | 14 | ++ | +++ | ++ |
| 9140 | 17 | 0 | 35 | + | − | + |
| 1082 | 18 | +5 | 15 | ++ | + | + |
| 4033 | 19 | −2 | 15 | + | − | − |

TABLE 7

Cell-selectivity profiles of exemplary CPPs by fluorescence microscopy

| PEPTIDE ID | SEQ ID NO: | Peptide Charge | Peptide length aa | Fluorescent microscopy (10 μM, SF) bEnd.3 10 μM | 10 μM, 2.2 s | CHO 10 μM | 10 μM 2.2 s |
|---|---|---|---|---|---|---|---|
| 8093 | 9 | +5 | 19 | + | | + | |
| 0045 | 14 | +5 | 14 | ++ | | ++ | |
| 9170 | 15 | +9 | 18 | + | | +++ | |
| 0076 | 10 | −3 | 34 | − | + | − | |
| 4052 | 16 | +6 | 14 | ++ | | +++ | |
| 2113 | 13 | −11 | 41 | − | | − | |
| 5008 | 5 | +3 | 30 | + | | +++ | |

TABLE 8

Cell-selectivity profiles of exemplary CPPs by fluorescence microscopy

| PEPTIDE ID | SEQ ID NO: | Peptide Charge | Peptide length | Fluorescent microscopy (10 μM, SF) bEnd.3 | CHO |
|---|---|---|---|---|---|
| 3194 | 6 | −4 | 47 | + | − |
| 9190 | 3 | −7 | 64 | + | − |
| 1059 | 4 | +2 | 51 | + | ++ |
| 1115 | 7 | −6 | 70 | + | +/− |
| 0125 | 8 | −10 | 94 | ++* | NT |
| 9102 | 11 | −17 | 69 | + | − |
| 5112 | 12 | −16 | 69 | NT | NT |
| 9072 | 17 | +5 | 13 | ++ | ++ |
| 4063 | 2 | +5 | 14 | ++ | +++ |

TABLE 9

Cytotoxicity profiles of exemplary CPPs

| PEPTIDE ID | SEQ ID NO: | Peptide Charge | Peptide length | Cytotoxicity (10 μM) bEnd.3 (2, 24 hrs) | CHO (2, 24 hrs) |
|---|---|---|---|---|---|
| 8093 | 9 | +5 | 19 | − | − |
| 0045 | 14 | +5 | 14 | − | − |
| 9170 | 15 | +9 | 18 | − | − |
| 0076 | 10 | −3 | 34 | − | − |
| 4052 | 16 | +6 | 14 | − | − |

TABLE 9-continued

Cytotoxicity profiles of exemplary CPPs

| PEPTIDE ID | SEQ ID NO: | Peptide Charge | Peptide length | Cytotoxicity (10 μM) bEnd.3 (2, 24 hrs) | CHO (2, 24 hrs) |
|---|---|---|---|---|---|
| 2113 | 13 | −11 | 41 | NT | NT |
| 5008 | 5 | +3 | 30 | − | − |
| 9072 | 1 | +5 | 13 | − | − |
| 4063 | 2 | +5 | 14 | − | − |

Example 6

Confirmation of Cell Penetrating Activity of Serine-Substituted Peptides

This example confirms the functionality of exemplary cysteine-containing CPPs of the invention and exemplary modified versions of the peptides, e.g., derivatives, comprising one or more serine residues in place of the cysteine residues.

Exemplary unmodified cell-penetrating peptides of the invention, and exemplary modified versions of cell-penetrating peptides of the invention comprising cysteine-to-serine substitutions, were produced, according to standard procedures, and tested for their ability to deliver a cargo comprising a fluorophore to a CHO cell or HEK cell, essentially as described in Example 3 hereof. The amino acid sequences of the modified peptides are set forth in Table 10.

TABLE 10

Exemplary serine-substituted CPPs

| Unmodified Peptide ID | Unmodified Peptide SEQ ID NO: | Unmodified Peptide sequence | Modified Peptide ID | Modified Peptide SEQ ID NO | Modified Peptide Sequence |
|---|---|---|---|---|---|
| 0045 | 14 | PFLKRVPACLRLRR | 0045a | 24 | PFLKRVPASLRLRR |
| 9170 | 15 | RCGRASRCRVRWMRRRRI | 9170a | 25 | RSGRASRSRVRWMRRRRI |
| 4052 | 16 | WGCCGRSSRRRRTR | 4052a | 26 | WGSSGRSSRRRRTR |
| 5008 | 5 | PYSRPHVQLWYPNRESCRSLIRSLGP | 5008a | 27 | PYSRPHVQLWYPNRESSRSLIRSLGP |

Figure 45:
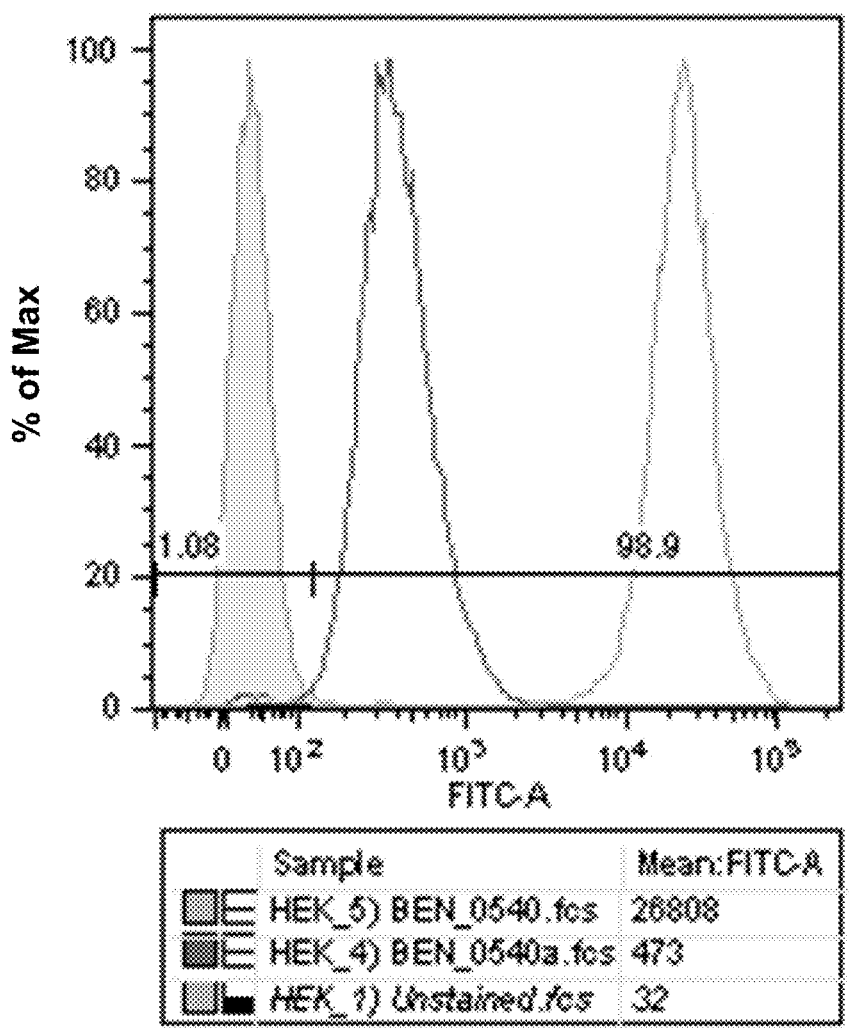
FIG. 45 provides a graphical representation showing the results of flow cytometry analysis of the uptake of 10 uM CPP of the invention, Peptide ID 0045 (shown here as "BEN_0540"; SEQ ID No. 14) and its serine substitution derivative, Peptide ID 0045a (shown here as "BEN_0540a"; SEQ ID No. 24) in HEK293 cells (corresponding data in CHO cells not shown).
Figure 46:
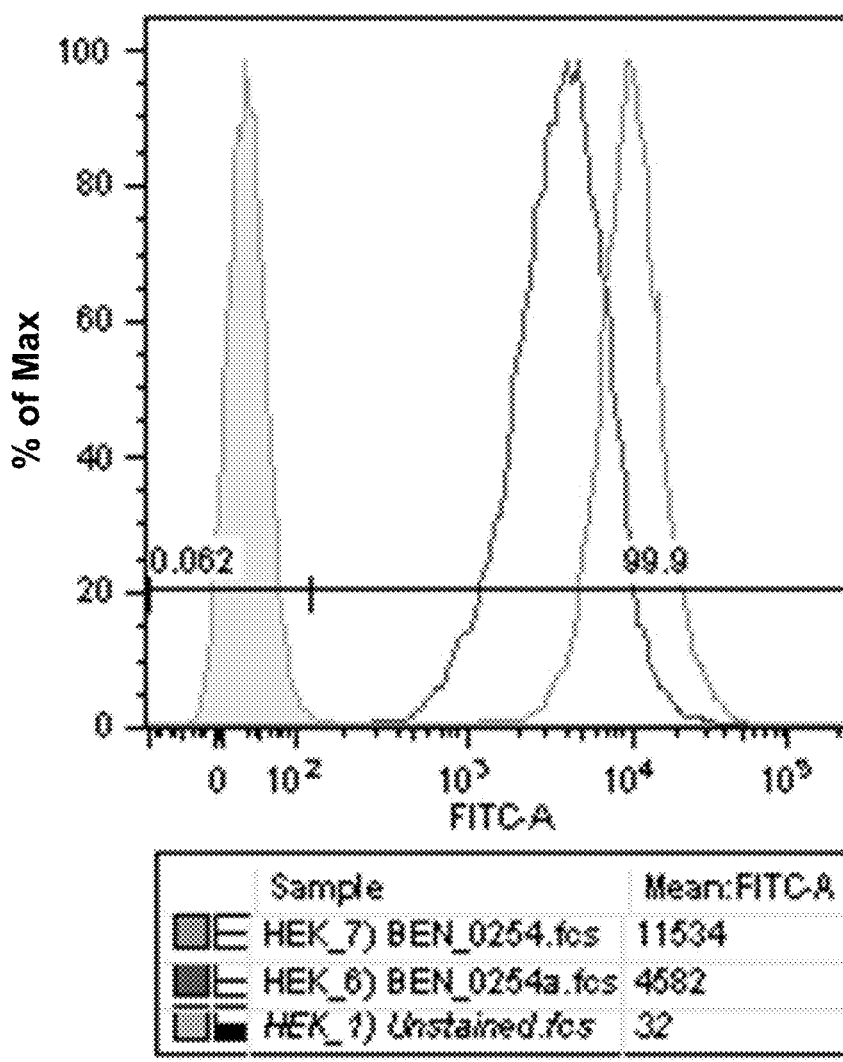
FIG. 46 provides a graphical representation showing the results of flow cytometry analysis of the uptake of 10 uM CPP of the invention, Peptide ID 4052 (shown here as "BEN_0254"; SEQ ID No. 16) and its serine substitution derivative, Peptide ID 4052a (shown here as "BEN_0254a"; SEQ ID No. 26) in HEK293 cells (corresponding data in CHO cells not shown).

Exemplary data presented in FIG. 45 and FIG. 46 demonstrate that both unmodified cell-penetrating peptides of the invention, and modified versions of the peptides wherein cysteine residues are substituted for serine residues, are functional in delivery of cargo to CHO cells (data not shown) and HEK cells.

Example 7

Delivery of a Neuroprotective Cargo with Exemplary CPPs of the Invention

This example demonstrates the ability of exemplary cell-penetrating peptides of the invention to deliver a peptide cargo to neural cells.

Peptides ID 4052 (SEQ ID NO: 16; Table 10), Peptides ID 4052a (SEQ ID NO: 26; Table 10), and TAT peptide (GRKKRRQRRRG; SEQ ID NO: 28) were each produced as fusions to the neuroprotective peptide PYC36 (GLQGRRRQGYQSIKP; SEQ ID NO: 29) described in WO 2008/034161. The fusion peptides were assayed for their ability to confer survival on primary cortical neuronal cultures by glutamate excitotoxicity assay as described in Example of WO 2008/034161.

Figure 47:
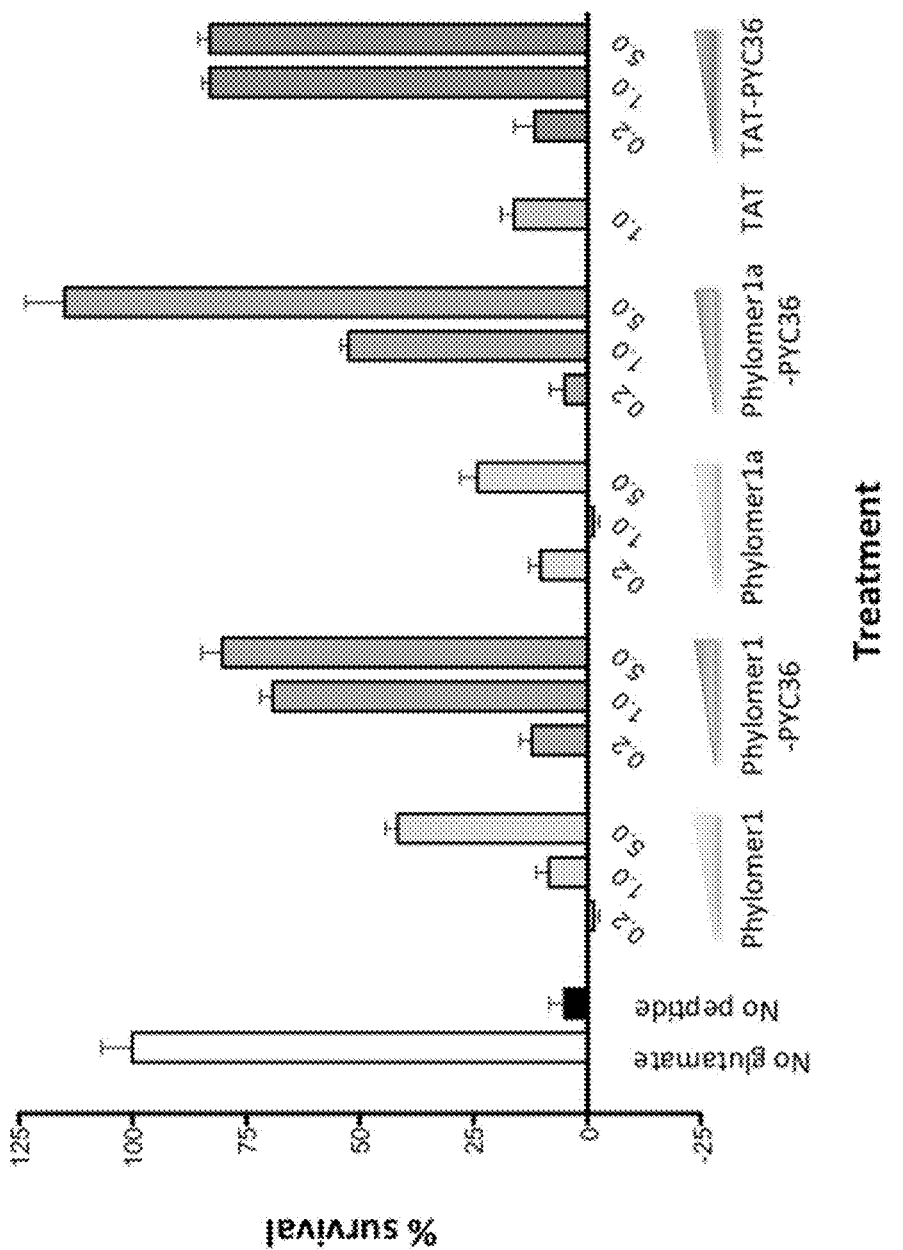
FIG. 47 provides a graphical representation showing the results of dose-dependent neuroprotective activity of certain peptides or CPP-cargo fusions following glutamate induced neural damage. Peptide ID 4052 is shown in this figure as "Peptide 1" and 4052a as "Peptide 1a". For example, at 1 uM, a fusion of PYC36 with Peptide ID 4052 shows equivalent to PYC36 delivered as a fusion using the prior-art TAT sequence, and at 5 uM PYC36 delivered with 4052a shows improved neuroprotection than that provided by PYC36 delivered as a TAT fusion. Treatment with PYC36 alone shows negligible neuroprotective activity (data not shown).

Data presented in FIG. 47 indicate that the exemplary CPPs of the invention can deliver a pharmacologically active cargo to a relevant tissue and produce an applicable and relevant biological response.

We claim:

1. A conjugate comprising:
   (i) a cell-penetrating peptide (CPP), or analog thereof, comprising an amino acid sequence at least 90% identical over the entire length of any one of SEQ ID NOs:11-13, wherein the cell-penetrating peptide is not a full-length protein that occurs in nature, and wherein the analog:
      (a) comprises one or more D-amino acid substitutes relative to the sequence of the cell penetrating peptide;
      (b) is a retro-inverso peptide analog of the cell penetrating peptide, or
      (c) comprises one or more non-naturally occurring amino acids, wherein each non-naturally amino acid is substituted for its natural counterpart in the sequence of the cell penetrating peptide, and
   (ii) a cargo for delivery in to a cell or sub-cellular location, wherein the cargo is associated with or covalently linked to the cell penetrating peptide or analog thereof, and wherein a cargo that is a peptide, polypeptide or protein is a second peptide, polypeptide or protein relative to the CPP.

2. A pharmaceutical composition comprising at least one conjugate according to claim 1 and a pharmaceutically-acceptable carrier or excipient.

3. The pharmaceutical composition according to claim 1 formulated for parenteral administration.

4. The conjugate according to claim 1, wherein the cargo is selected from the group consisting of: small molecules, carbohydrates, lipids, nucleic acids, cells, bacteriophage particles, virus particles, synthetic polymers, resins, latex particles, and dyes.

5. The conjugate according to claim 1, wherein the cargo is a second peptide, a polypeptide or a protein.

6. The conjugate according to claim 5, wherein the second peptide, polypeptide or protein is a therapeutic or diagnostic molecule.

7. The conjugate according to claim 1, wherein the cargo is covalently-linked to the cell-penetrating peptide or analog by a linker or spacer molecule.

8. The conjugate according to claim 1, wherein the conjugate is bound to a solid matrix comprising the cell-penetrating peptide or analog.

9. The conjugate according to claim 1, wherein the conjugate comprises at least one detectable molecule.

10. The conjugate according to claim 9, wherein the detectable molecule is selected from the group consisting of a haloalkane moiety, fluorophore, radioactive label, luminescent molecule, nanoparticle, contrast agent, a fluorescent compound, a cell-permeant FRET-paired fluorescent compound, and a quantum dot.

11. The conjugate according to claim 1 in an isolated form.

12. The conjugate according to claim 1, wherein the sequence of the cell-penetrating peptide or cell-penetrating analog thereof comprises the amino acid sequence of any one of SEQ ID NOs: 11-13.

13. The conjugate according to claim 1, wherein the cargo is selected from the group consisting of small molecules, carbohydrates, nucleic acids, and cells.

14. The conjugate according to claim 9, wherein the detectable molecule is selected from the group consisting of a haloalkane moiety, a luminescent molecule, a nanoparticle, a contrast agent, and a quantum dot.

\* \* \* \* \*